(12) United States Patent
Tschumperlin et al.

(10) Patent No.: US 12,264,163 B2
(45) Date of Patent: Apr. 1, 2025

(54) COMPOUNDS AND METHODS FOR TREATING FIBROTIC PATHOLOGIES

(71) Applicant: Mayo Foundation for Medical Education and Research, Rochester, MN (US)

(72) Inventors: Daniel J. Tschumperlin, Rochester, MN (US); Andrew J. Haak, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 646 days.

(21) Appl. No.: 17/625,244

(22) PCT Filed: Jul. 29, 2020

(86) PCT No.: PCT/US2020/044054
§ 371 (c)(1),
(2) Date: Jan. 6, 2022

(87) PCT Pub. No.: WO2021/021922
PCT Pub. Date: Feb. 4, 2021

(65) Prior Publication Data
US 2022/0275002 A1 Sep. 1, 2022

Related U.S. Application Data

(60) Provisional application No. 62/880,494, filed on Jul. 30, 2019, provisional application No. 62/880,594, filed on Jul. 30, 2019.

(51) Int. Cl.
| | | |
|---|---|---|
| *C07D 401/12* | (2006.01) | |
| *A61K 31/454* | (2006.01) | |
| *A61P 19/04* | (2006.01) | |
| *C07D 217/02* | (2006.01) | |
| *C07D 401/04* | (2006.01) | |
| *C07D 405/04* | (2006.01) | |
| *C07D 407/04* | (2006.01) | |
| *C07D 471/06* | (2006.01) | |
| *C07D 491/052* | (2006.01) | |
| *C07D 491/06* | (2006.01) | |
| *C07D 491/16* | (2006.01) | |

(52) U.S. Cl.
CPC .......... *C07D 491/16* (2013.01); *A61P 19/04* (2018.01); *C07D 217/02* (2013.01); *C07D 401/04* (2013.01); *C07D 405/04* (2013.01); *C07D 407/04* (2013.01); *C07D 471/06* (2013.01); *C07D 491/052* (2013.01); *C07D 491/06* (2013.01)

(58) Field of Classification Search
CPC .......................... C07D 401/12; A61K 31/454
See application file for complete search history.

(56) References Cited

U.S. PATENT DOCUMENTS

| | | |
|---|---|---|
| 4,963,568 A | 10/1990 | Schoenleber et al. |
| 5,304,121 A | 4/1994 | Sahatjian |
| 5,502,080 A | 3/1996 | Hitzig |
| 5,591,884 A | 1/1997 | DeNinno et al. |
| 5,621,133 A | 4/1997 | DeNinno et al. |
| 5,886,026 A | 3/1999 | Hunter et al. |
| 6,004,982 A | 12/1999 | Stupczewski et al. |
| 6,099,562 A | 8/2000 | Ding et al. |
| 6,713,506 B2 | 3/2004 | Dou et al. |
| 6,803,031 B2 | 10/2004 | Rabinowitz et al. |
| 8,859,001 B2 | 10/2014 | Levite et al. |
| 2008/0114080 A1 | 5/2008 | Chen |
| 2009/0005394 A1 | 1/2009 | Harbeson |
| 2009/0247483 A1 | 10/2009 | Mitchell et al. |
| 2013/0338145 A1 | 12/2013 | Mitchell et al. |
| 2015/0157584 A1 | 6/2015 | Guan et al. |
| 2016/0032384 A1 | 2/2016 | Murphy et al. |
| 2017/0174713 A1 | 6/2017 | Du et al. |
| 2019/0151270 A1 | 5/2019 | Ashby |
| 2021/0038561 A1 | 2/2021 | Tschumperlin et al. |
| 2023/0346740 A1 | 11/2023 | Tschumperlin et al. |
| 2024/0043396 A1 | 2/2024 | Haak et al. |
| 2024/0252463 A1 | 8/2024 | Tschumperlin et al. |

FOREIGN PATENT DOCUMENTS

| | | |
|---|---|---|
| WO | WO 1990015056 | 12/1990 |
| WO | WO 1996038435 | 12/1996 |
| WO | WO 1997006799 | 2/1997 |
| WO | WO 2006012640 | 2/2006 |
| WO | WO 2010124005 | 10/2010 |
| WO | WO 2011069051 | 6/2011 |
| WO | WO 2017132661 | 8/2017 |
| WO | WO 2019152733 | 8/2019 |
| WO | WO 2020145364 | 7/2020 |

OTHER PUBLICATIONS

"Interstitial Lung Disease", Mayo Clinic, Jul. 21, 2017. Accessed Mar. 10, 2022. Available from: <https://www.mayoclinic.org/diseases-conditions/interstitial-lung-disease/symptoms-causes/syc-20353108 >. (Year: 2017).
"Pain and IPF: What's the deal", Pulmonary Fibrosis News, Nov. 13, 2017. Accessed Mar. 17, 2022. Available from <https://www.pulmonaryfibrosisnews.com/2017/11/13/ipf-pain-what-is-going-on-how-to-alleviate-it/> (Year: 2017).
Andersen et al., "Dopamine receptor agonists: selectivity and dopamine D1 receptor efficacy," Eur. J. Pharmacology, Jun. 12, 1990, 188(6):335-347.
Bai et al., "Yes-associated protein regulates the hepatic response after bile duct ligation," Hepatology, Sep. 2012, 56(3):1097-1107.
Bonner et al., "Facile synthesis of octahydrobenzo[h]isoquinolines: Novel and highly potent D1 dopamine agonists," Bioorg. Med. Chemistry, Sep. 15, 2010, 18(18):6763-6770.

(Continued)

*Primary Examiner* — Bruck Kifle
(74) *Attorney, Agent, or Firm* — Fish & Richardson P.C.

(57) ABSTRACT

The present application provides methods for treating or preventing diseases and conditions associated with tissue fibrosis.

13 Claims, 104 Drawing Sheets

Specification includes a Sequence Listing.

(56) References Cited

OTHER PUBLICATIONS

Brogden et al., "Fenoldapam: A Review of its Pharmacodynamic and Pharmacokinetic Properties and Intravenous Clinical Potential in the Management of Hypertensive Urgencies and Emergencies," Drugs, Oct. 1997, 54(4):634-650.
Cohen, Rachel. "Dopamine and Chronic Pain", Rachel Cohen, South West Spine and Pain Center, May 13, 2015, Accessed Mar. 10, 2022. Available from: <https://www.southwestspineandpain.com/blog/dopamine-and-chronic-pain>. (Year: 2015).
DeNinno et al., "Synthesis and Dopaminergic Activity of 3-Substituted 1-(Aminomethyl)-3,4-dihydro-5,6-dihydroxy-1H-2-benzopyrans: Characterization of an Auxiliary Binding Region in the D1 Receptor," J. Med. Chemistry, Aug. 1, 1991, 34(8):2561-2569.
Dupont et al., "Role of YAP/TAZ in mechanotransduction," Nature, Jun. 8, 2011, 474:179-183.
Elbediwy et al., "Integrin signalling regulates YAP and TAZ to control skin homeostasis," Development, May 2016, 143(10):1674-1687.
Elbediwy et al., "YAP and TAZ in epithelial stem cells: A sensor for cell polarity, mechanical forces and tissue damage," Bioessays, Jul. 2016, 38(7):644-653.
Flock et al., "Selectivity determinants of GPCR-G-protein binding," Nature, May 18, 2017, 545(7654):317-322.
Grove et al., "YAP/TAZ initiate and maintain Schwann cell myelination," eLife, Jan. 26, 2017, 6:e20982, 27 pages.
Gu et al., "Soft matrix is a natural stimulator for cellular invasiveness," Mol. Biol. Cell, Feb. 15, 2014, 25(4):457-469.
Gurevich, Eugenia, et al. "G protein-coupled receptor kinases as regulators of dopamine receptor functions", Pharmacol Res. (Sep. 2016) 111:1-16, pp. 1-38. (Year: 2016).
Hahn et al., "Characterization of the peripheral and central effects of SK&F 82526, a novel dopamine receptor agonist," J. Pharmacol. Exp. Therapeutics, Nov. 1982, 223(2):305-313.
Hansen et al., "YAP and TAZ: a nexus for Hippo signaling and beyond," Trends Cell Biology, Sep. 2015, 25(9):499-513.
Hauser et al., Trends in GPCR drug discovery: new agents, targets and indications, Nat. Rev. Drug Discovery, Dec. 2017, 16(12):829-842.
Huang et al., "Matrix Stiffness-Induced Myofibroblast Differentiation is Mediated by Intrinsic Mechanotransduction," Am. J. Respir. Cell Mol. Biology, Sep. 2012, 47(3):340-348.
Ilium, "Is nose-to-brain transport of drugs in man a reality?," J. Pharm. Pharmacology, Jan. 2004, 56(1):3-17.
Ilium, "Transport of drugs from the nasal cavity to the central nervous system," Eur. J. Pharm. Sciences, Jul. 2000, 11(1):1-18.
Imajo et al., "Dual role of YAP and TAZ in renewal of the intestinal epithelium," Nat. Cell Biology, Jan. 2015, 17(1):7-19.
Insel et al., "GPCR expression in tissues and cells: Are the optimal receptors being used as drug targets?," Brit. J. Pharmacology, Mar. 2012, 165(6):1613-1616.
Jorgenson et al., "TAZ activation drives fibroblast spheroid growth, expression of profibrotic paracrine signals, and context-dependent ECM gene expression," Am. J. Physiol. Cell Physiology, Mar. 2017, 312(3):C277-C285.
Kim et al., "cAMP/PKA signalling reinforces the LATS-YAP pathway to fully 25 suppress YAP in response to actin cytoskeletal changes," EMBO Journal, May 29, 2013, 32(11):1543-1555.
Kim et al., "YAP/TAZ regulates sprouting angiogenesis and vascular barrier maturation," J. Clin. Investigation, Aug. 14, 2017, 127(9):3441-3461.
Klecker et al., "Stereoselective metabolism of fenoldapam and its metabolites in human liver microsomes, cytosol, and slices," J. Cardiovasc. Pharmacology, Jul. 1997, 30(1):69-74.
Kordes, Claus, et al. "Stellate cells are mesenchymal stem cells", European Journal of Medical Research, (2014), vol. 19, Suppl. 1:S6, pp. 1-2. (Year: 2014).
Kuo et al., "Analysis of the myosin-II-responsive focal adhesion proteome reveals a role for β-Pix in negative regulation of focal adhesion maturation," Nat. Cell Biology, Apr. 2011, 13(4):383-393.
Levasseur et al., "Targeted Disruption of YAP and TAZ Impairs the Maintenance of the Adrenal Cortex," Endocrinology, Nov. 2017, 158(11):3738-3753.
Le Witt, "Subcutaneously administered apomorphine: pharmacokinetics and metabolism," Neurology, Mar. 23, 2004, 62(6 Suppl 4):S8-11.
Liang et al., "Yap/Taz Deletion in Gli+ Cell-Derived Myofibroblasts Attenuates Fibrosis," J. Am. Soc. Nephrology, Nov. 2017, 28(11):3278-3290.
Lin et al., "YAP is essential for mechanical force production and epithelial cell proliferation during lung branching morphogenesis," eLife, Mar. 21, 2017, 6:e21130, 25 pages.
Liu et al., "Feedback amplification of fibrosis through matrix stiffening and COX-2 suppression," J. Cell Biology, Aug. 2010, 190(4):693-706.
Liu et al., "Mechanosignaling through YAP and TAZ drives fibroblast activation and fibrosis," Am. J. Physiol. Lung Cell Mol. Physiology, Feb. 2015, 308(4):L344-L357.
Mannaerts et al., "The Hippo pathway effector YAP controls mouse hepatic stellate cell activation," J. Hepatology, Sep. 2015, 63(3):679-688.
Marinkovic et al., "Improved throughput traction microscopy reveals pivotal role for matrix stiffness in fibroblast contractility and TGF-β responsiveness," Am. J. Physiol. Lung Cell Mol. Physiology, Aug. 2012, 303(3):L169-L180.
Marinkovic et al., "Matrices of Physiologic Stiffness Potently Inactivate Idiopathic Pulmonary Fibrosis Fibroblasts," Am. J. Respir. Cell. Mol. Biology, Apr. 2013, 48(4):422-430.
Martin et al., "PAK proteins and YAP-1 signalling downstream of integrin beta-5 1 in myofibroblasts promote liver fibrosis," Nat. Communication, Aug. 18, 2016, 7:12502, 11 pages.
Martin, "The Discovery of Novel Selective D1 Dopaminergic Agonists: A-68930, A-77636, A-86929, and ABT-413," Int. J. Med. Chemistry, May 2011, 2011:424535, 9 pages.
Mih et al., "Matrix stiffness reverses the effect of actomyosin tension on cell proliferation," J. Cell Science, Oct. 2012, 125:5974-5983.
Miranda et al., "TGF-beta1 regulates the expression and transcriptional activity of TAZ protein via a Smad3-independent, myocardin-related transcription factor-mediated mechanism," J. Biol. Chemistry, 292(36):14902-14920.
Mirones et al., "Dopamine Mobilizes Mesenchymal Progenitor Cells Through D2-Class Receptors and Their PI3K/AKT Pathway," Stem Cells, May 8, 2014, 32(9):2529-2538.
Noguchi et al., "TAZ contributes to pulmonary fibrosis by activating profibrotic functions of lung fibroblasts," Sci. Reports, Feb. 14, 2017, 7:42595, 11 pages.
PCT International Preliminary Report on Patentability in International Appln. No. PCT/US2020/044054, dated Feb. 1, 2022, 7 pages.
PCT International Search Report and Written Opinion in International Appln. No. PCT/US2020/044054, dated Jan. 5, 2021, 12 pages.
Perumal et al., "Morin attenuates diethylnitrosamine-induced rat liver fibrosis and hepatic stellate cell activation by co-ordinated regulation of Hippo/Yap and TGF beta 1/Smad signaling," Biochimie, Sep. 2017, 140:10-19.
Piersma et al., "TGF-beta, WNT, and YAP/TAZ Converge," Front. Medicine, Sep. 3, 2015, 2:59, 14 pages.
Piersma et al., "YAP1 is a Driver of Myofibroglast Differentiation in Normal and Diseased Fibroblasts," Am. J. Pathology, Oct. 10, 2015, 185(12):3326-3337.
Pubchem CID 23643862, "(6Ar)-5,6,6a,7-Tetrahydro-3,6-dimethyl-4H-dibenzo[de,g]quinoline-10,11-diol," Jan. 14, 2008, 7 pages.
Pubchem CID 57340494, "(1S)-10-Methyl-15-azatetracyclo[7.7.1.02,7.013,17]heptadec-2(7),3,5,9,11,13(17)-hexaene-5,6-diol," Jul. 7, 2012, 6 pages.
Rahaman et al., "TRPV4 mediates myofibroblast differentiation and pulmonary fibrosis in mice," J. Clin. Investigation, Nov. 3, 2014, 124(12):5225-5238.

(56) References Cited

OTHER PUBLICATIONS

Snead et al., "G protein-coupled receptor (GPCR) regulation of cardiac fibrosis," FASEB Journal, Apr. 2012, 26(S1):1059.10.
Southan et al., "The IUPHAR/BPS Guide to Pharmacology in 2016: towards curated quantitative interactions between 1300 protein targets and 6000 ligands," Nucleic Acids Research, Jan. 2016, 44(Database Issue):D1054-D1068.
Szeto et al., "YAP/TAZ Are Mechanoregulators of TGF-beta-Smad Signaling and Renal Fibrogenesis," J. Am. Soc. Nephrology, Oct. 2016, 27(10):3117-3128.
Tang et al., "Snail/Slug-YAP/TAZ complexes cooperatively regulate mesenchymal stem cell function and bone formation," Cell Cycle, Jan. 2017, 16(5):399-405.
Totaro et al., "YAP/TAZ link cell mechanics to Notch signalling to control epidermal stem cell fate," Nat. Communications, May 17, 2017, 8:15206, 13 pages.
Townsend et al., "Constrictive pericarditis and pleuropulmonary fibrosis secondary to cabergoline treatment for Parkinson's disease," Heart, Aug. 2004, 90(8):e47, 2 pages.
Trissel et al., "Stability of fenoldopam mesylate in two infusion solutions," Am. J. Health Syst. Pharmacy, May 1, 2002, 59(9):846-848.
Tschumperlin et al., "Biomechanical regulation of mesenchymal cell function," Curr. Opin. Rheumatology, Jan. 2013, 25(1):92-100.
Wang et al., "Hepatocyte TAZ/WWTR1 Promotes Inflammation and Fibrosis in Nonalcoholic Steatohepatitis," Cell Metabolism, 24(6):848-862.
Wang et al., "Integrin-YAP/TAZ-JNK cascade mediates atheroprotective effect of unidirectional shear flow," Nature, Dec. 22, 2016, 540(7634):579-582.
Whitehead et al., "Overexpression of the PSMB9 component of the proteasome in early stage, node negative breast cancer is prognostic for an increased risk of early relapse or death," Proc. Amer. Assoc. Cancer Research, May 2005, 65(9 Supplement):740.
Wilborn et al., "Cultured Lung Fibroblasts Isolated from Patients with Idiopathic Pulmonary Fibrosis Have a Diminished Capacity to Synthesize Prostaglandin E2 and to Express Cyclooxygenase-2," J. Clin. Investigation, Apr. 1995, 95(4):1861-1868.
Wynn, "Common and unique mechanisms regulate fibrosis in various fibroproliferative diseases," J. Clin. Investigation, Mar. 2007, 117(3):524-529.
Yu et al., "Protein kinase A activates the Hippo pathway to modulate cell proliferation and differentiation," Genes Development, Jun. 2013, 27(11):1223-1232.
Yu et al., "Regulation of the Hippo-YAP Pathway by G-Protein-Coupled Receptor Signaling," Cell, Aug. 2012, 150(4):780-791.
Zanconato et al., "YAP/TAZ as therapeutic targets in cancer," Curr. Opin. Pharmacology, 29:26-33.
Zhang et al., "Omega-3 PUFAs ameliorate liver fibrosis and inhibit hepatic stellate cells proliferation and activation by promoting YAP/TAZ degradation," Sci. Reports, Jul. 2016, 6:30029, 14 pages.
Zhao et al., "The Hippo-YAP pathway in organ size control and tumorigenesis: an updated version," Genes Development, May 2010, 24(9):862-874.
Zhou et al., "G protein-coupled receptors: bridging the gap from the extracellular signals to the Hippo pathway," Acta Biochim. Biophys. Sinica, Jan. 2015, 47(1):10-15.
Zhou et al., "Inhibition of mechanosensitive signaling in myofibroblasts ameliorates experimental pulmonary fibrosis," J. Clin. Investigation, Feb. 22, 2013, 123(3):1096-1108.
Zhubanchaliyev et al., "Targeting Mechanotransduction at the Transcriptional Level: YAP and BRD4 are Novel Therapeutic Targets for the Reversal of Liver Fibrosis," Front. Pharmacology, Dec. 2016, 7:462, 11 pages.
Extended Search Report in European Appln. No. 20847742.2, dated Aug. 30, 2022, 7 pages.
Beaulieu et al., "The physiology, signaling, and pharmacology of dopamine receptors," Pharmacol. Rev., Mar. 2011, 63(1):182-217.

Bell et al., "Optimization of novel nipecotic bis(amide) inhibitors of the Rho/MKL1/SRF transcriptional pathway as potential anti-metastasis agents," Bioorg. Med. Chem. Lett., Jul. 2013, 23(13):3826-3832.
Boyd et al., "Dopamine receptor signaling and current and future antipsychotic drugs," Handb. Exp. Pharmacol., Jan. 2012, 212:53-86.
Breslin et al., "Three-dimensional cell culture: the missing link in drug discovery," Drug Discov. Today, Mar. 2013, 18(5-6):240-249.
Choi et al., "GPCR-mediated YAP/TAZ inactivation in fibroblasts via EPAC1/2, RAP2C, and MAP4K7," J. Cell. Physiol., Nov. 2021, 236(11):7759-7774.
Diaz-Espinosa et al., "Dopamine D1 receptor stimulates cathepsin K-dependent degradation and resorption of collagen I in lung fibroblasts," J. Cell. Sci., Dec. 2020, 133(23):jcs248278.
Dong et al., "[Expression of dopamine receptor D2 and adenosine receptor A2A in human retinal pigment epithelium]," Zhonghua Yan Ke Za Zhi, Dec. 2007, 43(12):1110-1113 (with English Abstract).
Extended European Search Report in European Appln. No. 24167069.4, dated Jun. 11, 2024, 7 pages.
Extended Search Report in European Appln. No. 19747631.0 dated Mar. 11, 2021, 7 pages.
Friedlander, "Fibrosis and diseases of the eye," J. Clin. Invest., Mar. 2007, 117(3):576-586.
Gao et al., "Dopamine receptor signaling regulates fibrotic activation of retinal pigmented epithelial cells," Am. J. Physiol. Cell. Physiol., Jul. 2022, 323(1):C116-C124.
Gray et al., "Impaired β-arrestin recruitment and reduced desensitization by non-catechol agonists of the D1 dopamine receptor," Nat. Commun., Feb. 2018, 9(1):674.
Guha et al., "Stimulation of the D5 dopamine receptor acidifies the lysosomal pH of retinal pigmented epithelial cells and decreases accumulation of autofluorescent photoreceptor debris," J. Neurochem., Aug. 2012, 122(4):823-833.
Haak et al., "Selective YAP/TAZ inhibition in fibroblasts via dopamine receptor D1 agonism reverses fibrosis," Sci. Transl. Med., Oct. 2019, 11(516):eaau6296, 16 pages.
Haak et al., "Targeting GPCR Signaling for Idiopathic Pulmonary Fibrosis Therapies," Trends Pharmacol. Sci., Mar. 2020, 41(3):172-182.
Hazim et al., "Rapid differentiation of the human RPE cell line, ARPE-19, induced by nicotinamide," Exp. Eye Res., Feb. 2019, 179:18-24.
Idrees et al., "Proliferative Vitreoretinopathy: A Review," Int. Ophthalmol. Clin., Jan. 2019, 59(1):221-240.
Insel et al., "cAMP and Epac in the regulation of tissue fibrosis," Br. J. Pharmacol., May 2012, 166(2):447-456.
Jiang et al., "Reversible Treatment of Pressure Overload-Induced Left Ventricular Hypertrophy through Drd5 Nucleic Acid Delivery Mediated by Functional Polyaminoglycoside," Adv. Sci., Jan. 2021, 8(5):2003706.
Kirchhof et al., "Pathogenesis of proliferative vitreoretinopathy. Modulation of retinal pigment epithelial cell functions by vitreous and macrophages," Dev. Ophthalmol., 1989, 15:1-53.
Kita et al., "Role of TGF-β in proliferative vitreoretinal diseases and ROCK as a therapeutic target," Proc. Natl. Acad. Sci. USA, Nov. 2008, 105(45):17504-17509.
Martucci et al., "Is there a relationship between dopamine and rhegmatogenous retinal detachment?" Neural Regen. Res., Feb. 2020, 15(2):311-314.
Miller et al., "Minireview: Fibronectin in retinal disease," Exp. Biol. Med., Jan. 2017, 242(1):1-7.
Ming et al., "Retinal pigment epithelial cells secrete neurotrophic factors and synthesize dopamine: possible contribution to therapeutic effects of RPE cell transplantation in Parkinson's disease," J. Transl. Med., Jun. 2009, 7:53.
Mou et al., "Dopamine receptor agonists ameliorate bleomycin-induced pulmonary fibrosis by repressing fibroblast differentiation and proliferation," Biomed. Pharmacother., Jul. 2021, 139:111500.
Mudhar et al., "A brief review of the histopathology of proliferative vitreoretinopathy (PVR)," Eye, Feb. 2020, 34(2):246-250.

(56) References Cited

OTHER PUBLICATIONS

Mystek et al., "New insights into the model of dopamine D1 receptor and G-proteins interactions," Biochim. Biophys. Acta, Mar. 2015, 1853:594-603.

Orita et al., "Effect of prostaglandin E2 on collagen gel contraction in mouse retinal pigment epithelium cells," Abstract, Presented at the proceedings of the ARVO Annual Meeting, Invest. Ophthalmol. Vis. Sci., Jun. 2013, 54(15):2008.

PCT International Preliminary Report on Patentability in International Appln. No. PCT/US2019/016178, dated Aug. 4, 2020, 9 pages.

PCT International Preliminary Report on Patentability in International Appln. No. PCT/US2022/014045, mailed on Aug. 10, 2023, 8 pages.

PCT International Search Report and Written Opinion in International Appln. No. PCT/US2019/016178, dated Jun. 10, 2019, 13 pages.

PCT International Search Report and Written Opinion in International Appln. No. PCT/US2022/014045, mailed on Jun. 8, 2022, 11 pages.

Popovic et al., "Revisiting loxapine: a systematic review," Ann. Gen. Psychiatry, Apr. 2015, 14:15.

Qing et al., "Dopamine receptor D2 antagonism normalizes profibrotic macrophage-endothelial crosstalk in non-alcoholic steatohepatitis," J. Hepatol., Feb. 2022, 76(2):394-406.

Roy et al., "Retinal fibrosis in diabetic retinopathy," Exp. Eye Res., Jan. 2016, 142:71-75.

Seagle et al., "Melanin photoprotection in the human retinal pigment epithelium and its correlation with light-induced cell apoptosis," Proc. Natl. Acad. Sci. USA, Jun. 2005, 102(25):8978-8983.

Si et al., "Synthesis and dopamine receptor affinities of N-alkyl-11-hydroxy-2-methoxynoraporphines: N-alkyl substituents determine D1 versus D2 receptor selectivity," J. Med. Chem., Feb. 2008, 51(4):983-987.

Sipos et al., "Synthesis and neuropharmacological characterization of 2-O-substituted apomorphines," Bioorg. Med. Chem., Apr. 2008, 16(8):4563-4568.

Sparrow et al., "The retinal pigment epithelium in health and disease," Curr. Mol. Med., Dec. 2010, 10(9):802-823.

Sriram et al., "G Protein-Coupled Receptors as Targets for Approved Drugs: How Many Targets and How Many Drugs?," Mol. Pharmacol., Apr. 2018, 93(4):251-258.

Takahashi et al., "Tumor Necrosis Factor-$\alpha$ Regulates Transforming Growth Factor-$\beta$-dependent Epithelial-Mesenchymal Transition by Promoting Hyaluronan-CD44-Moesin Interaction2," J. Biol. Chem., Feb. 2010, 285(6):4060-4073.

Tamiya et al., "Role of epithelial-mesenchymal transition in proliferative vitreoretinopathy," Exp. Eye Res., Jan. 2016, 142:26-31.

Tinter et al., "Pleuropulmonary fibrosis after long-term treatment with the dopamine agonist pergolide for Parkinson Disease," Arch. Neurol., Aug. 2005, 62(8):1290-1295.

Yamada et al., "Oxidized low density lipoproteins induce a pathologic response by retinal pigmented epithelial cells," J. Neurochem., May 2008, 105(4):1187-1197.

Yin et al., "Transplantation of human retinal pigment epithelium cells in the treatment for Parkinson disease," CNS Neurosci. Ther., Dec. 2012, 18(12):1012-1020.

Zhao et al., "Dopamine receptor D2 inhibition alleviates diabetic hepatic stellate cells fibrosis by regulating the TGF-$\beta$1/Smads and NFκB pathways," Clin. Exp. Pharmacol. Physiol., Mar. 2021, 48(3):370-380.

Zhou et al., "Role of Epithelial-Mesenchymal Transition in Retinal Pigment Epithelium Dysfunction," Front. Cell. Dev. Biol., Jun. 2020, 8:501.

U.S. Appl. No. 18/265,472, filed Jun. 6, 2023, Andrew J. Haak, Published as U.S. 2024/0043396.

U.S. Appl. No. 18/422,541, filed Jan. 25, 2024, Daniel J. Tschumperlin, Pending.

U.S. Appl. No. 16/965,122, filed Jul. 27, 2020, Daniel J. Tschumperlin, Published as U.S. Publication No. 2021/0038561.

U.S. Appl. No. 17/934,009, filed Sep. 21, 2022, Daniel J. Tschumperlin, Pending.

(CTC-3)

(CTC-3)

(CTC-6)

(CTC-6)

| R example | EC50 (potency, µM) | Intrinsic Activity (efficacy) |
|---|---|---|
| H (A68930) | 0.005 | 71 |
| OH | 0.004 | 110 |
| OCH₃ | 0.007 | 107 |
| CF₃ | 0.005 | 134 |

DeNirro et al. United States Patent: 5,621,133. 1997

(example 2)

DHX = dihydrexidine
DNS = dinapsoline
DNX = dinoxyline (example 1)

COMPOUNDS AND METHODS FOR TREATING FIBROTIC PATHOLOGIES

CROSS-REFERENCE TO RELATED APPLICATIONS

This application is a National Stage application under 35 U.S.C. § 371 of International Application No. PCT/US2020/044054, having an International Filing Date of Jul. 29, 2020, which claims priority to U.S. Provisional Patent Application Ser. No. 62/880,494, filed on Jul. 30, 2019, and U.S. Provisional Patent Application Ser. No. 62/880,594, filed on Jul. 30, 2019, the entire contents of which are hereby incorporated by reference.

SEQUENCE LISTING

This application contains a Sequence Listing that has been submitted electronically as an ASCII text file named 07039_1920WO1 ST25.txt. The ASCII text file, created on Jul. 27, 2020, is 11 kilobytes in size. The material in the ASCII text file is hereby incorporated by reference in its entirety.

TECHNICAL FIELD

This invention relates to compounds (e.g., isochromane compounds) that inhibit YAP/TAZ in fibroblasts and are useful in treating diseases and conditions associated with tissue fibrosis.

BACKGROUND

Tissue fibrosis across all organs affects a vast population of people. In the U.S. alone over half a million people are affected by liver (>400 k) and lung (>100 k) fibrosis. These diseases remain very challenging to treat clinically. In examples such as idiopathic pulmonary fibrosis (IPF) and scleroderma, therapeutic options are extremely limited. In fact, for this group of diseases, the five year survival rate can be as bleak as many late stage aggressive cancers.

SUMMARY

Tissue fibrosis is characterized by uncontrolled deposition and diminished clearance of fibrous connective tissue proteins, and ultimately leads to fatal, end-stage organ scarring. Yes-associated protein 1 (YAP) and transcriptional coactivator with PDZ-binding motif (TAZ) play a role in the mesenchymal cell activation that drives tissue fibrosis (Refs. 1-4). YAP and TAZ are downstream transcriptional effectors of multiple pro-fibrotic stimuli in mesenchymal cells (See e.g., Ref. 5), and their expression in other cells and tissues is essential to regeneration and homeostasis (See e.g., Ref. 6), complicating efforts to target them therapeutically (See e.g., Ref. 7).

In one general aspect, the present application provides methods for inhibiting YAP and TAZ in mesenchymal cells via GPCR agonism. The data presented herein demonstrates the efficacy of this approach in murine models of lung and liver fibrosis. $G\alpha_s$-coupled dopamine receptor D1 is preferentially expressed in lung and liver mesenchymal cells relative to other major resident cells of these organs. Agonism of the D1 receptor selectively inhibits YAP/TAZ function in mesenchymal cells, and shifts their phenotype in a YAP/TAZ dependent fashion from pro-fibrotic to fibrosis-resolving, effectively reversing in vitro extracellular matrix accumulation and stiffening and reversing in vivo tissue fibrosis. This finding demonstrates a cell-selective approach to inhibiting a target that drives tissue fibrosis, and establishes $G\alpha_s$ agonism as a strategy for generating a fibrosis-resolving mesenchymal phenotype.

In one general aspect, the present application provides a compound of Formula (I):

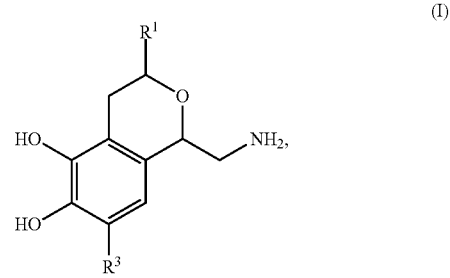

or a pharmaceutically acceptable salt thereof, wherein $R^1$ and $R^3$ are as described herein.

In another general aspect, the present disclosure provides a compound of Formula (II):

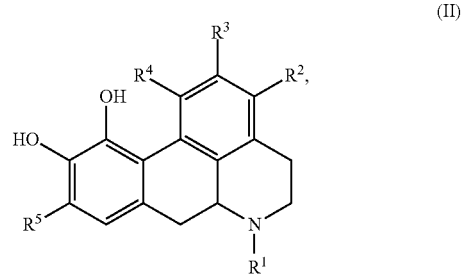

or a pharmaceutically acceptable salt thereof, wherein $R^1$, $R^2$, $R^3$, $R^4$ and $R^5$ are as described herein.

In another general aspect, the present disclosure provides a compound of Formula (III):

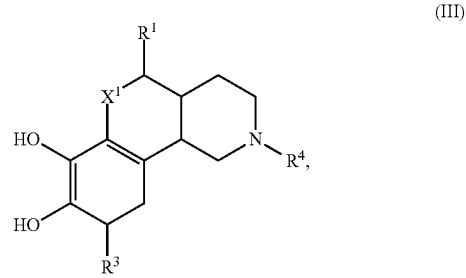

or a pharmaceutically acceptable salt thereof, wherein $X^1$, $R^1$, $R^3$, and $R^4$ are as described herein.

In another general aspect, the present disclosure provides a compound of Formula (IV):

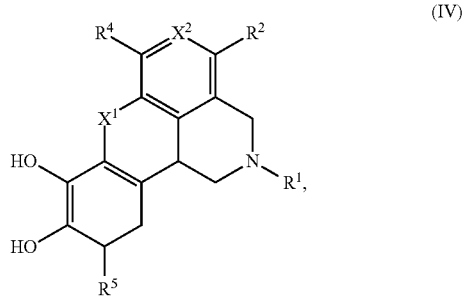

or a pharmaceutically acceptable salt thereof, wherein $X^1$, $X^2$, $R^1$, $R^2$, $R^4$ and $R^5$ are as described herein.

In another general aspect, the present disclosure provides a pharmaceutical composition comprising a compound of any one of the Formulae described herein, or a pharmaceutically acceptable salt thereof, and a pharmaceutically acceptable carrier.

In another general aspect, the present application provides a method of agonizing a $G\alpha_S$ protein coupled receptor in a cell, the method comprising contacting the cell with an effective amount of a compound of any one of the Formulae described herein, or a pharmaceutically acceptable salt thereof.

In another general aspect, the present application provides a method of promoting YAP/TAZ phosphorylation in a cell, the method comprising contacting the cell with an effective amount of a compound of any one of the Formulae described herein, or a pharmaceutically acceptable salt thereof.

In another general aspect, the present application provides a method of inhibiting YAP/TAZ function in a cell, the method comprising contacting the cell with an effective amount of a compound of any one of the Formulae described herein, or a pharmaceutically acceptable salt thereof.

In another general aspect, the present application provides a method of inhibiting expression of a profibrotic gene in a cell, the method comprising contacting the cell with an effective amount of a compound of any one of the Formulae described herein, or a pharmaceutically acceptable salt thereof.

In another general aspect, the present application provides a method of reducing nuclear localization of YAP/TAZ in a cell, the method comprising contacting the cell with an effective amount of a compound of any one of the Formulae described herein, or a pharmaceutically acceptable salt thereof.

In another general aspect, the present application provides a method of inhibiting expressing of α-smooth muscle actin (αSMA) in a cell, the method comprising contacting the cell with an effective amount of a compound of any one of the Formulae described herein, or a pharmaceutically acceptable salt thereof.

In another general aspect, the present application provides a method of inhibiting extra-cellular matrix production and deposition by a cell, the method comprising contacting the cell with an effective amount of a compound of any one of the Formulae described herein, or a pharmaceutically acceptable salt thereof.

In another general aspect, the present application provides a method of enhancing extra-cellular matrix degradation by a cell, the method comprising contacting the cell with an effective amount of a compound of any one of the Formulae described herein, or a pharmaceutically acceptable salt thereof.

In yet another general aspect, the present application provides a method of treating or preventing a fibrotic pathology, the method comprising administering to a subject in need thereof a therapeutically effective amount of a compound of any one of the Formulae described herein, or a pharmaceutically acceptable salt thereof, or a pharmaceutical composition comprising same.

Unless otherwise defined, all technical and scientific terms used herein have the same meaning as commonly understood by one of ordinary skill in the art to which the present application belongs. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the present application will be apparent from the following detailed description and figures, and from the claims.

DETAILED DESCRIPTION

Figure 1:
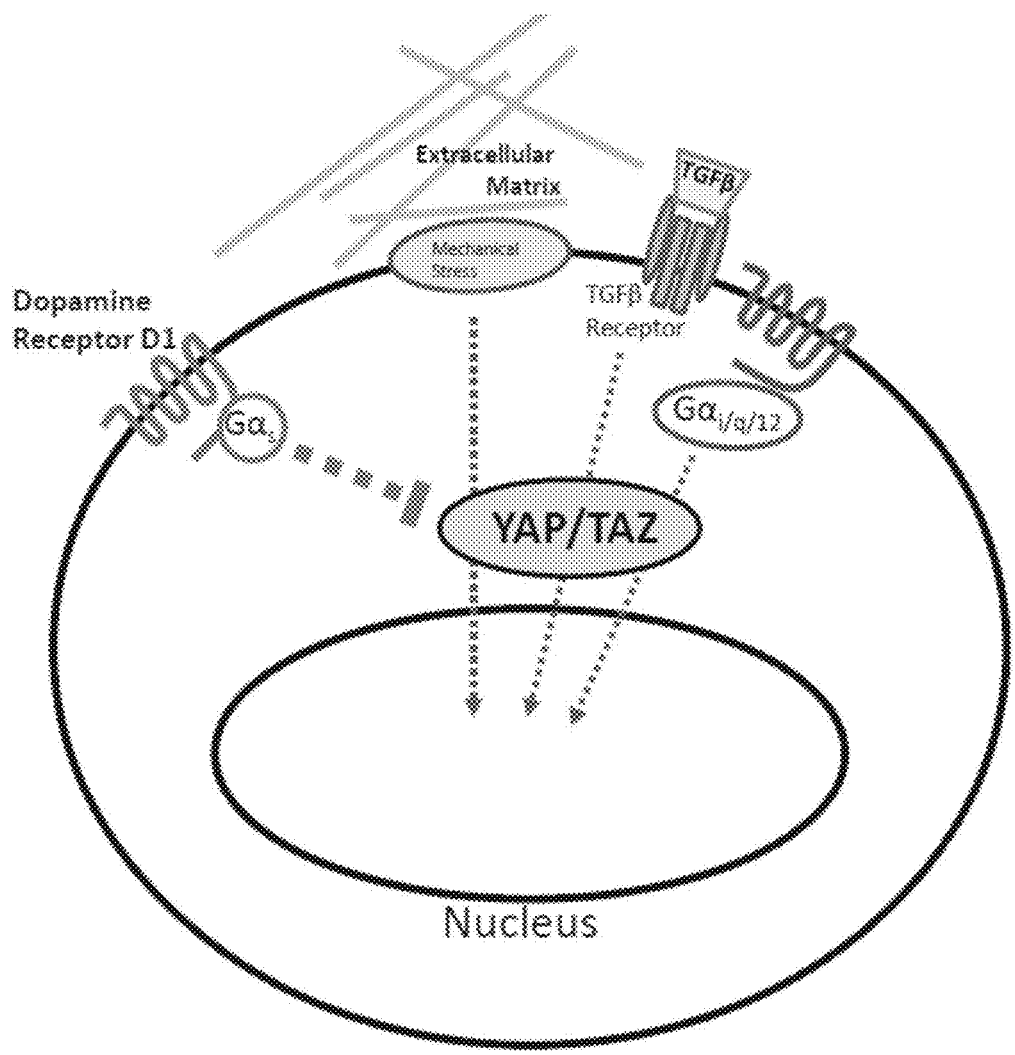
FIG. 1 contains a schematic representation of molecular mechanism by which transcription factor YAP/TAZ promotes tissue fibrosis. YAP/TAZ nuclear localization and activity is mediated by multiple profibrotic signaling pathways. Activation of the D1 dopamine receptor inhibits nuclear localization and activity of YAP/TAZ in fibroblasts.

Tissue fibrosis can occur in multiple vital organs including heart, lung, liver, and kidney. Fibrosis is a progressive process which, through multiple mechanisms, transforms a normal healthy organ into an architecturally and functionally compromised tissue. From a clinical standpoint they represent a serious problem as the therapeutic options remain minimal and the prognosis is generally very poor. Dopamine receptors, which are almost exclusively researched as part of the central nervous system, are actually highly expressed in the periphery as well in select tissues and cells in the body. These receptors signal through downstream pathways which play a major role in tissue fibrosis. One example of such receptors is a $G\alpha_s$-coupled receptor, such as a dopamine receptor D1 (DRD1). As described in the present disclosure, agonising dopamine receptors leads to treatment or prevention of tissue fibrosis in multiple organs.

YAP and TAZ are transcriptional co-activators and central effectors of the Hippo pathway (Ref. 8). Originally identified based on their roles in organ growth and size control during tissue morphogenesis, the Hippo pathway and YAP/TAZ in adult tissues regulate epithelial and endothelial homeostasis (Ref. 9-13), stem cell function (Ref. 14-16) and tissue regeneration (Ref. 9,17,18). Roles for YAP and TAZ in mesenchymal cell activation and fibrosis in multiple organs (Ref. 19-22), including the lung and liver (Ref. 2), was also shown. An array of mechanical and biochemical signals have been implicated as upstream regulators of YAP and TAZ, with multiple pro-fibrotic stimuli including matrix stiffness, TGFβ/SMAD, MRTF/SRF, and WNT (Ref. 5, 23, 24) signaling all potentially involved.

G protein coupled receptors are linked to effector proteins from four main classes of G-proteins (e.g., Gα$_{12/13}$, Gα$_{q/11}$, Gα$_{i/o}$ or Gα$_s$). In some instances, G protein coupled receptor stimulates YAP/TAZ nuclear translocation and transcriptional activity. In other instances, G protein coupled receptors inhibit YAP/TAZ nuclear localization and activity via elevation of cAMP (see, e.g., FIG. 1, 2).

In some embodiments, activation (agonism) of a G protein coupled receptor results in YAP/TAZ hyper phosphorylation and inactivation under physiological conditions (e.g., agonism of the receptor prevents YAP/TAZ nuclear localization). This is in contrast to inactivation (antagonism) of G protein coupled receptor, which stimulates YAP/TAZ nuclear translocation and transcriptional activity, which results in expression of profibrotic genes, such as Acta2 (αSMA), Ctgf (Connective tissue growth factor), Fn1 (Fibronectin), Col1a1 (Collagen I), and Col1a2 (Collagen II).

In some embodiments, the present disclosure provides a method of agonizing a G protein coupled receptor in a cell, the method comprising contacting the cell with any one of compounds described herein, or a pharmaceutically acceptable salt thereof. In such embodiments, the compound selectively agonizes the Gα$_s$ receptor (e.g., the compound is 100-fold, 50-fold, or 10-fold selective to Gα$_s$ protein coupled receptor as compared to Gα$_{12/13}$, Gα$_{q/11}$ or Gα$_{i/o}$ protein coupled receptor, or any combination of the aforementioned).

In some embodiments, the cell is a mesenchymal cell (e.g., the G protein coupled receptor is expressed in a mesenchymal cell). In some embodiments, the mesenchymal cell is a fibroblast (e.g., pulmonary, cardiac, hepatic, renal or dermal fibroblast) or a stellate cell (e.g., pancreatic stellate cell, hepatic stellate cell, podocyte, or osteocyte). In some embodiments, the G protein coupled receptor is preferentially expressed in mesenchymal cells as compared to epithelial or endothelial cells of a tissue (e.g., lung tissue or liver tissue). In one example, the G protein coupled receptor is preferentially expressed in pulmonary fibroblasts over alveolar epithelial cells. In another example, the G protein coupled receptor is preferentially expressed in hepatic stellate cells over hepatocytes.

In some embodiments, the G protein coupled receptor is Gα$_S$ receptor. In one example, Gα$_S$ receptor is expressed preferentially in the mesenchymal cell. In some embodiments, the Gα$_s$ protein coupled receptor is a dopamine receptor (e.g., D1, D2, D3, D4, or D5 dopamine receptor). In some embodiments the dopamine receptor is a dopamine receptor D1 (DRD1). In one example, the methods of the present disclosure include selectively agonizing the dopamine receptor D1 (e.g., the compound of Formula (I) is 100-fold, 50-fold, or 10-fold selective to D1 dopamine receptor as compared to D2, D3, D4, or D5 receptor, or any combination of the aforementioned).

Figure 2:
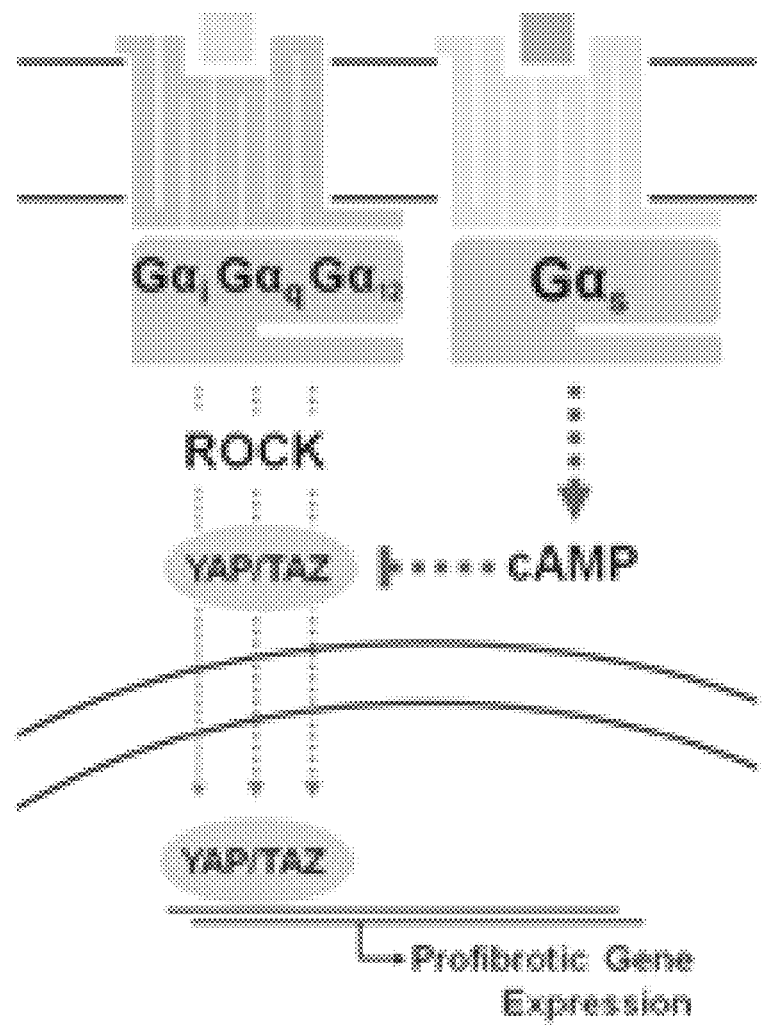
FIG. 2 contains a scheme showing that $G\alpha_s$-coupled Dopamine Receptor D1 is selectively expressed in pulmonary fibroblasts. The scheme shows regulation of YAP/TAZ transcription co-factor activity by GPCR signaling. Receptors which couple to $G\alpha_s$ elevate cAMP and induce phosphorylation of YAP/TAZ which blocks nuclear localization. Receptors which couple to $Galph\alpha_{i/q/12}$ promote nuclear localization and activity of YAP/TAZ, e.g., through Rho-kinase (ROCK).

Referring to FIGS. 1 and 2, without being bound by a theory, it is believed that agonism of a G protein coupled receptor results in YAP/TAZ phosphorylation and subsequent degradation of YAP/TAZ in the cell. In some embodiments, the YAP/TAZ phosphorylation comprises phosphorylation of YAP serine 127. In some embodiments, the YAP/TAZ phosphorylation comprises phosphorylation of TAZ serine 89. In some embodiments, the YAP/TAZ phosphorylation comprises phosphorylation of YAP serine 127 and phosphorylation of TAZ serine 89. Hence, in some embodiments, the present disclosure provides a method of promoting YAP phosphorylation in a cell, the method comprising contacting the cell with any one of compounds described herein, or a pharmaceutically acceptable salt thereof. Because the compounds of the present disclosure promote degradation of the YAP/TAZ protein complex, in some embodiments, the present disclosure provides a method of reducing nuclear localization of YAP/TAZ in a cell, the method comprising contacting the cell with any one of the compounds of the present disclosure, or a pharmaceutically acceptable salt thereof. Hence, the compounds of this disclosure render YAP/TAZ unable to perform its cellular function. In some embodiments, the present disclosure provides a method of inhibiting YAP/TAZ function in a cell, the method comprising contacting the cell with any one of the compounds of the present disclosure, or a pharmaceutically acceptable salt thereof. Examples of the YAP/TAZ cellular functions include expression of profibrotic genes in the cell and production of fibrotic biomolecules (e.g., actin, collagen) by the cell. Generally, these fibrotic biomolecules constitute extra-cellular matrix surrounding the cell. Suitable examples of profibrotic genes include Acta2 (αSMA), Ctgf (Connective tissue growth factor), Fn1 (Fibronectin), Col1a1 (Collagen I), and Col1a2 (Collagen II). In some embodiments, the present disclosure provides a method of inhibiting expression of α-smooth muscle actin (αSMA) in a cell, the method comprising contacting the cell with any one of the compounds of the present disclosure, or a pharmaceutically acceptable salt thereof. Concomitantly, in some embodiments, the present disclosure provides a method of inhibiting production and deposition of extra-cellular matrix by a cell, the method comprising contacting the cell with any one of the compounds of the present disclosure, or a pharmaceutically acceptable salt thereof. In some embodiments, inhibiting YAP/TAZ function in a cell by the compound of the present disclosure results in a prevention of accumulation of extracellular matrix in a tissue.

Without being bound by a theory, it is believed that agonism of a G protein coupled receptor reverses fiber formation and extracellular matrix accumulation (e.g., a G protein coupled receptor agonism leads to removing the fiber and extracellular matrix from a tissue). Hence, in some embodiments, the present disclosure provides a method enhancing extra-cellular matrix degradation by a cell, the method comprising contacting the cell with any one of the compounds of the present disclosure, or a pharmaceutically acceptable salt thereof.

In some embodiments, the fiber formation, or fibrosis, is induced in a tissue by trauma or tissue injury. Normally, cells generate just the right amount of tissue to replace old tissue or repair tissue damage. Excessive connective tissue generation (e.g., in response to trauma or injury) results in pathological accumulation of fibrotic tissue (e.g., extracellular matrix proteins) leading to organ or tissue thickening and scarring.

In some embodiments, the present disclosure provides a method of treating or preventing a fibrotic pathology in a subject, the method comprising administering to the subject in need thereof a therapeutically effective amount of any one of the compounds described herein, or a pharmaceutically acceptable salt thereof. In some embodiments, the subject in need of treatment of fibrotic pathology is diagnosed with fibrotic pathology by a treating physician.

In some embodiments, the fibrotic pathology is interstitial lung disease (ILD). In some embodiments, fibrotic pathology is lung tissue fibrosis, e.g., pulmonary fibrosis (PF) or idiopathic pulmonary fibrosis (IPF). Despite the name, cystic fibrosis is not considered an interstitial lung disease or predominantly a fibrotic pathology. Cystic fibrosis results from impaired ion transport, mucus dysfunction, and failure to effectively clear pathogens from the airways, which eventually results in scarring of the airways and lungs.

In some embodiments, fibrotic pathology is a liver tissue fibrosis, e.g., cirrhosis or biliary atresia. In some embodiments, fibrotic pathology is a heart tissue fibroses (cardiac fibrosis), e.g., atrial fibrosis, endomyocardial fibrosis, or post-myocardial infarction scarring. In some embodiments, fibrotic pathology is a brain tissue fibrosis, e.g., glial scar. In some embodiments, fibrotic pathology is arterial stiffness, arthrofibrosis (knee, shoulder, elbow, or other joints), kidney fibrosis (e.g., chronic kidney disease and fibrosis), liver fibrosis, nonalcoholic fatty liver, nonalcoholic steatohepatitis, Crohn's disease (intestinal scarring), Dupuytren's contracture (scar tissue in hands or fingers), skin tissue fibrosis, e.g., keloid (a scar on the skin), mediastinal fibrosis (soft tissue of the mediastinum), Peyronie's disease (scar in a penial tissue), nephrogenic systemic fibrosis, progressive massive fibrosis, retroperitoneal fibrosis (scar on the soft tissue of the retroperitoneum) or adhesive capsulitis.

In some embodiments, the subject in need of prevention of fibrotic pathology is diagnosed with tissue trauma or injury by a treating physician. Suitable examples of tissue injury include injury caused by inhaled substances (e.g., silica or asbestos), drug-induced injury (injury caused by an antibiotic or an anticancer drug), tissue injury caused by autoimmune disease (e.g., rheumatoid arthritis, sclerosis, such as systemic sclerosis, lupus), injury caused by infection (e.g., tuberculosis, pneumonia, respiratory virus), or sarcoidosis.

Exemplary Therapeutic Compounds

Compounds of Formula (I)

In some embodiments, the present disclosure provides a compound of Formula

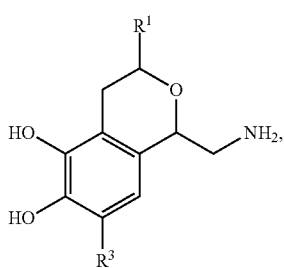

(I)

or a pharmaceutically acceptable salt thereof, wherein:
$R^1$ is selected from HO—$C_{1-6}$ alkyl, $NH_2$—$C_{1-6}$ alkyl, 5-6-membered heteroaryl ring comprising 1 to 5 heteroatoms selected from N, O, and S, and 3-10-membered heterocycloalkyl ring comprising 1 to 3 heteroatoms independently selected from N, O, and S;
wherein said heteroaryl ring and heterocycloalkyl ring are each optionally substituted with 1, 2, or 3 substituents independently selected from $R^2$;
each $R^2$ is independently selected from halo, OH, $C_{1-3}$ alkoxy, SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, $C_{1-3}$ alkoxy, SH, $NH_2$, $C_{1-3}$ alkylamino, and di($C_{1-3}$ alkyl)amino; and
$R^3$ is selected from H and halo.

In some embodiments, the present disclosure provides a compound of Formula (I):

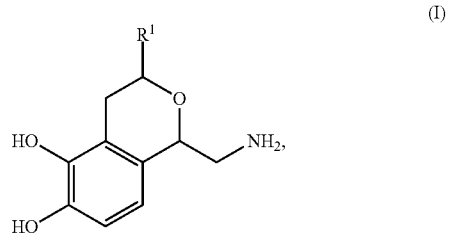

(I)

or a pharmaceutically acceptable salt thereof, wherein:
$R^1$ is selected from HO—$C_{1-6}$ alkyl, $NH_2$—$C_{1-6}$ alkyl, 5-6-membered heteroaryl ring comprising 1 or 2 heteroatoms selected from N, O, and S, and 3-7-membered heterocycloalkyl ring comprising 1 or 2 heteroatoms selected from N, O, and S;
wherein said heteroaryl ring and heterocycloalkyl ring are each optionally substituted with 1, 2, or 3 substituents independently selected from $R^2$; and
each $R^2$ is independently selected from OH, SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino, and di($C_{1-3}$ alkyl)amino.

In some embodiments, $R^1$ is 5-6-membered heteroaryl ring comprising 1 to 5 heteroatoms selected from N, O, and S, which is optionally substituted with 1, 2, or 3 substituents independently selected from $R^2$.

In some embodiments, $R^1$ is 5-6-membered heteroaryl ring comprising 1 or 2 heteroatoms selected from N, O, and S, which is optionally substituted with 1, 2, or 3 substituents independently selected from $R^2$.

In some embodiments, $R^1$ is 5-membered heteroaryl ring comprising 1 or 2 heteroatoms selected from N, O, and S, which is optionally substituted with 1, 2, or 3 substituents independently selected from $R^2$.

In some embodiments, $R^1$ is selected from thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl, each of which is optionally substituted with 1, 2, or 3 substituents independently selected from $R^2$.

In some embodiments, $R^1$ is 6-membered heteroaryl ring comprising 1 or 2 N atoms, which is optionally substituted with 1, 2, or 3 substituents independently selected from $R^2$.

In some embodiments, $R^1$ is selected from pyridinyl, pyrimidinyl, pyrazinyl, diazinyl, triazinyl, tetrazinyl, and pentazinyl, each of which is optionally substituted with 1, 2, or 3 substituents independently selected from $R^2$.

In some embodiments, $R^1$ is selected from pyridyl, pyrazinyl, pyrimidinyl, and pyridazinyl, each of which is optionally substituted with 1, 2, or 3 substituents independently selected from $R^2$.

In some embodiments, $R^1$ is selected from pyridinyl, pyrimidinyl, and pyrazinyl, each of which is optionally substituted with 1, 2, or 3 substituents independently selected from $R^2$.

In some embodiments, $R^1$ is pyridinyl, optionally substituted with 1, 2, or 3 substituents independently selected from $R^2$.

In some embodiments, the compound of Formula (I) is:

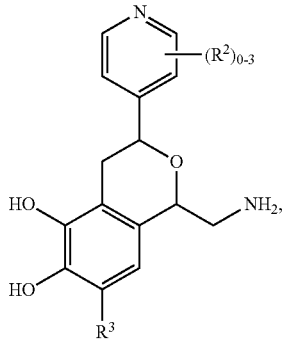

or a pharmaceutically acceptable salt thereof.

In some embodiments, the compound of Formula (I) is:

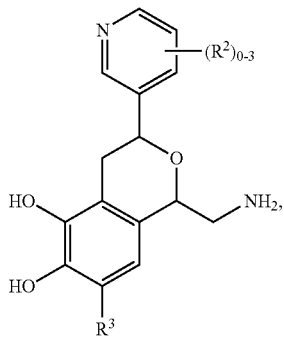

or a pharmaceutically acceptable salt thereof.

In some embodiments, the compound of Formula (I) is:

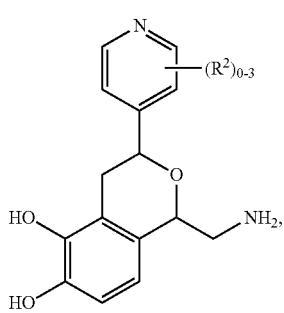

or a pharmaceutically acceptable salt thereof.

In some embodiments, the compound of Formula (I) is:

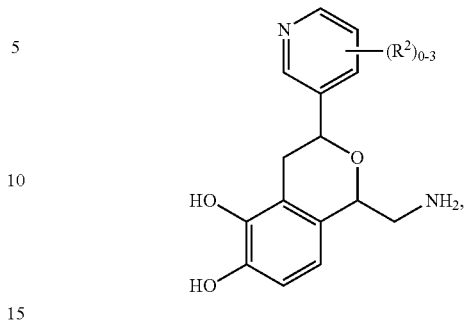

or a pharmaceutically acceptable salt thereof.

In some embodiments, $R^1$ is 3-10-membered heterocycloalkyl ring comprising 1 to 3 heteroatoms independently selected from N, O, and S, which is optionally substituted with 1, 2, or 3 substituents independently selected from $R^2$.

In some embodiments, $R^1$ is 3-7-membered heterocycloalkyl ring comprising 1 or 2 heteroatoms selected from N, O, and S, which is optionally substituted with 1, 2, or 3 substituents independently selected from $R^2$.

In some embodiments, $R^1$ is 3-membered heterocycloalkyl ring comprising 1 heteroatom selected from N, O, and S, which is optionally substituted with 1, 2, or 3 substituents independently selected from $R^2$. Examples of such rings include aziridinyl and oxiranyl.

In some embodiments, $R^1$ is 4-membered heterocycloalkyl ring comprising 1 heteroatom selected from N, O, and S, which is optionally substituted with 1, 2, or 3 substituents independently selected from $R^2$. Examples of such rings include oxetanyl and azetidinyl.

In some embodiments, $R^1$ is 5-membered heterocycloalkyl ring comprising 1 or 2 heteroatoms selected from N, O, and S, which is optionally substituted with 1, 2, or 3 substituents independently selected from $R^2$. Examples of such rings include tetrahydrofuranyl, pyrrolidinyl, isoxazolidinyl, imidazolidinyl, and thiazolidinyl.

In some embodiments, $R^1$ is 6-membered heterocycloalkyl ring comprising 1 or 2 heteroatoms selected from N, O, and S, which is optionally substituted with 1, 2, or 3 substituents independently selected from $R^2$. Examples of such rings include morpholinyl, thiomorpholinyl, tetrahydropyranyl, piperazinyl, and piperidinyl.

In some embodiments, $R^1$ is 7-membered heterocycloalkyl ring comprising 1 or 2 heteroatoms selected from N, O, and S, which is optionally substituted with 1, 2, or 3 substituents independently selected from $R^2$.

In some embodiments, $R^1$ is 8-membered heterocycloalkyl ring comprising 1 or 2 heteroatoms selected from N, O, and S, which is optionally substituted with 1, 2, or 3 substituents independently selected from $R^2$.

In some embodiments, $R^1$ is 9-membered heterocycloalkyl ring comprising 1 or 2 heteroatoms selected from N, O, and S, which is optionally substituted with 1, 2, or 3 substituents independently selected from $R^2$.

In some embodiments, $R^1$ is 10-membered heterocycloalkyl ring comprising 1 or 2 heteroatoms selected from N, O, and S, which is optionally substituted with 1, 2, or 3 substituents independently selected from $R^2$.

In some embodiments, $R^1$ is selected from tetrahydropyranyl, piperidinyl, tetrahydrofuranyl, pyrrolidinyl, pyranyl, morpholinyl, oxazinyl, dioxanyl, dioxinyl, diazinanyl, triazinanyl, trioxanyl, azepinyl, azepinyl, oxepanyl, oxepinyl, diazepanyl, diazepinyl, azocanyl, azocinyl, oxocanyl, oxocinyl, azonanyl, azoninyl, oxonanyl, and oxoninyl, each of which is optionally substituted with 1, 2, or 3 substituents independently selected from $R^2$.

In some embodiments, $R^1$ is selected from tetrahydropyranyl, piperidinyl, tetrahydrofuranyl, and pyrrolidinyl, each of which is optionally substituted with 1, 2, or 3 substituents independently selected from $R^2$.

In some embodiments, $R^1$ is selected from tetrahydropyranyl and piperidinyl, each of which is optionally substituted with 1, 2, or 3 substituents independently selected from $R^2$.

In some embodiments, $R^1$ is tetrahydropyranyl, optionally substituted with 1, 2, or 3 substituents independently selected from R.

In some embodiments, $R^1$ is piperidinyl, optionally substituted with 1, 2, or 3 substituents independently selected from $R^2$.

In some embodiments, the compound of Formula (I) is:

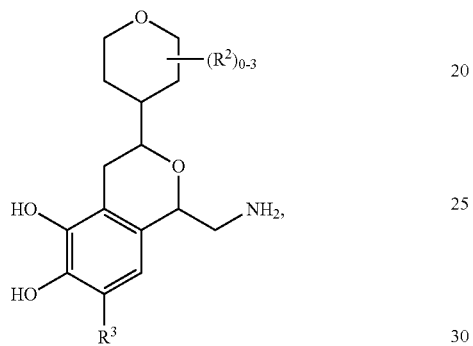

or a pharmaceutically acceptable salt thereof.

In some embodiments, the compound of Formula (I) is:

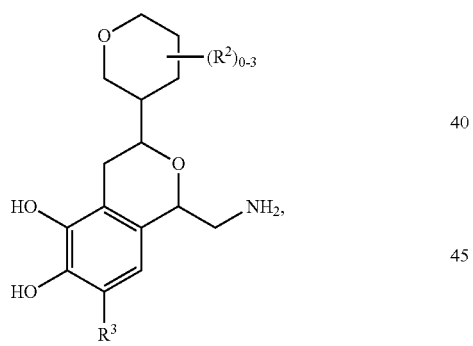

or a pharmaceutically acceptable salt thereof.

In some embodiments, the compound of Formula (I) is:

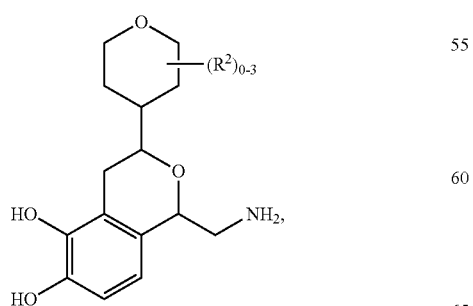

or a pharmaceutically acceptable salt thereof.

In some embodiments, the compound of Formula (I) is:

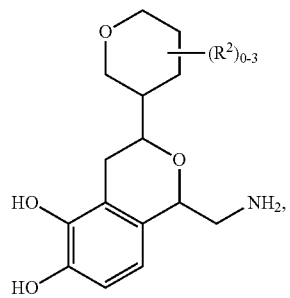

or a pharmaceutically acceptable salt thereof.

In some embodiments, the compound of Formula (I) is:

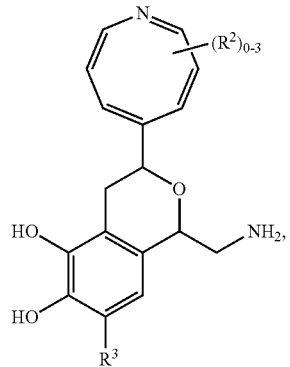

or a pharmaceutically acceptable salt thereof.

In some embodiments, the compound of Formula (I) is:

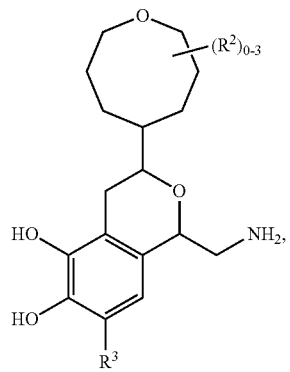

or a pharmaceutically acceptable salt thereof.

In some embodiments, $R^1$ is selected from HO—$C_{1-6}$ alkyl and $NH_2$—$C_{1-6}$ alkyl.

In some embodiments, $R^1$ is HO—$C_{1-6}$ alkyl.

In some embodiments, $R^1$ is $NH_2$—$C_{1-6}$ alkyl.

In some embodiments, $R^2$ is independently selected from halo, OH, $C_{1-3}$ alkoxy, $C_{1-3}$ alkyl, and $C_{1-3}$ haloalkyl.

In some embodiments, $R^2$ is selected from OH, $NH_2$, $C_{1-3}$ alkyl, HO—$C_{1-3}$ alkyl, and $NH_2$—$C_{1-3}$ alkyl. In some embodiments, $R^2$ is selected from OH and $NH_2$. In some embodiments, $R^2$ is OH. In some embodiments, $R^2$ is $NH_2$.

In some embodiments, $R^2$ is $C_{1-3}$ alkyl. In some embodiments, $R^2$ is HO—$C_{1-3}$ alkyl. In some embodiments, $R^2$ is $NH_2$—$C_{1-3}$ alkyl.

In some embodiments, $R^3$ is H.

In some embodiments, $R^3$ is halo.

In some embodiments, $R^3$ is selected from Cl, F, and Br. In some embodiments, $R^3$ is Cl. In some embodiments, $R^3$ is F. In some embodiments, $R^3$ is Br.

In some embodiments, the compound of Formula (I) is selected from any one of the following compounds:

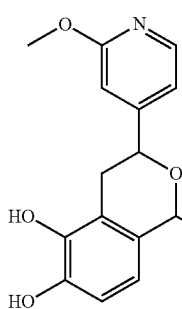
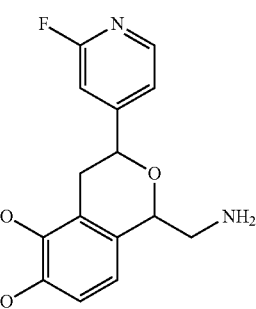
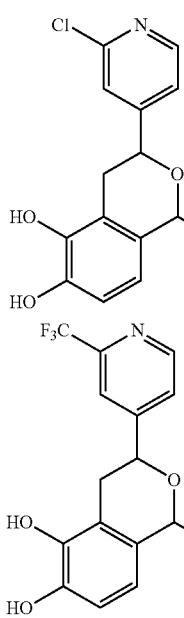
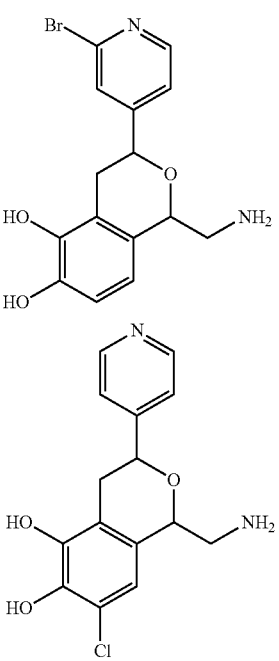
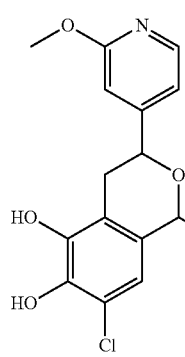
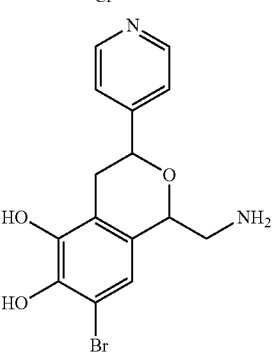
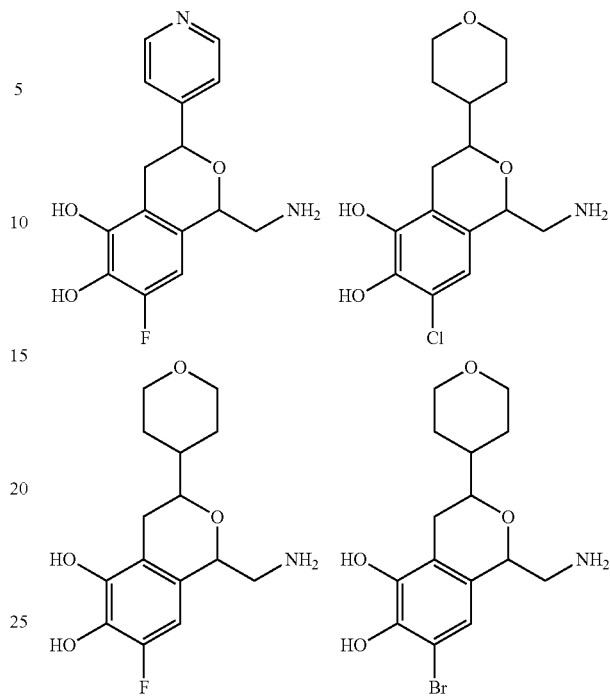

or a pharmaceutically acceptable salt thereof.

In some embodiments, the compound of Formula (I) is selected from any one of the following compounds:

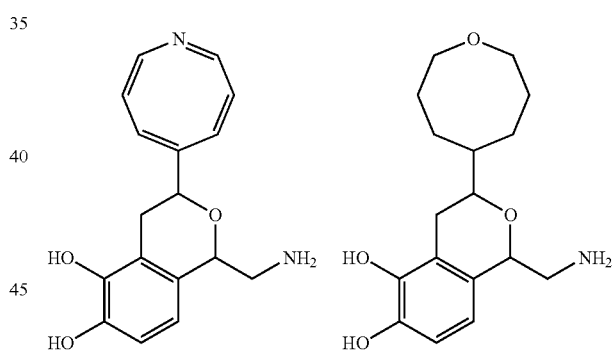

or a pharmaceutically acceptable salt thereof.

In some embodiments, the compound of Formula (I) is selected from any one of the following compounds:

(CTC-1)

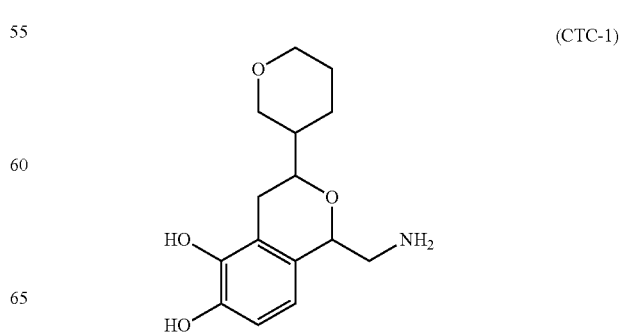

-continued (CTC-2)

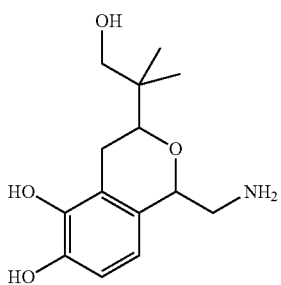

(CTC-3)

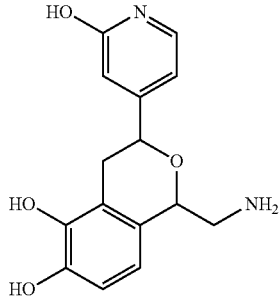

(CTC-7)

(CTC-6)

(3-Me-CTC-6)

-continued (2-OH-CTC-6)

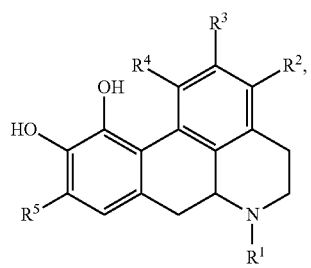

or a pharmaceutically acceptable salt thereof.

Compounds of Formula (II)

In some embodiments, the present disclosure provides a compound of Formula (II):

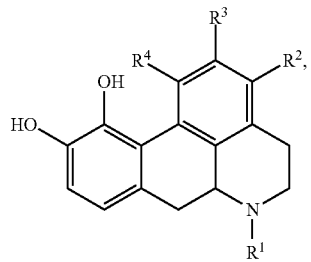

(II)

or a pharmaceutically acceptable salt thereof, wherein:
$R^1$ is selected from H and $C_{1-3}$ alkyl, wherein said $C_{1-3}$ alkyl is optionally substituted with OH, SH, $NH_2$, $C_{1-3}$ alkylamino, or di($C_{1-3}$ alkyl)amino;
$R^2$, $R^3$, and $R^4$ are each independently selected from H, OH, SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino, and di($C_{1-3}$ alkyl)amino; and
$R^5$ is selected from H and halo.

In some embodiments of the compound of Formula (II), when $R^5$ is H:
(i) at least one of $R^2$, $R^3$, and $R^4$ is not H;
(ii) if $R^2$ is H and $R^3$ is OH, then $R^4$ is not H or OH; and
(iii) if $R^2$ is OH, then at least one of $R^3$ and $R^4$ is not H.

In some embodiments, the present disclosure provides a compound of Formula (II):

(II)

or a pharmaceutically acceptable salt thereof, wherein:
$R^1$ is selected from H and $C_{1-3}$ alkyl, wherein said $C_{1-3}$ alkyl is optionally substituted with OH, SH, $NH_2$, $C_{1-3}$ alkylamino, or di($C_{1-3}$ alkyl)amino; and $R^2$, $R^3$, and $R^4$ are each independently selected from H, OH, SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino, and di($C_{1-3}$ alkyl)amino.

In some embodiments of the compound of Formula (II), at least one of $R^2$, $R^3$, and $R^4$ is not H. In some embodiments of the compound of Formula (II), if $R^2$ is H and $R^3$ is OH, then $R^4$ is not H or OH. In some embodiments of the compound of Formula (II), if $R^2$ is OH, then at least one of $R^3$ and $R^4$ is not H.

In some embodiments of the compound of Formula (II):
(i) at least one of $R^2$, $R^3$, and $R^4$ is not H;
(ii) if $R^2$ is H and $R^3$ is OH, then $R^4$ is not H or OH; and
(iii) if $R^2$ is OH, then at least one of $R^3$ and $R^4$ is not H.

In some embodiments, $R^1$ is H.

In some embodiments, $R^1$ is $C_{1-3}$ alkyl (e.g., methyl, ethyl, propyl, isopropyl).

In some embodiments, $R^1$ is selected from HO—$C_{1-3}$ alkyl and $NH_2$—$C_{1-3}$ alkyl. In some embodiments, $R^1$ is HO—$C_{1-3}$ alkyl. In some embodiments, $R^1$ is $NH_2$—$C_{1-3}$ alkyl.

In some embodiments, at least one of $R^2$, $R^3$, and $R^4$ is selected from OH, SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino, and di($C_{1-3}$ alkyl)amino.

In some embodiments, at least one of $R^2$, $R^3$, and $R^4$ is selected from SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino and di($C_{1-3}$ alkyl)amino.

In some embodiments, at least one of $R^2$, $R^3$, and $R^4$ is selected from $NH_2$, $C_{1-3}$ alkyl, HO—$C_{1-3}$ alkyl, and $NH_2$—$C_{1-3}$ alkyl.

In some embodiments, at least one of $R^2$, $R^3$, and $R^4$ is $C_{1-3}$ alkyl.

In some embodiments, $R^2$ is selected from OH, SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino, and di($C_{1-3}$ alkyl)amino.

In some embodiments, $R^2$ is selected from SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino, and di($C_{1-3}$ alkyl)amino.

In some embodiments, $R^2$ is selected from OH, $NH_2$, $C_{1-3}$ alkyl, HO—$C_{1-3}$ alkyl, and $NH_2$—$C_{1-3}$ alkyl. In some embodiments, $R^2$ is selected from $NH_2$, $C_{1-3}$ alkyl, HO—$C_{1-3}$ alkyl, and $NH_2$—$C_{1-3}$ alkyl. In some embodiments, $R^2$ is selected from $C_{1-3}$ alkyl, HO—$C_{1-3}$ alkyl, and $NH_2$—$C_{1-3}$ alkyl. In some embodiments, $R^2$ is selected from $C_{1-3}$ alkyl and HO—$C_{1-3}$ alkyl. In some embodiments, $R^2$ is $C_{1-3}$ alkyl (e.g., methyl, ethyl, propyl, isopropyl). In some embodiments, $R^2$ is HO—$C_{1-3}$ alkyl. In some embodiments, $R^2$ is $NH_2$—$C_{1-3}$ alkyl. In some embodiments, $R^2$ is OH. In some embodiments, $R^2$ is $NH_2$. In some embodiments, $R^2$ is H.

In some embodiments, $R^3$ is selected from OH, SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino, and di($C_{1-3}$ alkyl)amino.

In some embodiments, $R^3$ is selected from SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino, and di($C_{1-3}$ alkyl)amino.

In some embodiments, $R^3$ is selected from OH, $NH_2$, $C_{1-3}$ alkyl, HO—$C_{1-3}$ alkyl, and $NH_2$—$C_{1-3}$ alkyl. In some embodiments, $R^3$ is selected from $NH_2$, $C_{1-3}$ alkyl, HO—$C_{1-3}$ alkyl, and $NH_2$—$C_{1-3}$ alkyl. In some embodiments, $R^3$ is selected from $C_{1-3}$ alkyl, HO—$C_{1-3}$ alkyl, and $NH_2$—$C_{1-3}$ alkyl. In some embodiments, $R^3$ is selected from $C_{1-3}$ alkyl and HO—$C_{1-3}$ alkyl. In some embodiments, $R^3$ is $C_{1-3}$ alkyl (e.g., methyl, ethyl, propyl, isopropyl). In some embodiments, $R^3$ is HO—$C_{1-3}$ alkyl. In some embodiments, $R^3$ is $NH_2$—$C_{1-3}$ alkyl. In some embodiments, $R^3$ is OH. In some embodiments, $R^3$ is $NH_2$. In some embodiments, $R^3$ is H.

In some embodiments, $R^4$ is selected from OH, SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino, and di($C_{1-3}$ alkyl) amino.

In some embodiments, $R^4$ is selected from SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino, and di($C_{1-3}$ alkyl)amino.

In some embodiments, $R^4$ is selected from OH, $NH_2$, $C_{1-3}$ alkyl, HO—$C_{1-3}$ alkyl, and $NH_2$—$C_{1-3}$ alkyl. In some embodiments, $R^4$ is selected from $NH_2$, $C_{1-3}$ alkyl, HO—$C_{1-3}$ alkyl, and $NH_2$—$C_{1-3}$ alkyl. In some embodiments, $R^4$ is selected from $C_{1-3}$ alkyl, HO—$C_{1-3}$ alkyl, and $NH_2$—$C_{1-3}$ alkyl. In some embodiments, $R^4$ is selected from $C_{1-3}$ alkyl and HO—$C_{1-3}$ alkyl. In some embodiments, $R^4$ is $C_{1-3}$ alkyl (e.g., methyl, ethyl, propyl, isopropyl). In some embodiments, $R^4$ is HO—$C_{1-3}$ alkyl. In some embodiments, $R^4$ is $NH_2$—$C_{1-3}$ alkyl. In some embodiments, $R^4$ is OH. In some embodiments, $R^4$ is $NH_2$. In some embodiments, $R^4$ is H.

In some embodiments:
$R^3$ is OH; and
$R^2$ is selected from SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino and di($C_{1-3}$ alkyl)amino.

In some embodiments:
$R^3$ is OH; and
$R^2$ is selected from OH, $NH_2$, $C_{1-3}$ alkyl, HO—$C_{1-3}$ alkyl, and $NH_2$—$C_{1-3}$ alkyl.

In some embodiments:
$R^3$ is OH; and
$R^4$ is selected from SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino and di($C_{1-3}$ alkyl)amino.

In some embodiments:
$R^3$ is OH; and
$R^4$ is selected from $NH_2$, $C_{1-3}$ alkyl, HO—$C_{1-3}$ alkyl, and $NH_2$—$C_{1-3}$ alkyl.

In some embodiments:
$R^4$ is OH; and
$R^3$ is selected from H, SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino and di($C_{1-3}$ alkyl)amino.

In some embodiments:
$R^4$ is OH; and
$R^3$ is selected from H, $NH_2$, $C_{1-3}$ alkyl, HO—$C_{1-3}$ alkyl, and $NH_2$—$C_{1-3}$ alkyl.

In some embodiments:
$R^2$ is OH; and
at least one of $R^3$ and $R^4$ is selected from OH, SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino and di($C_{1-3}$ alkyl)amino.

In some embodiments:
$R^2$ is OH; and
at least one of $R^3$ and $R^4$ is selected from OH, $NH_2$, $C_{1-3}$ alkyl, HO—$C_{1-3}$ alkyl, and $NH_2$—$C_{1-3}$ alkyl.

In some embodiments, $R^3$ is OH and $R^2$ is $C_{1-3}$ alkyl. In some embodiments, $R^3$ is $C_{1-3}$ alkyl and $R^2$ is OH. In some embodiments, $R^3$ is OH and $R^4$ is $C_{1-3}$ alkyl. In some embodiments, $R^3$ is $C_{1-3}$ alkyl and $R^4$ is OH.

In some embodiments:
$R^5$ is halo; and
$R^2$, $R^3$, and $R^4$ are each independently selected from H, OH, SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino, and di($C_{1-3}$ alkyl)amino.

In some embodiments, $R^2$, $R^3$, and $R^4$ are each independently selected from H, OH, and $C_{1-3}$ alkyl. In some embodiments, $R^2$, $R^3$, and $R^4$ are each H.

In some embodiments, $R^5$ is H. In some embodiments, $R^5$ is halo. In some embodiments, $R^5$ is selected from Cl, Br, and F. In some embodiments, $R^5$ is Cl. In some embodiments, $R^5$ is Br. In some embodiments, $R^5$ is F.

In some embodiments, the compound of Formula (I) is:

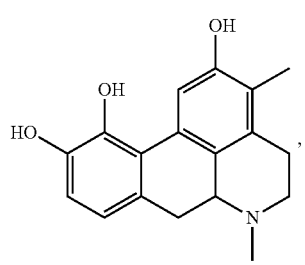

(compound 1)

or a pharmaceutically acceptable salt thereof.
In some embodiments, the compound of Formula (I) is:

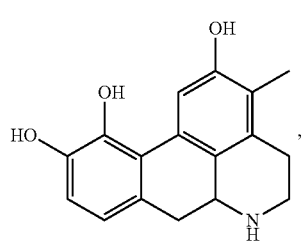

(compound 2)

or a pharmaceutically acceptable salt thereof.
In some embodiments, the compound of Formula (II) is selected from any one of the following compounds:

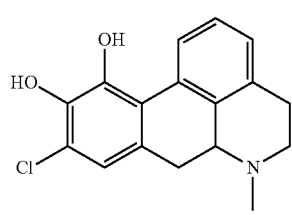

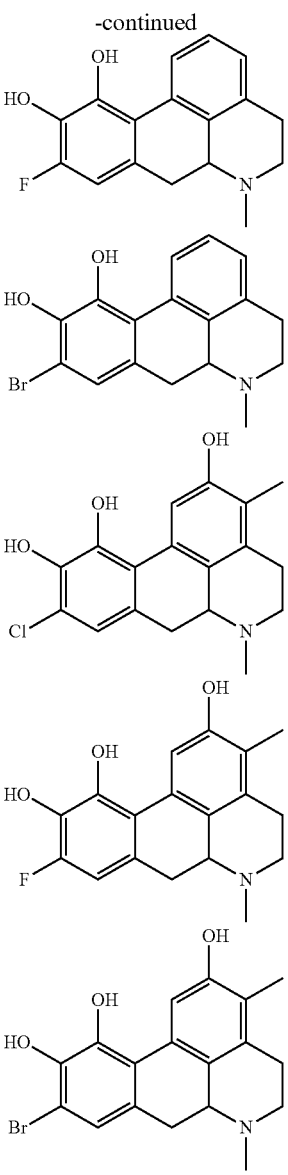

or a pharmaceutically acceptable salt thereof.

Compounds of Formula (II)

In some embodiments, the present disclosure provides a compound of Formula (III):

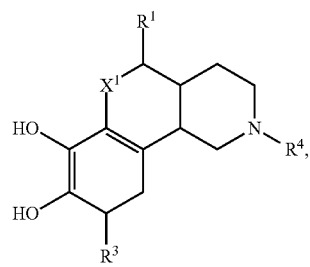

(III)

or a pharmaceutically acceptable salt thereof, wherein:
$X^1$ is selected from $CH_2$ and O;
$R^1$ is selected from HO—$C_{1-6}$ alkyl, $NH_2$—$C_{1-6}$ alkyl, 5-6-membered heteroaryl ring comprising 1 to 5 heteroatoms selected from N, O, and S, and 3-10-membered heterocycloalkyl ring comprising 1 to 3 heteroatoms independently selected from N, O, and S;

wherein said heteroaryl ring and heterocycloalkyl ring are each optionally substituted with 1, 2, or 3 substituents independently selected from $R^2$;

each $R^2$ is independently selected from halo, OH, $C_{1-3}$ alkoxy, SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, $C_{1-3}$ alkoxy, SH, $NH_2$, $C_{1-3}$ alkylamino, and di($C_{1-3}$ alkyl)amino;

$R^3$ is selected from H and halo; and $R^4$ is selected from H and $C_{1-3}$ alkyl, wherein said $C_{1-3}$ alkyl is optionally substituted with OH, SH, $NH_2$, $C_{1-3}$ alkylamino, or di($C_{1-3}$ alkyl)amino.

In some embodiments, $X^1$ is $CH_2$. In some embodiments, $X^1$ is O.

In some embodiments, $R^3$ is H. In some embodiments, $R^3$ is halo. In some embodiments, $R^3$ is selected from Cl, Br, and F. In some embodiments, $R^3$ is Cl. In some embodiments, $R^3$ is Br. In some embodiments, $R^3$ is F.

In some embodiments, $R^4$ is selected from H and $C_{1-3}$ alkyl.

In some embodiments, $R^4$ is H. In some embodiments, $R^4$ is $C_{1-3}$ alkyl.

In some embodiments, $R^1$ is 5-6-membered heteroaryl ring comprising 1 to 5 heteroatoms selected from N, O, and S, which is optionally substituted with 1, 2, or 3 substituents independently selected from $R^2$.

In some embodiments, $R^1$ is 5-6-membered heteroaryl ring comprising 1 or 2 heteroatoms selected from N, O, and S, which is optionally substituted with 1, 2, or 3 substituents independently selected from R.

In some embodiments, $R^1$ is 5-membered heteroaryl ring comprising 1 or 2 heteroatoms selected from N, O, and S, which is optionally substituted with 1, 2, or 3 substituents independently selected from R.

In some embodiments, $R^1$ is selected from thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl, each of which is optionally substituted with 1, 2, or 3 substituents independently selected from $R^2$.

In some embodiments, $R^1$ is 6-membered heteroaryl ring comprising 1 or 2 N atoms, which is optionally substituted with 1, 2, or 3 substituents independently selected from $R^2$.

In some embodiments, $R^1$ is selected from pyridinyl, pyrimidinyl, pyrazinyl, diazinyl, triazinyl, tetrazinyl, and pentazinyl, each of which is optionally substituted with 1, 2, or 3 substituents independently selected from $R^2$.

In some embodiments, $R^1$ is selected from pyridyl, pyrazinyl, pyrimidinyl, and pyridazinyl, each of which is optionally substituted with 1, 2, or 3 substituents independently selected from R.

In some embodiments, $R^1$ is selected from pyridinyl, pyrimidinyl, and pyrazinyl, each of which is optionally substituted with 1, 2, or 3 substituents independently selected from R.

In some embodiments, $R^1$ is pyridinyl, optionally substituted with 1, 2, or 3 substituents independently selected from $R^2$.

In some embodiments, the compound of Formula (III) has formula:

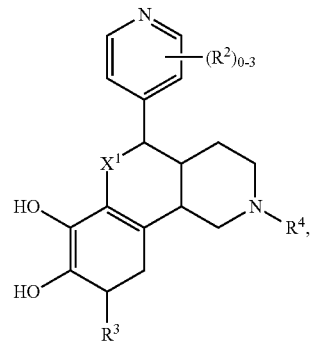

or a pharmaceutically acceptable salt thereof.

In some embodiments, the compound of Formula (III) has formula:

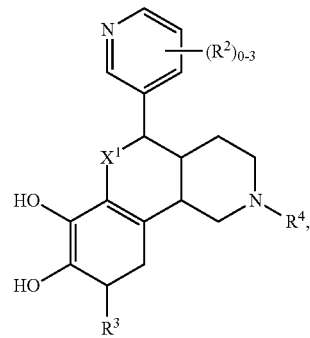

or a pharmaceutically acceptable salt thereof.

In some embodiments, $R^1$ is 3-10-membered heterocycloalkyl ring comprising 1 to 3 heteroatoms independently selected from N, O, and S, which is optionally substituted with 1, 2, or 3 substituents independently selected from R.

In some embodiments, $R^1$ is 3-7-membered heterocycloalkyl ring comprising 1 or 2 heteroatoms selected from N, O, and S, which is optionally substituted with 1, 2, or 3 substituents independently selected from R.

In some embodiments, $R^1$ is 3-membered heterocycloalkyl ring comprising 1 heteroatom selected from N, O, and S, which is optionally substituted with 1, 2, or 3 substituents independently selected from $R^2$. Examples of such rings include aziridinyl and oxiranyl.

In some embodiments, $R^1$ is 4-membered heterocycloalkyl ring comprising 1 heteroatom selected from N, O, and S, which is optionally substituted with 1, 2, or 3 substituents independently selected from $R^2$. Examples of such rings include oxetanyl and azetidinyl.

In some embodiments, $R^1$ is 5-membered heterocycloalkyl ring comprising 1 or 2 heteroatoms selected from N, O, and S, which is optionally substituted with 1, 2, or 3 substituents independently selected from R. Examples of such rings include tetrahydrofuranyl, pyrrolidinyl, isoxazolidinyl, imidazolidinyl, and thiazolidinyl.

In some embodiments, $R^1$ is 6-membered heterocycloalkyl ring comprising 1 or 2 heteroatoms selected from N, O, and S, which is optionally substituted with 1, 2, or 3 substituents independently selected from $R^2$. Examples of such rings include morpholinyl, thiomorpholinyl, tetrahydropyranyl, piperazinyl, and piperidinyl.

In some embodiments, $R^1$ is 7-membered heterocycloalkyl ring comprising 1 or 2 heteroatoms selected from N, O, and S, which is optionally substituted with 1, 2, or 3 substituents independently selected from R.

In some embodiments, $R^1$ is 8-membered heterocycloalkyl ring comprising 1 or 2 heteroatoms selected from N, O, and S, which is optionally substituted with 1, 2, or 3 substituents independently selected from $R^2$.

In some embodiments, $R^1$ is 9-membered heterocycloalkyl ring comprising 1 or 2 heteroatoms selected from N, O, and S, which is optionally substituted with 1, 2, or 3 substituents independently selected from $R^2$.

In some embodiments, $R^1$ is 10-membered heterocycloalkyl ring comprising 1 or 2 heteroatoms selected from N, O, and S, which is optionally substituted with 1, 2, or 3 substituents independently selected from $R^2$.

In some embodiments, $R^1$ is selected from tetrahydropyranyl, piperidinyl, tetrahydrofuranyl, pyrrolidinyl, pyranyl, morpholinyl, oxazinyl, dioxanyl, dioxinyl, diazinanyl, triazinanyl, trioxanyl, azepanyl, azepinyl, oxepanyl, oxepinyl, diazepanyl, diazepinyl, azocanyl, azocinyl, oxocanyl, oxocinyl, azonanyl, azoninyl, oxonanyl, and oxoninyl, each of which is optionally substituted with 1, 2, or 3 substituents independently selected from $R^2$.

In some embodiments, $R^1$ is selected from tetrahydropyranyl, piperidinyl, tetrahydrofuranyl, and pyrrolidinyl, each of which is optionally substituted with 1, 2, or 3 substituents independently selected from $R^2$.

In some embodiments, $R^1$ is selected from tetrahydropyranyl and piperidinyl, each of which is optionally substituted with 1, 2, or 3 substituents independently selected from $R^2$.

In some embodiments, $R^1$ is tetrahydropyranyl, optionally substituted with 1, 2, or 3 substituents independently selected from $R^2$. In some embodiments, $R^1$ is any one of $R^1$ described herein for Formula (I).

In some embodiments, the compound of Formula (III) has formula:

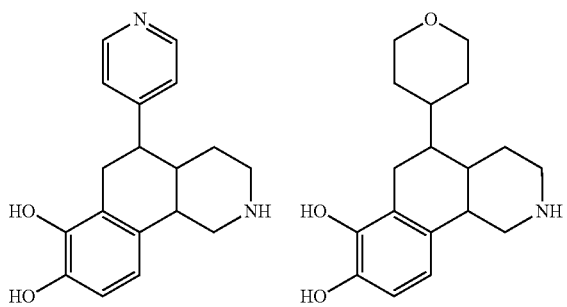

or a pharmaceutically acceptable salt thereof.

In some embodiments, the compound of Formula (III) has formula:

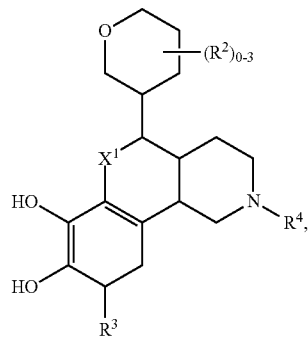

or a pharmaceutically acceptable salt thereof.

In some embodiments, $R^1$ is selected from HO—$C_{1-6}$ alkyl and $NH_2$—$C_{1-6}$ alkyl.

In some embodiments, $R^1$ is HO—$C_{1-6}$ alkyl.

In some embodiments, $R^1$ is $NH_2$—$C_{1-6}$ alkyl.

In some embodiments, each $R^2$ is independently selected from halo, OH, $C_{1-3}$ alkoxy, $C_{1-3}$ alkyl, and $C_{1-3}$ haloalkyl. In some embodiments, $R^2$ is any of the $R^2$ groups described herein for the compound of Formula (I). In some embodiments, $R^2$ is selected from OH, $NH_2$, $C_{1-3}$ alkyl, HO—$C_{1-3}$ alkyl, and $NH_2$—$C_{1-3}$ alkyl. In some embodiments, $R^2$ is selected from OH and $NH_2$. In some embodiments, $R^2$ is OH. In some embodiments, $R^2$ is $NH_2$. In some embodiments, $R^2$ is $C_{1-3}$ alkyl. In some embodiments, $R^2$ is HO—$C_{1-3}$ alkyl. In some embodiments, $R^2$ is $NH_2$—$C_{1-3}$ alkyl.

In some embodiments, the compound of Formula (III) is selected from any one of the following compounds:

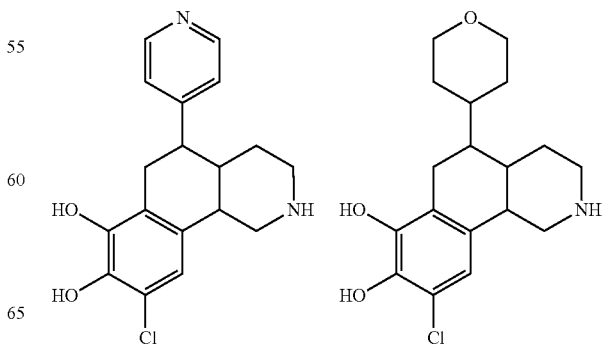

35
-continued
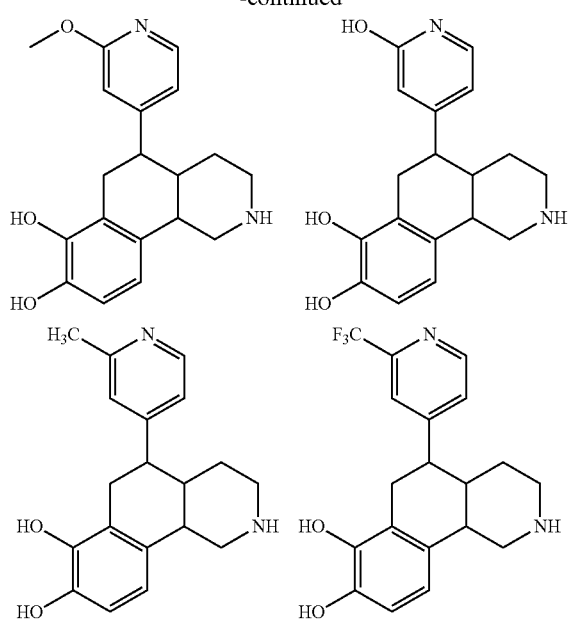
36
-continued
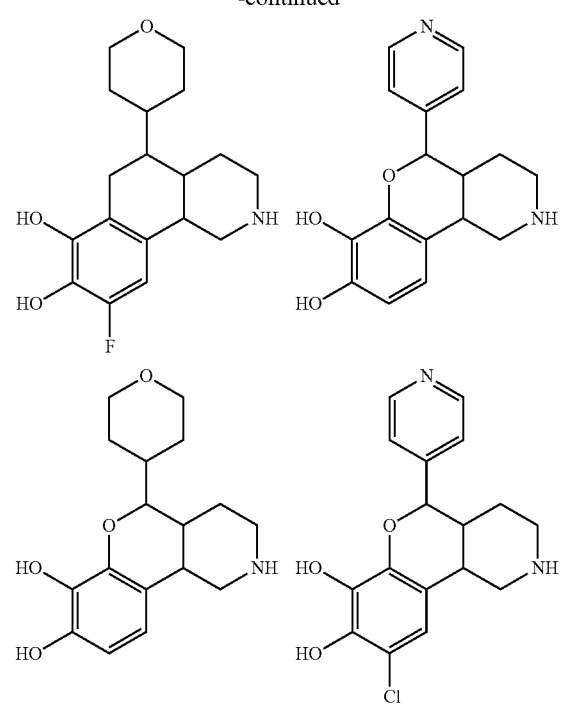
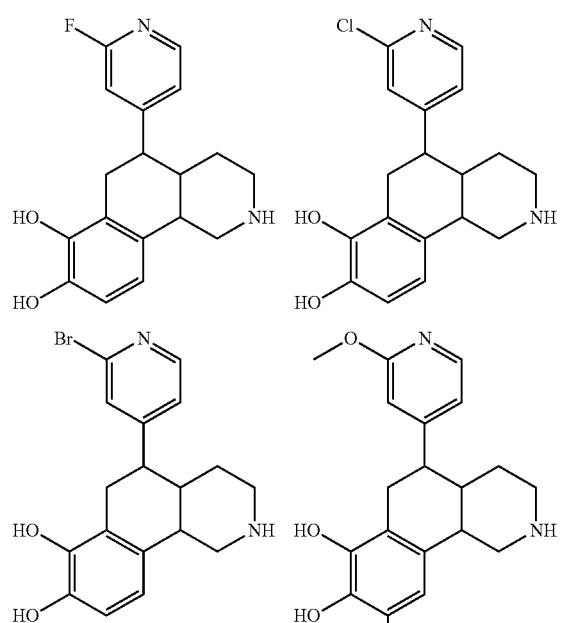
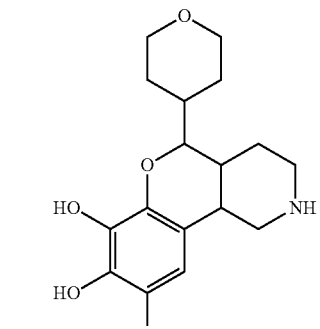
(example 2)
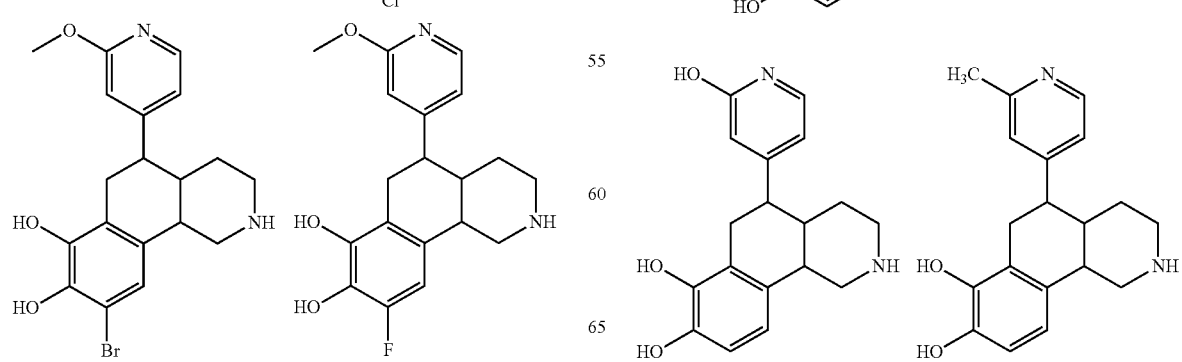

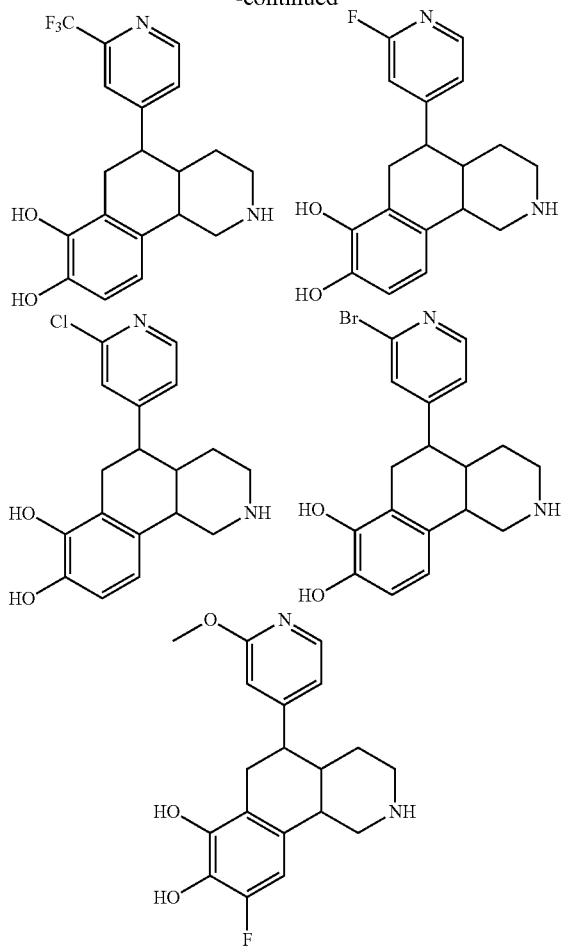

or a pharmaceutically acceptable salt thereof.

Compounds of Formula (IV)

In some embodiments, the present disclosure provides a compound of Formula (IV):

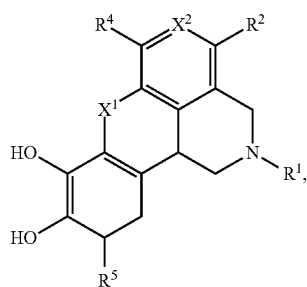

or a pharmaceutically acceptable salt thereof, wherein:
$X^1$ is selected from $CH_2$ and O;
$X^2$ is selected from $CR^3$ and N;
$R^1$ is selected from H and $C_{1-3}$ alkyl, wherein said $C_{1-3}$ alkyl is optionally substituted with OH, SH, $NH_2$, $C_{1-3}$ alkylamino, or di($C_{1-3}$ alkyl)amino;
$R^5$ is selected from H and halo; and
$R^2$, $R^3$, and $R^4$ are each independently selected from H, OH, SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino, and di($C_{1-3}$ alkyl)amino.

In some embodiments of the compound of Formula (IV), if $R^5$ is H and $X^2$ is $CR^3$, then at least one of $R^2$, $R^3$, and $R^4$ is not H.

In some embodiments, $X^1$ is $CH_2$. In some embodiments, $X^1$ is O.

In some embodiments, $R^1$ is selected from H and $C_{1-3}$ alkyl.

In some embodiments, $R^1$ is H. In some embodiments, $R^1$ is $C_{1-3}$ alkyl (e.g., methyl, ethyl, propyl, isopropyl). In some embodiments, $R^1$ is selected from HO—$C_{1-3}$ alkyl and $NH_2$—$C_{1-3}$ alkyl. In some embodiments, $R^1$ is HO—$C_{1-3}$ alkyl. In some embodiments, $R^1$ is $NH_2$—$C_{1-3}$ alkyl.

In some embodiments, $R^5$ is H. In some embodiments, $R^5$ is halo. In some embodiments, $R^5$ is selected from Cl, Br, and F. In some embodiments, $R^5$ is Cl. In some embodiments, $R^5$ is Br. In some embodiments, $R^5$ is F.

In some embodiments, $X^2$ is N. In some embodiments, $X^2$ is $CR^3$.

In some embodiments, at least one of $R^2$, $R^3$, and $R^4$ is selected from OH, SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino, and di($C_{1-3}$ alkyl)amino.

In some embodiments, at least one of $R^2$, $R^3$, and $R^4$ is selected from SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino and di($C_{1-3}$ alkyl)amino.

In some embodiments, at least one of $R^2$, $R^3$, and $R^4$ is selected from $NH_2$, $C_{1-3}$ alkyl, HO—$C_{1-3}$ alkyl, and $NH_2$—$C_{1-3}$ alkyl.

In some embodiments, at least one of $R^2$, $R^3$, and $R^4$ is $C_{1-3}$ alkyl.

In some embodiments, $R^2$ is selected from OH, SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino, and di($C_{1-3}$ alkyl)amino.

In some embodiments, $R^2$ is selected from SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino, and di($C_{1-3}$ alkyl)amino.

In some embodiments, $R^2$ is selected from OH, $NH_2$, $C_{1-3}$ alkyl, HO—$C_{1-3}$ alkyl, and $NH_2$—$C_{1-3}$ alkyl. In some embodiments, $R^2$ is selected from $NH_2$, $C_{1-3}$ alkyl, HO—$C_{1-3}$ alkyl, and $NH_2$—$C_{1-3}$ alkyl. In some embodiments, $R^2$ is selected from $C_{1-3}$ alkyl, HO—$C_{1-3}$ alkyl, and $NH_2$—$C_{1-3}$ alkyl. In some embodiments, $R^2$ is selected from $C_{1-3}$ alkyl and HO—$C_{1-3}$ alkyl. In some embodiments, $R^2$ is $C_{1-3}$ alkyl (e.g., methyl, ethyl, propyl, isopropyl). In some embodiments, $R^2$ is HO—$C_{1-3}$ alkyl. In some embodiments, $R^2$ is $NH_2$—$C_{1-3}$ alkyl. In some embodiments, $R^2$ is OH. In some embodiments, $R^2$ is $NH_2$. In some embodiments, $R^2$ is H.

In some embodiments, $R^3$ is selected from OH, SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino, and di($C_{1-3}$ alkyl)amino.

In some embodiments, $R^3$ is selected from SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino, and di($C_{1-3}$ alkyl)amino.

In some embodiments, $R^3$ is selected from OH, $NH_2$, $C_{1-3}$ alkyl, HO—$C_{1-3}$ alkyl, and $NH_2$—$C_{1-3}$ alkyl. In some embodiments, $R^3$ is selected from $NH_2$, $C_{1-3}$ alkyl, HO—$C_{1-3}$ alkyl, and $NH_2$—$C_{1-3}$ alkyl. In some embodiments, $R^3$ is selected from $C_{1-3}$ alkyl, HO—$C_{1-3}$ alkyl, and $NH_2$—$C_{1-3}$ alkyl. In some embodiments, $R^3$ is selected from $C_{1-3}$ alkyl and HO—$C_{1-3}$ alkyl. In some embodiments, $R^3$ is $C_{1-3}$ alkyl (e.g., methyl, ethyl, propyl, isopropyl). In some embodiments, $R^3$ is HO—$C_{1-3}$ alkyl. In some embodiments, $R^3$ is $NH_2$—$C_{1-3}$ alkyl. In some embodiments, $R^3$ is OH. In some embodiments, $R^3$ is $NH_2$. In some embodiments, $R^3$ is H.

In some embodiments, $R^4$ is selected from OH, SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino, and di($C_{1-3}$ alkyl)amino.

In some embodiments, $R^4$ is selected from SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino, and di($C_{1-3}$ alkyl)amino.

In some embodiments, $R^4$ is selected from OH, $NH_2$, $C_{1-3}$ alkyl, HO—$C_{1-3}$ alkyl, and $NH_2$—$C_{1-3}$ alkyl. In some embodiments, $R^4$ is selected from $NH_2$, $C_{1-3}$ alkyl, HO—$C_{1-3}$ alkyl, and $NH_2$—$C_{1-3}$ alkyl. In some embodiments, $R^4$ is selected from $C_{1-3}$ alkyl, HO—$C_{1-3}$ alkyl, and $NH_2$—$C_{1-3}$ alkyl. In some embodiments, $R^4$ is selected from $C_{1-3}$ alkyl and HO—$C_{1-3}$ alkyl. In some embodiments, $R^4$ is $C_{1-3}$ alkyl (e.g., methyl, ethyl, propyl, isopropyl). In some embodiments, $R^4$ is HO—$C_{1-3}$ alkyl. In some embodiments, $R^4$ is $NH_2$—$C_{1-3}$ alkyl. In some embodiments, $R^4$ is OH. In some embodiments, $R^4$ is $NH_2$. In some embodiments, $R^4$ is H.

In some embodiments, the compound of Formula (IV) has formula:

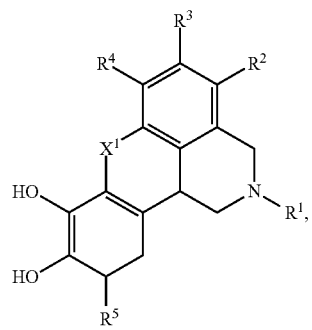

or a pharmaceutically acceptable salt thereof.

In some embodiments:

$R^5$ is halo; and $R^2$, $R^3$, and $R^4$ are each independently selected from H, OH, SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino, and di($C_{1-3}$ alkyl)amino.

In some embodiments, $R^2$, $R^3$, and $R^4$ are each independently selected from H, OH, and $C_{1-3}$ alkyl. In some embodiments, $R^2$, $R^3$, and $R^4$ are each H.

In some embodiments:

$R^3$ is H;

$R^5$ is H; and $R^2$ and $R^4$ are each independently selected from OH and $C_{1-3}$ alkyl.

In some embodiments, the compound of Formula (IV) has formula:

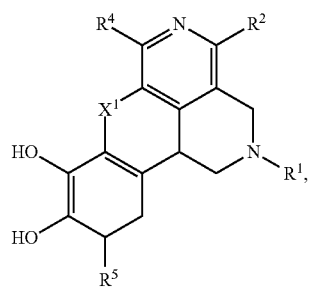

or a pharmaceutically acceptable salt thereof.

In some embodiments, $R^2$ and $R^4$ are each independently selected from H, halo, OH, $C_{1-3}$ alkoxy, $C_{1-3}$ alkyl, and $C_{1-3}$ haloalkyl.

In some embodiments, the compound of Formula (IV) is selected from any one of the following compounds:

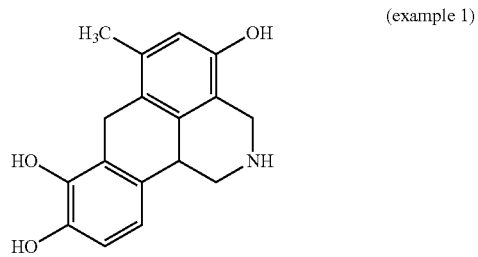

(example 1)

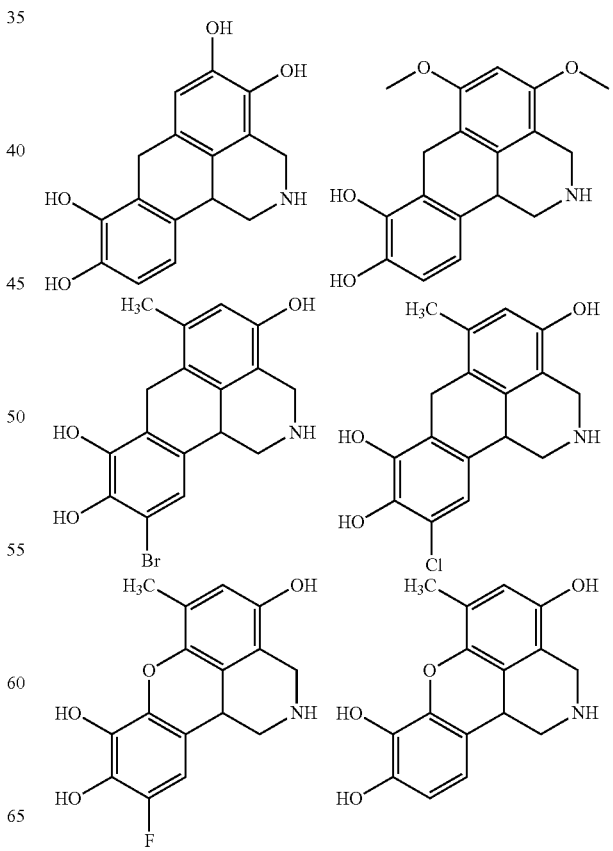

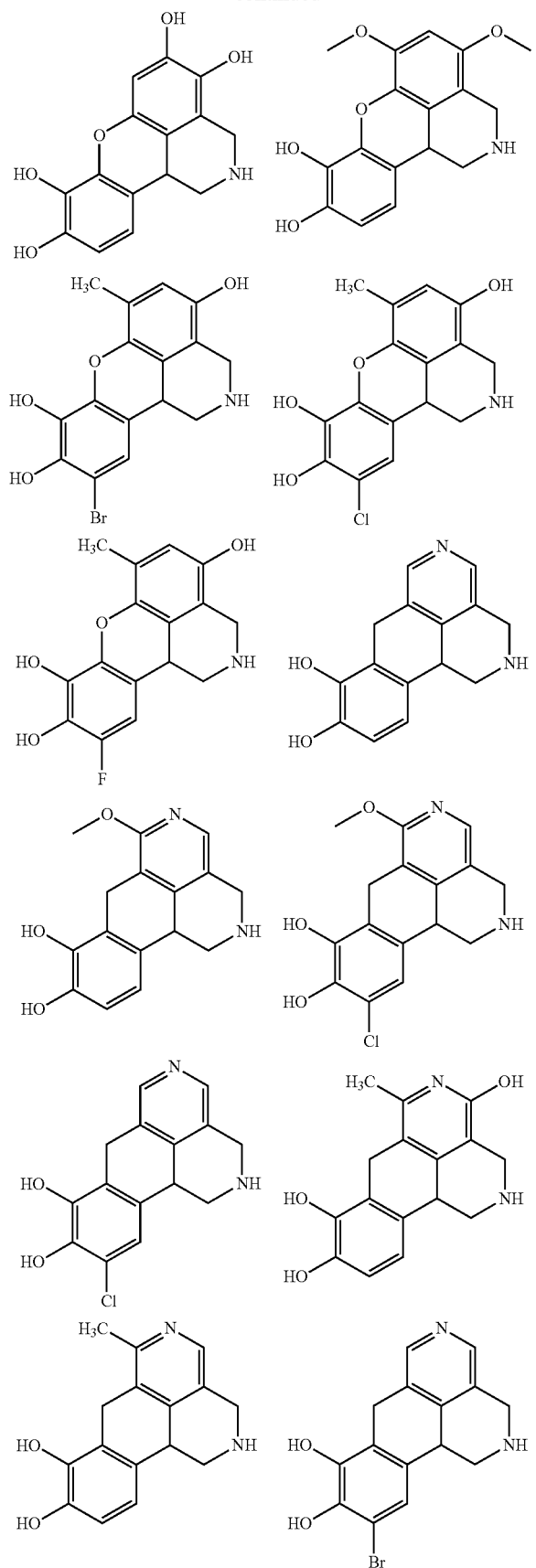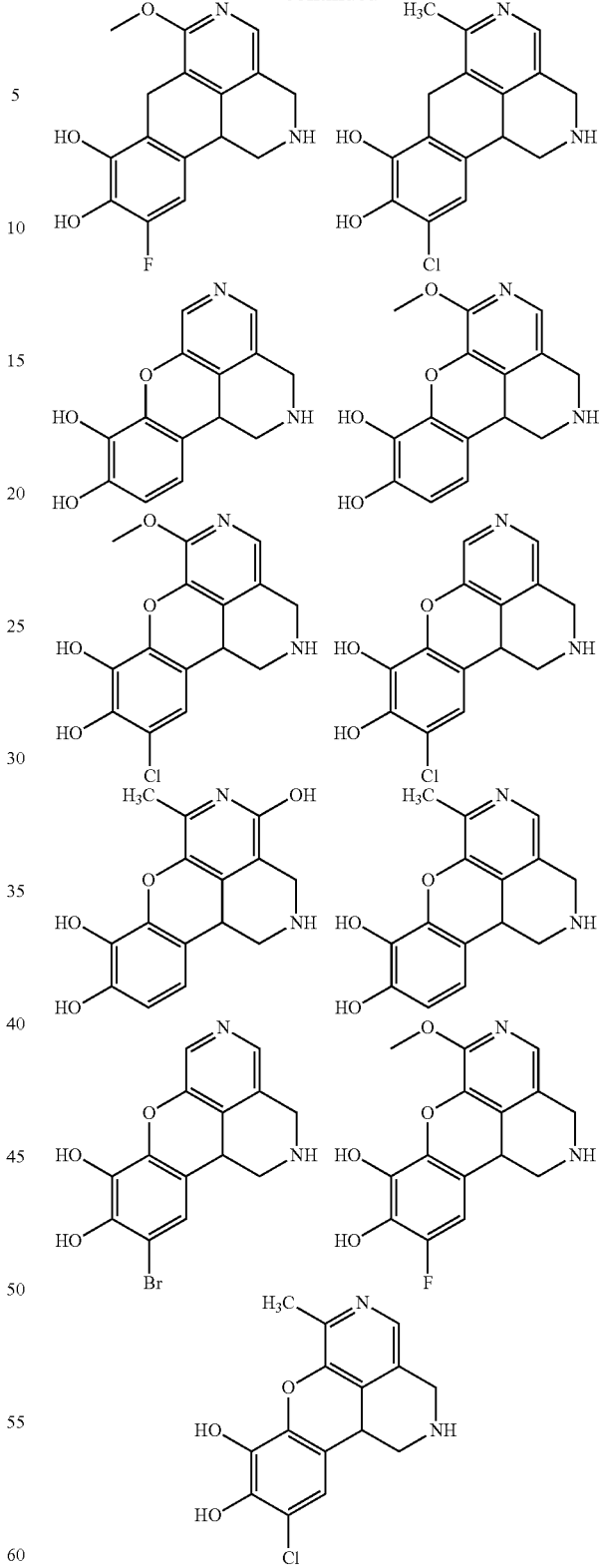
or a pharmaceutically acceptable salt thereof.
In some embodiments, the the compound of any one of the foregoing Formulae is hydrophilic. In such embodiments, the structure of the compound contains hydrogen bond donor (HBD) atoms that are capable of forming hydrogen bonds with molecules of water and with the amino acids within the active site of a G protein coupled receptor. In some embodiments, the compound of any one of the foregoing Formulae contains at least 2, 3, 4, 5, or 6 HBD atoms (e.g., heteroatoms such as O, N or S). In some embodiments, the compound of any one of the foregoing Formulae contains at least one hydroxyl group (e.g., 1, 2, 3, 4, 5, or 6 hydroxyl groups). In some embodiments, the compound of any one of the foregoing Formulae contains amino groups (e.g., 1, 2, 3, 4, 5, or 6 amino groups).

In some embodiments, the compound of any one of the foregoing Formulae does not penetrate the blood brain barrier or only an insignificant amount of the compound of any one of the foregoing Formulae penetrates the blood brain barrier after the compound is administered to a subject (e.g., not more than about 0.1 wt. %, about 1 wt. %, about 5 wt. %, about 10 wt. %, or about 20 wt. % of the amount of the compound administered to the subject penetrates the blood brain barrier). In one example, the compound of any one of the foregoing Formulae is ineffective or only weakly effective in treating central nervous system (CNS) disorders due to its hydrophilicity and subsequent inability to penetrate the blood bran barrier.

Pharmaceutical Compositions and Formulations

The present application also provides pharmaceutical compositions comprising an effective amount of a compound of the present disclosure, or a pharmaceutically acceptable salt thereof, and a pharmaceutically acceptable carrier. The pharmaceutical composition may also comprise at least one of any one of the additional therapeutic agents described. In certain embodiments, the application also provides pharmaceutical compositions and dosage forms comprising any one the additional therapeutic agents described herein (e.g., in a kit). The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of the present application include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

The compositions or dosage forms may contain any one of the compounds and therapeutic agents described herein in the range of 0.005% to 100% with the balance made up from the suitable pharmaceutically acceptable excipients. The contemplated compositions may contain 0.001%-100% of any one of the compounds and therapeutic agents provided herein, in one embodiment 0.1-95%, in another embodiment 75-85%, in a further embodiment 20-80%, wherein the balance may be made up of any pharmaceutically acceptable excipient described herein, or any combination of these excipients.

Routes of Administration and Dosage Forms

The pharmaceutical compositions of the present application include those suitable for any acceptable route of administration. Acceptable routes of administration include, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intranasal, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal.

Compositions and formulations described herein may conveniently be presented in a unit dosage form, e.g., tablets, capsules (e.g., hard or soft gelatin capsules), sustained release capsules, and in liposomes, and may be prepared by any methods well known in the art of pharmacy. See, for example, Remington: The Science and Practice of Pharmacy, Lippincott Williams & Wilkins, Baltimore, MD (20th ed. 2000). Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In some embodiments, any one of the compounds and therapeutic agents disclosed herein are administered orally. Compositions of the present application suitable for oral administration may be presented as discrete units such as capsules, sachets, granules or tablets each containing a predetermined amount (e.g., effective amount) of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption. In the case of tablets for oral use, carriers that are commonly used include lactose, sucrose, glucose, mannitol, and silicic acid and starches. Other acceptable excipients may include: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added. Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions or infusion solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, saline (e.g., 0.9% saline solution) or 5% dextrose solution, immediately prior to use. Extemporaneous injection solutions and suspensions may be prepared from sterile powders, granules and tablets. The injection solutions may be in the form, for example, of a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of the present application may be administered in the form of suppositories for rectal administration. These compositions can be prepared by mixing a compound of the present application with a suitable non-irritating excipient which is solid at room temperature but liquid at the rectal temperature and therefore will melt in the rectum to release the active components. Such materials include cocoa butter, beeswax, and polyethylene glycols.

The pharmaceutical compositions of the present application may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, for example, U.S. Pat. No. 6,803,031. Additional formulations and methods for intranasal administration are found in Ilium, L., *J Pharm Pharmacol*, 56:3-17, 2004 and Ilium, L., *Eur J Pharm Sci* 11:1-18, 2000.

The topical compositions of the present disclosure can be prepared and used in the form of an aerosol spray, cream, emulsion, solid, liquid, dispersion, foam, oil, gel, hydrogel, lotion, mousse, ointment, powder, patch, pomade, solution, pump spray, stick, towelette, soap, or other forms commonly employed in the art of topical administration and/or cosmetic and skin care formulation. The topical compositions can be in an emulsion form. Topical administration of the pharmaceutical compositions of the present application is especially useful when the desired treatment involves areas or organs readily accessible by topical application. In some embodiments, the topical composition comprises a combination of any one of the compounds and therapeutic agents disclosed herein, and one or more additional ingredients, carriers, excipients, or diluents including absorbents, anti-irritants, anti-acne agents, preservatives, antioxidants, coloring agents/pigments, emollients (moisturizers), emulsifiers, film-forming/holding agents, fragrances, leave-on exfoliants, prescription drugs, preservatives, scrub agents, silicones, skin-identical/repairing agents, slip agents, sunscreen actives, surfactants/detergent cleansing agents, penetration enhancers, and thickeners.

The compounds and therapeutic agents of the present application may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the present application provides an implantable drug release device impregnated with or containing a compound or a therapeutic agent, or a composition comprising a compound of the present application or a therapeutic agent, such that said compound or therapeutic agent is released from said device and is therapeutically active.

Dosages and Regimens

In the pharmaceutical compositions of the present application, a therapeutic compound is present in an effective amount (e.g., a therapeutically effective amount).

Effective doses may vary, depending on the diseases treated, the severity of the disease, the route of administration, the sex, age and general health condition of the subject, excipient usage, the possibility of co-usage with other therapeutic treatments such as use of other agents and the judgment of the treating physician.

In some embodiments, an effective amount of a therapeutic compound can range, for example, from about 0.001 mg/kg to about 500 mg/kg (e.g., from about 0.001 mg/kg to about 200 mg/kg; from about 0.01 mg/kg to about 200 mg/kg; from about 0.01 mg/kg to about 150 mg/kg; from about 0.01 mg/kg to about 100 mg/kg; from about 0.01 mg/kg to about 50 mg/kg; from about 0.01 mg/kg to about 10 mg/kg; from about 0.01 mg/kg to about 5 mg/kg; from about 0.01 mg/kg to about 1 mg/kg; from about 0.01 mg/kg to about 0.5 mg/kg; from about 0.01 mg/kg to about 0.1 mg/kg; from about 0.1 mg/kg to about 200 mg/kg; from about 0.1 mg/kg to about 150 mg/kg; from about 0.1 mg/kg to about 100 mg/kg; from about 0.1 mg/kg to about 50 mg/kg; from about 0.1 mg/kg to about 10 mg/kg; from about 0.1 mg/kg to about 5 mg/kg; from about 0.1 mg/kg to about 2 mg/kg; from about 0.1 mg/kg to about 1 mg/kg; or from about 0.1 mg/kg to about 0.5 mg/kg).

In some embodiments, an effective amount of a therapeutic compound is about 0.1 mg/kg, about 0.5 mg/kg, about 1 mg/kg, about 2 mg/kg, or about 5 mg/kg.

The foregoing dosages can be administered on a daily basis (e.g., as a single dose or as two or more divided doses, e.g., once daily, twice daily, thrice daily) or non-daily basis (e.g., every other day, every two days, every three days, once weekly, twice weekly, once every two weeks, once a month). The compounds and compositions described herein can be administered to the subject in any order. A first therapeutic agent, such as a compound of the present disclosure, can be administered prior to or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before or after), or concomitantly with the administration of a second therapeutic agent, such as an anti-fibrotic agent described herein, to a subject in need of treatment. Thus, the compound of the present disclosure, or a composition containing the compound, can be administered separately, sequentially or simultaneously with the second therapeutic agent, such as an anti-fibrotic agent described herein. When the compound of the present disclosure, or a pharmaceutically acceptable salt thereof, and a second or third therapeutic agent are administered to the subject simultaneously, the therapeutic agents may be administered in a single dosage form (e.g., tablet, capsule, or a solution for injection or infusion).

In some embodiments, the second (additional) therapeutic agent is a drug that is useful in treating or preventing a fibrotic pathology. Suitable examples of such drugs include nintedanib, pirfenidone, or prednisone, or immunosuppressants, such as cyclophosphamide, azathioprine, methotrexate, penicillamine, and cyclosporine.

In some embodiments, the additional therapeutic agent is dopamine, or a pharmaceutically acceptable salt thereof.

In some embodiments, the additional therapeutic agent is a dopamine receptor agonist. In some embodiments, the dopamine receptor agonist is selected from: ABT-413, A-86929, dihydrexidine (DHX), dinapsoline, dinoxyline, doxanthrine, SKF-81297, SKF-82958, SKF-38393, fenoldopam, 6-Br-APB, stepholidine, A-68930, A-77636, CY-208-243, SKF-89145, SKF-89626, 7,8-dihydroxy-5-phenyl-octahydrobenzo[h]isoquinoline, cabergoline, pergolide, R(−)-2,10,11-trihydroxyaporphine, (R)-(−)-apomorphine, R(−)-propylnorapomorphine, R(+)-6-bromo-APB, R(−)-2,10,11-trihydroxy-N-propyl-noraporphine, 6,7-ADTN, mesulergine, N-methyldopamine, 4-hydroxyphenethylamine, cabergoline, 3-hydroxyphenethylamine, pramipexole, PD-168077, fenoldopam, (±)-PD 128-907, (+)-2-(N-phenylethyl-N-propyl)amino-5-hydroxytetralin, bromocriptine, ropinirole, LY-163-502, dipropyldopamine, B-HT 920, piribedil, (+)-UH 232, pergolide, (−)-quinpirole, R(−)-2,11-dihydroxy-10-methoxyapomorphine, or a pharmaceutically acceptable salt thereof.

In some embodiments, the second (additional) therapeutic agent is an anti-inflammatory drug. Suitable examples of such drugs include NSAIDs such as celecoxib, rofecoxib, ibuprofen, naproxen, aspirin, diclofenac, sulindac, oxaprozin, piroxicam, indomethacin, meloxicam, fenoprofen, diflunisal, methotrexate, BAY 11-7082, or a pharmaceutically acceptable salt thereof. Suitable examples of steroid anti-inflammatory agents include cortisol, corticosterone, hydrocortisone, aldosterone, deoxycorticosterone, triamcinolone, bardoxolone, bardoxolone methyl, triamcinolone, cortisone, prednisone, and methylprednisolone, or a pharmaceutically acceptable salt thereof.

Kits

The present invention also includes pharmaceutical kits useful, for example, in the treatment of disorders, diseases and conditions referred to herein, which include one or more containers containing a pharmaceutical composition comprising a therapeutically effective amount of a compound of the present disclosure. Such kits can further include, if desired, one or more of various conventional pharmaceutical kit components, such as, for example, containers with one or more pharmaceutically acceptable carriers, additional containers, etc. Instructions, either as inserts or as labels, indicating quantities of the components to be administered, guidelines for administration, and/or guidelines for mixing the components, can also be included in the kit.

Definitions

As used herein, the term "about" means "approximately" (e.g., plus or minus approximately 10% of the indicated value).

As used herein, the term "compound" as used herein is meant to include all stereoisomers, geometric isomers, tautomers, and isotopes of the structures named or depicted. Compounds herein identified by name or structure as one particular tautomeric form are intended to include other tautomeric forms unless otherwise specified.

The terms "pharmaceutical" and "pharmaceutically acceptable" are employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal. In some embodiments, the cell is a mesenchymal cell. In some embodiments, the cell is a fibroblast (e.g., cardiac, dermal or lung fibroblast). In some embodiments, the cell is a hepatic stellate cell.

As used herein, the term "contacting" refers to the bringing together of indicated moieties or items in an in vitro system, an ex vivo system, or an in vivo system. For example, "contacting" a cell with a compound provided herein includes the act of administering that compound to a mammal (e.g., a human) containing that cell as well as, for example, introducing that compound into a cell culture containing that cell.

As used herein, the term "mammal" includes, without limitation, mice, rats, other rodents, rabbits, dogs, cats, swine, cattle, sheep, horses, elephants, deer, non-human primates (e.g., monkeys and apes), house pets, and humans.

As used herein, the phrase "effective amount" or "therapeutically effective amount" refers to the amount of active compound or pharmaceutical agent that elicits the biological or medicinal response in a tissue, system, mammal, or human that is being sought by a researcher, veterinarian, medical doctor, or other clinician.

As used herein the term "treating" or "treatment" refers to 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

As used herein, the term "preventing" or "prevention" of a disease, condition or disorder refers to decreasing the risk of occurrence of the disease, condition or disorder in a subject or group of subjects (e.g., a subject or group of subjects predisposed to or susceptible to the disease, condition or disorder). In some embodiments, preventing a disease, condition or disorder refers to decreasing the possibility of acquiring the disease, condition or disorder and/or its associated symptoms. In some embodiments, preventing a disease, condition or disorder refers to completely or almost completely stopping the disease, condition or disorder from occurring.

As used herein, the term "pharmaceutically acceptable salt" refers to a salt that is formed between an acid and a basic group of the compound, such as an amino functional group, or a base and an acidic group of the compound, such as a carboxyl functional group. In some embodiments, the compound is a pharmaceutically acceptable acid addition salt. In some embodiments, acids commonly employed to form pharmaceutically acceptable salts of the therapeutic compounds described herein include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

In some embodiments, bases commonly employed to form pharmaceutically acceptable salts of the therapeutic compounds described herein include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2—OH—(C1-C6)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

As used herein, the phrase "optionally substituted" means unsubstituted or substituted. The substituents are independently selected, and substitution can be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, without limitation, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, the term "$C_{n-m}$ haloalkyl", employed alone or in combination with other terms, refers to an alkyl group having from one halogen atom to 2s+1 halogen atoms that may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, the term "amino" refers to a group of formula —$NH_2$.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms. Suitable examples of alkylamino groups include N-methylamino, N-ethylamino, N-propylamino (e.g., N-(n-propyl)amino and N-isopropylamino), N-butylamino (e.g., N-(n-butyl)amino and N-(tert-butyl)amino), and the like.

As used herein, the term "di $C_{n-m}$ alkylamino" refers to a group of formula —$N(alkyl)_2$, wherein each alkyl group independently has n to m carbon atoms. In some embodiments, each alkyl group has 1 to 6, 1 to 4, or 1 to 3 carbon atoms. Suitable examples of dialkylamino groups include N,N-methylehtylamino, N,N-diethylamino, N,N-propylethylamino, N,N-butylisopropylamino, and the like.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, the term "HO—$C_{1-3}$ alkyl" refers to a group of formula —($C_{1-3}$ alkylene)-OH. As used herein, the term "$NH_2$—$C_{1-3}$ alkyl" refers to a group of formula —($C_{1-3}$ alkylene)-$NH_2$.

As used herein, "halo" refers to F, Cl, Br, or I. In some embodiments, a halo is F, Cl, or Br.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur, and oxygen. In some embodiments, any ring-forming N in a heteroaryl moiety can be an N-oxide. In some embodiments, the heteroaryl is a 5-10 membered monocyclic or bicyclic heteroaryl having 1, 2, 3, or 4 heteroatom ring members independently selected from nitrogen, sulfur, and oxygen. In some embodiments, the heteroaryl is a 5-6 monocyclic heteroaryl having 1 or 2 heteroatom ring members independently selected from nitrogen, sulfur, and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls include, without limitation, thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls include, without limitation, pyridyl, pyrazinyl, pyrimidinyl, triazinyl, and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, 7-, 8-, 9-, or 10-membered heterocycloalkyl groups. Heterocycloalkyl groups can also include spirocycles. Example heterocycloalkyl groups include, without limitation, pyrrolidin-2-one, 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by 1 or 2 independently selected oxo or sulfido groups (e.g., C(O), S(O), C(S), or S(O)$_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl is a monocyclic 4-6 membered heterocycloalkyl having 1 or 2 heteroatoms independently selected from nitrogen, oxygen, or sulfur and having one or more oxidized ring members. In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more oxidized ring members.

EXAMPLES

Materials and Methods

Cell culture: Cells were all maintained in EMEM (ATCC) containing 10% FBS, unless otherwise noted. IMR-90 embryonic lung fibroblasts and NIH-3T3 mouse fibroblasts were purchased from ATCC. Doxycycline-inducible Tet-On NIH3T3 expressing TAZ4SA or control empty vector were described previously. Normal Human Alveolar Epithelial Cells (NHAEpCs), Normal Human Microvascular Endothelial Cells (NHMVECs), Normal Human Lung Fibroblasts (NHLFs), and Human Dermal Fibroblasts (HDFs) were purchased from Lonza and were cultured in the proprietary media per Lonza's recommendation. Human Adult Cardiac Fibroblasts (HACFs) and Hepatic Stellate Cells (HSCs) were purchased from ScienCell and were cultured in the proprietary media per ScienCell's recommendation. Hepatocytes were purchased from Samsara and were cultured in the proprietary media per Samsara's recommendation. All additional experiments with pulmonary fibroblasts used primary human lung fibroblasts isolated by explant culture from the lungs of subjects diagnosed with IPF who underwent lung transplantation, or donors whose organs were rejected for transplantation (non-IPF), generously provided by Peter Bitterman and Craig Henke at the University of Minnesota under a protocol approved by the University of Minnesota Institutional Review Board. All primary cell culture experiments were performed with cells at passage six or less.

Chemicals and Reagents: Dimethyl sulfoxide (DMSO), Y-27632, endothelin 1 (ET-1), and ascorbic acid were purchased from Sigma-Aldrich. Dihydrexidine (DHX), SKF-81297, fenoldopam, forskolin, and prostaglandin E2 were purchased from Tocris Bioscience. lysophosphatidic acid (LPA), and serotonin (5-HT) were purchased from Cayman Chemical. SCH 39166 was purchased from Santa Cruz Biotechnology. TGFβ1 was purchased from eBioscience.

GPCRome Profiling and qPCR: GPCRome profiling was performed according to the manufacturer's suggestions (Qiagen). Cells were grown in their recommended growth media for 24 hours prior to RNA isolation using RNeasy Plus Mini Kit (Qiagen) according to manufacturer's instructions. Isolated RNA (1000 ng) was then used to synthesize cDNA using the RT$^2$ First Strand Kit (Qiagen) and the G Protein Coupled Receptors 384HT PCR Array was analyzed using a LightCycler 480 (Roche). Data are shown as 1/Ct (FIG. 3), GAPDH for fibroblast and epithelial cell datasets were nearly identical (17.39 and 17.41 respectively). Raw Ct values for all receptors are available (Table 1).

TABLE 1

Receptors marked (*) were identified to exclusively couple to Gα$_s$ (See e.g., Ref. 21)

| Uni Gene | Gen Bank | Symbol | Description | Fibroblast cT | Aveolar Epithelial cT |
|---|---|---|---|---|---|
| Hs.377783 | NM_001118 | ADCYAP1R1 | Adenylate cyclase activating polypeptide 1 (pituitary) receptor type I | 34.98 | 34.41 |
| Hs.77867 | NM_000674 | ADORA1 | Adenosine A1 receptor | 29.7 | 27.95 |
| Hs.197029 | NM_000675 | ADORA2A | Adenosine A2a receptor | 32.49 | 30.97 |

TABLE 1-continued

Receptors marked (*) were identified to exclusively couple to Gα$_s$ (See e.g., Ref. 21)

| Uni Gene | Gen Bank | Symbol | Description | Fibroblast cT | Aveolar Epithelial cT |
|---|---|---|---|---|---|
| Hs.167046 | NM_000676 | ADORA2B | Adenosine A2b receptor | 26.82 | 26.08 |
| Hs.281342 | NM_000677 | ADORA3 | Adenosine A3 receptor | 37.78 | 35.78 |
| Hs.709175 | NM_033303 | ADRA1A | Adrenergic, alpha-1A-, receptor | 34.69 | 33.45 |
| Hs.368632 | NM_000679 | ADRA1B | Adrenergic, alpha-1B-, receptor | 32.9 | 29.79 |
| Hs.557 | NM_000678 | ADRA1D | Adrenergic, alpha-1D-, receptor | 29.16 | 32.89 |
| Hs.249159 | NM_000681 | ADRA2A | Adrenergic, alpha-2A-, receptor | 33.65 | 34.51 |
| Hs.247686 | NM_000682 | ADRA2B | Adrenergic, alpha-2B-, receptor | 36.07 | 40 |
| Hs.123022 | NM_000683 | ADRA2C | Adrenergic, alpha-2C-, receptor | 33.79 | 33.89 |
| Hs.99913 | NM_000684 | ADRB1 | Adrenergic, beta-1-, receptor | 36.08 | 30.93 |
| Hs.591251 | NM_000024 | ADRB2 | Adrenergic, beta-2-, receptor, surface | 24.66 | 22.13 |
| Hs.2549 | NM_000025 | ADRB3 | Adrenergic, beta-3-, receptor | 33.1 | 34.93 |
| Hs.728754 | NM_031850 | AGTR1 | Angiotensin II receptor, type 1 | 26.71 | 31.48 |
| Hs.405348 | NM_000686 | AGTR2 | Angiotensin II receptor, type 2 | 35.14 | 40 |
| Hs.438311 | NM_005161 | APLNR | Apelin receptor | 36.26 | 36.72 |
| Hs.2131 | NM_000706 | AVPR1A | Arginine vasopressin receptor 1A | 33.8 | 32.59 |
| Hs.1372 | NM_000707 | AVPR1B | Arginine vasopressin receptor 1B | 30.85 | 27.69 |
| Hs.567240 | NM_000054 | AVPR2 | Arginine vasopressin receptor 2 (*) | 35.1 | 39 |
| Hs.194654 | NM_001702 | BAI1 | Brain-specific angiogenesis inhibitor 1 | 35.5 | 31.24 |
| Hs.524138 | NM_001703 | BAI2 | Brain-specific angiogenesis inhibitor 2 | 28.05 | 31.49 |
| Hs.13261 | NM_001704 | BAI3 | Brain-specific angiogenesis inhibitor 3 | 34.63 | 35.72 |
| Hs.525572 | NM_000710 | BDKRB1 | Bradykinin receptor B1 | 25.52 | 31.86 |
| Hs.654542 | NM_000623 | BDKRB2 | Bradykinin receptor B2 | 29.25 | 32.77 |
| Hs.121484 | NM_001727 | BRS3 | Bombesin-like receptor 3 | 34.59 | 34.82 |
| Hs.591148 | NM_004054 | C3AR1 | Complement component 3a receptor 1 | 31.75 | 31.58 |
| Hs.2161 | NM_001736 | C5AR1 | Complement component 5a receptor 1 | 30.59 | 30.75 |
| Hs.489127 | NM_001742 | CALCR | CALCITONIN RECEPTOR | 38.19 | 37.02 |
| Hs.470882 | NM_005795 | CALCRL | Calcitonin receptor-like | 31.19 | 28.81 |
| Hs.435615 | NM_000388 | CASR | Calcium-sensing receptor | 31.32 | 31.84 |
| Hs.146346 | NM_001296 | CCBP2 | Chemokine binding protein 2 | 27.74 | 27.65 |
| Hs.129 | NM_000730 | CCKAR | Cholecystokinin A receptor | 32.43 | 36.62 |
| Hs.203 | NM_176875 | CCKBR | Cholecystokinin B receptor | 34.99 | 39.34 |
| Hs.301921 | NM_001295 | CCR1 | Chemokine (C-C motif) receptor 1 | 30.53 | 30.92 |
| Hs.278446 | NM_016602 | CCR10 | Chemokine (C-C motif) receptor 10 | 29.82 | 28.25 |
| Hs.511794 | NM_001123396 | CCR2 | Chemokine (C-C motif) receptor 2 | 34.75 | 33.51 |
| Hs.506190 | NM_001837 | CCR3 | Chemokine (C-C motif) receptor 3 | 33.35 | 36.14 |
| Hs.184926 | NM_005508 | CCR4 | Chemokine (C-C motif) receptor 4 | 32.99 | 34.95 |
| Hs.450802 | NM_000579 | CCR5 | Chemokine (C-C motif) receptor 5 | 32.86 | 32.49 |
| Hs.46468 | NM_004367 | CCR6 | Chemokine (C-C motif) receptor 6 | 33.77 | 30.9 |
| Hs.370036 | NM_001838 | CCR7 | Chemokine (C-C motif) receptor 7 | 30.45 | 32.7 |
| Hs.113222 | NM_005201 | CCR8 | Chemokine (C-C motif) receptor 8 | 36.9 | 40 |
| Hs.225946 | NM_006641 | CCR9 | Chemokine (C-C motif) receptor 9 | 33.71 | 35.12 |
| Hs.729361 | NM_016557 | CCRL1 | Chemokine (C-C motif) receptor-like 1 | 24.68 | 29.02 |
| Hs.535713 | NM_003965 | CCRL2 | Chemokine (C-C motif) receptor-like 2 | 32.82 | 26.46 |
| Hs.466039 | NM_001784 | CD97 | CD97 molecule | 23.15 | 23.23 |
| Hs.252387 | NM_014246 | CELSR1 | Cadherin, EGF LAG seven-pass G-type receptor 1 | 29.57 | 27.06 |
| Hs.57652 | NM_001408 | CELSR2 | Cadherin, EGF LAG seven-pass G-type receptor 2 | 32.54 | 31.57 |
| Hs.631926 | NM_001407 | CELSR3 | Cadherin, EGF LAG seven-pass G-type receptor 3 | 32.97 | 31.12 |
| Hs.632119 | NM_000738 | CHRM1 | Cholinergic receptor, muscarinic 1 | 40 | 35.56 |
| Hs.535891 | NM_000739 | CHRM2 | Cholinergic receptor, muscarinic 2 | 26.19 | 31.13 |
| Hs.7138 | NM_000740 | CHRM3 | Cholinergic receptor, muscarinic 3 | 36.75 | 36.74 |
| Hs.248100 | NM_000741 | CHRM4 | Cholinergic receptor, muscarinic 4 | 30.1 | 29.43 |
| Hs.584747 | NM_012125 | CHRM5 | Cholinergic receptor, muscarinic 5 | 31.48 | 31.18 |
| Hs.197143 | NM_004072 | CMKLR1 | CHEMOKINE-LIKE RECEPTOR 1 | 34.55 | 34.77 |
| Hs.75110 | NM_016083 | CNR1 | Cannabinoid receptor 1 (brain) | 36.13 | 33.43 |
| Hs.73037 | NM_001841 | CNR2 | Cannabinoid receptor 2 (macrophage) | 27.88 | 26.15 |
| Hs.300684 | NM_014478 | CRCP | CGRP receptor component | 24.2 | 23.45 |
| Hs.417628 | NM_004382 | CRHR1 | Corticotropin releasing hormone receptor 1 | 33 | 32.61 |
| Hs.729970 | NM_001883 | CRHR2 | Corticotropin releasing hormone receptor 2 | 35.59 | 35.16 |
| Hs.78913 | NM_001337 | CX3CR1 | Chemokine (C-X3-C motif) receptor 1 | 35.81 | 36.67 |
| Hs.194778 | NM_000634 | CXCR1 | Chemokine (C-X-C motif) receptor 1 | 38.63 | 34.23 |
| Hs.846 | NM_001557 | CXCR2 | Chemokine (C-X-C motif) receptor 2 | 26.1 | 25.7 |
| Hs.198252 | NM_001504 | CXCR3 | Chemokine (C-X-C motif) receptor 3 | 31.54 | 30.31 |
| Hs.593413 | NM_003467 | CXCR4 | Chemokine (C-X-C motif) receptor 4 | 33.79 | 27.46 |
| Hs.113916 | NM_001716 | CXCR5 | Chemokine (C-X-C motif) receptor 5 | 34.73 | 31.79 |
| Hs.34526 | NM_006564 | CXCR6 | Chemokine (C-X-C motif) receptor 6 | 29.43 | 28.22 |
| Hs.471751 | NM_020311 | CXCR7 | Chemokine (C-X-C motif) receptor 7 | 29.5 | 29.02 |
| Hs.201300 | NM_006639 | CYSLTR1 | Cysteinyl leukotriene receptor 1 | 34.63 | 35.83 |
| Hs.253706 | NM_020377 | CYSLTR2 | Cysteinyl leukotriene receptor 2 | 36.85 | 35.32 |
| Hs.153381 | NM_002036 | DARC | Duffy blood group, chemokine receptor | 40 | 37.48 |
| Hs.2624 | NM_000794 | DRD1 | Dopamine receptor D1 (*) | 26.47 | 40 |
| Hs.73893 | NM_000795 | DRD2 | Dopamine receptor D2 | 32.97 | 30.29 |

TABLE 1-continued

Receptors marked (*) were identified to exclusively couple to Gα$_s$ (See e.g., Ref. 21)

| Uni Gene | Gen Bank | Symbol | Description | Fibroblast cT | Aveolar Epithelial cT |
|---|---|---|---|---|---|
| Hs.121478 | NM_000796 | DRD3 | Dopamine receptor D3 | 32.27 | 33.02 |
| Hs.99922 | NM_000797 | DRD4 | Dopamine receptor D4 | 33.5 | 33.22 |
| Hs.380681 | NM_000798 | DRD5 | Dopamine receptor D5 (*) | 35.72 | 35 |
| Hs.183713 | NM_001957 | EDNRA | Endothelin receptor type A | 24.05 | 28.15 |
| Hs.82002 | NM_000115 | EDNRB | Endothelin receptor type B | 27.72 | 27.09 |
| Hs.132314 | NM_022159 | ELID1 | EGF, latrophilin and seven transmembrane domain containing 1 | 25.5 | 27.01 |
| Hs.2375 | NM_001974 | EMR1 | Egf-like module containing, mucin-like, hormone receptor-like 1 | 31.03 | 32.47 |
| Hs.482562 | NM_001992 | F2R | Coagulation factor II (thrombin) receptor | 20.46 | 23.5 |
| Hs.154299 | NM_005242 | F2RL1 | Coagulation factor II (thrombin) receptor-like 1 | 23.32 | 20.47 |
| Hs.42502 | NM_004101 | F2RL2 | Coagulation factor II (thrombin) receptor-like 2 | 23.34 | 29.22 |
| Hs.137574 | NM_003950 | F2RL3 | Coagulation factor II (thrombin) receptor-like 3 | 32.52 | 30.04 |
| Hs.248127 | NM_005303 | FFAR1 | Free fatty acid receptor 1 | 34.82 | 33.99 |
| Hs.248056 | NM_005306 | FFAR2 | Free fatty acid receptor 2 | 40 | 36.9 |
| Hs.248055 | NM_005304 | FFAR3 | Free fatty acid receptor 3 | 35.52 | 35.47 |
| Hs.753 | NM_002029 | FPR1 | Formyl peptide receptor 1 | 35.8 | 40 |
| Hs.99855 | NM_001462 | FPR2 | Formyl peptide receptor 2 | 33.2 | 34.11 |
| Hs.445466 | NM_002030 | FPR3 | Formyl peptide receptor 3 | 33.45 | 33.8 |
| Hs.1428 | NM_181446 | FSHR | Follicle stimulating hormone receptor | 35.87 | 35.7 |
| Hs.94234 | NM_003505 | FZD1 | Frizzled family receptor 1 | 23.26 | 25.3 |
| Hs.31664 | NM_007197 | FZD10 | Frizzled family receptor 10 | 37.64 | 31.86 |
| Hs.142912 | NM_001466 | FZD2 | Frizzled family receptor 2 | 26.96 | 25.31 |
| Hs.40735 | NM_017412 | FZD3 | Frizzled family receptor 3 (*) | 29.18 | 25.21 |
| Hs.19545 | NM_012193 | FZD4 | Frizzled family receptor 4 | 25.59 | 27.44 |
| Hs.17631 | NM_003468 | FZD5 | Frizzled family receptor 5 | 29.48 | 25.43 |
| Hs.591863 | NM_003506 | FZD6 | Frizzled family receptor 6 | 23.58 | 22.69 |
| Hs.173859 | NM_003507 | FZD7 | Frizzled family receptor 7 | 25.43 | 28.28 |
| Hs.302634 | NM_031866 | FZD8 | Frizzled family receptor 8 | 28.64 | 27.28 |
| Hs.647029 | NM_003508 | FZD9 | Frizzled family receptor 9 | 33.01 | 33.15 |
| Hs.167017 | NM_001470 | GABBR1 | Gamma-aminobutyric acid (GABA) B receptor, 1 | 29.81 | 30.5 |
| Hs.198612 | NM_005458 | GABBR2 | Gamma-aminobutyric acid (GABA) B receptor, 2 | 23.5 | 29.12 |
| Hs.272191 | NM_001480 | GALR1 | Galanin receptor 1 | 37.82 | 35.83 |
| Hs.666366 | NM_003857 | GALR2 | GALANIN RECEPTOR 2 | 34.97 | 33.03 |
| Hs.158353 | NM_003614 | GALR3 | Galanin receptor 3 | 35.06 | 40 |
| Hs.208 | NM_000160 | GCGR | Glucagon receptor (*) | 40 | 33.78 |
| Hs.767 | NM_000823 | GHRHR | Growth hormone releasing hormone receptor (*) | 32.27 | 32.5 |
| Hs.248115 | NM_004122 | GHSR | Growth hormone secretagogue receptor | 35.58 | 33.62 |
| Hs.658534 | NM_000164 | GIPR | Gastric inhibitory polypeptide receptor (*) | 31.28 | 29.57 |
| Hs.389103 | NM_002062 | GLP1R | Glucagon-like peptide 1 receptor | 40 | 37.36 |
| Hs.248202 | NM_004246 | GLP2R | Glucagon-like peptide 2 receptor | 35.47 | 37.79 |
| Hs.407587 | NM_000406 | GNRHR | Gonadotropin-releasing hormone receptor | 33.11 | 32.34 |
| Hs.160954 | NM_170699 | GPBAR1 | G protein-coupled bile acid receptor 1 (*) | 32.49 | 31.71 |
| Hs.20961 | NM_001505 | GPER | G protein-coupled estrogen receptor 1 | 28.52 | 28.89 |
| Hs.184907 | NM_005279 | GPR1 | G protein-coupled receptor 1 | 26.65 | 26.31 |
| Hs.350569 | NM_054021 | GPR101 | G protein-coupled receptor 101 (*) | 34.32 | 35.07 |
| Hs.256897 | NM_153840 | GPR110 | G protein-coupled receptor 110 | 33.06 | 26.43 |
| Hs.715357 | NM_153839 | GPR111 | G protein-coupled receptor 111 | 33.75 | 29.59 |
| Hs.381354 | NM_153834 | GPR112 | G protein-coupled receptor 112 | 40 | 40 |
| Hs.631878 | NM_153835 | GPR113 | G protein-coupled receptor 113 | 34.24 | 31.19 |
| Hs.187884 | NM_153837 | GPR114 | G protein-coupled receptor 114 | 31.86 | 30.84 |
| Hs.710050 | NM_153838 | GPR115 | G protein-coupled receptor 115 | 40 | 23.51 |
| Hs.362806 | NM_015234 | GPR116 | G protein-coupled receptor 116 | 27.99 | 21.72 |
| Hs.496762 | NM_178471 | GPR119 | G protein-coupled receptor 119 (*) | 35.63 | 35.98 |
| Hs.123034 | NM_005288 | GPR12 | G protein-coupled receptor 12 | 33.54 | 34.47 |
| Hs.435183 | NM_001083909 | GPR123 | G protein-coupled receptor 123 | 34.4 | 36.7 |
| Hs.708086 | NM_032777 | GPR124 | G protein-coupled receptor 124 | 27.98 | 34.7 |
| Hs.99195 | NM_145290 | GPR125 | G protein-coupled receptor 125 | 24.46 | 24.44 |
| Hs.715560 | NM_020455 | GPR126 | G protein-coupled receptor 126 | 22.45 | 20.94 |
| Hs.334511 | NM_032787 | GPR128 | G protein-coupled receptor 128 | 36.17 | 35.28 |
| Hs.532504 | NM_013345 | GPR132 | G protein-coupled receptor 132 | 28.86 | 27.48 |
| Hs.656751 | NM_198827 | GPR133 | G protein-coupled receptor 133 | 27.94 | 29.87 |
| Hs.647573 | NM_022571 | GPR135 | G protein-coupled receptor 135 | 28.69 | 30.03 |
| Hs.446875 | NM_001002911 | GPR139 | G protein-coupled receptor 139 | 30.45 | 29.85 |
| Hs.688230 | NM_181791 | GPR141 | G protein-coupled receptor 141 | 37.06 | 39.01 |
| Hs.574368 | NM_181790 | GPR142 | G protein-coupled receptor 142 | 35.8 | 34.46 |
| Hs.74124 | NM_000273 | GPR143 | G protein-coupled receptor 143 | 34.13 | 27.12 |
| Hs.454099 | NM_001161808 | GPR144 | G protein-coupled receptor 144 | 33.57 | 34.42 |

TABLE 1-continued

Receptors marked (*) were identified to exclusively couple to Gα$_s$ (See e.g., Ref. 21)

| Uni Gene | Gen Bank | Symbol | Description | Fibroblast cT | Aveolar Epithelial cT |
|---|---|---|---|---|---|
| Hs.729332 | NM_138445 | GPR146 | G protein-coupled receptor 146 | 31.74 | 30.75 |
| Hs.452574 | NM_207364 | GPR148 | G protein-coupled receptor 148 | 35.2 | 35.27 |
| Hs.688231 | NM_001038705 | GPR149 | G protein-coupled receptor 149 | 31.07 | 30.7 |
| Hs.563128 | NM_005290 | GPR15 | G protein-coupled receptor 15 | 36.47 | 34.66 |
| Hs.143315 | NM_199243 | GPR150 | G protein-coupled receptor 150 | 32.57 | 33.87 |
| Hs.483732 | NM_194251 | GPR151 | G protein-coupled receptor 151 | 33.16 | 32 |
| Hs.567997 | NM_206997 | GPR152 | G protein-coupled receptor 152 | 30.54 | 30.27 |
| Hs.531581 | NM_207370 | GPR153 | G protein-coupled receptor 153 | 27.19 | 27.2 |
| Hs.333358 | NM_153002 | GPR156 | G protein-coupled receptor 156 | 32.07 | 31.58 |
| Hs.632367 | NM_024980 | GPR157 | G protein-coupled receptor 157 | 27.57 | 25.28 |
| Hs.499108 | NM_020752 | GPR158 | G protein-coupled receptor 158 | 33.68 | 31.79 |
| Hs.231320 | NM_014373 | GPR160 | G protein-coupled receptor 160 | 29.28 | 24 |
| Hs.271809 | NM_153832 | GPR161 | G protein-coupled receptor 161 | 25.87 | 24.7 |
| Hs.631654 | NM_014449 | GPR162 | G protein-coupled receptor 162 | 26.71 | 28.97 |
| Hs.46453 | NM_005291 | GPR17 | G protein-coupled receptor 17 | 31.26 | 30.45 |
| Hs.549152 | NM_013308 | GPR171 | G protein-coupled receptor 171 | 33.11 | 32.54 |
| Hs.661815 | NM_018969 | GPR173 | G protein-coupled receptor 173 | 28.15 | 30.92 |
| Hs.326713 | NM_032553 | GPR174 | G protein-coupled receptor 174 | 38.4 | 38.98 |
| Hs.37196 | NM_007223 | GPR176 | G protein-coupled receptor 176 | 21.97 | 23.55 |
| Hs.462915 | NM_001004334 | GPR179 | G protein-coupled receptor 179 | 33.88 | 32.21 |
| Hs.631765 | NM_005292 | GPR18 | G protein-coupled receptor 18 | 29.78 | 29.19 |
| Hs.483909 | NM_007264 | GPR182 | G protein-coupled receptor 182 | 32.29 | 31.2 |
| Hs.784 | NM_004951 | GPR183 | G protein-coupled receptor 183 | 27.5 | 27.52 |
| Hs.657862 | NM_006143 | GPR19 | G protein-coupled receptor 19 | 31.65 | 32.27 |
| Hs.188859 | NM_005293 | GPR20 | G protein-coupled receptor 20 | 34.57 | 34.59 |
| Hs.728941 | NM_005294 | GPR21 | G protein-coupled receptor 21 | 31.02 | 29.77 |
| Hs.657277 | NM_005295 | GPR22 | G protein-coupled receptor 22 | 31.47 | 29.99 |
| Hs.534316 | NM_005298 | GPR25 | G protein-coupled receptor 25 | 37.46 | 38.18 |
| Hs.12751 | NM_153442 | GPR26 | G protein-coupled receptor 26 (*) | 34.83 | 34.88 |
| Hs.591653 | NM_018971 | GPR27 | G protein-coupled receptor 27 | 28.07 | 29.67 |
| Hs.66542 | NM_005281 | GPR3 | G protein-coupled receptor 3 (*) | 26.17 | 26.56 |
| Hs.248124 | NM_005299 | GPR31 | G protein-coupled receptor 31 | 31 | 30.4 |
| Hs.515555 | NM_001506 | GPR32 | G protein-coupled receptor 32 | 36.07 | 33.68 |
| Hs.495989 | NM_005300 | GPR34 | G protein-coupled receptor 34 | 31.49 | 30.5 |
| Hs.239891 | NM_005301 | GPR35 | G protein-coupled receptor 35 | 34.2 | 33.59 |
| Hs.406094 | NM_005302 | GPR37 | G protein-coupled receptor 37 | 24.85 | 26.61 |
| Hs.132049 | NM_004767 | GPR37L1 | G protein-coupled receptor 37 like 1 | 32.8 | 30.17 |
| Hs.432395 | NM_001508 | GPR39 | G protein-coupled receptor 39 | 28.53 | 25.46 |
| Hs.17170 | NM_005282 | GPR4 | G protein-coupled receptor 4 | 29.13 | 28.77 |
| Hs.299567 | NM_004778 | PTGDR2 | Prostaglandin D2 receptor 2 | 37.67 | 37.96 |
| Hs.590903 | NM_007227 | GPR45 | G protein-coupled receptor 45 | 33.14 | 35.04 |
| Hs.567390 | NM_004224 | GPR50 | G protein-coupled receptor 50 | 34.9 | 34.67 |
| Hs.673850 | NM_005684 | GPR52 | G protein-coupled receptor 52 | 31.7 | 31.63 |
| Hs.114545 | NM_005683 | GPR55 | G protein-coupled receptor 55 | 33.55 | 33.22 |
| Hs.513633 | NM_005682 | GPR56 | G protein-coupled receptor 56 | 26.56 | 24.79 |
| Hs.46332 | NM_005284 | GPR6 | G protein-coupled receptor 6 | 36.18 | 37.9 |
| Hs.709782 | NM_031936 | GPR61 | G protein-coupled receptor 61 (*) | 37.71 | 35.49 |
| Hs.232213 | NM_080865 | GPR62 | G protein-coupled receptor 62 | 35.19 | 35.44 |
| Hs.632612 | NM_030784 | GPR63 | G protein-coupled receptor 63 | 28.62 | 28.31 |
| Hs.146978 | NM_005756 | GPR64 | G protein-coupled receptor 64 | 30.16 | 29.06 |
| Hs.513440 | NM_003608 | GPR65 | G protein-coupled receptor 65 (*) | 32.03 | 32.56 |
| Hs.8882 | NM_003485 | GPR68 | G protein-coupled receptor 68 | 25.81 | 30.14 |
| Hs.696596 | NM_006794 | GPR75 | G protein-coupled receptor 75 | 25.52 | 26.2 |
| Hs.534412 | NM_018485 | GPR77 | G protein-coupled receptor 77 | 36.11 | 34.31 |
| Hs.350588 | NM_080819 | GPR78 | G protein-coupled receptor 78 (*) | 32.78 | 32.56 |
| Hs.664795 | NM_080817 | GPR82 | G protein-coupled receptor 82 | 31.72 | 30.15 |
| Hs.272385 | NM_016540 | GPR83 | G protein-coupled receptor 83 | 30.91 | 30.45 |
| Hs.306199 | NM_020370 | GPR84 | G protein-coupled receptor 84 | 35.03 | 33.96 |
| Hs.152009 | NM_018970 | GPR85 | G protein-coupled receptor 85 | 27.77 | 31.55 |
| Hs.591292 | NM_023915 | GPR87 | G protein-coupled receptor 87 | 32.93 | 25.64 |
| Hs.170053 | NM_022049 | GPR88 | G protein-coupled receptor 88 | 30.94 | 30.86 |
| Hs.383403 | NM_170776 | GPR97 | G protein-coupled receptor 97 | 32.72 | 32 |
| Hs.591777 | NM_032119 | GPR98 | G protein-coupled receptor 98 | 35.7 | 28.62 |
| Hs.631733 | NM_003979 | GPRC5A | G protein-coupled receptor, family C, group 5, member A | 23.58 | 17.06 |
| Hs.148685 | NM_016235 | GPRC5B | G protein-coupled receptor, family C, group 5, member B | 29.27 | 22.56 |
| Hs.446438 | NM_018653 | GPRC5C | G protein-coupled receptor, family C, group 5, member C | 33.92 | 25.51 |
| Hs.644599 | NM_018654 | GPRC5D | G protein-coupled receptor, family C, group 5, member D | 29.49 | 25.92 |
| Hs.266745 | NM_148963 | GPRC6A | G protein-coupled receptor, family C, group 6, member A | 34.22 | 39.42 |
| Hs.128848 | NM_000831 | GRIK3 | Glutamate receptor, ionotropic, kainate 3 | 40 | 40 |

TABLE 1-continued

Receptors marked (*) were identified to exclusively couple to Gα$_s$ (See e.g., Ref. 21)

| Uni Gene | Gen Bank | Symbol | Description | Fibro-blast cT | Aveolar Epithelial cT |
|---|---|---|---|---|---|
| Hs.32945 | NM_000838 | GRM1 | Glutamate receptor, metabotropic 1 | 36.87 | 34.53 |
| Hs.121510 | NM_000839 | GRM2 | Glutamate receptor, metabotropic 2 | 32.26 | 32.67 |
| Hs.590575 | NM_000840 | GRM3 | Glutamate receptor, metabotropic 3 | 36.87 | 32.92 |
| Hs.654847 | NM_000841 | GRM4 | Glutamate receptor, metabotropic 4 | 33.12 | 32.9 |
| Hs.147361 | NM_000842 | GRM5 | Glutamate receptor, metabotropic 5 | 31.84 | 30.8 |
| Hs.248131 | NM_000843 | GRM6 | Glutamate receptor, metabotropic 6 | 35.33 | 33.24 |
| Hs.606393 | NM_000844 | GRM7 | Glutamate receptor, metabotropic 7 | 33.68 | 32.69 |
| Hs.449625 | NM_000845 | GRM8 | Glutamate receptor, metabotropic 8 | 34.05 | 40 |
| Hs.567282 | NM_005314 | GRPR | Gastrin-releasing peptide receptor | 28.1 | 30.68 |
| Hs.610873 | NM_032554 | HCAR1 | Hydroxycarboxylic acid receptor 1 | 31.72 | 30.02 |
| Hs.524812 | NM_177551 | HCAR2 | Hydroxycarboxylic acid receptor 2 | 33.92 | 32.17 |
| Hs.388226 | NM_001525 | HCRTR1 | Hypocretin (orexin) receptor 1 | 33.89 | 33.48 |
| Hs.151624 | NM_001526 | HCRTR2 | Hypocretin (orexin) receptor 2 | 37.99 | 35.2 |
| Hs.1570 | NM_000861 | HRH1 | Histamine receptor H1 | 25.73 | 28.32 |
| Hs.247885 | NM_022304 | HRH2 | Histamine receptor H2 | 32.13 | 31.68 |
| Hs.251399 | NM_007232 | HRH3 | Histamine receptor H3 | 31.47 | 31.07 |
| Hs.287388 | NM_021624 | HRH4 | Histamine receptor H4 | 33.14 | 31.81 |
| Hs.247940 | NM_000524 | HTR1A | 5-hydroxytryptamine (serotonin) receptor 1A | 35.62 | 40 |
| Hs.123016 | NM_000863 | HTR1B | 5-hydroxytryptamine (serotonin) receptor 1B | 29.48 | 28.24 |
| Hs.121482 | NM_000864 | HTR1D | 5-hydroxytryptamine (serotonin) receptor 1D | 33.86 | 30.01 |
| Hs.1611 | NM_000865 | HTR1E | 5-hydroxytryptamine (serotonin) receptor 1E | 40 | 37.33 |
| Hs.248136 | NM_000866 | HTR1F | 5-hydroxytryptamine (serotonin) receptor 1F | 33.26 | 35.72 |
| Hs.654586 | NM_000621 | HTR2A | 5-hydroxytryptamine (serotonin) receptor 2A | 32.74 | 33.32 |
| Hs.421649 | NM_000867 | HTR2B | 5-hydroxytryptamine (serotonin) receptor 2B | 29.09 | 28.81 |
| Hs.149037 | NM_000868 | HTR2C | 5-hydroxytryptamine (serotonin) receptor 2C | 36.23 | 40 |
| Hs.413899 | NM_000869 | HTR3A | 5-hydroxytryptamine (serotonin) receptor 3A | 33.43 | 31.46 |
| Hs.241377 | NM_006028 | HTR3B | 5-hydroxytryptamine (serotonin) receptor 3B | 33.91 | 33.52 |
| Hs.483773 | NM_000870 | HTR4 | 5-hydroxytryptamine (serotonin) receptor 4 | 34.83 | 34.95 |
| Hs.65791 | NM_024012 | HTR5A | 5-hydroxytryptamine (serotonin) receptor 5A | 35.84 | 34.13 |
| Hs.22180 | NM_000871 | HTR6 | 5-hydroxytryptamine (serotonin) receptor 6 | 35.5 | 36.22 |
| Hs.73739 | NM_000872 | HTR7 | 5-hydroxytryptamine (serotonin) receptor 7 (adenylate cyclase-coupled) (*) | 27.89 | 30.19 |
| Hs.208229 | NM_032551 | KISS1R | KISS1 receptor | 34.04 | 32.88 |
| Hs.705413 | NM_002303 | LEPR | Leptin receptor | 26.57 | 24.8 |
| Hs.502176 | NM_018490 | LGR4 | Leucine-rich repeat containing G protein-coupled receptor 4 | 24.47 | 28.09 |
| Hs.658889 | NM_003667 | LGR5 | Leucine-rich repeat containing G protein-coupled receptor 5 | 33.8 | 33.2 |
| Hs.468490 | NM_000233 | LHCGR | Luteinizing hormone/choriogonadotropin receptor | 35.45 | 34.77 |
| Hs.126667 | NM_057159 | LPAR1 | Lysophosphatidic acid receptor 1 | 22.02 | 23.12 |
| Hs.122575 | NM_004720 | LPAR2 | Lysophosphatidic acid receptor 2 | 29.18 | 25.33 |
| Hs.674915 | NM_012152 | LPAR3 | Lysophosphatidic acid receptor 3 | 27.34 | 29.24 |
| Hs.522701 | NM_005296 | LPAR4 | Lysophosphatidic acid receptor 4 | 31.29 | 35.52 |
| Hs.155538 | NM_020400 | LPAR5 | Lysophosphatidic acid receptor 5 | 33.23 | 31.2 |
| Hs.123464 | NM_005767 | LPAR6 | Lysophosphatidic acid receptor 6 | 28.73 | 26.09 |
| Hs.654658 | NM_014921 | LPHN1 | Latrophilin 1 | 33.57 | 29.74 |
| Hs.24212 | NM_012302 | LPHN2 | Latrophilin 2 | 23.44 | 22.42 |
| Hs.28391 | NM_015236 | LPHN3 | Latrophilin 3 | 34.52 | 28.43 |
| Hs.655431 | NM_181657 | LTB4R | Leukotriene B4 receptor | 32.26 | 31.3 |
| Hs.130685 | NM_019839 | LTB4R2 | Leukotriene B4 receptor 2 | 31.26 | 29.47 |
| Hs.99900 | NM_002377 | MAS1 | MAS1 oncogene | 36 | 38.64 |
| Hs.513829 | NM_002386 | MC1R | Melanocortin 1 receptor (alpha melanocyte stimulating hormone receptor) (*) | 30.35 | 29.34 |
| Hs.248144 | NM_000529 | MC2R | Melanocortin 2 receptor (adrenocorticotropic hormone) (*) | 40 | 40 |
| Hs.248018 | NM_019888 | MC3R | Melanocortin 3 receptor (*) | 30.98 | 34.42 |
| Hs.532833 | NM_005912 | MC4R | Melanocortin 4 receptor (*) | 35.44 | 34.64 |
| Hs.248145 | NM_005913 | MC5R | Melanocortin 5 receptor (*) | 31.57 | 31.76 |
| Hs.248122 | NM_005297 | MCHR1 | Melanin-concentrating hormone receptor 1 | 34 | 32.94 |

TABLE 1-continued

Receptors marked (*) were identified to exclusively couple to Gα$_s$ (See e.g., Ref. 21)

| Uni Gene | Gen Bank | Symbol | Description | Fibroblast cT | Aveolar Epithelial cT |
|---|---|---|---|---|---|
| Hs.591342 | NM_032503 | MCHR2 | Melanin-concentrating hormone receptor 2 | 37.38 | 36.01 |
| Hs.527802 | NM_198923 | MRGPRD | MAS-related GPR, member D | 31.31 | 30.07 |
| Hs.706565 | NM_001039165 | MRGPRE | MAS-related GPR, member E | 31.61 | 31.18 |
| Hs.118513 | NM_145015 | MRGPRF | MAS-related GPR, member F | 25.45 | 31.62 |
| Hs.730306 | NM_001164377 | MRGPRG | MAS-related GPR, member G | 27.3 | 27.83 |
| Hs.711459 | NM_147199 | MRGPRX1 | MAS-related GPR, member X1 | 37.05 | 38.5 |
| Hs.350566 | NM_054030 | MRGPRX2 | MAS-related GPR, member X2 | 25.94 | 30.83 |
| Hs.380177 | NM_054031 | MRGPRX3 | MAS-related GPR, member X3 | 34.05 | 40 |
| Hs.632138 | NM_054032 | MRGPRX4 | MAS-related GPR, member X4 | 35.65 | 35.67 |
| Hs.243467 | NM_005958 | MTNR1A | Melatonin receptor 1A | 34.82 | 33.03 |
| Hs.569039 | NM_005959 | MTNR1B | Melatonin receptor 1B | 30.7 | 30.61 |
| Hs.654478 | NM_002511 | NMBR | Neuromedin B receptor | 32.99 | 34.44 |
| Hs.471619 | NM_006056 | NMUR1 | Neuromedin U receptor 1 | 33.93 | 32.54 |
| Hs.283093 | NM_020167 | NMUR2 | Neuromedin U receptor 2 | 34.63 | 34.07 |
| Hs.248117 | NM_005285 | NPBWR1 | Neuropeptides B/W receptor 1 | 36.11 | 34.44 |
| Hs.248118 | NM_005286 | NPBWR2 | Neuropeptides B/W receptor 2 | 37.46 | 36.74 |
| Hs.302026 | NM_022146 | NPFFR1 | Neuropeptide FF receptor 1 | 34.41 | 34.73 |
| Hs.99231 | NM_053036 | NPFFR2 | Neuropeptide FF receptor 2 | 40 | 29.59 |
| Hs.490330 | NM_000906 | NPR1 | Natriuretic peptide receptor A | 28.76 | 28.04 |
| Hs.78518 | NM_003995 | NPR2 | Natriuretic peptide receptor B | 25.45 | 25.75 |
| Hs.237028 | NM_000908 | NPR3 | Natriuretic peptide receptor B | 26.24 | 27.09 |
| Hs.652373 | NM_207172 | NPSR1 | Neuropeptide S receptor 1 | 34.05 | 34.78 |
| Hs.519057 | NM_000909 | NPY1R | Neuropeptide Y receptor Y1 | 32.34 | 30.81 |
| Hs.37125 | NM_000910 | NPY2R | Neuropeptide Y receptor Y2 | 30.61 | 29.84 |
| Hs.598503 | NM_006174 | NPY5R | Neuropeptide Y receptor Y5 | 38.24 | 35.21 |
| Hs.590869 | NM_002531 | NTSR1 | Neurotensin receptor 1 (high affinity) | 27.66 | 32.7 |
| Hs.131138 | NM_012344 | NTSR2 | Neurotensin receptor 2 | 34.14 | 33.3 |
| Hs.677835 | NM_181745 | O3FAR1 | Omega-3 fatty acid receptor 1 | 35.31 | 32.92 |
| Hs.67896 | NM_007346 | OGFR | Opioid growth factor receptor | 26.18 | 25.76 |
| Hs.656404 | NM_001708 | OPN1SW | Opsin 1 (cone pigments), short-wave-sensitive | 24.49 | 24.73 |
| Hs.534399 | NM_014322 | OPN3 | Opsin 3 | 26.3 | 24.9 |
| Hs.283922 | NM_033282 | OPN4 | Opsin 4 | 33.61 | 33.56 |
| Hs.213717 | NM_181744 | OPN5 | Opsin 5 | 40 | 32.7 |
| Hs.372 | NM_000911 | OPRD1 | Opioid receptor, delta 1 | 30.86 | 29.97 |
| Hs.106795 | NM_000912 | OPRK1 | Opioid receptor, kappa 1 | 34.64 | 34.46 |
| Hs.2859 | NM_000913 | OPRL1 | Opiate receptor-like 1 | 33.94 | 31.44 |
| Hs.2353 | NM_000914 | OPRM1 | Opioid receptor, mu 1 | 35.48 | 37.77 |
| Hs.352218 | NM_080818 | OXGR1 | Oxoglutarate (alpha-ketoglutarate) receptor 1 | 40 | 37.8 |
| Hs.2820 | NM_000916 | OXTR | Oxytocin receptor | 25.26 | 25.31 |
| Hs.654526 | NM_002563 | P2RY1 | Purinergic receptor P2Y, G-protein coupled, 1 | 29.28 | 29.49 |
| Hs.296433 | NM_198333 | P2RY10 | Purinergic receptor P2Y, G-protein coupled, 10 | 40 | 40 |
| Hs.166168 | NM_002566 | P2RY11 | Purinergic receptor P2Y, G-protein coupled, 11 | 31.61 | 31.58 |
| Hs.591281 | NM_022788 | P2RY12 | Purinergic receptor P2Y, G-protein coupled, 12 | 32.42 | 32.59 |
| Hs.546396 | NM_176894 | P2RY13 | Purinergic receptor P2Y, G-protein coupled, 13 | 33.65 | 33.98 |
| Hs.2465 | NM_014879 | P2RY14 | Purinergic receptor P2Y, G-protein coupled, 14 | 34.63 | 34.32 |
| Hs.339 | NM_002564 | P2RY2 | Purinergic receptor P2Y, G-protein coupled, 2 | 35.47 | 27.48 |
| Hs.673854 | NM_002565 | P2RY4 | Pyrimidinergic receptor P2Y, G-protein coupled, 4 | 34.14 | 32.57 |
| Hs.16362 | NM_004154 | P2RY6 | Pyrimidinergic receptor P2Y, G-protein coupled, 6 | 34.56 | 31.31 |
| Hs.111377 | NM_178129 | P2RY8 | Purinergic receptor P2Y, G-protein coupled, 8 | 36.9 | 40 |
| Hs.509067 | NM_002609 | PDGFRB | Platelet-derived growth factor receptor, beta polypeptide | 27.58 | 32.28 |
| Hs.458573 | NM_006207 | PDGFRL | Platelet-derived growth factor receptor-like | 26.52 | 27.21 |
| Hs.524719 | NM_005972 | PPYR1 | Pancreatic polypeptide receptor 1 | 29 | 28.22 |
| Hs.248119 | NM_004248 | PRLHR | Prolactin releasing hormone receptor | 32.86 | 32.31 |
| Hs.683206 | NM_138964 | PROKR1 | Prokineticin receptor 1 | 40 | 35.42 |
| Hs.375029 | NM_144773 | PROKR2 | Prokineticin receptor 2 | 35.49 | 34.73 |
| Hs.709174 | NM_000952 | PTAFR | Platelet-activating factor receptor | 31.98 | 29.55 |
| Hs.306831 | NM_000953 | PTGDR | Prostaglandin D2 receptor (DP) (*) | 25.3 | 24.34 |
| Hs.159360 | NM_000955 | PTGER1 | Prostaglandin E receptor 1 (subtype EP1), 42 kDa | 32.17 | 29.07 |

TABLE 1-continued

Receptors marked (*) were identified to exclusively couple to $G\alpha_s$ (See e.g., Ref. 21)

| Uni Gene | Gen Bank | Symbol | Description | Fibroblast cT | Aveolar Epithelial cT |
|---|---|---|---|---|---|
| Hs.2090 | NM_000956 | PTGER2 | Prostaglandin E receptor 2 (subtype EP2), 53 kDa (*) | 25.8 | 25.86 |
| Hs.445000 | NM_198715 | PTGER3 | Prostaglandin E receptor 3 (subtype EP3) | 26.95 | 29.88 |
| Hs.199248 | NM_000958 | PTGER4 | Prostaglandin E receptor 4 (subtype EP4) | 26.62 | 25.16 |
| Hs.654365 | NM_000959 | PTGFR | Prostaglandin F receptor (FP) | 27.13 | 33.28 |
| Hs.458324 | NM_000960 | PTGIR | Prostaglandin I2 (prostacyclin) receptor (IP) | 28.32 | 30.43 |
| Hs.1019 | NM_000316 | PTH1R | Parathyroid hormone 1 receptor | 33.51 | 32.47 |
| Hs.570296 | NM_005048 | PTH2R | Parathyroid hormone 2 receptor | 36.11 | 36.96 |
| Hs.368977 | NM_198179 | QRFPR | Pyroglutamylated RFamide peptide receptor | 34.89 | 40 |
| Hs.1544 | NM_002921 | RGR | Retinal G protein coupled receptor | 33.43 | 33.89 |
| Hs.247565 | NM_000539 | RHO | Rhodopsin | 31.99 | 32.3 |
| Hs.658310 | NM_006583 | RRH | Retinal pigment epithelium-derived rhodopsin homolog | 33.04 | 32.26 |
| Hs.591686 | NM_021634 | RXFP1 | Relaxin/insulin-like family peptide receptor 1 | 33.24 | 36.53 |
| Hs.680763 | NM_130806 | RXFP2 | Relaxin/insulin-like family peptide receptor 2 | 33.27 | 32.82 |
| Hs.170146 | NM_016568 | RXFP3 | Relaxin/insulin-like family peptide receptor 3 | 33.21 | 33.03 |
| Hs.449914 | NM_181885 | RXFP4 | Relaxin/insulin-like family peptide receptor 4 | 34 | 32.75 |
| Hs.154210 | NM_001400 | S1PR1 | Sphingosine-1-phosphate receptor 1 | 26.42 | 28.45 |
| Hs.655405 | NM_004230 | S1PR2 | Sphingosine-1-phosphate receptor 2 | 23.97 | 25.2 |
| Hs.585118 | NM_005226 | S1PR3 | Sphingosine-1-phosphate receptor 3 | 25.59 | 26.58 |
| Hs.662006 | NM_003775 | S1PR4 | Sphingosine-1-phosphate receptor 4 | 33.52 | 30.76 |
| Hs.501561 | NM_030760 | S1PR5 | Sphingosine-1-phosphate receptor 5 | 37.46 | 36.16 |
| Hs.42091 | NM_002980 | SCTR | Secretin receptor | 40 | 40 |
| Hs.522087 | NM_005866 | SIGMAR1 | Sigma non-opioid intracellular receptor 1 | 21.57 | 22.06 |
| Hs.437846 | NM_005631 | SMO | Smoothened, frizzled family receptor | 27.8 | 30.67 |
| Hs.591915 | NM_052918 | SORCS1 | Sortilin-related VPS10 domain containing receptor 1 | 32.14 | 33.05 |
| Hs.479099 | NM_020777 | SORCS2 | Sortilin-related VPS10 domain containing receptor 2 | 32.76 | 32.61 |
| Hs.671950 | NM_014978 | SORCS3 | Sortilin-related VPS10 domain containing receptor 3 | 40 | 30.11 |
| Hs.248160 | NM_001049 | SSTR1 | Somatostatin receptor 1 | 23.91 | 29.84 |
| Hs.514451 | NM_001050 | SSTR2 | Somatostatin receptor 2 | 32.93 | 32.08 |
| Hs.225995 | NM_001051 | SSTR3 | Somatostatin receptor 3 | 33.57 | 33.23 |
| Hs.673846 | NM_001052 | SSTR4 | Somatostatin receptor 4 | 31.45 | 31.61 |
| Hs.449840 | NM_001053 | SSTR5 | Somatostatin receptor 5 | 40 | 37.35 |
| Hs.279575 | NM_033050 | SUCNR1 | Succinate receptor 1 | 34.48 | 34.88 |
| Hs.375030 | NM_138327 | TAAR1 | Trace amine associated receptor 1 | 35.07 | 34.03 |
| Hs.272382 | NM_014626 | TAAR2 | Trace amine associated receptor 2 | 36.98 | 40 |
| Hs.248198 | NM_003967 | TAAR5 | Trace amine associated receptor 5 | 27.07 | 30.8 |
| Hs.434196 | NM_175067 | TAAR6 | Trace amine associated receptor 6 | 33.81 | 33.85 |
| Hs.434116 | NM_175057 | TAAR9 | Trace amine associated receptor 9 (gene/pseudogene) | 35.81 | 40 |
| Hs.633301 | NM_001058 | TACR1 | Tachykinin receptor 1 | 28.18 | 31.06 |
| Hs.88372 | NM_001057 | TACR2 | Tachykinin receptor 2 | 28.21 | 29.21 |
| Hs.942 | NM_001059 | TACR3 | Tachykinin receptor 3 | 31.34 | 31.62 |
| Hs.442530 | NM_001060 | TBXA2R | Thromboxane A2 receptor | 29.62 | 31.6 |
| Hs.656790 | NM_032027 | TM2D1 | TM2 domain containing 1 | 24.13 | 23.97 |
| Hs.3022 | NM_003301 | TRHR | Thyrotropin-releasing hormone receptor | 32.54 | 32.8 |
| Hs.160411 | NM_000369 | TSHR | Thyroid stimulating hormone receptor | 34.52 | 35.82 |
| Hs.192720 | NM_018949 | UTS2R | Urotensin 2 receptor | 32.55 | 31.77 |
| Hs.348500 | NM_004624 | VIPR1 | Vasoactive intestinal peptide receptor 1 | 34.58 | 26.91 |
| Hs.585052 | NM_003382 | VIPR2 | Vasoactive intestinal peptide receptor 2 (*) | 35.05 | 33.28 |
| Hs.248116 | NM_005283 | XCR1 | Chemokine (C motif) receptor 1 | 35.03 | 32.98 |
| Hs.227656 | NM_004736 | XPR1 | Xenotropic and polytropic retrovirus receptor 1 | 23.47 | 22.49 |
| Hs.592355 | NM_002046 | GAPDH | Glyceraldehyde-3-phosphate dehydrogenase | 17.39 | 17.41 |

For all other in vitro experiments, cells were treated as indicated prior to RNA isolation using RNeasy Plus Mini Kit (Qiagen) according to manufacturer's instructions. Isolated RNA (250 ng) was then used to synthesize cDNA using SuperScript VILO (Invitrogen). Quantitative PCR was performed using FastStart Essential DNA Green Master (Roche) and analyzed using a LightCycler 96 (Roche). Data are expressed as a fold change by ΔΔCt relative to GAPDH. For in vivo experiments, tissue was immediately frozen, and stored at −80° C. RNA isolation, cDNA synthesis, and qPCR analysis were performed as above. Primers used for qPCR are shown in Table 2.

TABLE 2

| Human Primer | | Sequence | |
|---|---|---|---|
| DRD 1 | F:<br>R: | CCCAGCCCTATCAGTCATATTG,<br>AGGATTCATCTGCGAGTTCAG | SEQ ID NOs:<br>1 and 2 |
| CTGF | F:<br>R: | GTCCAGCACGAGGCTCA,<br>TCGCCTTCGTGGTCCTC | SEQ ID NOs:<br>3 and 4 |
| COL1A1 | F:<br>R: | AAGGGACACAGAGGTTTCAGTGG,<br>CAGCACCAGTAGCACCATCATTTC | SEQ ID NOs:<br>5 and 6 |
| ACTA2 | F:<br>R: | GTGAAGAAGAGGACAGCACTG,<br>CCCATTCCCACCATC ACC | SEQ ID NOs:<br>7 and 8 |
| FN1 | F:<br>R: | TGTCAGTCAAAGCAAGCCCG,<br>TTAGGACGCTCATAAGTGTCACCC | SEQ ID NOs:<br>9 and 10 |
| TGM2 | F:<br>R: | TCAGCTACAATGGGATCTTGG,<br>AAGGCAGTCACGGTATTTCTC | SEQ ID NOs:<br>11 and 12 |
| LOX | F:<br>R: | ACATTCGCTACACAGGACATC,<br>TTCCCACTTCAGAACACCAG | SEQ ID NOs:<br>13 and 14 |
| LOXL1 | F:<br>R: | TGCCAGTGGATCGACATAAC,<br>GAAACGTAGCGACCTGTGTAG | SEQ ID NOs:<br>15 and 16 |
| LOXL2 | F:<br>R: | GTGCAGCGACAAAAGGATTC,<br>GCGGTAGGTTGAGAGGATG | SEQ ID NOs:<br>17 and 18 |
| LOXL3 | F:<br>R: | AGCGAAAAGAGGGTCAACG,<br>TGTCATTGGCACGATAGAACTC | SEQ ID NOs:<br>19 and 20 |
| LOXL4 | F:<br>R: | GTGGCAGAGTCAGATTTCTCC,<br>TTGTTCCTGAGACGCTGTTC | SEQ ID NOs:<br>21 and 22 |
| PLAU | F:<br>R: | GGGAGATGAAGTTTGAGGTGG,<br>AGATGGTCTGTATAGTCCGGG | SEQ ID NOs:<br>23 and 24 |
| PLAT | F:<br>R: | AAACCCAGATCGAGACTCAAAG,<br>ACCCATTCCCAAAGTAGCAG | SEQ ID NOs:<br>25 and 26 |
| CTSK | F:<br>R: | CTCCTTCCAGTTTTACAGCAAAG,<br>TTTCCCCAGTTTTCTCCCC | SEQ ID NOs:<br>27 and 28 |
| MMP14 | F:<br>R: | TGCCTACCGACAAGATTGATG,<br>ATCCCTTCCCAGACTTTGATG | SEQ ID NOs:<br>29 and 30 |
| Mouse Primer | | Sequence | |
| Drd1 | F:<br>R: | CCCGTAGCCATTATGATCGTC,<br>AGAGCATTCGACAGGGTTTC | SEQ ID NOs:<br>31 and 32 |
| Pdgfra | F:<br>R: | TCCTTCTACCACCTCAGCGAG,<br>CCGGATGGTCACTCTTTAGGAAG | SEQ ID NOs:<br>33 and 34 |
| Epcam | F:<br>R: | TTGCTCCAAACTGGCGTCTA,<br>ACGTGATCTCCGTGTCCTTGT | SEQ ID NOs:<br>35 and 36 |
| Pecam 1 | F:<br>R: | CTGCCAGTCCGAAAATGGAAC,<br>CTTCATCCACTGGGGCTATC | SEQ ID NOs:<br>37 and 38 |
| Ptprc | F:<br>R: | GACAGAGTTAGTGAATGGAGACC,<br>AAAAGTTCGGAGAGTGTAGGC | SEQ ID NOs:<br>39 and 40 |
| Acta2 | F:<br>R: | GAGAAGCCCAGCCAGTCG,<br>CTCTTGCTCTGGGCTTCA | SEQ ID NOs:<br>41 and 42 |
| Ctgf | F:<br>R: | CCTGCGACCCACACAAG,<br>GACCCACCGAAGACACAG | SEQ ID NOs:<br>43 and 44 |
| Fn1 | F:<br>R: | CCAGCAGCATGATCAAAACAC,<br>GGTGGCTACATGTTAGAGTGTC | SEQ ID NOs:<br>45 and 46 |
| Col1a1 | F:<br>R: | ATCATAGCCATAGGACATCTGG,<br>CTGGACAGCCTGGACTTC | SEQ ID NOs:<br>47 and 48 |
| Yap1 | F:<br>R: | CTCTGAGTGATCCTCTGGTTC,<br>CCATAAGAACAAGACCACATCCT | SEQ ID NOs:<br>49 and 50 |
| WWtr1 | F:<br>R: | CTTGCTGGTGTTGGTGATTC,<br>ATCAGCCTCTGAATCATGTGAA | SEQ ID NOs:<br>51 and 52 |
| Alb | F:<br>R: | TGCTTTTTCCAGGGGTGTGTT,<br>TTACTTCCTGCACTAATTTGGCA | SEQ ID NOs:<br>53 and 54 |

Cell Sorting: FACS: PBS perfused mouse lungs were finely minced with a razor blade in a 100 mm petri dish in 1 mL of cold DMEM medium containing 0.2 mg/ml Liberase DL (Roche) and 100 U/ml DNase I (Roche). The mixture was transferred to 15 ml tubes and incubated at 37° C. for 30 min in a water bath. Enzymatic digestion was inactivated by adding DMEM medium containing 10% fetal bovine serum. The cell suspension was passed once through a 40 µm cell strainer (Fisher) to remove multicellular debris. Cells were then centrifuged at 1,300 r.p.m. at 4° C. for 10 min, washed once in PBS and resuspended in 0.2 ml of FACS buffer (1% BSA, 0.5 µM EDTA pH 7.4 in PBS). The single cell suspension was then incubated with anti-CD45-PerCp-Cy5.5, anti-CD31-PE, anti-PDGFRα-APC and anti-EpCAM-BV421 antibodies (1:200) (Biolegend) for 20 min on ice. After incubation, cells were washed with ice-cold FACS buffer and resuspended in 1 ml of FACS buffer. FACS sorting was conducted using a BD FACS Aria II (BD Biosciences). FACS-sorted epithelial cells, endothelial cells and fibroblasts were collected in 1.5 mL Eppendorf tubes containing RLT lysis buffer (Qiagen), which were subjected to mRNA extraction, complementary DNA synthesis and RT-PCR analysis. MACS: PBS perfused mouse lungs were finely minced with a razor blade in a 100 mm petri dish in 1 ml of MACs dissociation solution described in the MACS mouse lung dissociation kit. The mixture was transferred to 15 ml tubes and incubated at 37° C. for 30 min in a water bath. Enzymatic digestion was inactivated by adding DMEM containing 10% fetal bovine serum. The cell suspension was passed once through a 40 µm cell strainer (Fisher) to remove multicellular debris. Cells were then centrifuged at 1,350 r.p.m. at 4° C. for 10 min and supernatant aspirated. The samples were resuspended in 0.1 mL 15% BSA-autoMACS rinsing solution. The single cell suspension was then incubated with mouse anti-CD45 Micro-Beads (1:10) for 15 minutes at 4-8° C. Cells were then magnetically filtered using LS column (Miltenyi Biotec). Positively selected cells were pelleted at 1350 RPM at 4° C. and resuspended in RLT lysis buffer (Qiagen). Samples were then subjected to mRNA extraction, complementary DNA synthesis and RT-PCR analysis.

Immunofluorescence Microscopy: Cells were plated into 96 well plates (Corning 3603) in their specific growth media and allowed to attach (8 hours). Media was then exchanged for the indicated conditions for each experiment. Cells were fixed in 3.7% formalin (Sigma-Aldrich), permeabilized in 0.25% Triton X-100 (Sigma-Aldrich) and then blocked with 1% BSA for 1 h. Cells or tissue sections were incubated overnight with mouse monoclonal antibody against αSMA (Sigma-Aldrich F3777), and/or a rabbit monoclonal antibody against YAP/TAZ (Cell Signaling D24E4) diluted 1:200 in PBS with 1% BSA. Cells were then washed and exposed to flourescence-conjugated secondary antibodies (Invitrogen) diluted 1:1000 and DAPI (Thermo Fisher Scientific). Images were taken with a Cytation5 (BioTek) microscope. For scoring αSMA positive cells (FIG. 12), an observer blinded to the treatment conditions counted αSMA-positive cells using a visual threshold for bright fibrous staining; a minimum of 200 cells was counted for each condition. YAP/TAZ localization was quantified (FIGS. 6-10, 24-26, and 29-30) using Gen5 (Biotek) software. Images were taken at 4× magnification of both DAPI and YAP/TAZ staining. Objects were identified using the DAPI channel and a subpopulation of YAP/TAZ nuclear positive cells was counted based on nuclei where the average pixel intensity of the YAP/TAZ channel was greater than 85% of the average pixel intensity of all the nuclei in the control treated cells. Quantification of double positive (YAP/TAZ and αSMA) cells from lung tissue sections (FIG. 17-21) was performed similarly; however separate thresholds were established for both YAP/TAZ and αSMA. A minimum of 4000 cells was quantified for each mouse.

Traction Force Microscopy: Traction analysis was conducted as previously described. Briefly, polyacrylamide substrates with shear moduli of 6.4 kPa were prepared, and fluorescent sulfate-modified latex microspheres (0.2 µm, 505/515 ex/em) (FluoSpheres, Life Technologies) were conjugated to the gel surfaces after treatment with 1 mg/ml of dopamine hydrochloride (Sigma-Aldrich) in 50 mM HEPES solution (pH 8.5). IPF patient derived fibroblasts were plated on the gels overnight and treated as indicated before traction force measurements. Images of gel surface-conjugated fluorescent beads were acquired for each cell before and after trypsinization using a Nikon ECLIPSE Ti microscope at ×10 magnification. Traction forces were estimated by measuring bead displacement fields and computing corresponding traction fields using TractionsForAll (freely distributed program that calculates 2-D tractions exerted by an adherent cell on its substrate).

cAMP Assay: IPF patient derived fibroblasts were plated in EMEM containing 10% FBS overnight. Media was exchanged with EMEM containing 0.1% FBS for 24 hours. cAMP was measured using the cAMP-Glo™ Assay (Promega) according to manufacturer's suggestions. 20 minutes prior to cell lysis media was removed and cells were treated with "induction buffer" containing nonselective phosphodiesterase inhibitors and the indicated concentration of compound(s). Luminescence was measured on a Flexstation 3 (Molecular Devices) plate reader.

Western Blotting: Cells were plated in EMEM containing 10% FBS overnight. Media was exchanged with EMEM containing 0.1% FBS for 24 hours. Prior to protein isolation cells were treated with the indicated concentration of compounds for the indicated time. Total protein was isolated using RIPA buffer (pH 8.0) containing Pierce Phosphatase Inhibitor (Thermo) and Halt Protease Inhibitor Cocktail (Thermo). Lysate total protein concentration was determined using Pierce BCA Protein Assay Kit (Thermo) and samples were run on a 10% polyacrylamide gel. Blots were incubated overnight with primary antibodies: pYAP (Ser 127, Cell Signaling D9W21), YAP/TAZ (Cell Signaling D24E4), GAPDH (Cell Signaling 14C10), HSC70 (Santa Cruz sc-7298), αSMA (Abcam ab5694), and fibronectin (Santa Cruz sc-9068) diluted 1:1000 in Li-Cor Odyssey Blocking Buffer. Blots were washed with TBS-Tween before 60 minute incubation with IR-dye-conjugated secondary antibodies (Li-Cor) diluted 1:10,000. Plates were imaged via a Li-Cor OdysseyXL system with quantification performed via densitometry.

Immuno-ECM Adapting from previously published methods, IPF patient-derived fibroblasts were plated to confluence in clear-bottom 96-well plates. After cells attached, the medium was swapped for EMEM containing 0.10% FBS±2 ng/mL TGF-β. After 48 hours the indicated concentration of DHX or DMSO control was added to each well and incubated for 24 hours. WST-1 viability reagent was added to each well (Sigma-Aldrich) and measured on a Flexstation 3 (Molecular Devices) plate reader. Cells were then fixed in 3.7% formalin (Sigma-Aldrich), and permeabilized in 0.25% Triton X-100 (Sigma-Aldrich). Wells were washed with tris-buffered saline (TBS) and blocked with Li-Cor Odyssey Blocking Buffer for 60 minutes before overnight incubation in a polyclonal rabbit antibody for fibronectin (Sigma sc-9068) or collagen I (Novus NB600-408) diluted 1:200 in blocking buffer. Wells were washed with TBS-Tween before 45 minute incubation with IR-dye-conjugated secondary antibody (Li-Cor #926-32211) diluted 1:400. Plates were imaged via a Li-Cor OdysseyXL system with quantification performed via densitometry. Data are expressed as IR intensity relative to WST-1 signal absorbance in order to account for any potential compound toxicity.

Matrix Remodeling Measured by Atomic Force Microscopy: NIH-3T3 cells were plated to confluence onto gelatin coated (Cell Biologics) AFM compatible tissue culture dishes (Willco) in DMEM containing 10% FBS. After cells attached overnight media was replaced with DMEM containing 2% FBS, 2 ng/mL TGFβ, and 20 µg/mL ascorbic acid to promote matrix deposition. After 72 hours, measurements were made using a BioScope Catalyst AFM (Bruker, MA, USA). Microindentations were performed using a 2.5 µm radius sphere-tipped probe (Novascan, IA, USA) with a spring constant determined at about 100 pN/nm by thermal fluctuation method. For each dish, 3 different areas were analyzed. Force curves were acquired with MIRO 2.0 (NanoScope 9.1; Bruker) at an indentation rate of 20 µm/s and a ramp size of 10 µm on different points. 75 force curves were performed per cell dish (25 per area). The Young's modulus E was determined by the fitting of force curve by Hertz model using NanoScope Analysis software (Bruker) and considering Poisson's ratio of 0.5. Media was exchanged for fresh DMEM containing 2% FBS, 2 ng/mL TGFβ, and 20 µg/mL ascorbic acid with the indicated concentration of DHX or 0.1% DMSO (vehicle control). After another 72 hours AFM measurements were made as before. The resulting cell-derived matrix was then decellularized with Phosphate-buffered saline (Gibco) containing: 0.5% (v/v) Triton X-100 (Sigma-Aldrich) and 20 mM NH$_4$OH (LabChem Inc.). Matrices were washed 3× with PBS and then plated with low passage (P3), NHLFs for 24 hours prior to RNA isolation.

RNA Interference: Cells were transfected using Lipofectamine RNAiMAX (Life Technologies) with 25 nM siGENOME siRNA SMARTpool (Dharmacon) targeting DRD1 (L-005477-00-0005) or a nontargeting SMARTpool (D-001810-10-05). Cells were cultured for 72 hours before collecting RNA. For the YAP/TAZ localization experiments, the cells were transfected in their 6-well plates for 48 hours prior to re-plating into 96-well plates for the immunofluorescence assays. See below for in vivo siRNA methodology.

Bleomycin Mouse Study: In the initial in vivo siRNA study (FIGS. 22 and 23A-23C), adult male age-matched C57BL/6N mice at 6-8 weeks of age were purchased from the National Cancer Institute (NCI)-Frederick Mouse Repository (Frederick, MD, USA). All experiments were performed in accordance with National Institute of Health guidelines and protocols approved by the Massachusetts General Hospital Subcommittee on Research Animal Care, and maintained all mice in a specific pathogen-free (SPF) environment certified by the American Association for Accreditation of Laboratory Animal Care (AAALAC). 6-8 weeks old mice were anesthetized with ketamine and xylazine before exposure of the trachea. Lung fibrosis was induced by intratracheal injection of bleomycin (50 μl at 1.2 U/kg) or phosphate buffered saline (PBS; as control) on day 0. After 14 days Small interfering RNA (siRNA) duplexes targeting mouse Yap (L-046247-01-0005) or Taz (L-058248-01-0005) mRNA (Dharmacon) or nontargeting control siRNA were administered in vivo by intratracheal instillation at a single dose of 25 μg (each siRNA) per mouse. On day 21 Mice were sacrificed and lungs harvested for collagen determination and biochemical analyses. To obtain BAL samples for total protein concentration determination, lungs were lavaged with six 0.5-mL aliquots of PBS. BAL samples were centrifuged at 3,000 g for 20 min at 4° C. and transferred the supernatants to siliconized low-binding Eppendorf tubes (PGC Scientifics) for subsequent analysis. Total protein concentration of the BAL fluid was determined by BCA Protein Assay Kit (Pierce). In the dihydrexidine treatment studies (FIG. 17-21), 8 week old female C57/BL6 mice were purchased from Charles River Laboratories. Mouse lung fibrosis was induced with bleomycin (BLEO; Fresenius Kabi) delivered intratracheally (3 U/kg) to the lungs using MicroSprayer® Aerosolizer (Penn-Century). The Sham mice received sterile 0.9% saline instead using identical methods. Mice were weighed every 24 hrs, and both groups were then randomized at day 10 into DHX and Control treatment groups, matching for the degree of weight change. DHX (5 mg/kg) was administered everyday intranasally (i.n.) dissolved in surfactant (infasurf) which has previously shown to aid in spreading to pulmonary aveoli for 14 days. The control groups of mice received the equivalent vehicle dose of surfactant. Following the final DHX treatment, mice were sacrificed and the right lungs were inflated with 4% paraformaldehyde (PFA) and further incubated in 4% PFA for 24 hours prior processing for paraffin embedding. The left lobe of the lung was snap frozen in liquid nitrogen for RNA isolation and hydroxyproline assay. Experimental procedures were approved by the Mayo Clinic Institutional Animal Care and Use Committee and the animals were handled in accordance with their guidelines.

Bile Duct Ligation: BDL was performed as previously described. Briefly, 8-10 weak old female C57BL/6N underwent either BDL or sham surgery. Mice were anesthetized on Day 0 following IACUC protocol, and the bile duct was ligated using sterile 3/0 silk ligatures. Sham surgery was performed by passing a silk ligature under the bile duct. Starting on Day 7, DHX (5 mg/kg) or vehicle control was administered everyday intraperitoneally (i.p.) for 14 days. Following the final DHX treatment, mice were sacrificed and the livers harvested for analysis of fibrosis.

Histological Scoring: Five μm thick sections were cut from Paraffin embedded lung tissues, and the sections were stained either with hematoxylin and eosin (H&E) or with Masson's Trichrome stain kit (Abcam). All H&E-stained slides and trichrome-stained slides were reviewed in a blinded fashion by a thoracic pathologist. The severity of interstitial and peribronchiolar lung immature and mature fibrosis was estimated on a numerical scale according to Ashcroft et al. For scoring purposes, all H&E stained slides were systematically scanned at 100× magnification and successive 100× fields were scored. Scoring was based on the following scale: 0 (no fibrosis), 1 (minimal interstitial and/or peribronchiolar thickening due to fibrosis), 3 (moderate thickening without obvious architectural distortion), 5 (increased fibrosis with formation of fibrous bands and/or small masses), 7 (severe architectural distortion with large areas of fibrosis and areas of honeycomb changes), and 8 (total fibrous obliteration of the field). The predominant score for each field was recorded. The mean of all scores was calculated for each case. Liver trichrome stained sections were computationally measured using Image J software. After converting each image in an RGB stack, the threshold was adjusted and kept at the same level for all the images.

Hydroxyproline: Hydroxyproline content was measured using a hydroxyproline assay kit (Biovision) according to the manufacture's instruction with slight modification. The lung tissues were weighed, homogenized in sterile water (10 mg of tissue per 100 μL $H_2O$) and hydrolyzed in 12N HCl in a pressure-tight, teflon capped vial at 120° C. for 3 hours followed by filtration through a 45 μm Spin-X® Centrifuge Tube filter (Corning). 10 μL of the hydrolyzed samples was dried in a Speed-Vac for 2 hours, followed by incubation with 100 μL of Chloramine T reagent for 5 minutes at room temperature and 100 μL of 4☐(dimethylamino) benzaldehyde (DMAB) for 90 minutes at 60° C. The absorbance of oxidized hydroxyproline was determined at 560 nm. Hyrdroxyproline concentrations were calculated from a standard curve generated using known concentrations of trans-4-hydroxyl-L-proline. The total amount of protein isolated from the weighed tissues was determined by using a protein assay kit (Bio-Rad, absorbance at 595 nm). The amount of collagen was expressed in μg/mg total protein.

Statistics: Groups were compared by one-way ANOVA with Tukey's multiple comparison's test. All statistical tests were carried out using GraphPad Prism 6 with statistical significance defined asp <0.05. Results are expressed throughout as the mean±standard error of the mean (SEM).

Example 1—Selective YAP and TAZ Targeting by Agonizing $G\alpha_s$ Receptors

To test whether nonselective YAP and TAZ targeting may be effective in a model of pulmonary fibrosis, YAP and TAZ siRNA were administered intratracheally to mice following bleomycin injury, a standard model of pulmonary fibrosis (FIG. 17-21). Non-selective targeting of YAP/TAZ in this context amplified fibrosis (measured by hydroxyproline assay), while also increasing lung injury and vascular leakage. Contrastingly, fibroblast selective genetic deletion of YAP and TAZ has shown promise in a kidney fibrosis model (See e.g., Ref. 25).

G protein-coupled receptors (GPCRs) make up the largest family of membrane receptors in the human genome, and have been prolific therapeutic targets, with their ligands account for >30% of all clinically approved drugs (See e.g., Ref. 26). GPCRs are linked to effector proteins from four main classes of G-proteins. Activation of receptors which couple to $G\alpha_{12/13}$, $G\alpha_{q/11}$ and $G\alpha_{i/o}$ stimulates YAP/TAZ nuclear translocation and transcriptional activity. In contrast, receptors which couple to $G\alpha_s$ inhibit YAP/TAZ nuclear localization and activity via elevation of cAMP (See e.g., Ref. 27-30) (FIG. 1,2).

Figure 3:
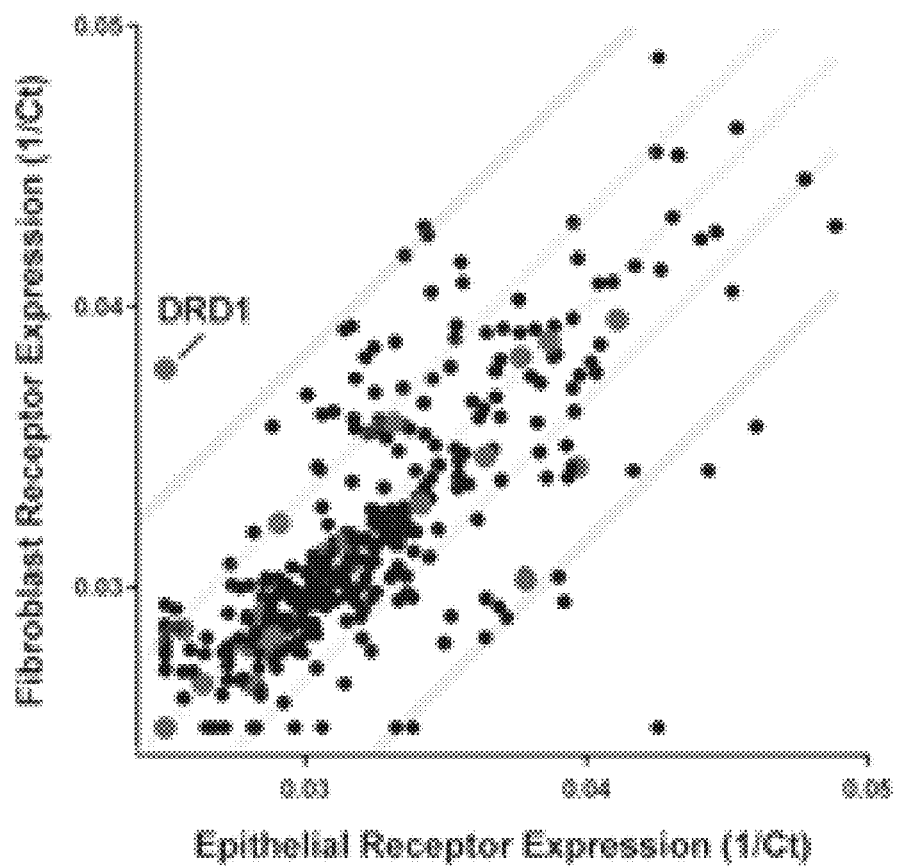
FIG. 3 contains a line plot showing GPCR expression profiling of cultured human alveolar epithelial cells and normal human pulmonary fibroblasts. Dopamine Receptor D1 (DRD1) transcripts are highly expressed in fibroblasts and not detected in epithelial cells. Red points indicate GPCRs which selectively couple to $G\alpha_s$. Orange diagonal line indicates 10-fold preferential expression, blue line 100-fold.
Figure 4:
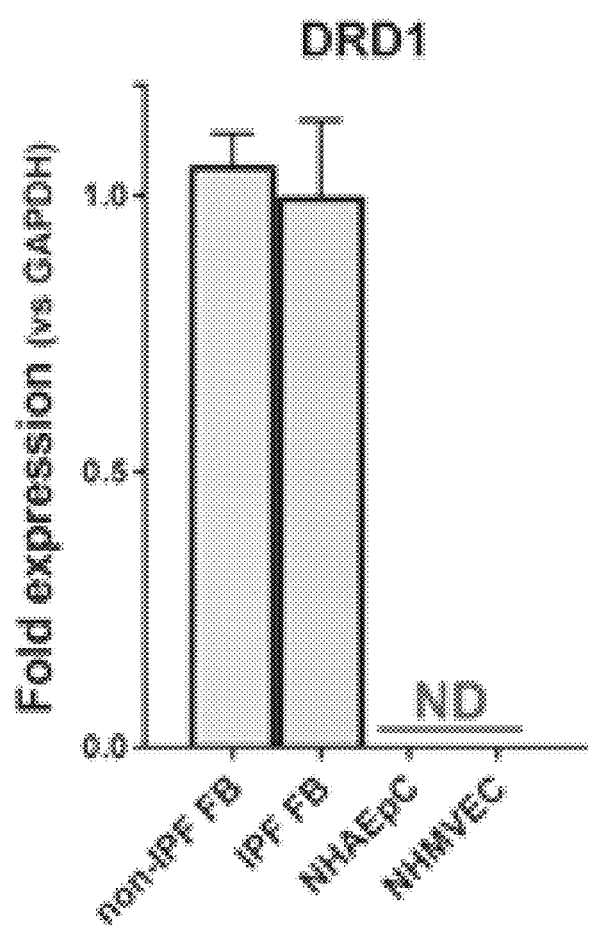
FIG. 4 contains a bar graph showing DRD1 expression in cultured non-IPF associated fibroblasts, IPF patient-derived fibroblasts, normal human alveolar epithelial cells (NHAEpC), and normal human microvasculature endothelial cells (NHMVEC), passage 6 or less. NHAEpC and NHMVEC, n=2. non-IPF FB and IPF FB, n=6.
Figure 5:
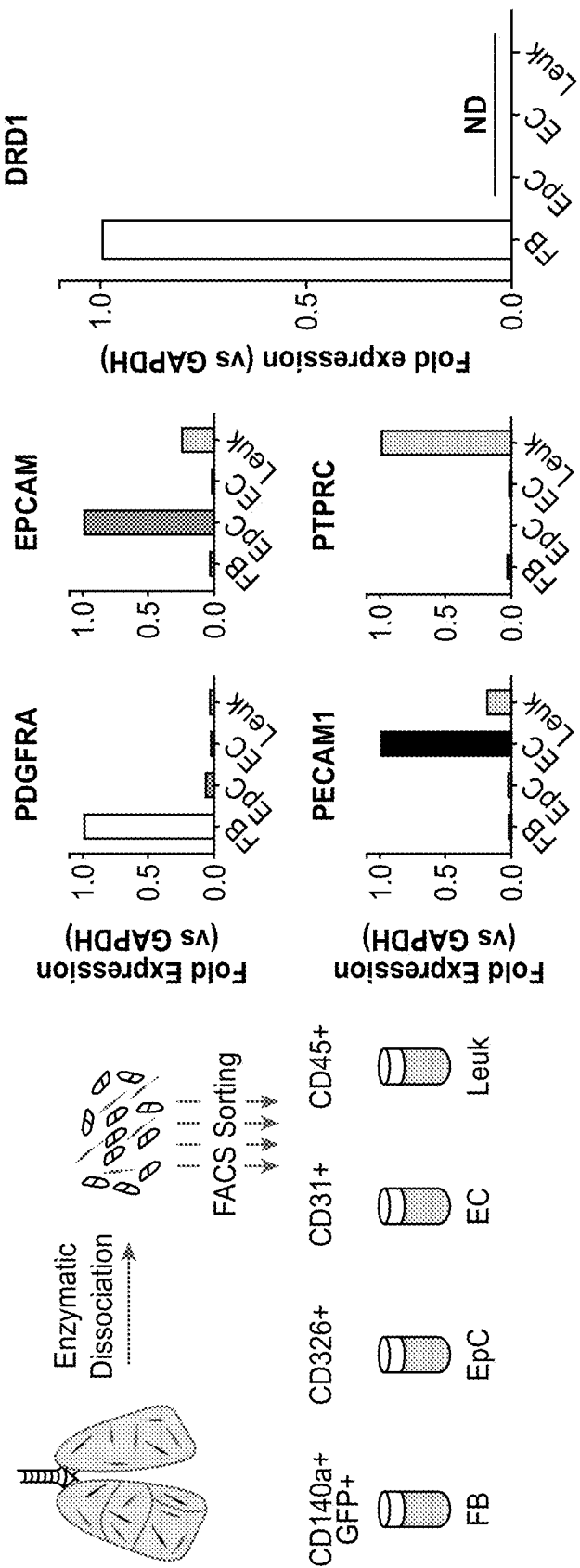
FIG. 5 shows expression of DRD1 in freshly isolated mouse lung fibroblasts (FB), epithelial (EpC), endothelial cells (EC), and leukocytes (Leuk). Lung from a healthy COL1A1-GFP expressing mouse was enzymatically digested then sorted for markers of fibroblasts (GFP+, CD140a+), epithelial cells (CD326+), endothelial cells (CD31+), and leukocytes (CD45+) followed by RNA isolation to validate selective populations and expression of Drd1.

GPCR expression varies across organs and even within adjacent cell types in the same tissue (See, e.g., Ref. 31). Therefore, RNA expression of the GPCRome was profiled in both primary adult human pulmonary fibroblasts and alveolar epithelial cells (FIG. 3), searching for receptors which exclusively couple to $G\alpha_s$ (See, e.g., Ref. 32) (larger dots, FIG. 3) and are expressed selectively in fibroblasts. Of the 28 $G\alpha_s$ coupled receptors, expression of the Dopamine Receptor D1 (DRD1) exhibited relatively high expression and pronounced enrichment in fibroblasts compared to alveolar epithelial cells (FIG. 3). Abundant transcripts for DRD1 in cultured normal human lung fibroblasts and fibroblasts derived from patients with idiopathic pulmonary fibrosis was determined by qPCR, and undetectable transcript levels of DRD1 in both primary human alveolar epithelial and microvasculature endothelial cells (FIG. 4). To further validate our findings in freshly isolated lung cell populations, we sorted mouse lung tissue into mesenchymal, epithelial, endothelial, and leukocyte enriched fractions (FIG. 5). As in cultured human cells we observed robust expression of DRD1 in the freshly isolated mesenchymal cells, but undetectable levels in other lung cell populations.

Figure 6:
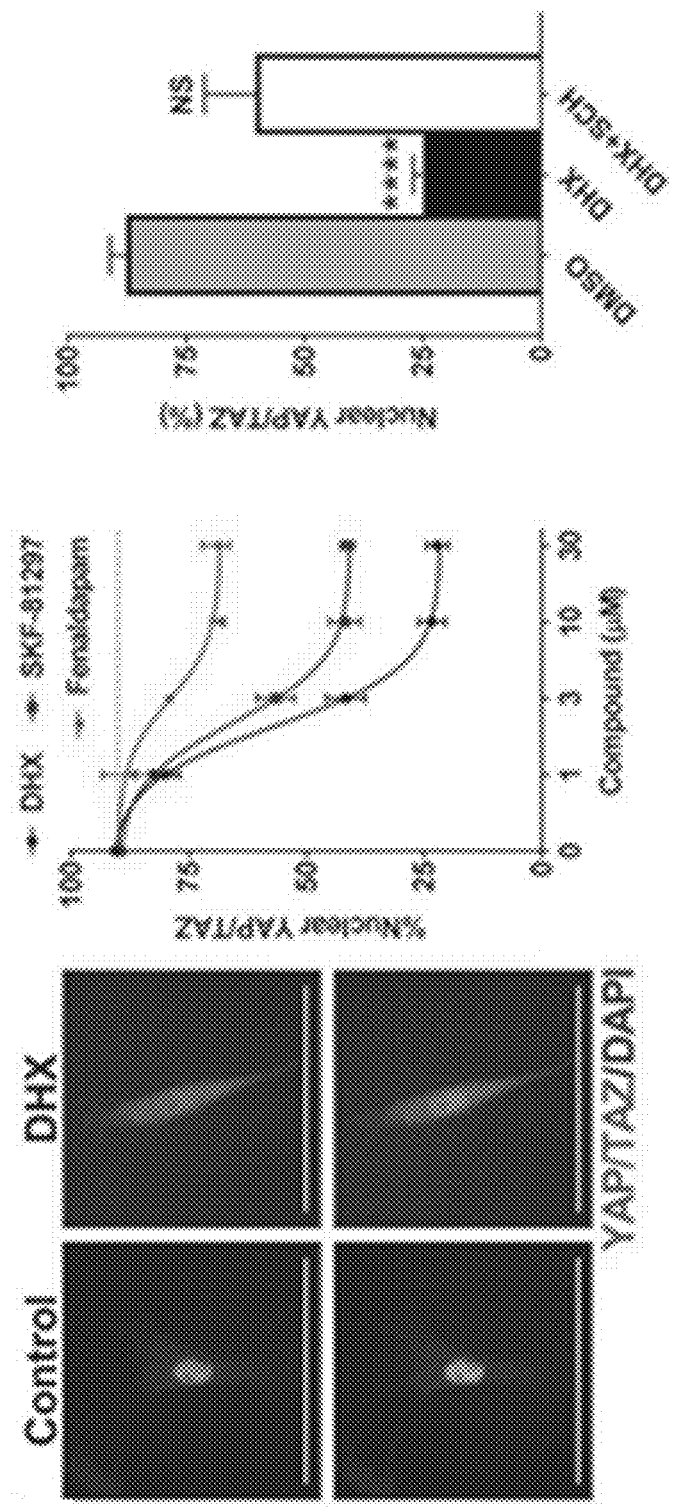
FIG. 6 shows that dopamine Receptor D1 agonism blocks YAP/TAZ nuclear localization. Selective agonists of dopamine receptor D1 with varying efficacy inhibit YAP/TAZ nuclear localization; this effect can be overcome by treatment with a DRD1 receptor antagonist (SCH 39166, 3 µM), (Dihydrexidine, 10 µM). IMR-90 cells treated 2 hours prior to fixation. N=4 (****p<0.0001 vs. 0.10% DMSO vehicle control). Scale bar represents 100 µm.
Figure 7:
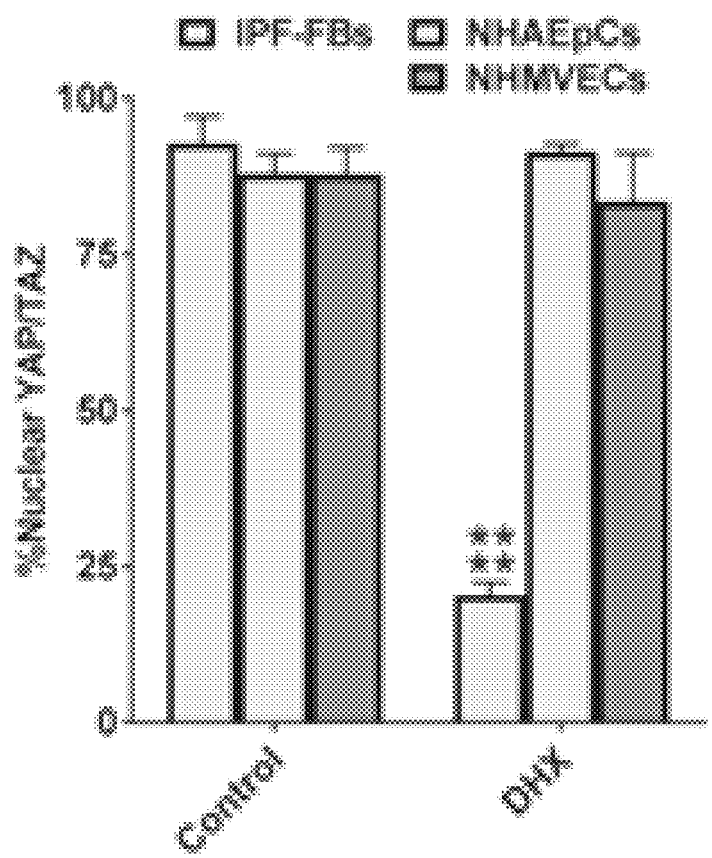
FIG. 7 shows that, consistent with DRD1 expression, D1 agonist (e.g., DHX) inhibits YAP/TAZ only in fibroblasts (IPF-FBs) but not in epithelial (NHEpCs) or endothelial (NHMVECs) cells. N=4 (****p<0.0001 vs. 0.1% DMSO vehicle control)

Example 2—DRD1 Agonists Selectively Inhibit YAP and TAZ Localization in Mesenchymal Cells Three selective DRD1 agonists (dihydrexidine, SKF-81297, fenoldopam) were tested for their ability to inhibit YAP/TAZ nuclear localization (FIG. 6, 24). Fibroblasts plated on stiff matrix (plastic) and lacking cell contact inhibition have abundant nuclear localization of YAP/TAZ (See e.g., Ref. 2). All three compounds reduced nuclear localization of YAP/TAZ, and their efficacy was consistent with previously described intrinsic activity of these ligands (See e.g., Ref. 33).

Figure 8:
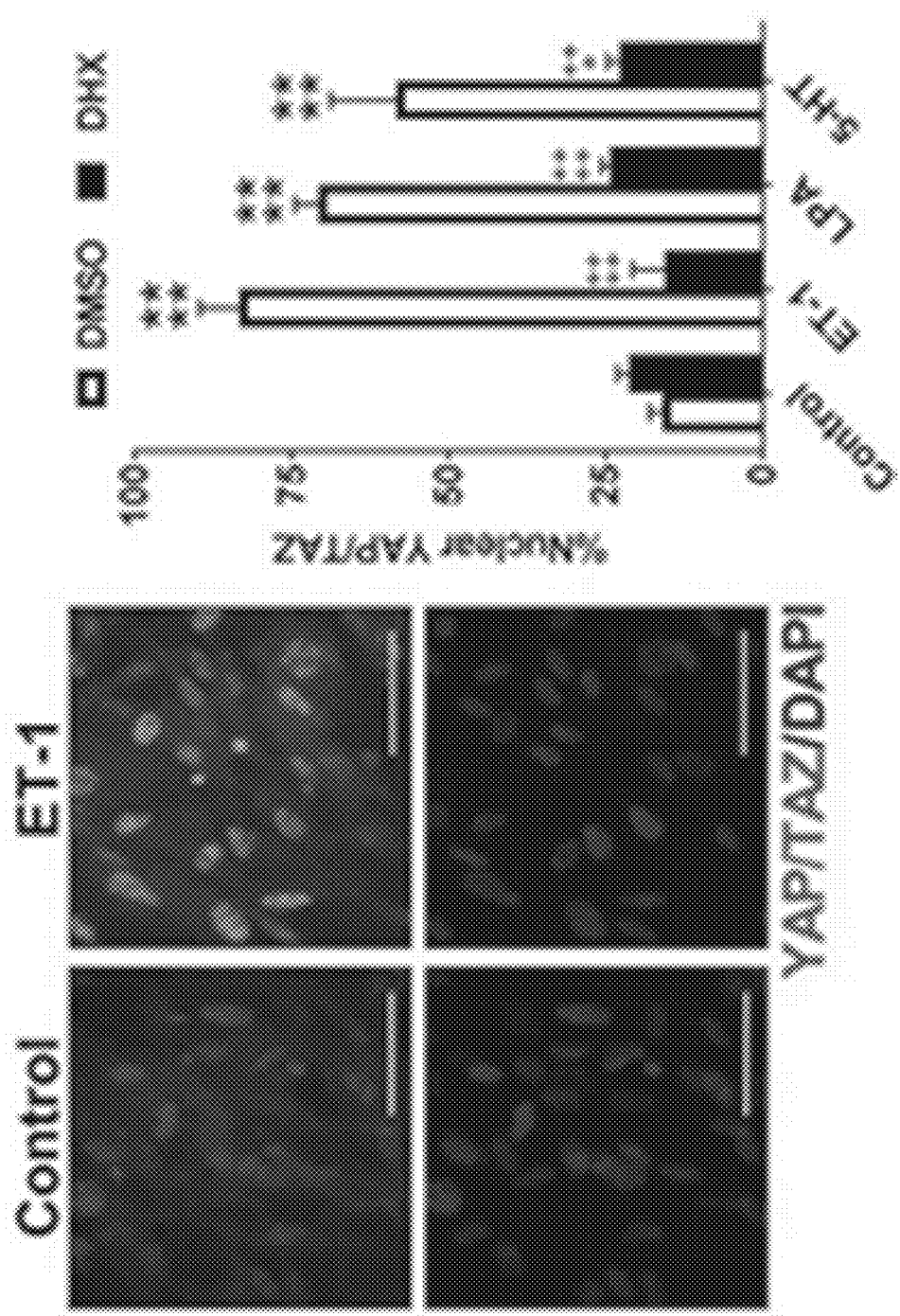
FIG. 8 shows that YAP/TAZ localization is induced through multiple ligands which stimulate receptors coupled to Galpha$_{i/q/12}$, endothelin 1 (ET-1: 100 nM), lysophosphatidic acid (LPA: 10 µM), and serotonin (5-HT: 1 µM). In each case DHX treatment (10 µM) can reverse this effect on YAP/TAZ. IMR-90 cells plated densely onto plastic cell culture plates for 24 hours in media containing 0.1% FBS, treated for 2 hours prior to fixation. N=4 (****p<0.0001 vs. 0.1% DMSO vehicle control), (++++p<0.0001 vs. the respective stimulated agonist ET-1, LPA, or 5-HT). Scale bar represents 100 µm.
Figure 9:
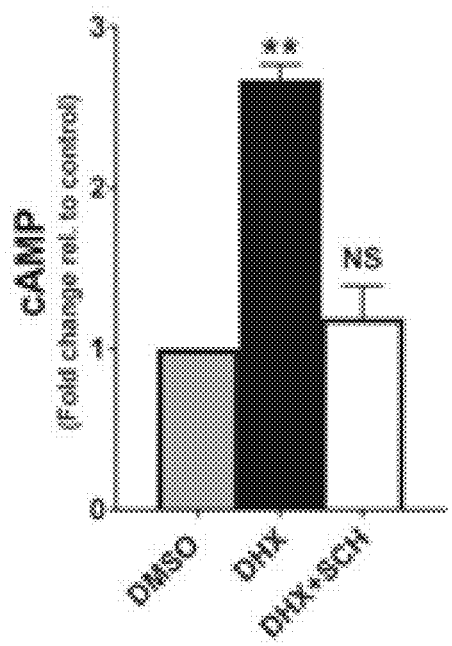
FIG. 9 contains a bar graph showing cAMP measured in IPF patient-derived fibroblasts treated for 20 minutes with DHX (10 µM)+/−SCH 39166 (3 µM). N=3 (**p<0.01 vs. 0.1% DMSO vehicle control).
Figure 10:
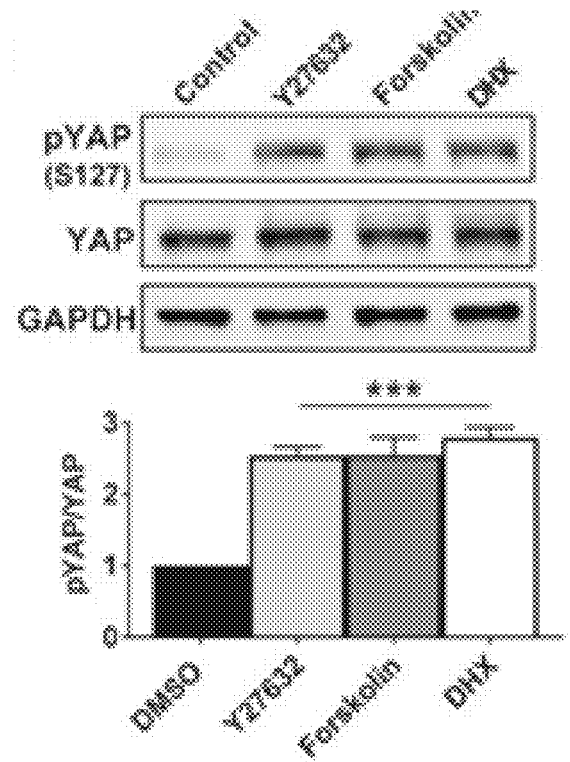
FIG. 10 shows phosphorylation of YAP by Rho-kinase inhibitor Y27632 (20 µM), direct cAMP stimulator Forskolin (10 µM), or DHX (10 µM). IMR-90 cells cultured for 24 hours in media containing 0.1% FBS, treated 2 hours prior to fixation. N=3 (***p<0.001 vs. 0.1% DMSO vehicle control).

The inhibition of YAP/TAZ nuclear localization by dihydrexidine (DHX) could be attenuated using a DRD1 selective antagonist (FIG. 24-26) or by treating the cells with DRD1-siRNA (FIG. 27-28), confirming the receptor-specific effects of DHX. Consistent with the previously defined mechanism whereby YAP/TAZ nuclear localization is controlled by cAMP-dependent phosphorylation of serine residues, promoting cytoplasmic retention or degradation, DHX elevated cAMP and promoted YAP serine 127 phosphorylation (See e.g., Ref. 27-30) (FIG. 9, 10). DHX was effective at inhibiting YAP/TAZ nuclear localization across a panel of mesenchymal cell types, including cardiac and dermal fibroblasts and hepatic stellate cells (FIG. 24-26), suggesting potentially broad relevance of this ligand for mesenchymal cell targeting of YAP and TAZ. DHX-mediated inhibition of YAP/TAZ nuclear localization was relatively sustained, and equally potent in normal lung fibroblasts and those derived from a patient with IPF, unlike the reduced potency of another GPCR ligand (PGE$_2$) with known anti-fibrotic effects in the lung (FIG. 24-26) (See e.g., Ref. 34). In contrast to these observations, DHX had no effect on YAP/TAZ localization in pulmonary epithelial and endothelial cells (FIG. 7), consistent with the absence of detectable transcripts for DRD1 in these cell types. Multiple GPCR ligands which are known to promote fibrosis couple to $G\alpha_i$, $G\alpha_q$, and $G\alpha_{12}$ which would in turn be expected to enhance YAP/TAZ nuclear localization in fibroblasts (See e.g., Ref. 28, 33). It was confirmed in confluent fibroblasts, which otherwise exhibit reduced nuclear localization of YAP/TAZ, showing that endothelin-1, lysophosphatidic acid and serotonin, all GPCR ligands implicated in promotion of fibrosis (See e.g., Ref. 35), enhance YAP/TAZ nuclear localization. DHX blocked nuclear localization of YAP/TAZ in responses to all three of these ligands, demonstrating the broad effects of GPCR ligands on YAP/TAZ in fibroblasts, and identifying DHX and stimulation of $G\alpha_s$/cAMP as an effective strategy for inhibiting both mechanical (stiff matrix) and biochemical regulation of YAP/TAZ nuclear localization (FIG. 8). The ability of selected dopamine receptor agonists to inhibit YAP/TAZ nuclear localization is shown in Table 3.

TABLE 3

| Compound | Nuclear localization (% of total cells) | | | |
|---|---|---|---|---|
| | IPF-1 | IPF-2 | IPF-3 | IPF-4 |
| DMSO | 89.96719 | 77.08034 | 76.3871 | 73.26695 |
| R(−)-2,10,11-Trihydroxyaporphine•HBr | 13.70637 | 22.14634 | 24.15385 | 17.75309 |
| Dihydrexidine | 13.22484 | 21.79444 | 27.63449 | 21.08058 |
| A 68930•HCl | 33.12535 | 30.59259 | 26.82353 | 10.25995 |
| (R)-(−)-Apomorphine•HCl | 29.20735 | 31.96825 | 27.47368 | 17.86425 |
| (±)-SKF-82958•HBr | 29.15385 | 38 | 38 | 12.28571 |
| CY 208-243 | 20.51748 | 39.79487 | 41.17073 | 19.81818 |
| R(−)-Propylnorapomorphine•HCl | 28.34884 | 26.70968 | 42.73684 | 29.03004 |
| R(+)-6-BROMO-APB•HBr | 28.36697 | 38 | 36 | 25.64706 |
| R(−)-2,10,11-Trihydroxy-N-propyl-noraporphine•HBr | 32.86874 | 35.25275 | 37.69697 | 25.35849 |
| A-77636•HCl•H$_2$O | 26.46154 | 30.88136 | 41.33333 | 37.78903 |
| Dopamine•HCl | 39.84783 | 59.28571 | 49.66667 | 49.50943 |
| 6,7-ADTN•HBr | 43.88865 | 44 | 65.5 | 52.64912 |
| Mesulergine•HCl | 37.81413 | 45.14286 | 78.625 | 45.14286 |
| SKF 38393•HBr | 69.5873 | 47.375 | 61.33333 | 35.79116 |
| N-Methyldopamine•HCl | 43.15829 | 46.73016 | 60.10526 | 70.44275 |
| 4-Hydroxyphenethylamine•HCl | 56.51852 | 45.69231 | 76.57143 | 43.3719 |
| Cabergoline | 57.01515 | 57.41176 | 45.95181 | 68.69498 |
| 3-Hydroxyphenethylamine•HCl | 48.95506 | 56.91892 | 69.25 | 58.37466 |
| Pramipexole Dihydrochloride Monohydrate | 64.92308 | 47.64912 | 65.5 | 58.96774 |
| PD 168077 maleate | 67.07869 | 42.44444 | 63.67568 | 68.4 |
| Fenoldopam•HCl | 68.09828 | 50.31884 | 66.63636 | 63 |
| (±)-PD 128,907•HCl | 60.13115 | 49.53846 | 78.47619 | 60.66187 |
| (±)-2-(N-phenylethyl-N-propyl)amino-5-hydroxytetralin•HCl | 68.85 | 60.85714 | 68 | 56.552 |
| Bromocriptine mesylate | 73.02879 | 52.81481 | 64.08696 | 64.59574 |
| Ropinirole HCl | 69.6036 | 58.68421 | 64.66099 | 65.69517 |
| LY-163,502•2HCl | 73.37074 | 60.97297 | 59.42857 | 66.48606 |
| Dipropyldopamine•HBr | 69.17914 | 74.36364 | 65.5 | 51.82253 |
| B-HT 920•2HCl | 75.67606 | 46.90411 | 64.78571 | 76.23529 |
| Piribedil•2HCl | 61.58491 | 85.76119 | 59.05263 | 59.63793 |
| (+)-UH 232 maleate | 61.9521 | 68 | 71.84615 | 67.26608 |
| Pergolide mesylate | 82.48669 | 69.37255 | 70.66667 | 65.57576 |
| (−)-Quinpirole•HCl | 80.11538 | 73.14851 | 80.53731 | 68.54475 |

TABLE 3-continued

| | Nuclear localization (% of total cells) | | | |
|---|---|---|---|---|
| Compound | IPF-1 | IPF-2 | IPF-3 | IPF-4 |
| R(−)-2,11-dihydroxy-10-methoxyapomorphine•HCl | 85.18283 | 74.66667 | 80.72727 | 80.45283 |

The ability of selected dopamine receptor agonists to inhibit expression of αSMA is shown in Table 4.

TABLE 4

| | αSMA intensity (% of DMSO control) | | | |
|---|---|---|---|---|
| Compound | IPF-1 | IPF-2 | IPF-3 | IPF-4 |
| DMSO | 100 | 100 | 100 | 100 |
| Dihydrexidine•HCl | 4.984838 | 0.04693 | 0.513048 | 12.03436 |
| A-77636•HCl•H$_2$O | 5.808214 | 0.71885 | 0.067655 | 12.42941 |
| R(−)-2,10,11-Trihydroxyaporphine•HBr | 2.887936 | 1.698043 | 7.646467 | 15.9942 |
| (±)-SKF-82958•HBr | 11.77987 | 4.966244 | 2.427766 | 9.32639 |
| A 68930•HCl | 12.40274 | 8.110719 | 3.24542 | 7.350053 |
| R(−)-Propylnorapomorphine•HCl | 5.081187 | 1.878811 | 5.560538 | 19.95755 |
| CY 208-243 | 21.01121 | 2.279688 | 2.610795 | 9.642782 |
| R(+)-6-bromo-APB•HBr | 11.25082 | 2.507086 | 0.850571 | 22.81622 |
| R(−)-2,10,11-Trihydroxy-N-propyl-noraporphine•HBr | 4.894616 | 8.436081 | 2.988195 | 25.60956 |
| (R)-(−)-Apomorphine•HCl | 7.067375 | 1.172584 | 0.961841 | 33.67351 |
| 6,7-ADTN•HBr | 37.14071 | 4.182238 | 9.908606 | 4.887935 |
| Dopamine•HCl | 35.24978 | 8.085496 | 26.56503 | 5.368141 |
| N-Methyldopamine•HCl | 43.19963 | 17.66949 | 28.99207 | 14.65662 |
| SKF 38393•HBr | 37.06277 | 26.81876 | 31.24847 | 20.7973 |
| Mesulergine•HCl | 35.50719 | 23.27498 | 40.01858 | 19.75155 |
| Dipropyldopamine•HBr | 48.72246 | 28.11431 | 40.33584 | 25.85713 |
| Bromocriptine mesylate | 54.0785 | 53.62163 | 61.14226 | 34.0979 |
| Pergolide mesylate | 65.01308 | 51.5948 | 63.61159 | 48.1321 |
| (±)-2-(N-phenylethyl-N-propyl)amino-5-hydroxytetralin•HCl | 65.43466 | 52.77428 | 60.4844 | 51.10147 |
| Piribedil•2HCl | 70.43668 | 61.52793 | 71.47113 | 41.19743 |
| Cabergoline | 76.91545 | 48.07228 | 77.14592 | 45.8402 |
| Fenoldopam•HCl | 77.33538 | 45.27138 | 69.40569 | 63.35173 |
| B-HT 920•2HCl | 74.97842 | 58.97091 | 70.11813 | 54.23016 |
| Ropinirole HCl | 72.18286 | 53.45179 | 78.99604 | 61.9799 |
| PD 168077 maleate | 75.26704 | 56.14917 | 75.76791 | 66.49739 |
| (+)-UH 232 maleate | 82.91486 | 63.85248 | 85.81355 | 65.71164 |
| LY-163,502•2HCl | 88.98983 | 72.85814 | 75.30018 | 86.7894 |
| (−)-Quinpirole•HCl | 84.60746 | 67.1295 | 85.40936 | 95.1307 |
| Pramipexole Dihydrochloride Monohydrate | 87.61601 | 73.21711 | 82.7588 | 89.93775 |
| (±)-PD 128,907•HCl | 83.67743 | 85.45062 | 94.2538 | 75.15364 |
| R(−)-2,11-dihydroxy-10-methoxyapomorphine•HCl | 91.84016 | 92.79975 | 81.85245 | 85.60691 |
| 3-Hydroxyphenethylamine•HCl | 88.58294 | 96.744 | 82.62473 | 99.8315 |
| 4-Hydroxyphenethylamine•HCl | 99.7156 | 93.43022 | 95.69317 | 88.2748 |

Figure 11:
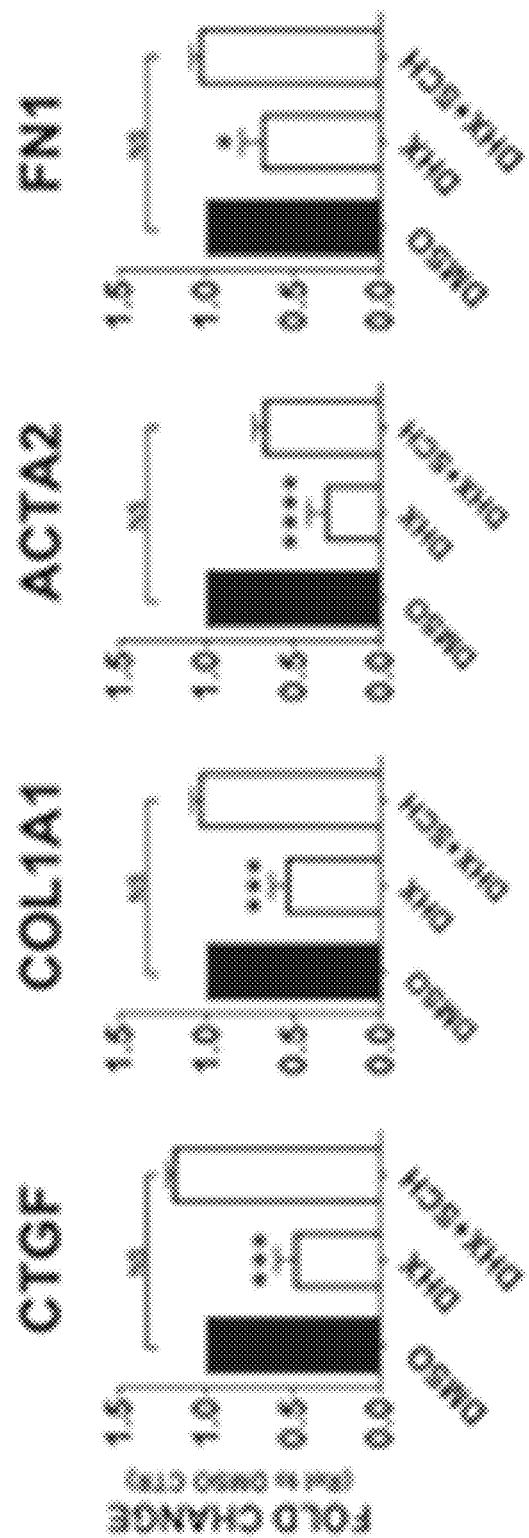
FIG. 11 shows that D1 agonist (e.g., DHX) reverses fibroblast matrix deposition, contraction and stiffening. DHX blocks profibrotic gene expression in IPF patient-derived fibroblasts. Genes which encode Connective tissue growth factor (CTGF), Collagen I (COL1A1), αSMA (ACTA2), and Fibronectin (FN1) are reduced by 24 hour treatment with DHX (10 µM), +/−SCH 39166 (3 µM). N=3 (**p<0.0001, *p<0.001, *p<0.05 vs. 0.1% DMSO vehicle control)
Figure 12:
FIG. 12 shows that D1 agonist (e.g., DHX) reverses TGFβ-induced αSMA+ stress fiber formation. IMR-90 cells pre-stimulated with 2 ng/mL TGFβ for 48 hours and then treated with DHX (10 µM)+2 ng/mL TGFβ for an additional 24 hours prior to fixation. Cells which are positive for αSMA were quantified by a blinded investigator and noted in the bottom right corner, a minimum of 300 cells in each experiment were quantified. N=3.
Figure 13:
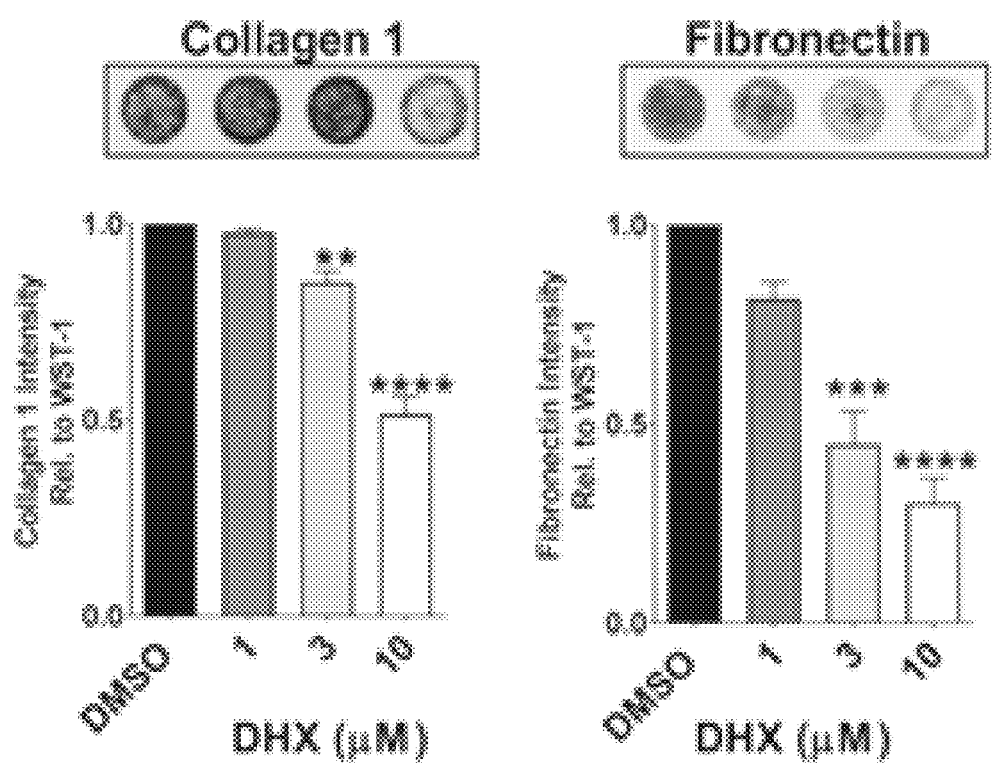
FIG. 13 shows that D1 agonist (e.g., DHX) reverses TGFβ-induced extracellular matrix accumulation. IPF patient-derived fibroblasts grown at confluence were pre-stimulated with 2 ng/mL TGFβ for 48 hours and then treated with DHX (10 µM)+2 ng/mL TGFβ for an additional 24 hours prior to fixation. Cell derived matrix is measured using antibodies for Collagen I and Fibronectin. N=3 (**p<0.0001, *p<0.001, p<0.01 vs. 0.1% DMSO vehicle control)
Figure 14:
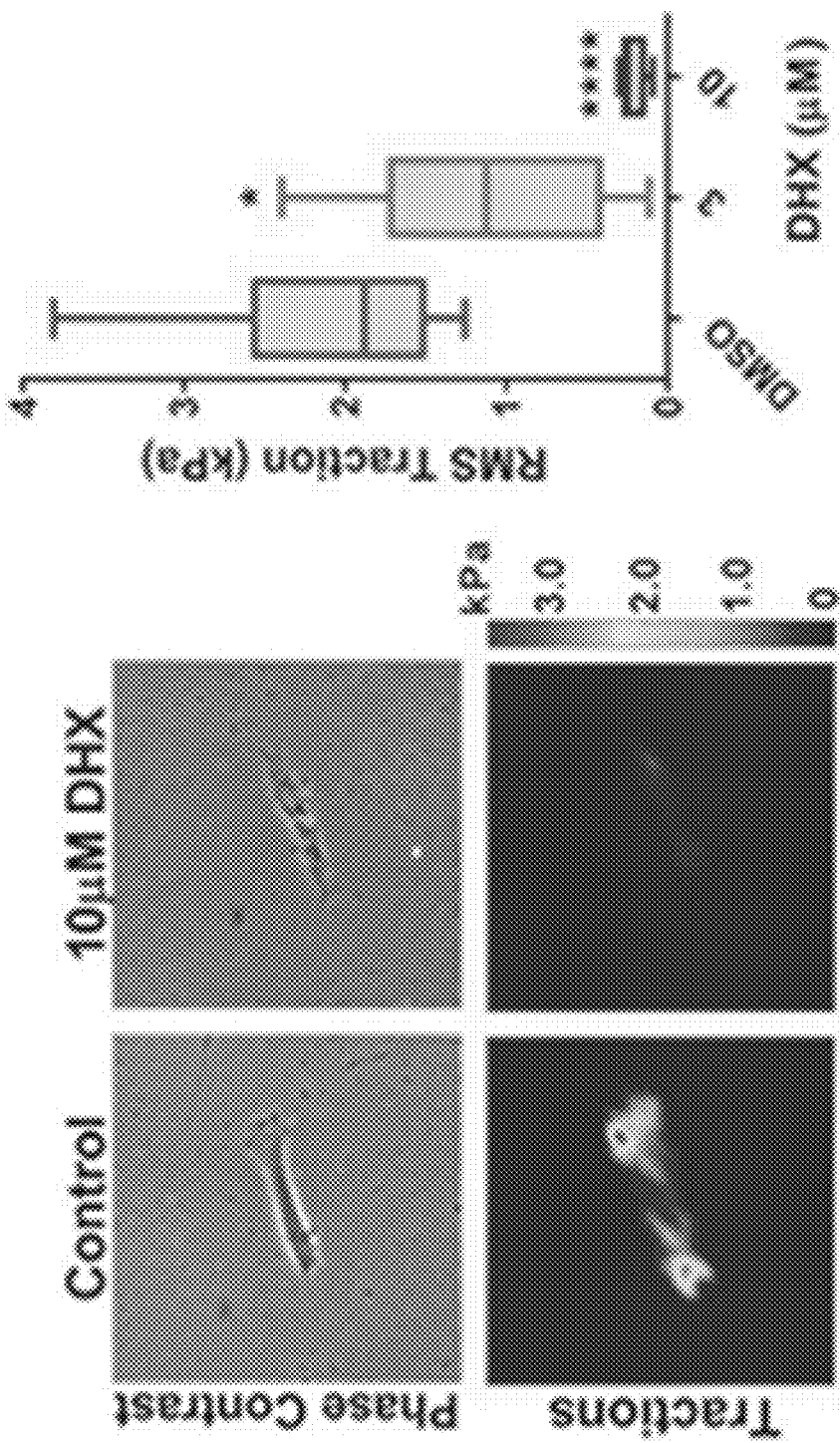
FIG. 14 shows that D1 agonist (e.g., DHX) attenuates IPF patient-derived fibroblast contractility measured by traction force microscopy. Representative traction maps are shown from cells plated onto 6.4 kPa matrices treated with the indicated concentration of DHX. RMS tractions were determined in two independent experiments; box and whisker plots show min to max, quartile, and mean from one representative experiment (**p<0.0001, *p<0.05 vs. 0.1% DMSO vehicle control).
Figure 27:
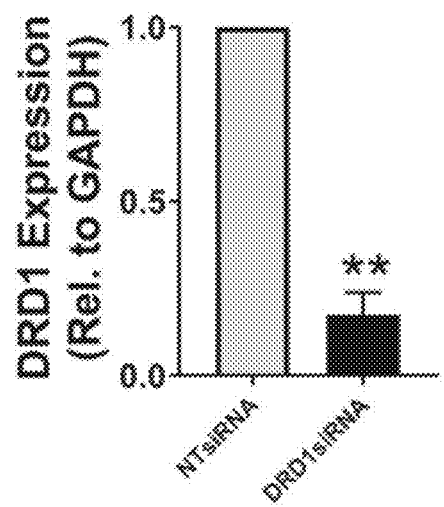
FIG. 27 shows that D1 agonist (e.g., DHX) inhibits pro-fibrotic gene expression through DRD1 agonism. siRNA treatment to knockdown DRD1.
Figure 28:
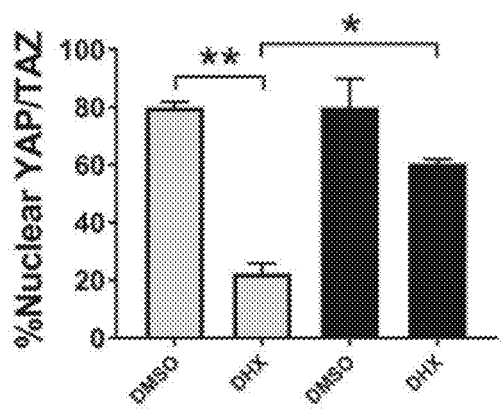
FIG. 28 shows reduced D1 agonist (e.g., DHX)-mediated inhibition of YAP/TAZ nuclear localization and pro-fibrotic gene expression in DRD1-siRNA treated cells. IMR-90 cells transfected with siRNA targeting DRD1 or NT siRNA for 72 hours prior to 2 hour (b) or 24 hour (c) treatment with DHX. N=2 for all (**$p<0.0001$, $p<0.01$, *$p<0.05$ vs. NTsiRNA).
Figure 28:
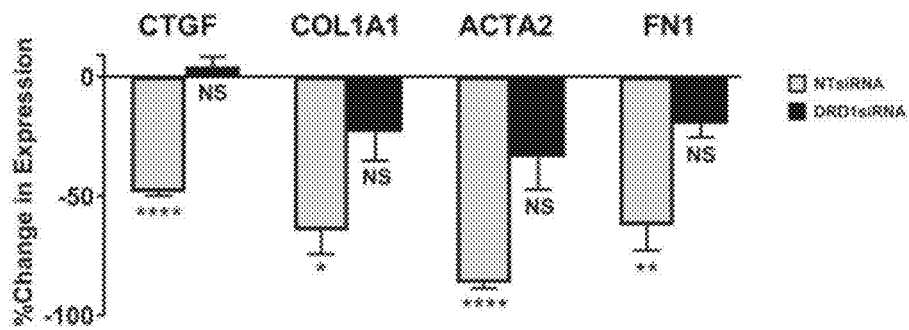
Figure 29:
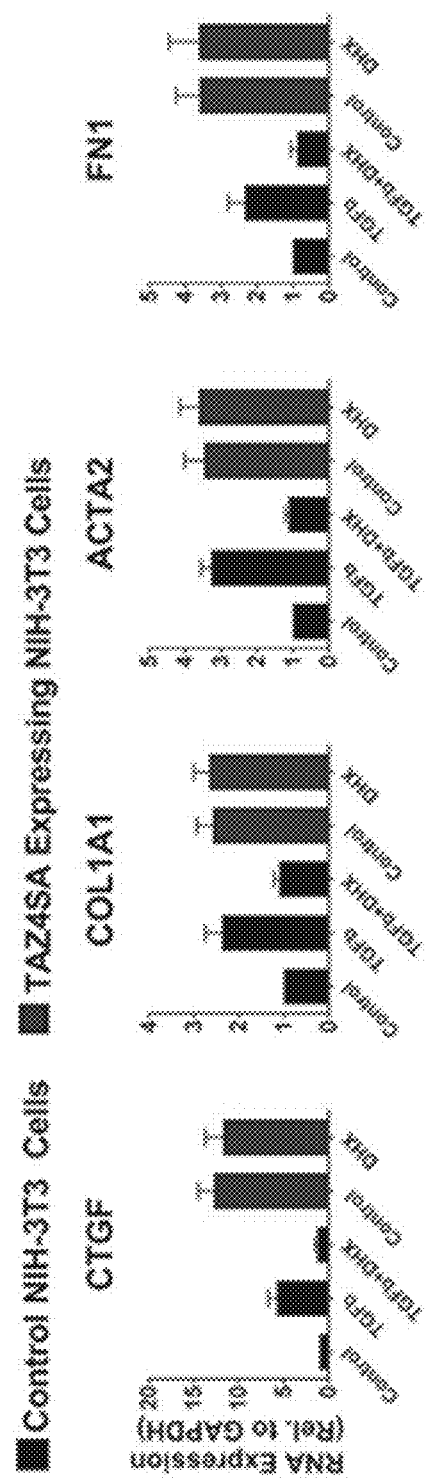
FIG. 29 shows that D1 agonist (e.g., DHX) inhibition of pro-fibrotic gene expression and matrix deposition requires inhibition of YAP/TAZ. DHX does not inhibit pro-fibrotic gene expression when fibroblasts express a constitutively active mutant TAZ (TAZ4SA). TAZ4SA expression was induced with 100 ng/mL doxycycline for 72 hours prior to treatment with 10 μM or the indicated concentration of dihydrexidine. For gene expression experiments efficacy of DHX in NIH-3T3 cells was validated with by DHX (10 μM) effect on TGFβ (24 hour, 2 ng/mL) induced gene expression. N=2 for all.
Figure 30:
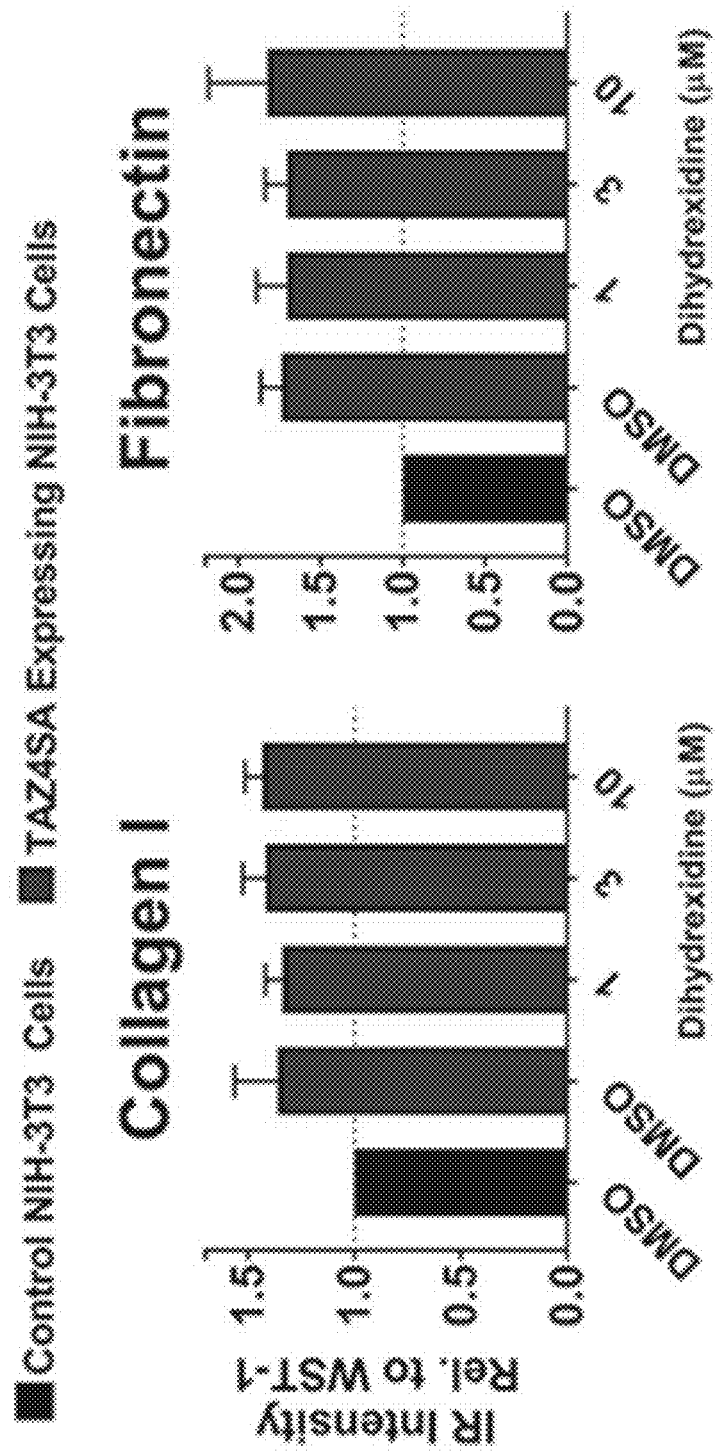
FIG. 30 shows that D1 agonist (e.g., DHX) inhibition of pro-fibrotic gene expression and matrix deposition requires inhibition of YAP/TAZ. DHX does not inhibit ECM deposition when fibroblasts express a constitutively active mutant TAZ (TAZ4SA). TAZ4SA expression was induced with 100 ng/mL doxycycline for 72 hours prior to treatment with 10 μM or the indicated concentration of dihydrexidine. For gene expression experiments efficacy of DHX in NIH-3T3 cells was validated with by DHX (10 μM) effect on TGFβ (24 hour, 2 ng/mL) induced gene expression. N=2 for all.
Figure 31:
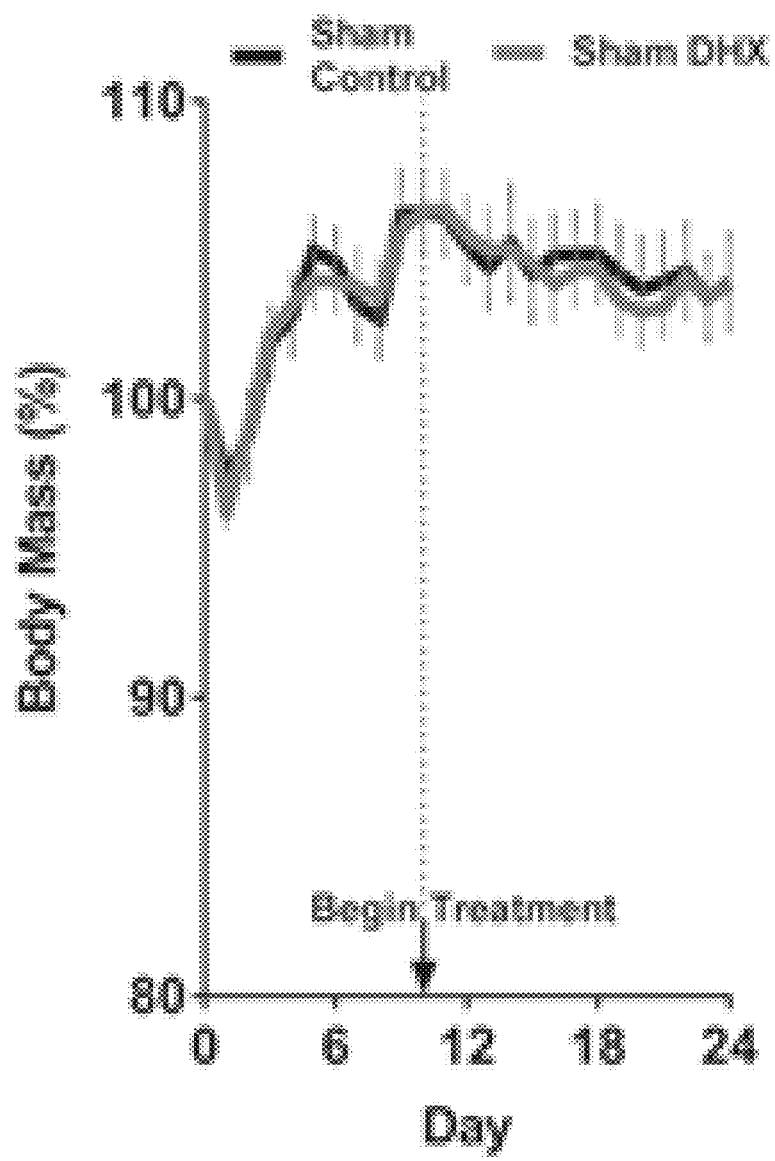
FIG. 31 shows that D1 agonist (e.g., DHX) alone does not affect lung matrix content or profibrotic gene expression. In normal healthy mice DHX did not alter body weight. n=6 mice per group.
Figure 32:
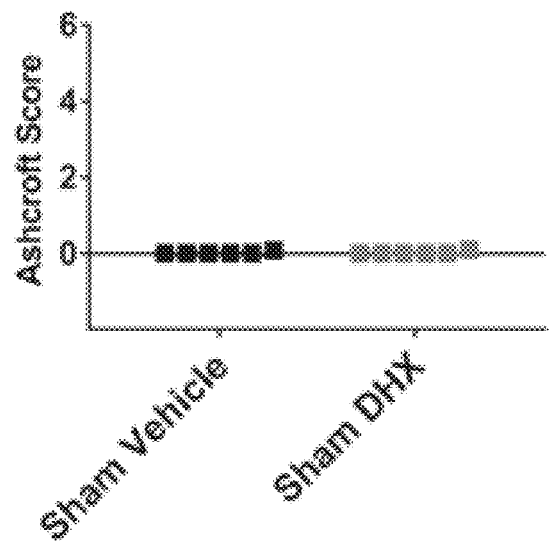
FIG. 32 shows that in normal healthy mice D1 agonist (e.g., DHX) did not alter lung histology n=6 mice per group.
Figure 33:
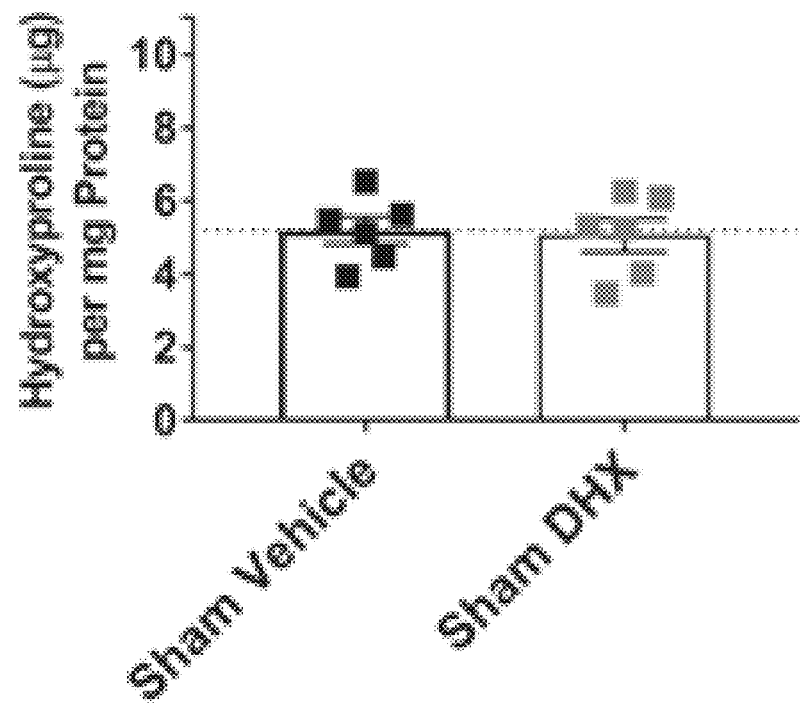
FIG. 33 shows that in normal healthy mice D1 agonist (e.g., DHX) did not alter lung collagen deposition. n=6 mice per group.
Figure 34:
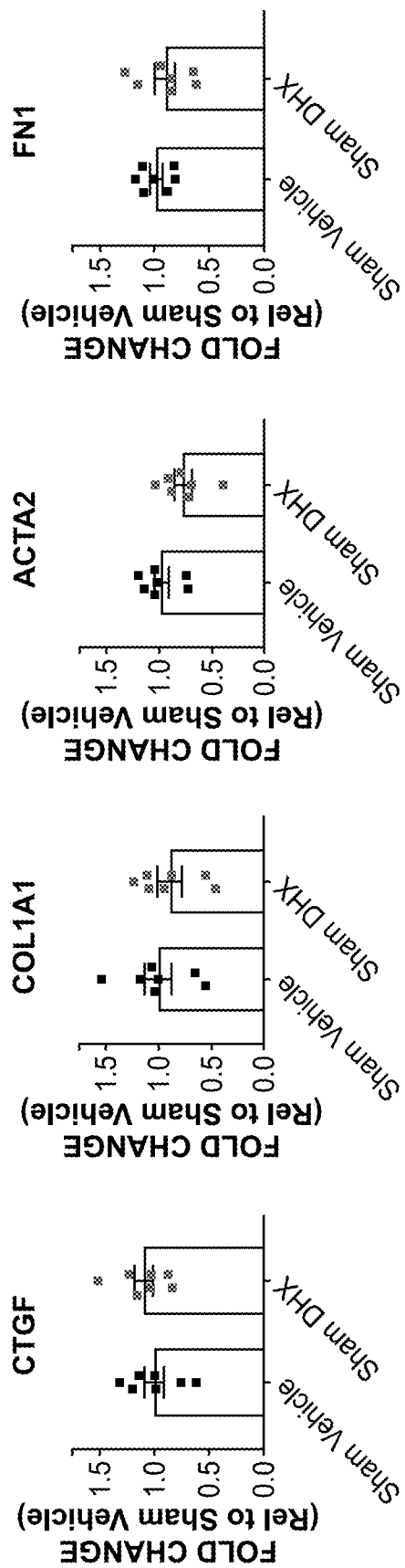
FIG. 34 shows that in normal healthy mice D1 agonist (e.g., DHX) did not alter expression of Ctgf, Col1a1, Acta2, and Fn1. n=6 mice per group.
Figure 35:
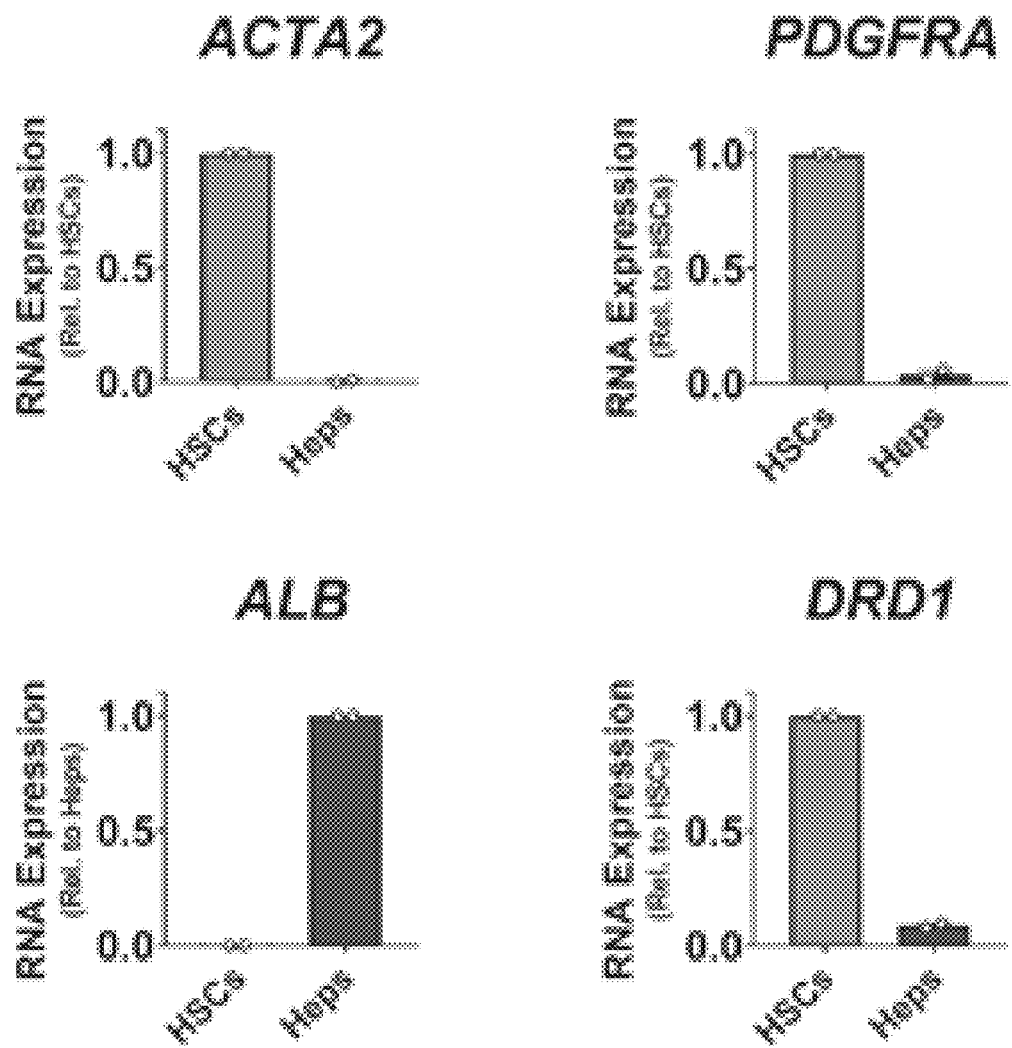
FIG. 35 shows that D1 agonist (e.g., DHX) reverses hepatic stellate cell activation and in vivo hepatic fibrosis. DRD1 is preferentially expressed in cultured human hepatic stellate cells (HSCs): ACTA2, PDGFRA positive, relative to cultured human hepatocytes (Heps): ALB positive. N=1.
Figure 36:
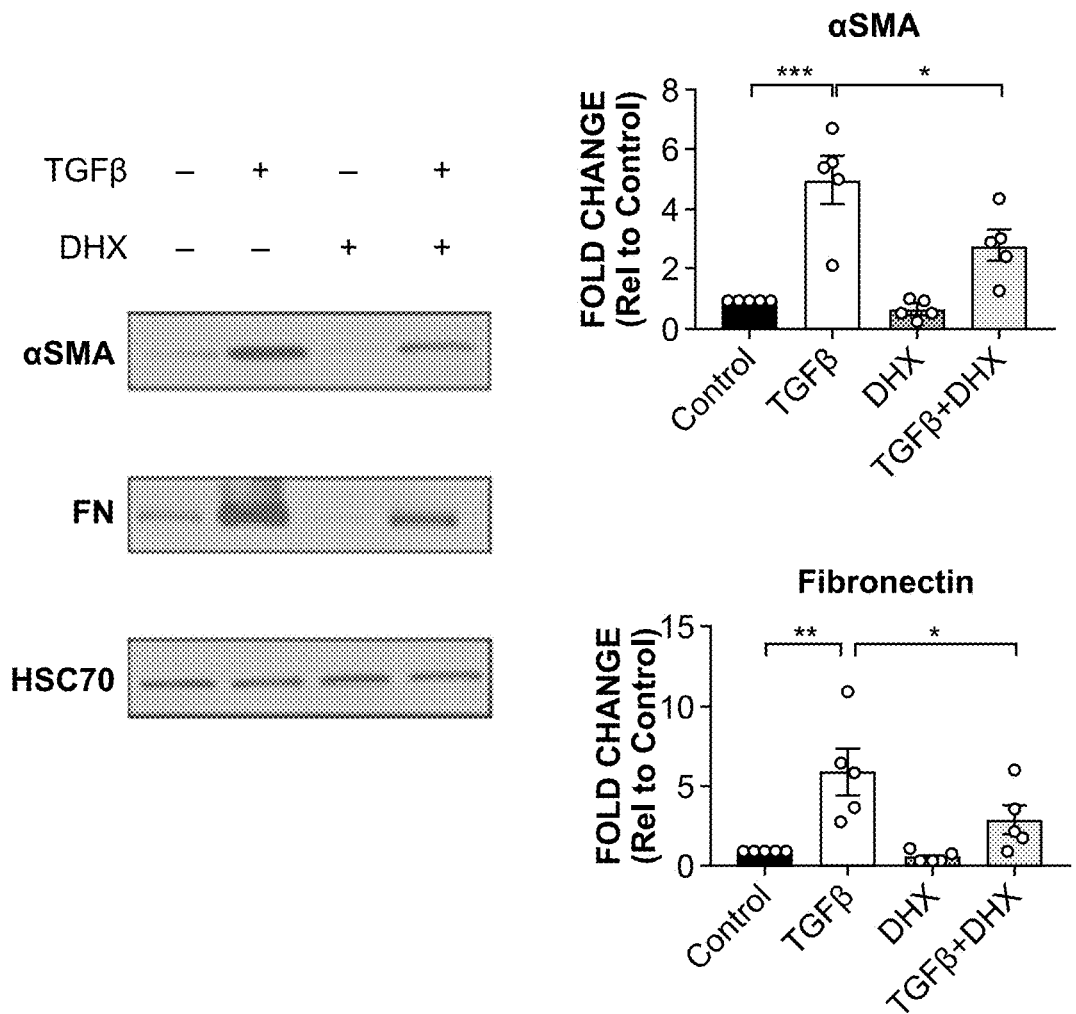
FIG. 36 shows that D1 agonist (e.g., DHX) inhibits TGFβ-mediated hepatic stellate cell activation in vitro. HSCs were stimulated with TGFβ for 48 hours+/−DHX (10 μM) prior to total protein isolation and western blot analysis of αSMA and Fibronectin. N=3 (*$p<0.001$, $p<0.01$, *$p<0.05$ vs. Control+TGFβ).
Figure 37:
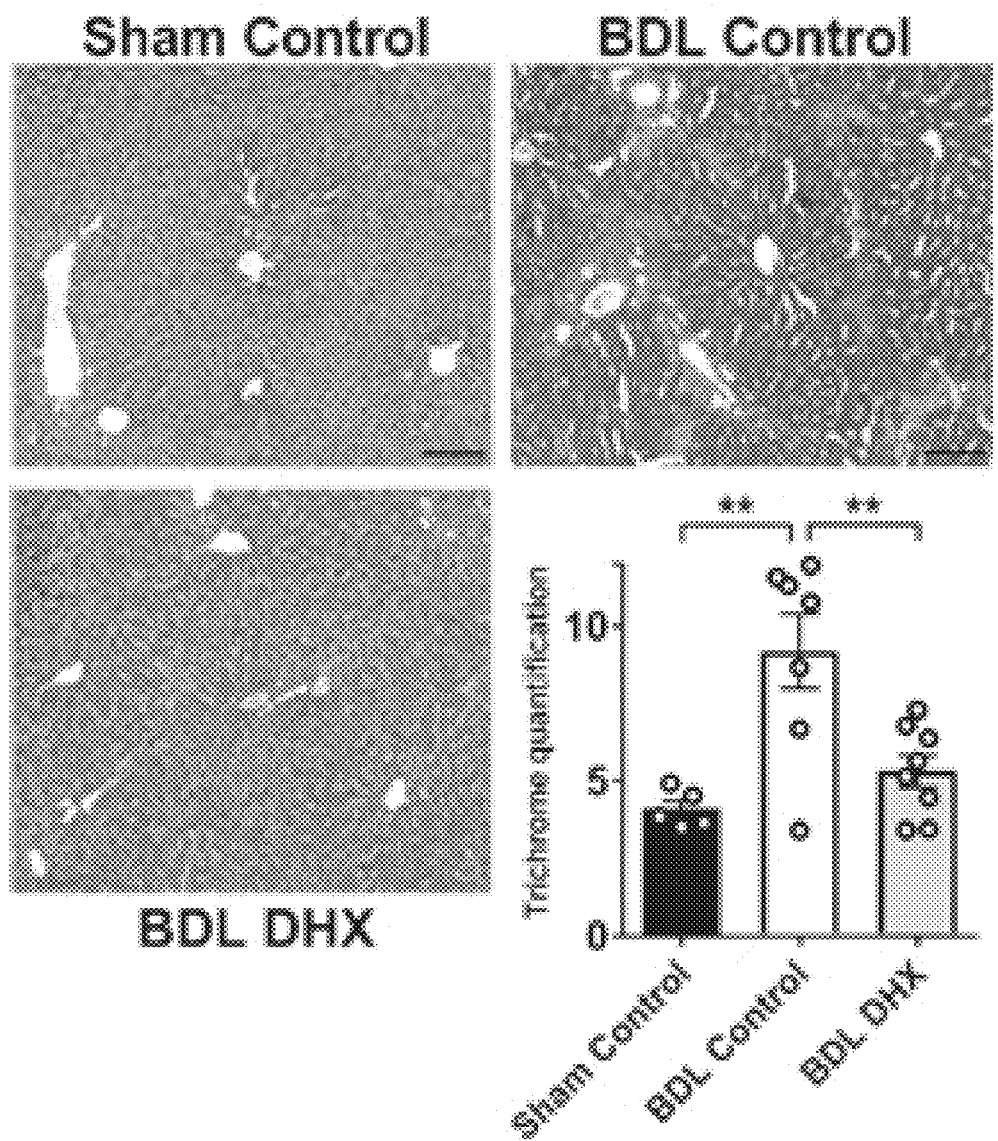
FIG. 37 shows that D1 agonist (e.g., DHX) reverses bile duct ligation (BDL)-mediated fibrosis in vivo measured by trichrome staining. Sham Control N=5, BDL Control N=7, and BDL DHX N=8 (**$p<0.01$ vs. BDL Control).
Figure 38:
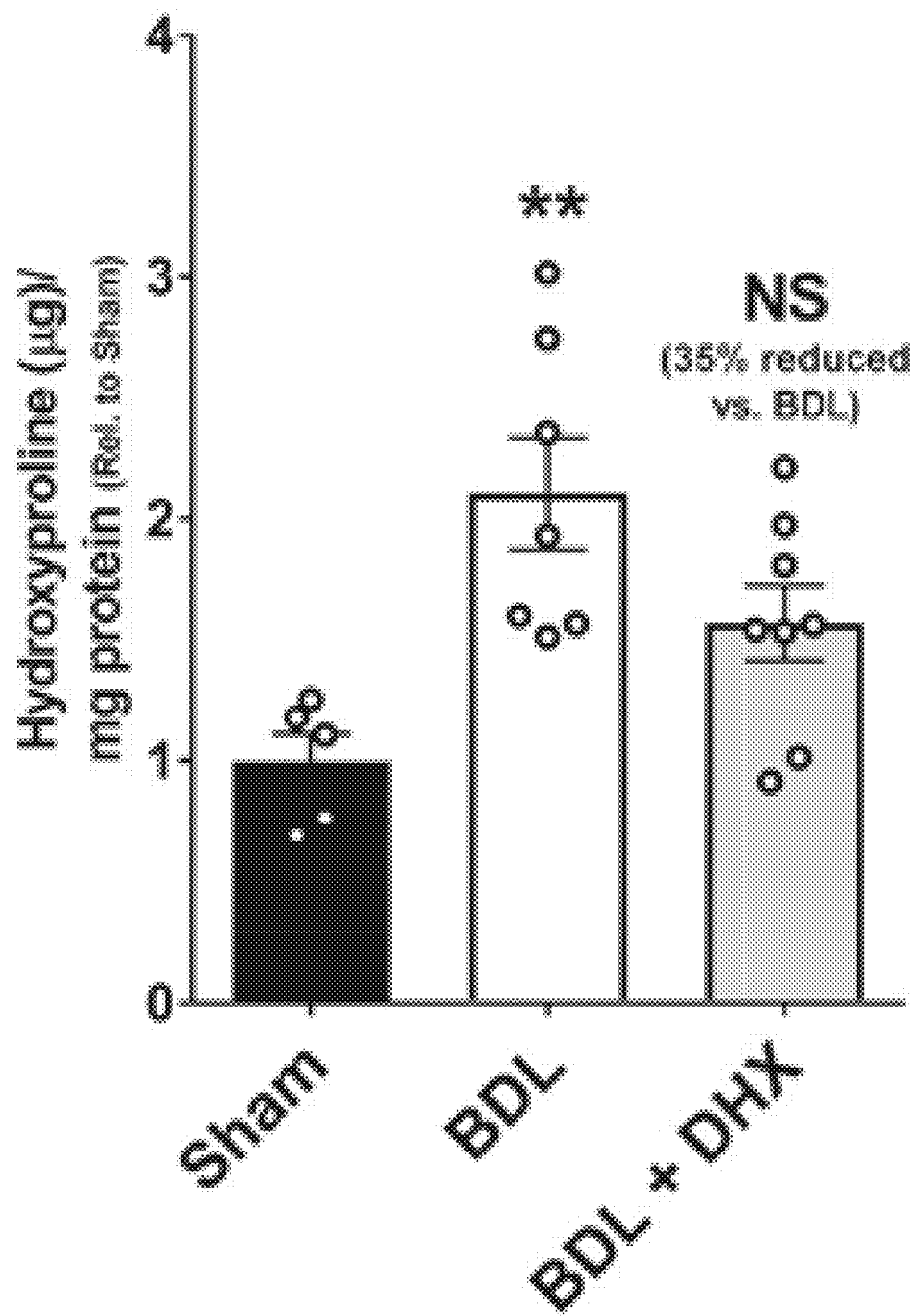
FIG. 38 shows that D1 agonist (e.g., DHX) reverses Bile duct ligation (BDL) mediated fibrosis in vivo measured by hydroxyproline. Sham Control N=5, BDL Control N=7, and BDL DHX N=8 (**$p<0.01$ vs. BDL Control).
Figure 39:
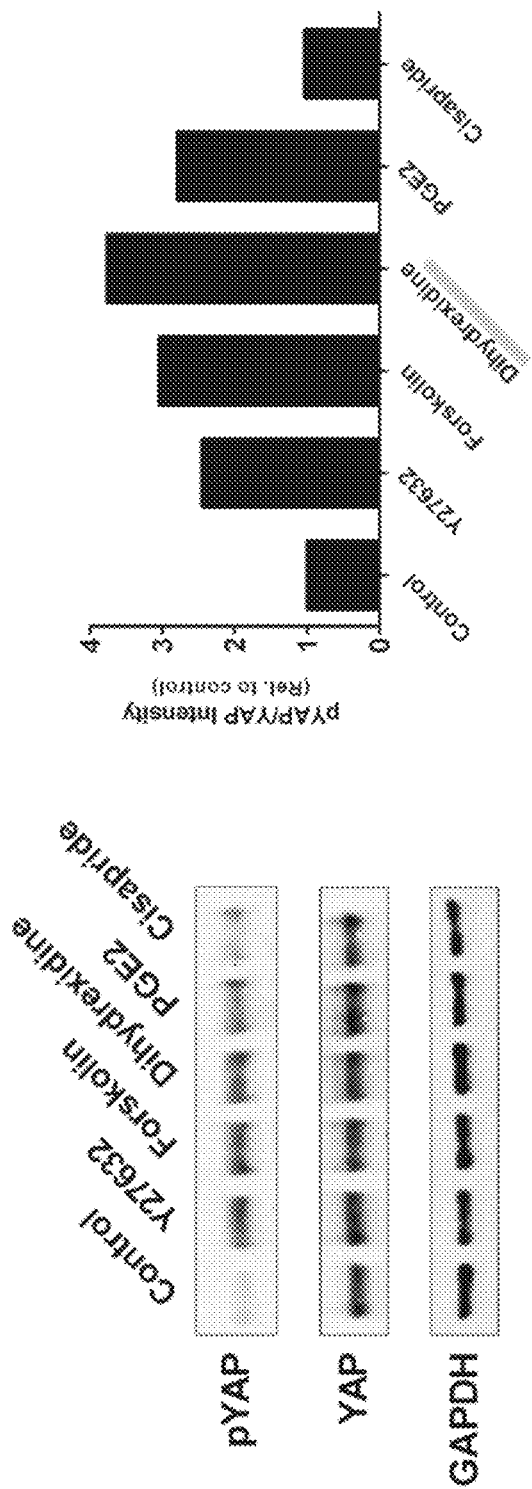
FIG. 39 shows that YAP phosphorylation blocks nuclear localization of pYAP.
Figure 40:
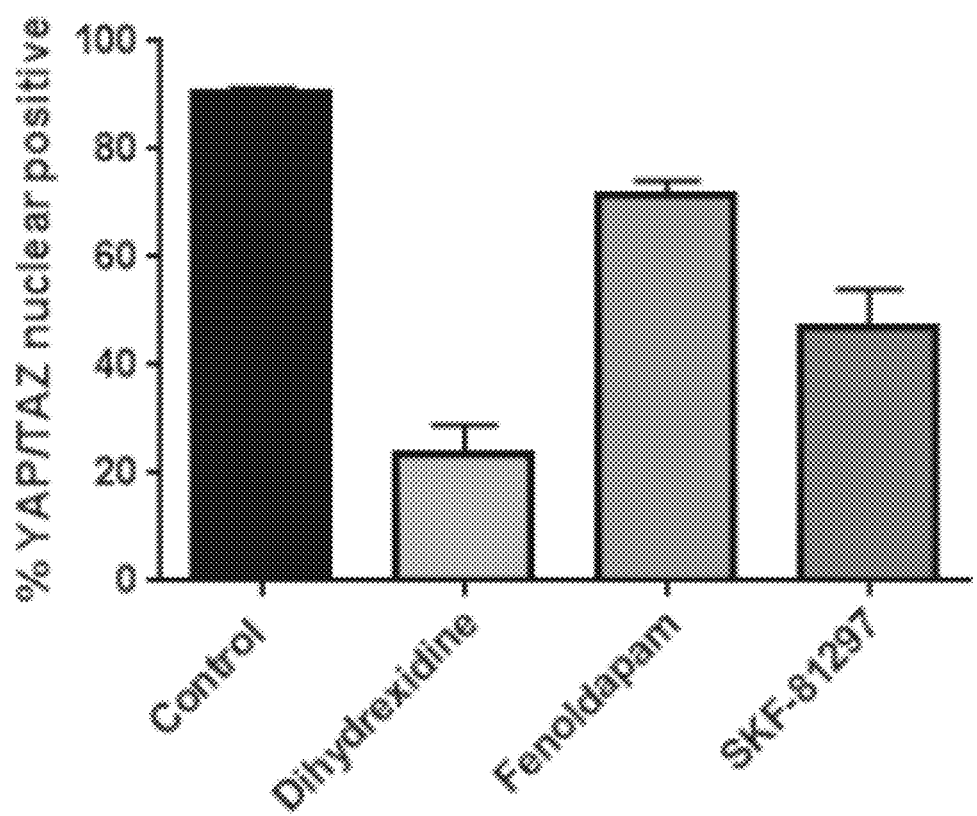
FIG. 40 shows that D1 receptor agonists targeting the same receptor and having diverse structures produce similar effect.
Figure 41:
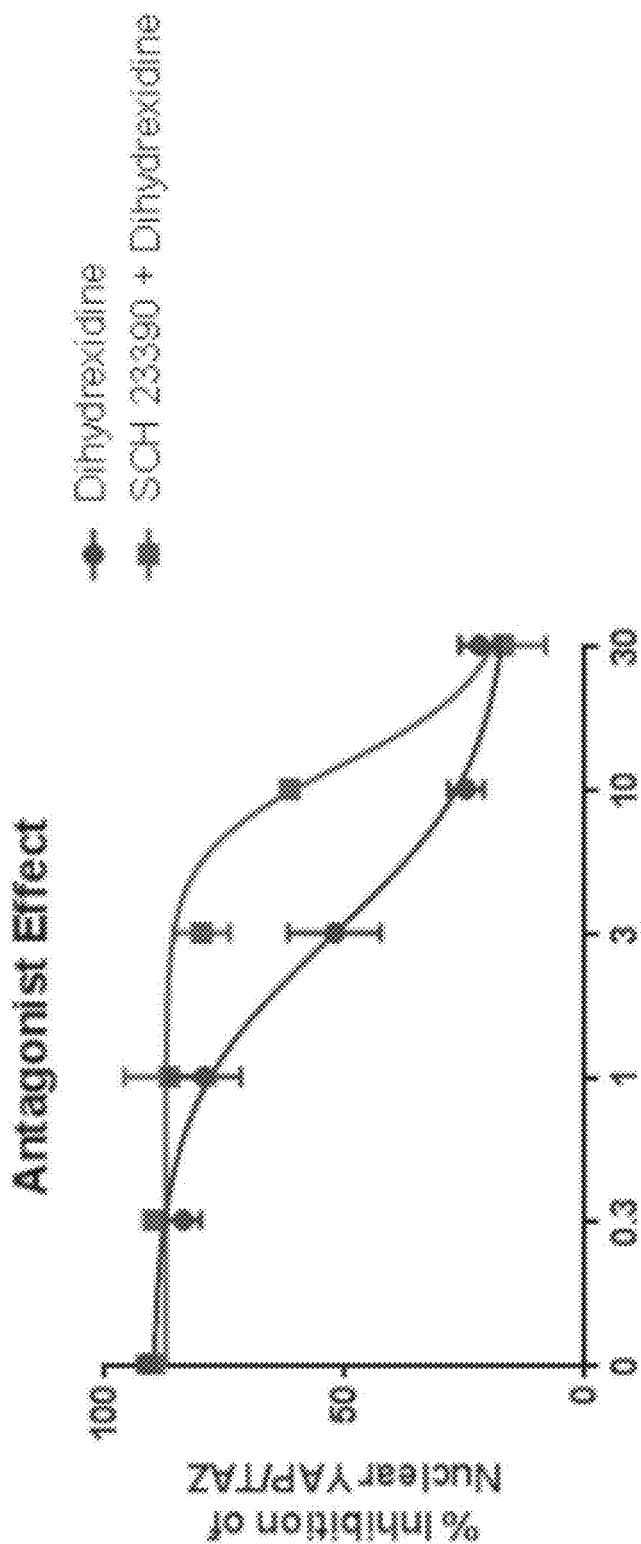
FIG. 41 shows that YAP inactivation by D1 agonist (e.g., DHX) are based on D1 receptor activity.
Figure 42:
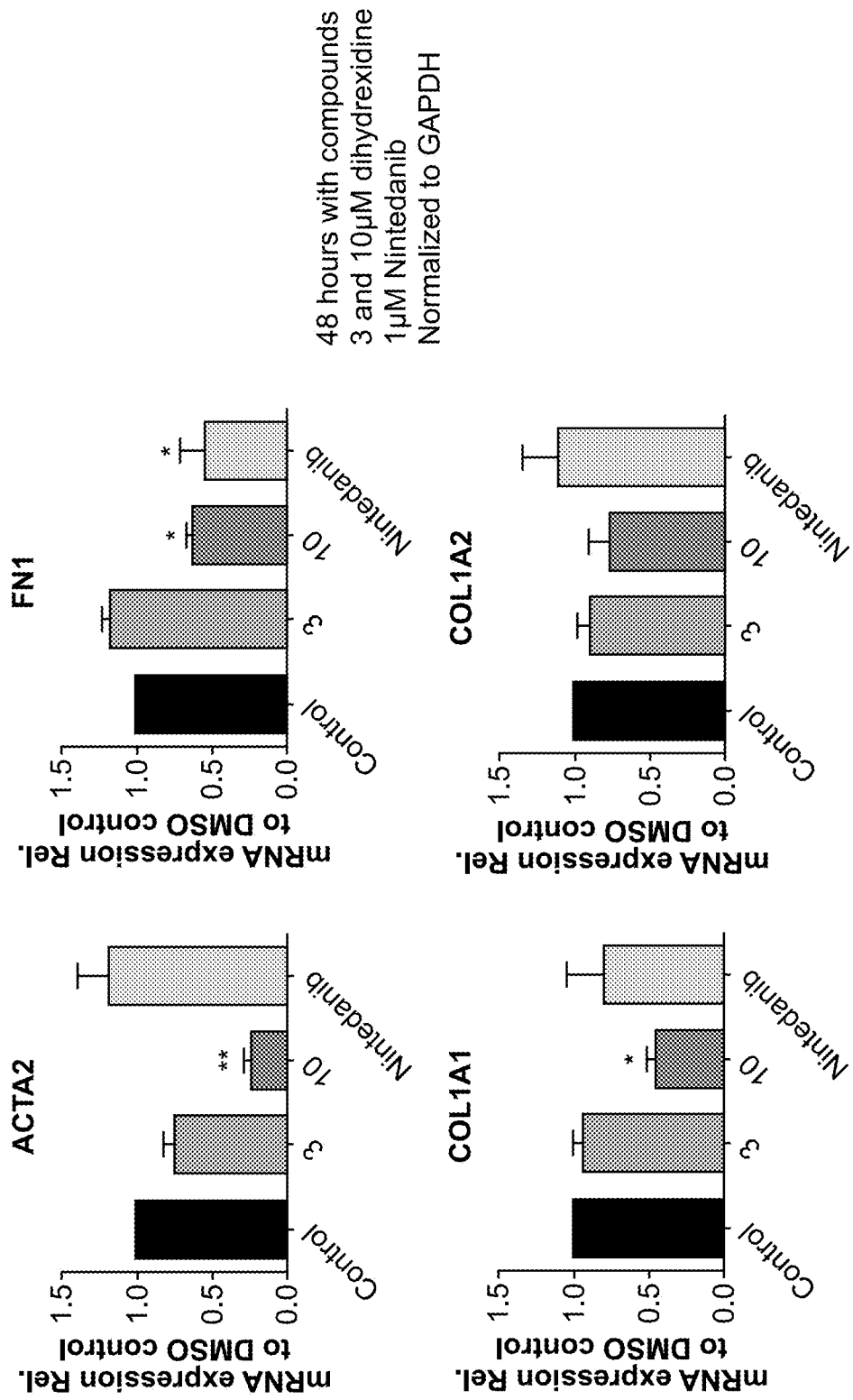
FIG. 42 shows that D1 receptor agonist reduces expression of multiple profibrotic genes in fibroblasts from patients with IPF.
Figure 43:
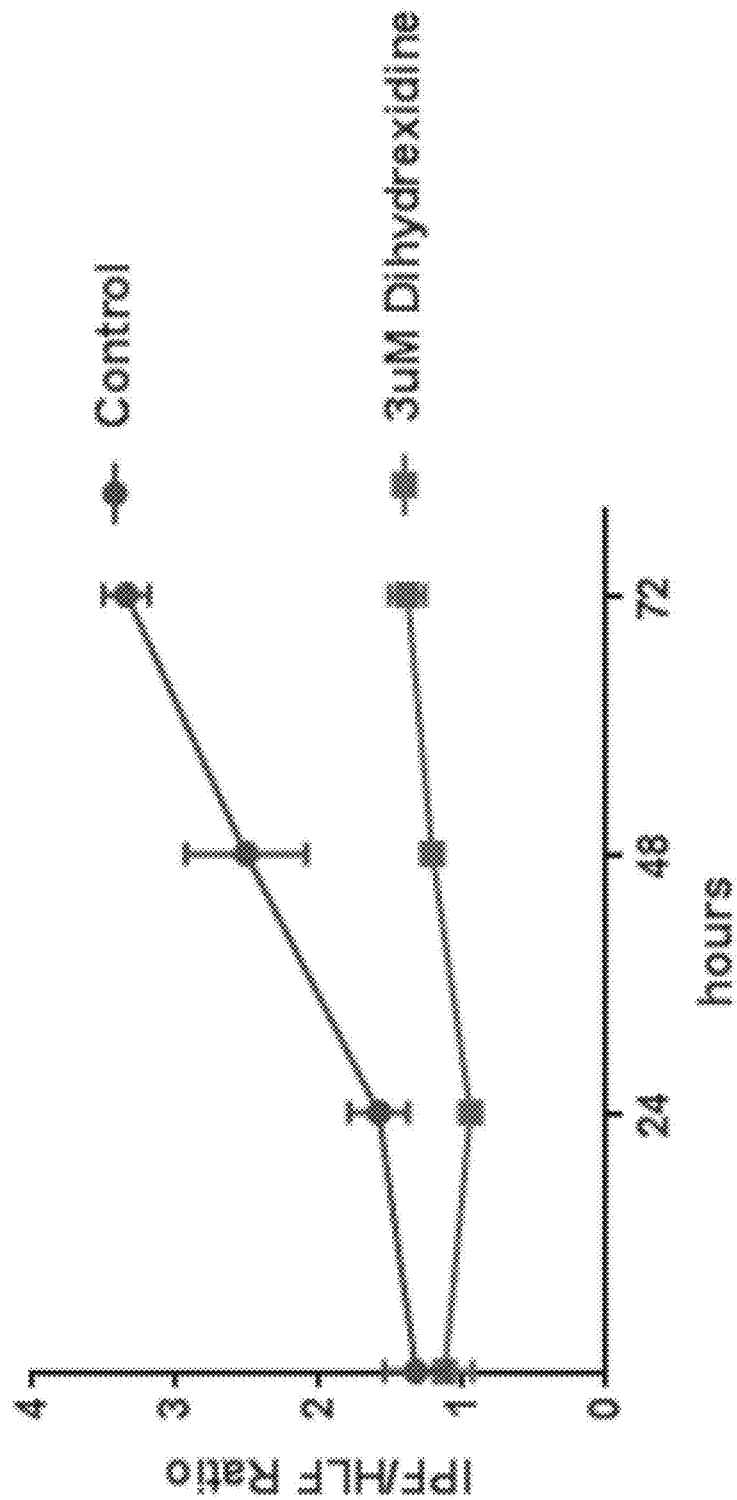
FIG. 43 shows that D1 receptor agonist (e.g., DHX) selectively slows proliferation in IPF fibroblasts. IPF fibroblast and Normal lung fibroblast co-culture proliferation. Cell are prelabelled with fluorescent dyes (red and green) and then cocultured at a ratio of about 1:1 in 96 well plates. Cell counts are determined every 24 hours and plotted as a ratio of IPF/HLF cells. In the control wells the IPF cells outgrow and take over the well. N=2.
Figure 44:
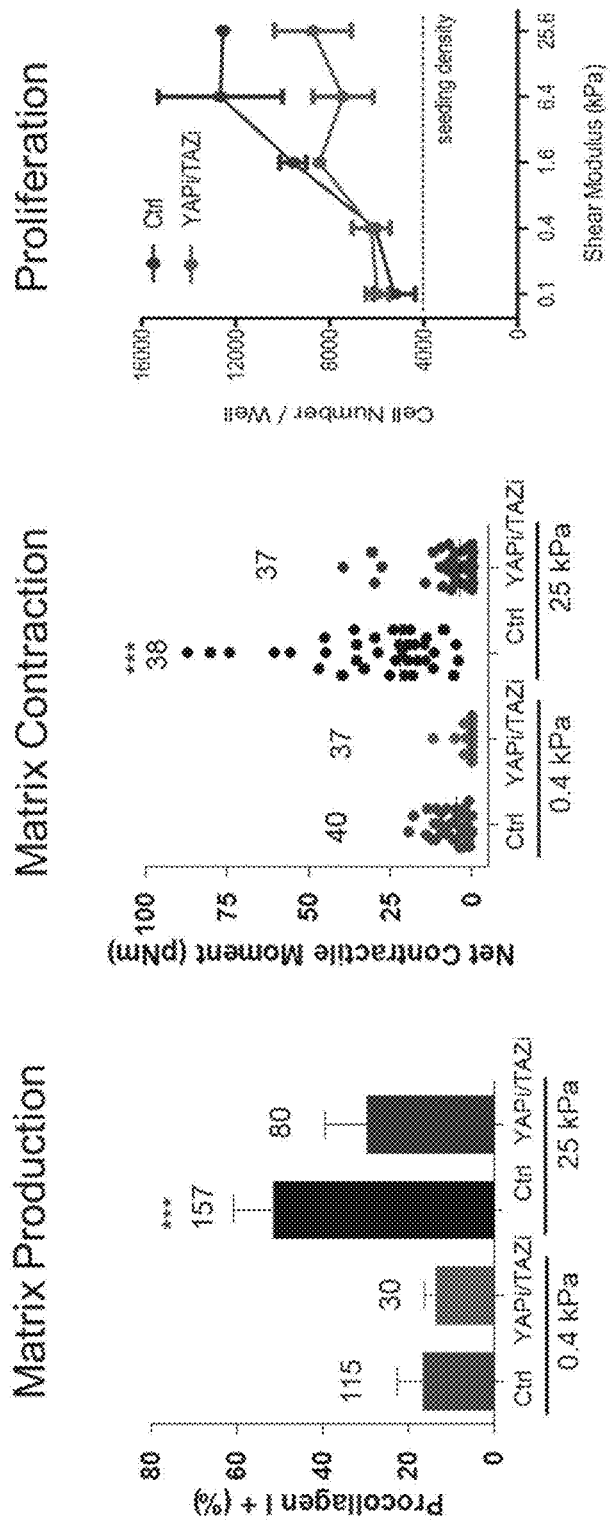
FIG. 44 shows that YAP/TAZ are necessary for matrix stiffness-dependent fibroblast activation.
Figure 45:
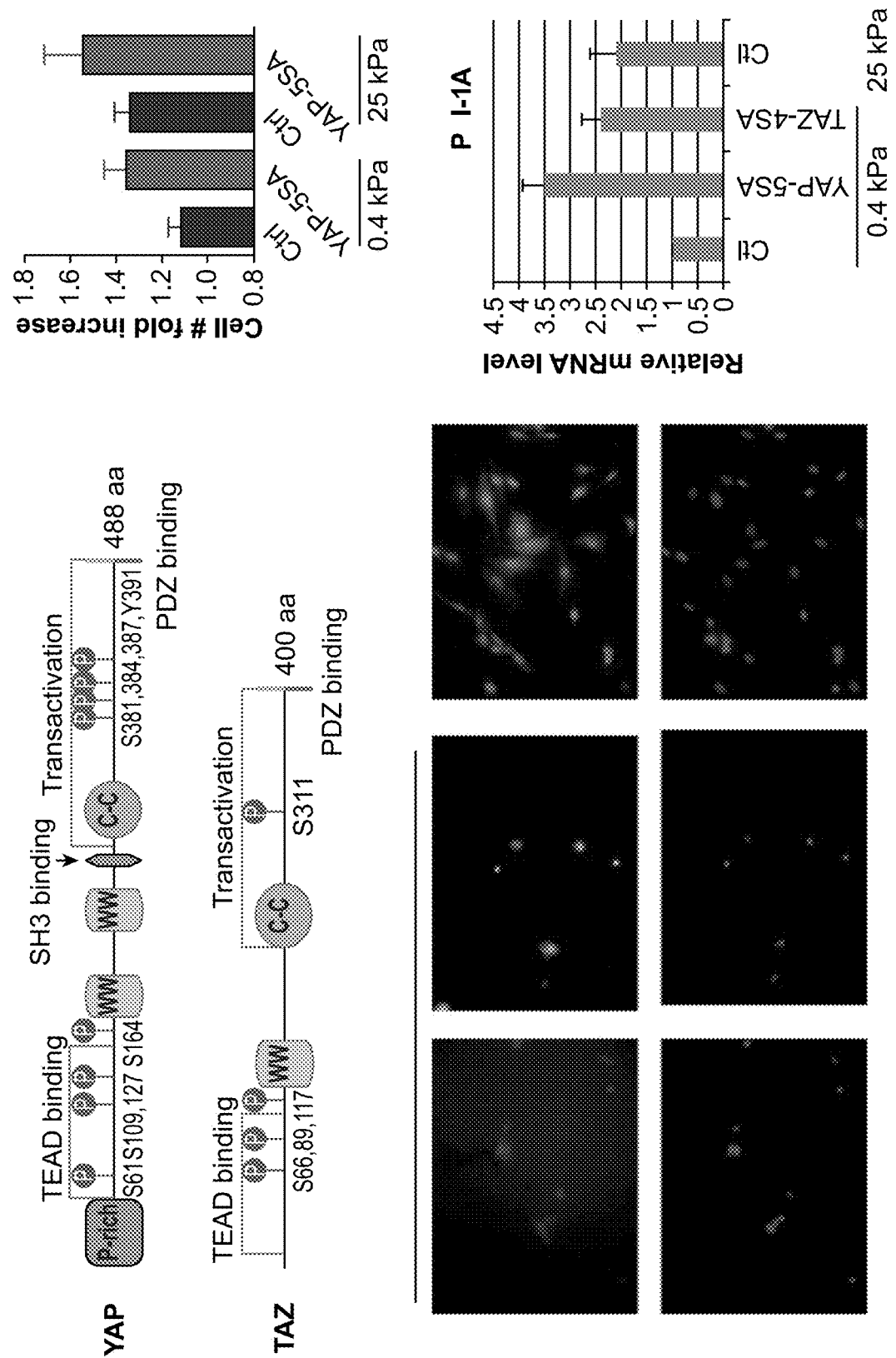
FIG. 45 shows that mutant YAP/TAZ are active on soft matrices in NIH 3T3 fibroblasts.
Figure 46:
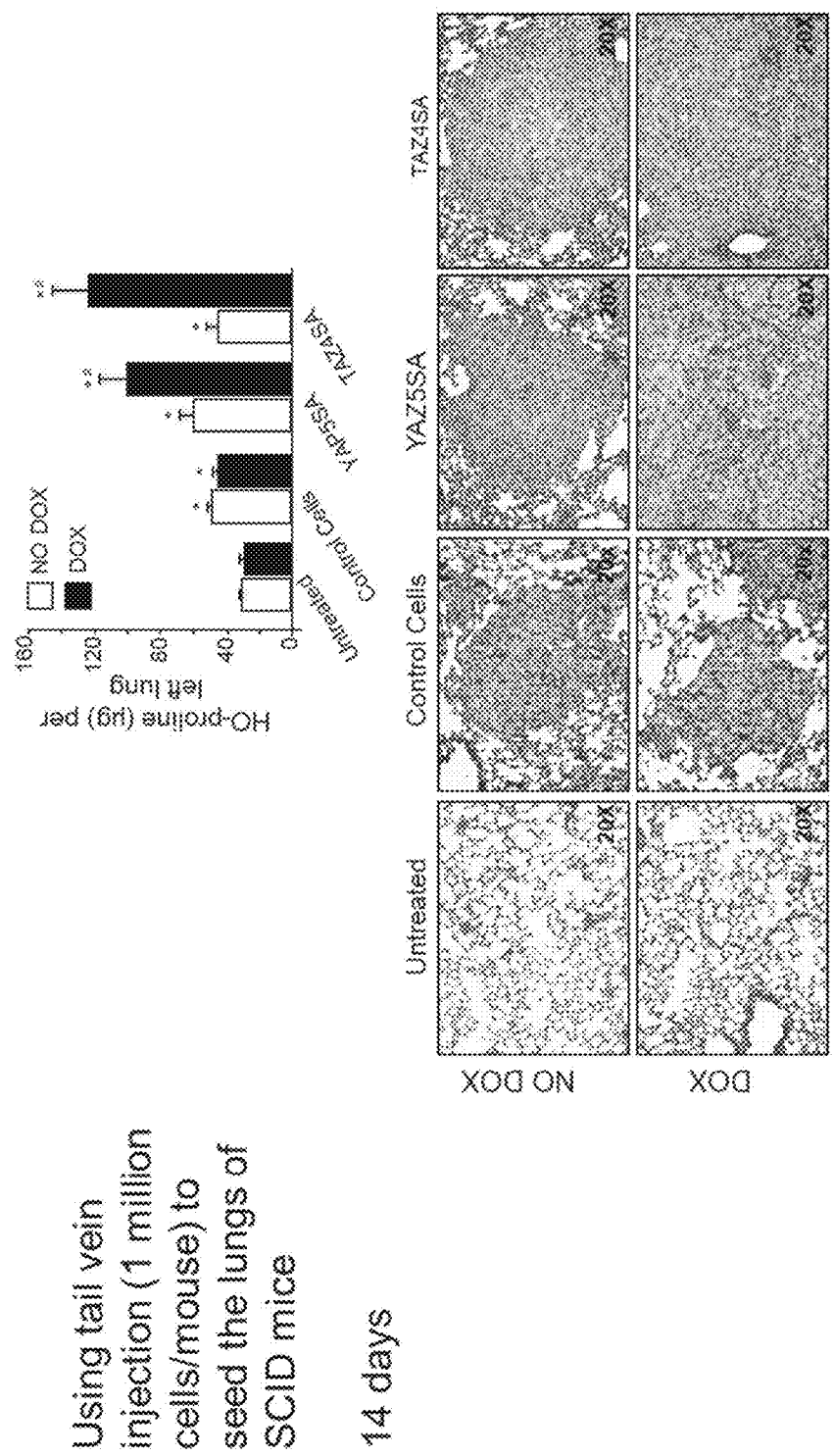
FIG. 46 shows that YAP/TAZ confer fibrogenic potential in vivo.
Figure 47:
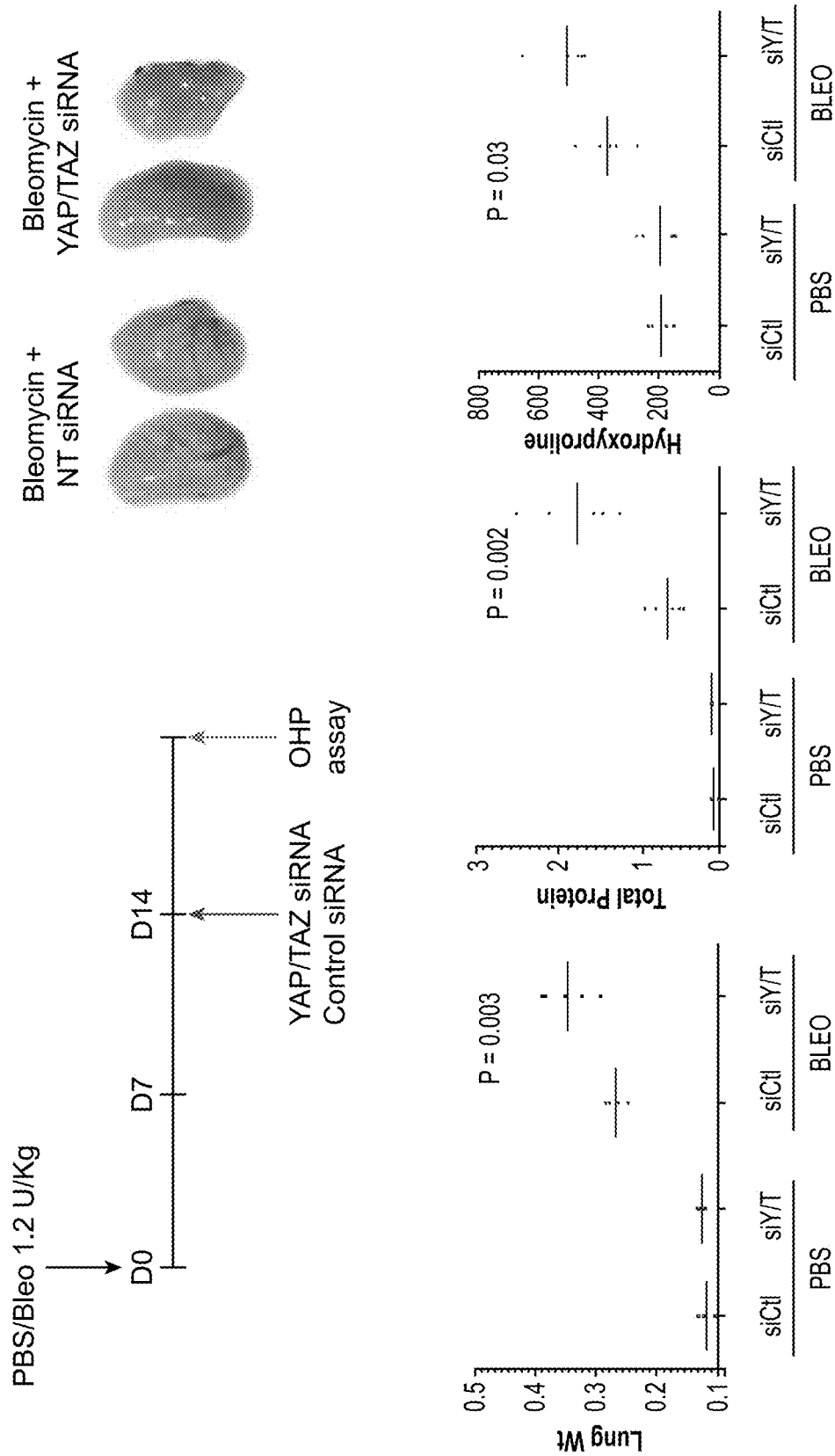
FIG. 47 shows that global YAP/TAZ targeting is not viable.
Figure 48:
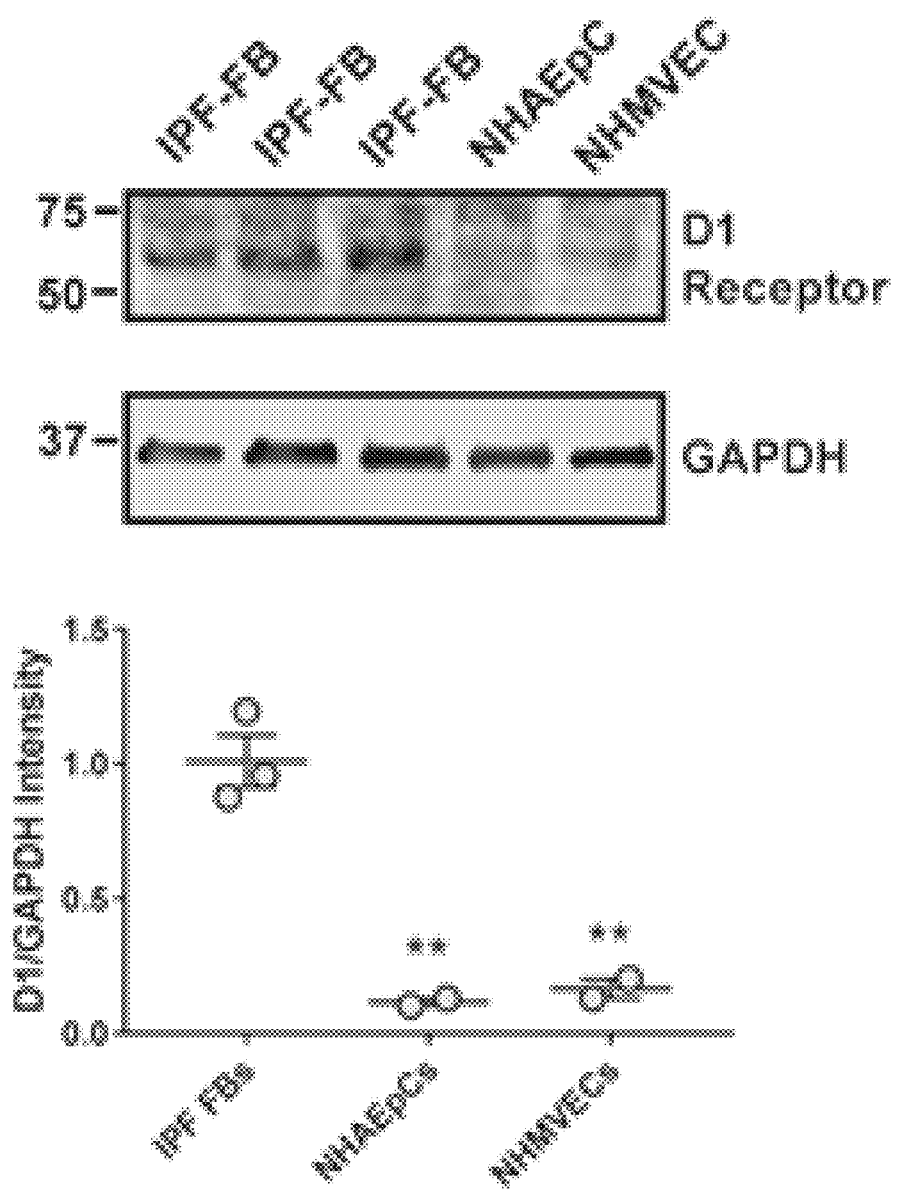
FIG. 48 shows Western blot protein expression of the D1 dopamine receptor from IPF patient derived fibroblasts, normal human alveolar epithelial cells (NHAEpC), and normal human microvasculature endothelial cells. NHAEpC and NHMVEC, N=2. non-IPF FB and IPF FB, N=3 different donor lines.
Figure 49:
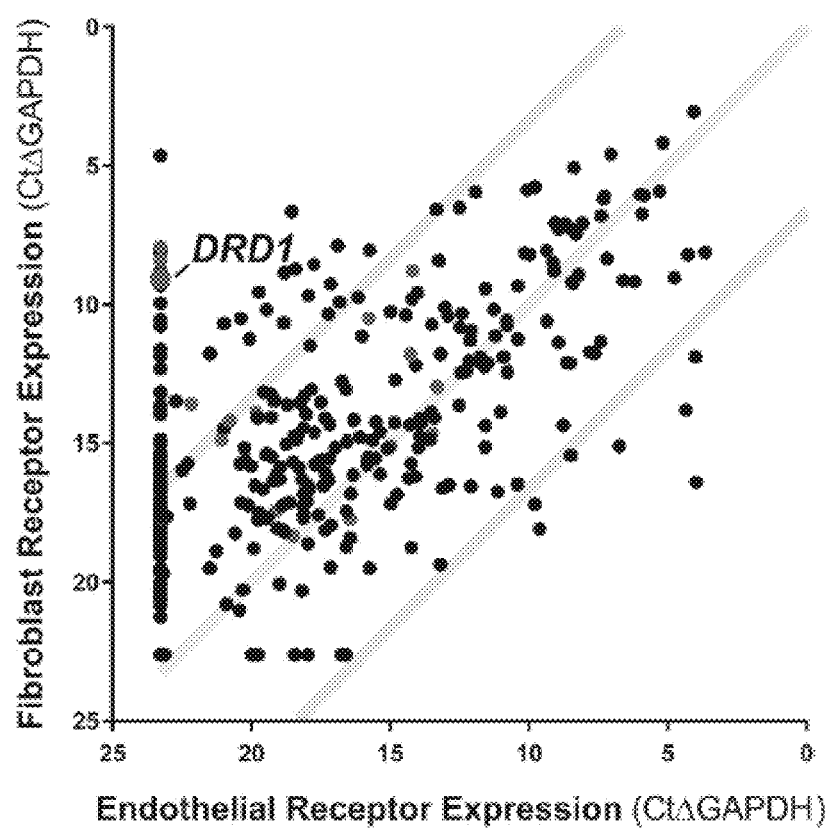
FIG. 49 shows GPCR expression profiling of primary cultured human pulmonary microvascular endothelial cells and normal human pulmonary fibroblasts. Red points indicate GPCRs that selectively couple to Gαs. Blue lines indicate 100-fold preferential expression. Prostaglandin receptors PTGER2 and PTGDR (red points directly above DRD1) were also selectively expressed in fibroblasts vs. endothelial cells, however both of these receptors were highly expressed in epithelial cells.
Figure 50A:
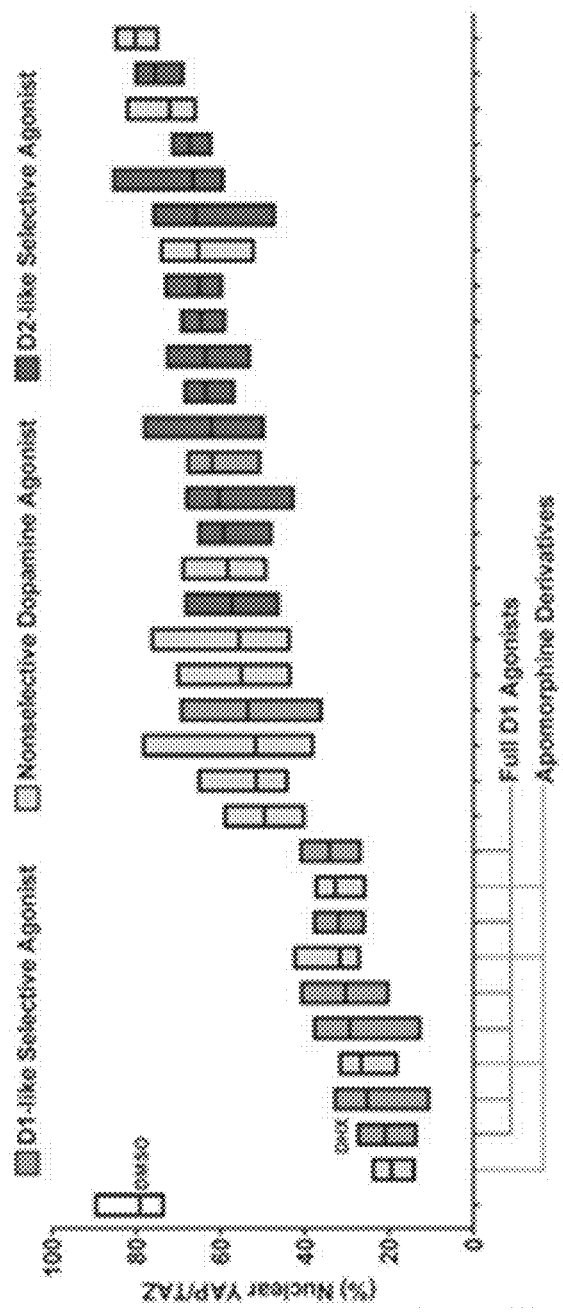
FIG. 50A shows that dopamine receptor D1 agonism blocks YAP/TAZ nuclear localization. D1 receptor selective agonists inhibit YAP/TAZ nuclear localization. IPF patient-derived lung fibroblasts cells treated 2 hours prior to fixation with diverse dopaminergic agonists (10 μM). N=4 different patient samples. % nuclear localization of YAP/TAZ was determined using automated imaging software. Scale bar represents 100 μm.
Figure 50B:
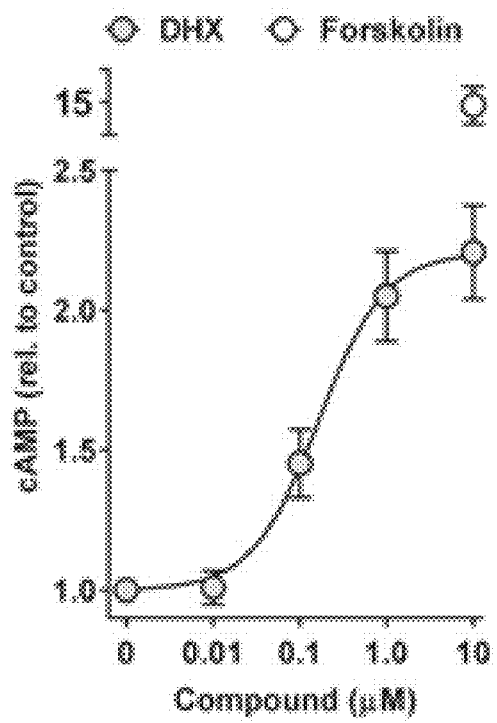
FIG. 50B shows cAMP measured in IPF patient-derived fibroblasts treated for 20 minutes with D1 receptor agonist (e.g., DHX). N=3.
Figure 50C:
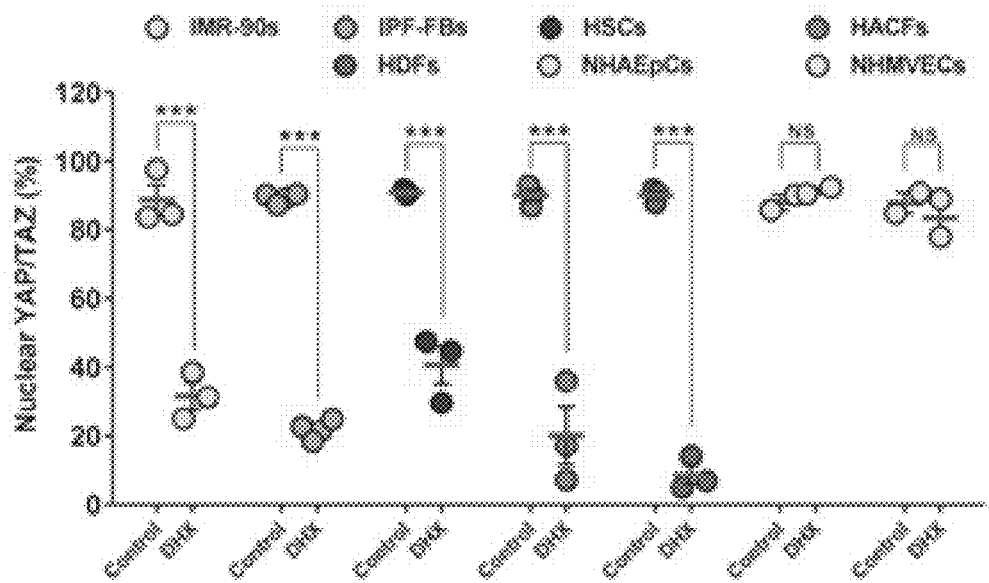
FIG. 50C shows that D1 receptor agonist (e.g., DHX) inhibits YAP/TAZ nuclear localization in fibroblasts from multiple organs: hepatic stellate cells (HSC), human adult cardiac fibroblasts (HACFs), and human dermal fibroblasts (HDFs) but not in lung alveolar epithelial (NHAEp) or endothelial (NHMVE) cells. N=3 (****$p<0.0001$ vs. 0.1% DMSO vehicle control).
Figure 51:
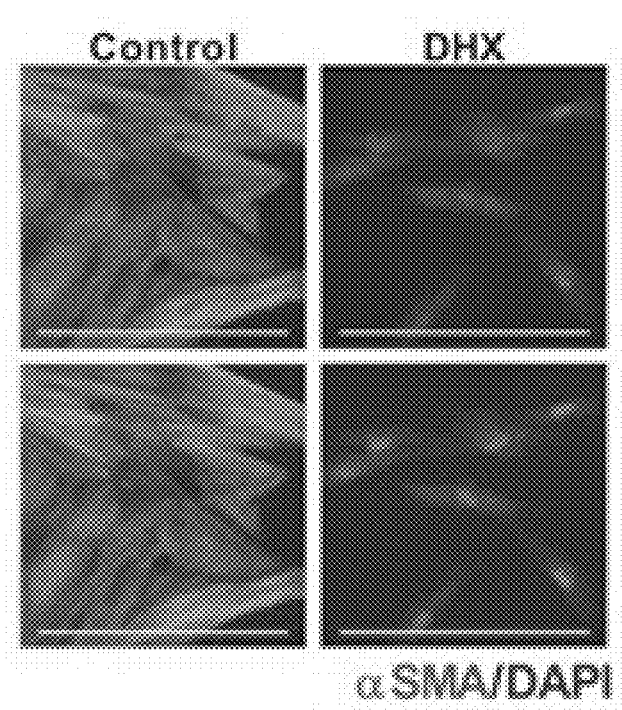
FIG. 51 shows that D1 receptor agonist (e.g., DHX) reverses fibroblast matrix deposition, contraction and stiffening. D1 receptor selective agonists inhibit fibroblast activation (Representative image: 1 µM dihydrexidine (DHX). IPF patient-derived lung fibroblasts cells treated for 72 hours prior to fixation with a library of diverse, mixed selectivity dopaminergic agonists (1 µM)+TGFβ. N=4 different patient samples. αSMA intensity was determined using automated imaging software. Scale bar represents 100 µm.
Figure 52:
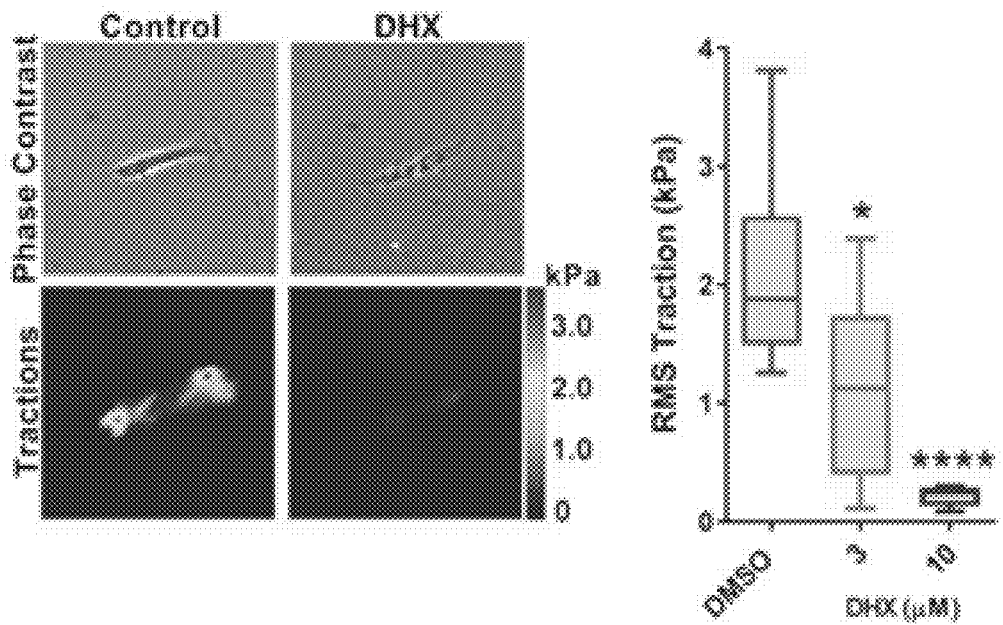
FIG. 52 shows that D1 receptor agonist (e.g., DHX) attenuates IPF fibroblast contractility measured by traction force microscopy. (****$p<0.0001$, *$p<0.05$ vs. 0.1% DMSO vehicle control).
Figure 53:
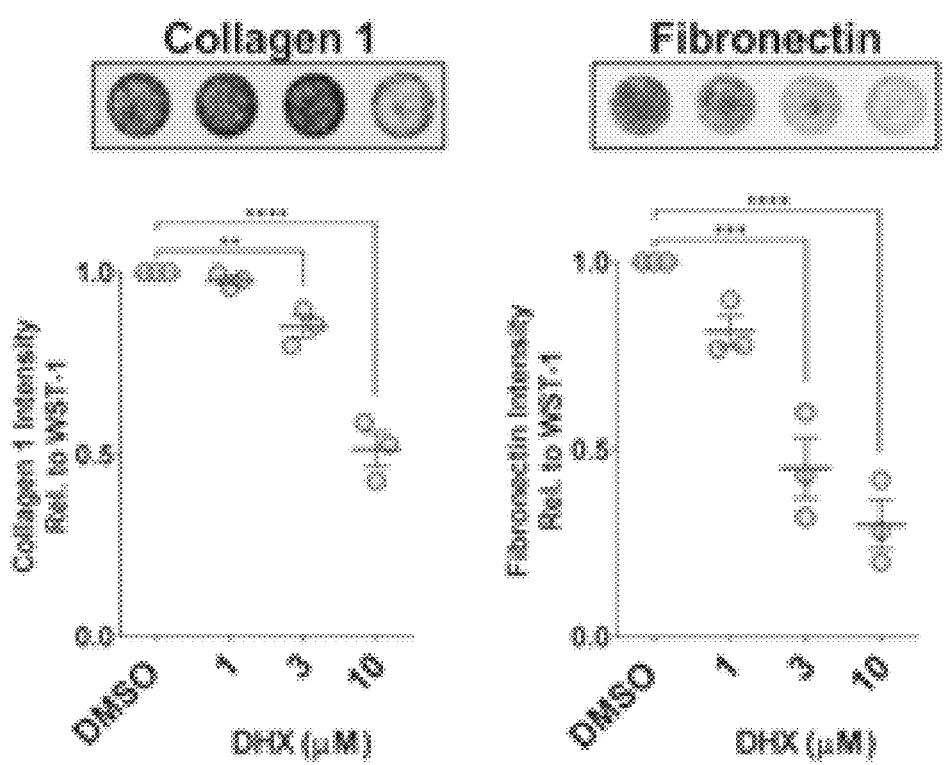
FIG. 53 shows that D1 receptor agonist (e.g., DHX) reverses extracellular matrix accumulation. IPF patient-derived fibroblasts pre-stimulated with 2 ng/mL TGFβ for 48 hours, then treated with DHX+2 ng/mL TGFβ for additional 24 hours. N=3 (**$p<0.0001$, *$p<0.001$, **$p<0.01$ vs. 0.1% DMSO vehicle control)
Figure 54:
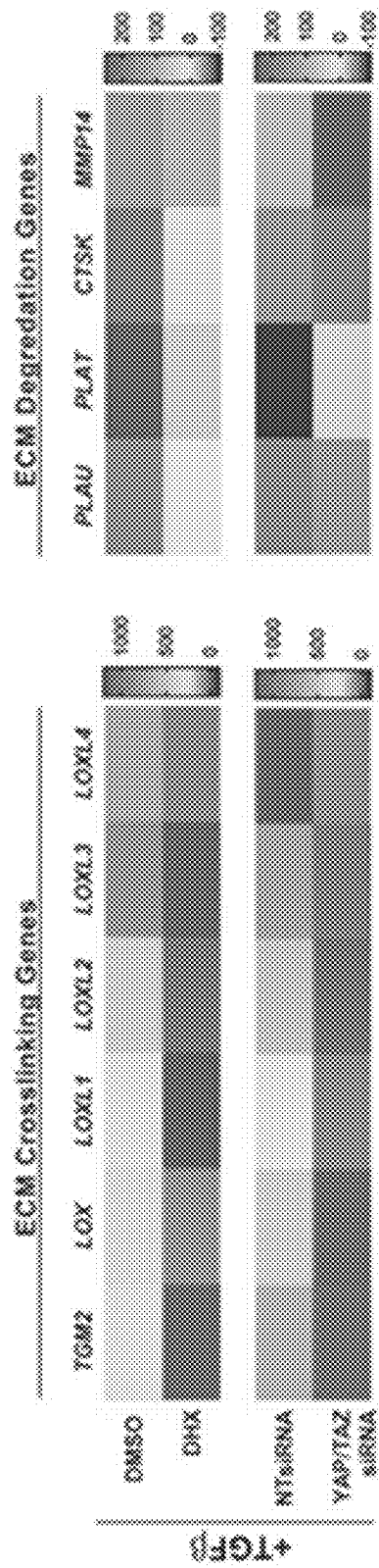
FIG. 54 shows that D1 receptor agonist (e.g., DHX) and YAP/TAZ siRNA modulate matrix crosslinking and degradation gene programs. IPF fibroblasts treated 24 hours with 2 ng/mL TGFβ+/−10 µM DHX or YAP and TAZ siRNA (>90% knockdown). N=3. Heat map indicates % change relative to unstimulated controls.
Figure 55:
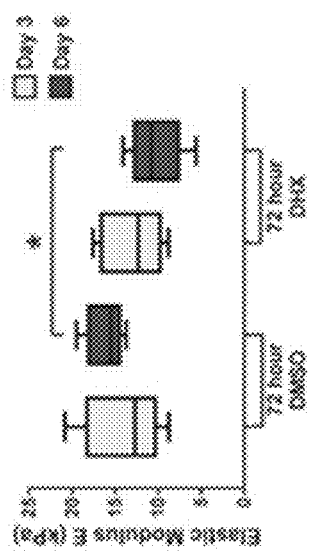
FIG. 55 shows that D1 receptor agonist (e.g., DHX) reverses extracellular matrix stiffening. IPF patient derived fibroblasts and their cell-derived matrices were characterized by AFM microindentation using a spherical tip after 72 hours, then treated+/−10 µM DHX in matrix deposition media for additional 72 hours and re-characterized. N=5 different patient samples. (*$p<0.05$ vs. 0.10% DMSO vehicle control).
Figure 55:
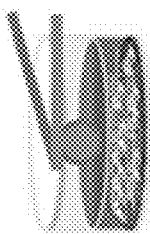
Figure 55:
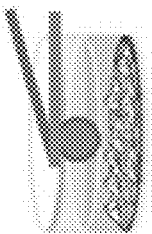
Figure 56:
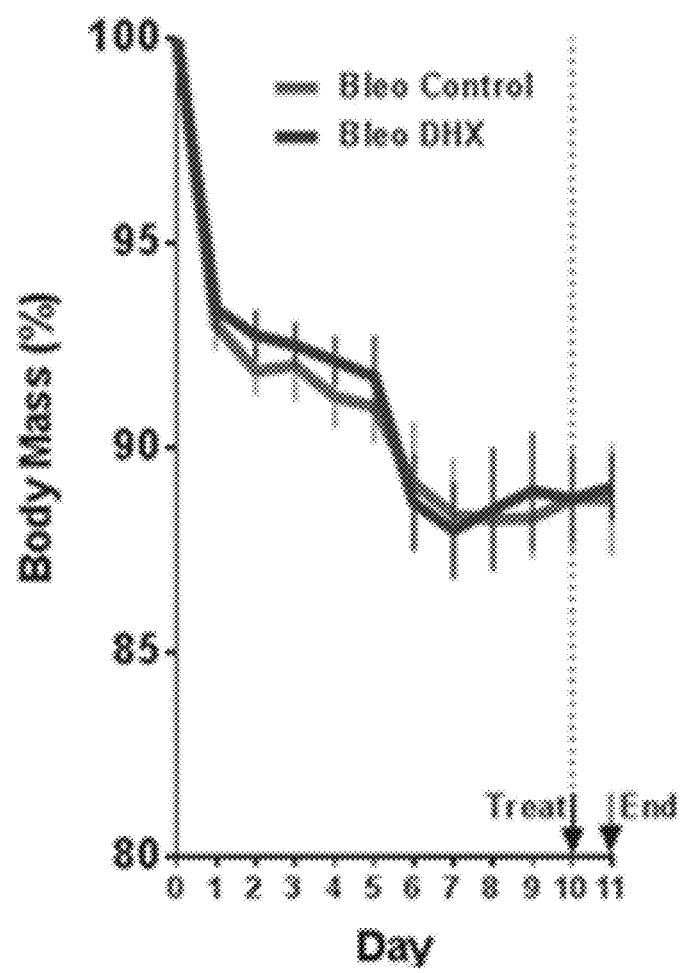
FIG. 56 shows that DHX selectively blocks expression of YAP/TAZ target genes in lung fibroblasts in vivo. Two groups of mice were injured intratracheally with bleomycin at day 0, on day 10 one group received two doses of DHX (2 and 24 hours prior to collecting lungs) and the other received vehicle control. On day 11 lungs were collected to flow sort fibroblasts, epithelial, and endothelial cells.
Figure 57:
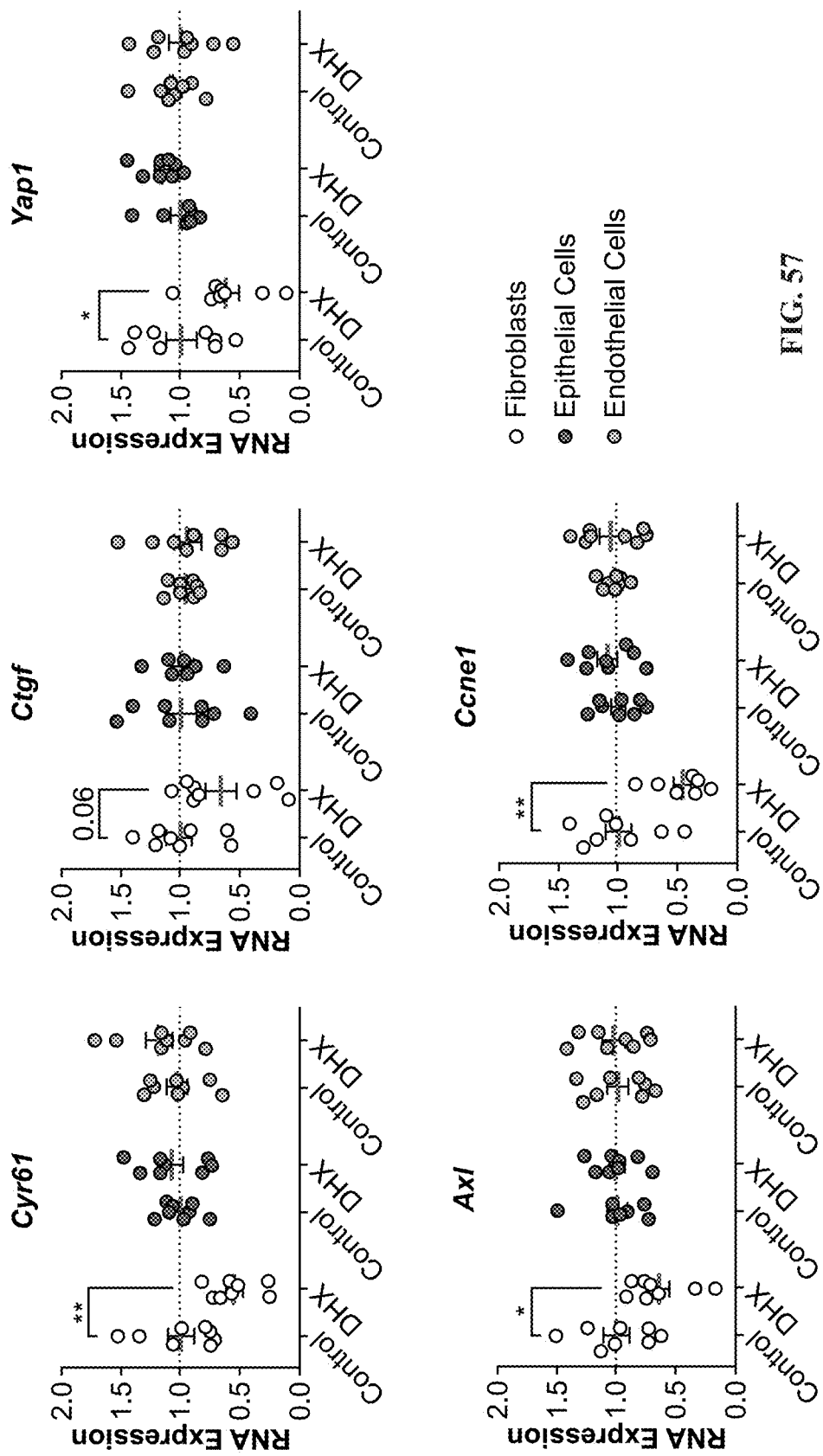
FIG. 57 shows changes in RNA expression of YAP/TAZ target genes from freshly isolated cells.
Figure 58A:
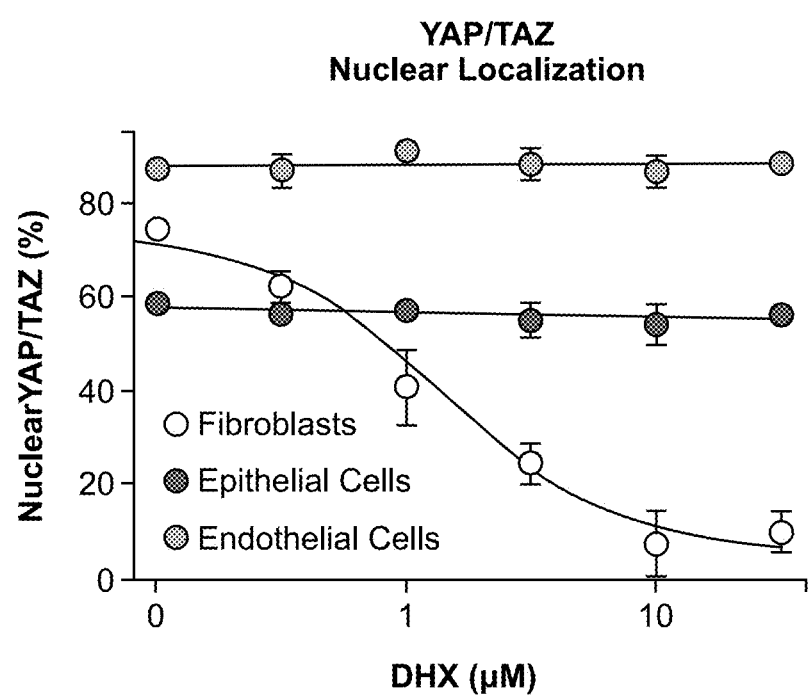
FIG. 58A shows that DRD1 agonism selectively blocks localization and activity of YAP/TAZ in lung fibroblasts. IPF derived lung fibroblasts, lung alveolar epithelial (NHAEp) and endothelial (NHMVE) cells were treated for 2 hours with DRD1 selective agonist (e.g., DHX)
Figure 58B:
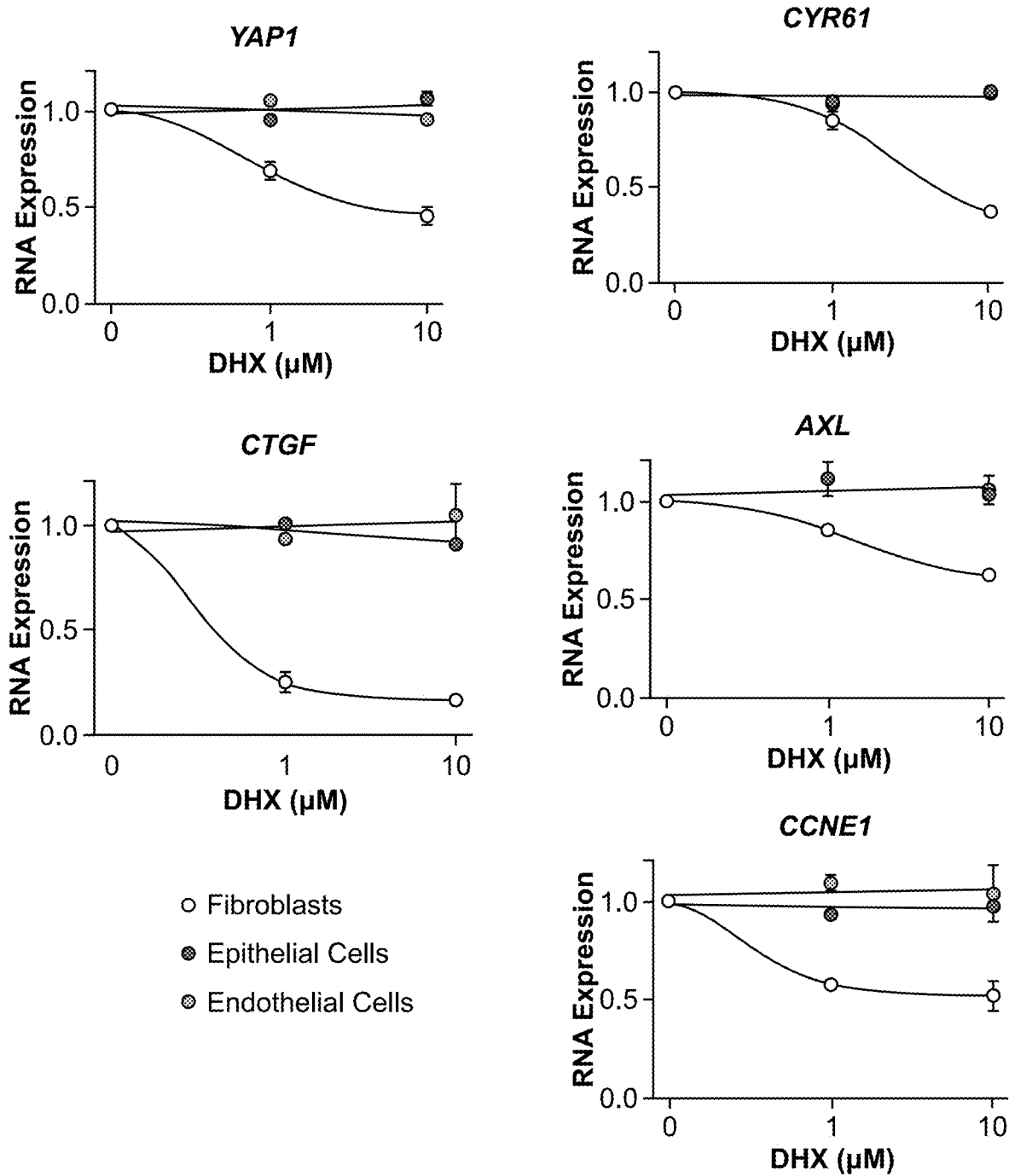
FIG. 58B shows results of an experiment where IPF derived lung fibroblasts, lung alveolar epithelial (NHAEp) and endothelial (NHMVE) cells were treated for 24 hours with DRD1 selective agonist prior to RNA isolation and measurement of YAP/TAZ target genes. N=2 technical replicates.
Figure 58C:
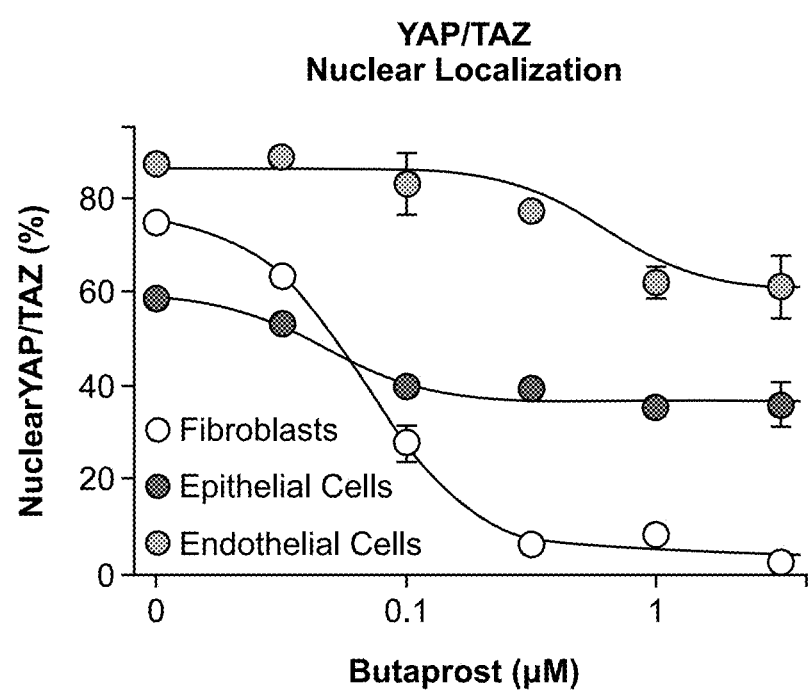
FIG. 58C shows results of an experiment where IPF derived lung fibroblasts, lung alveolar epithelial (NHAEp) and endothelial (NHMVE) cells were treated for 2 hours with butaprost (EP2 receptor agonist). DRD1 receptor is only expressed in fibroblasts while EP2 receptor, which also elevates cAMP, is expressed in all three cell types.
Figure 58D:
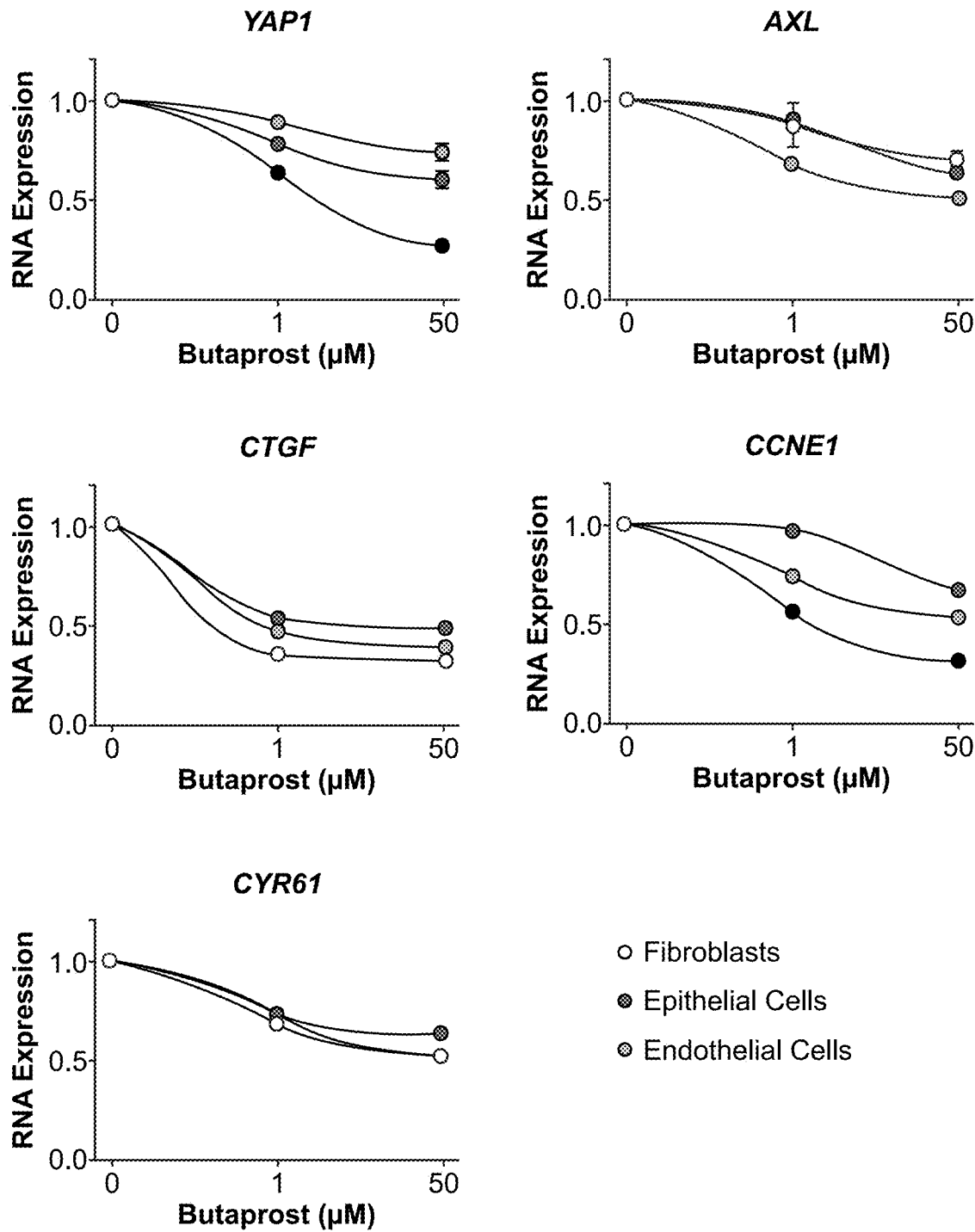
FIG. 58D shows results of an experiment where IPF derived lung fibroblasts, lung alveolar epithelial (NHAEp) and endothelial (NHMVE) cells were treated for 24 hours with butaprost (EP2 receptor agonist) prior to RNA isolation and measurement of YAP/TAZ target genes. N=2 technical replicates.
Figure 59A:
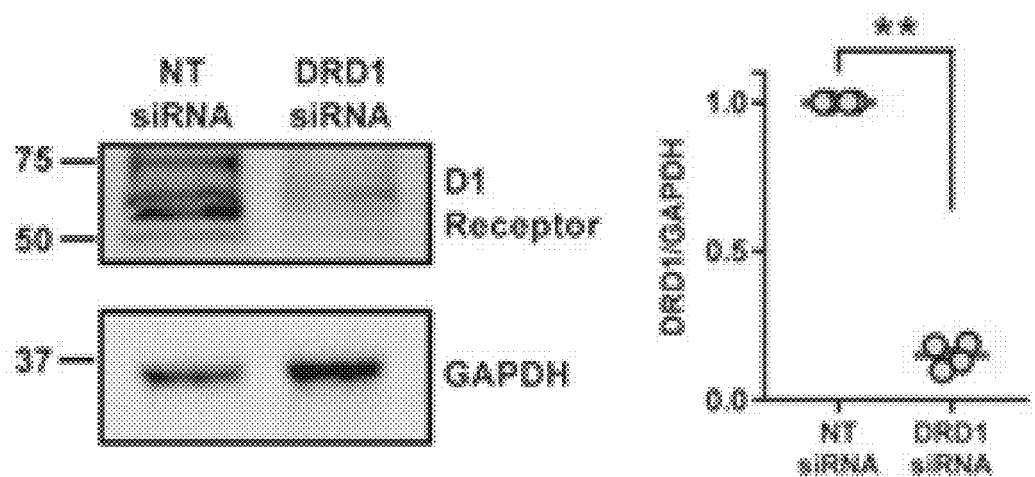
FIG. 59A shows that D1 receptor agonist (e.g., DHX) activity is dependent on DRD1 receptor.
Figure 59B:
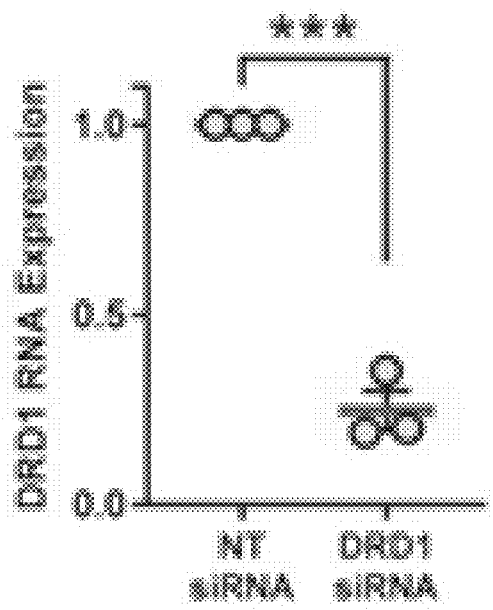
FIG. 59B shows that D1 receptor agonist (e.g., DHX) activity is dependent on DRD1 receptor.
Figure 59C:
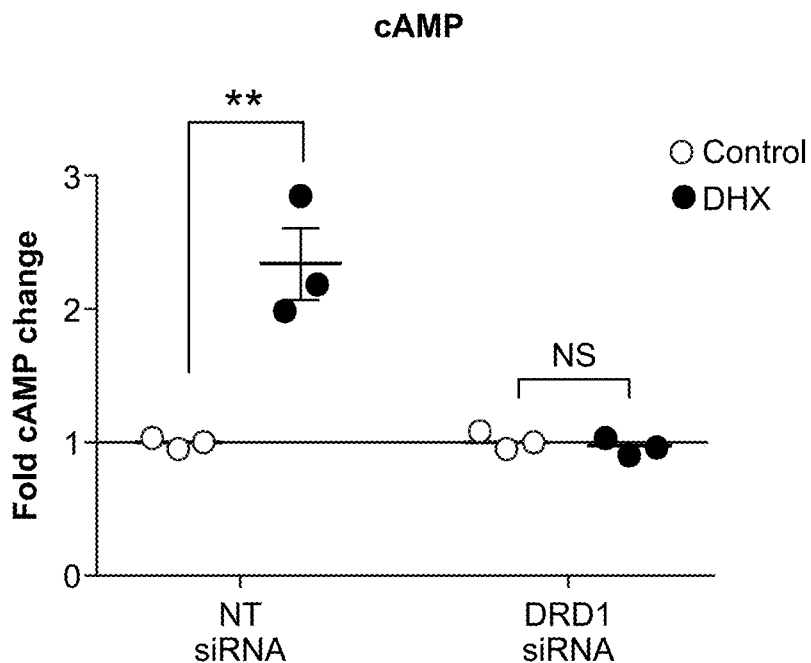
FIG. 59C shows that DRD1 siRNA treatment blocks DHX's elevation of cAMP. N=3, IMR-90 lung fibroblasts.
Figure 59D:
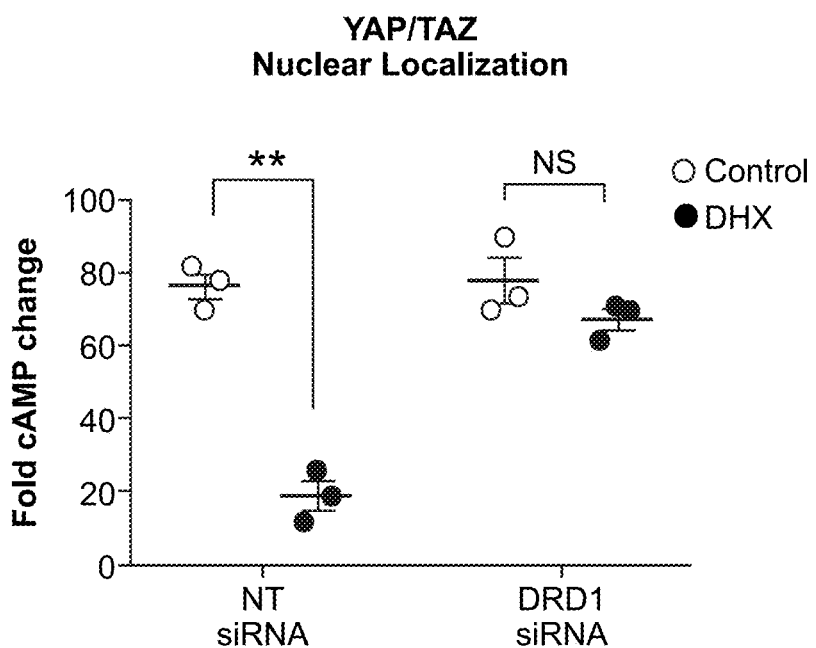
FIG. 59D shows that DRD1 siRNA treatment blocks inhibition of YAP/TAZ nuclear localization. N=3, IMR-90 lung fibroblasts.
Figure 59E:
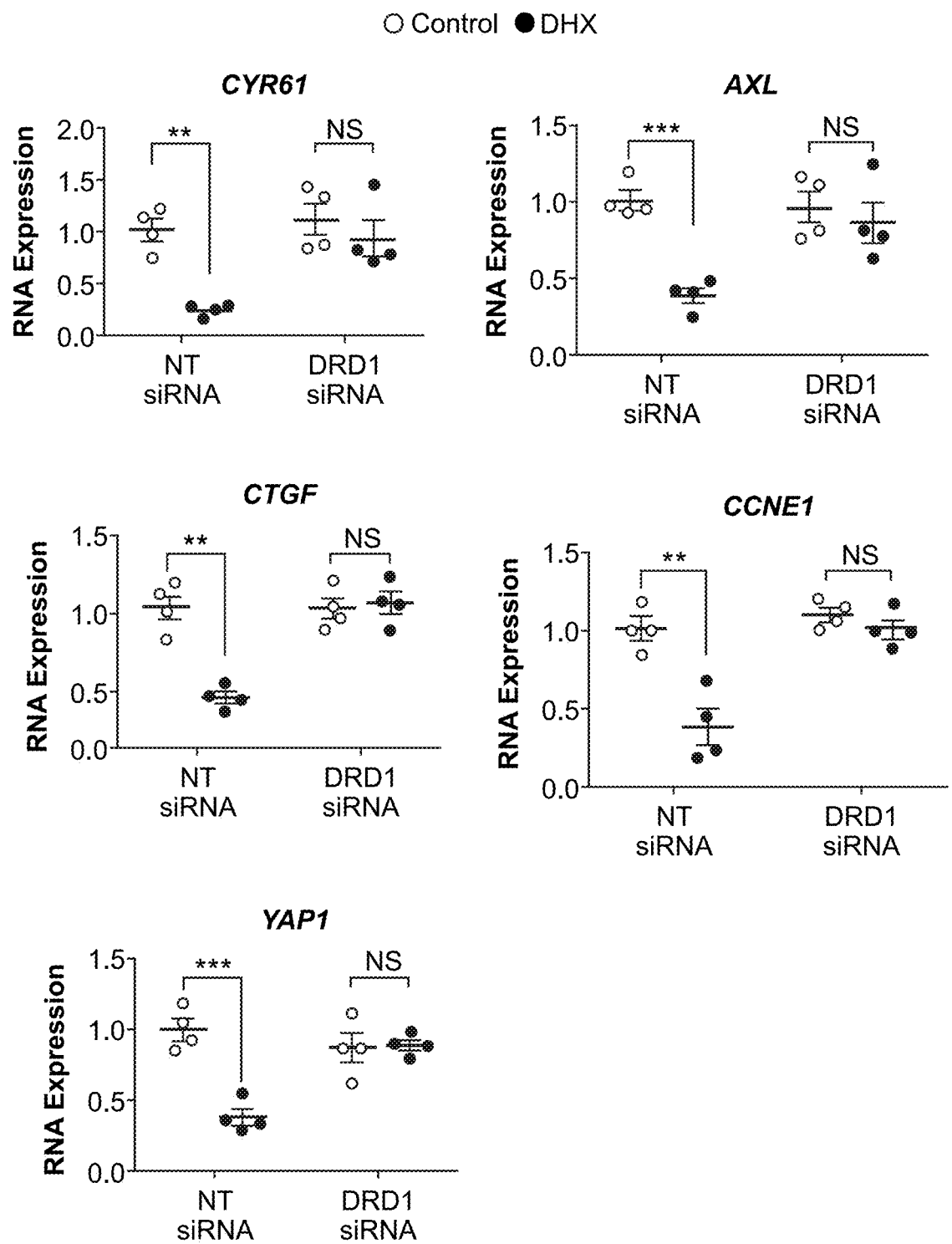
FIG. 59E shows that DRD1 siRNA treatment inhibition of YAP/TAZ target genes. N=3, IMR-90 lung fibroblasts.
Figure 59F:
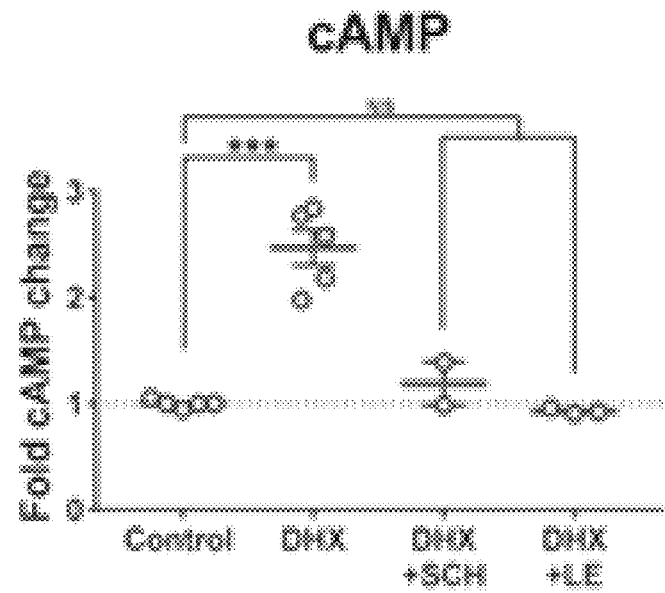
FIG. 59F shows that dopamine receptor D1 antagonists SCH-39166 and LE-300 block DHX's elevation of cAMP. N=3, IMR-90 lung fibroblasts.
Figure 59G:
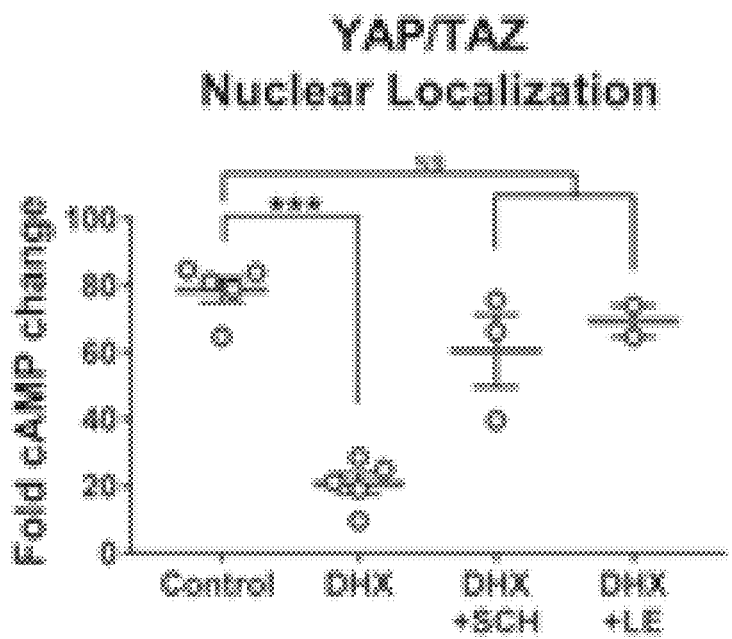
FIG. 59G shows that dopamine receptor D1 antagonists SCH-39166 and LE-300 block DHX's inhibition of YAP/TAZ nuclear localization. N=3, IMR-90 lung fibroblasts.
Figure 59H:
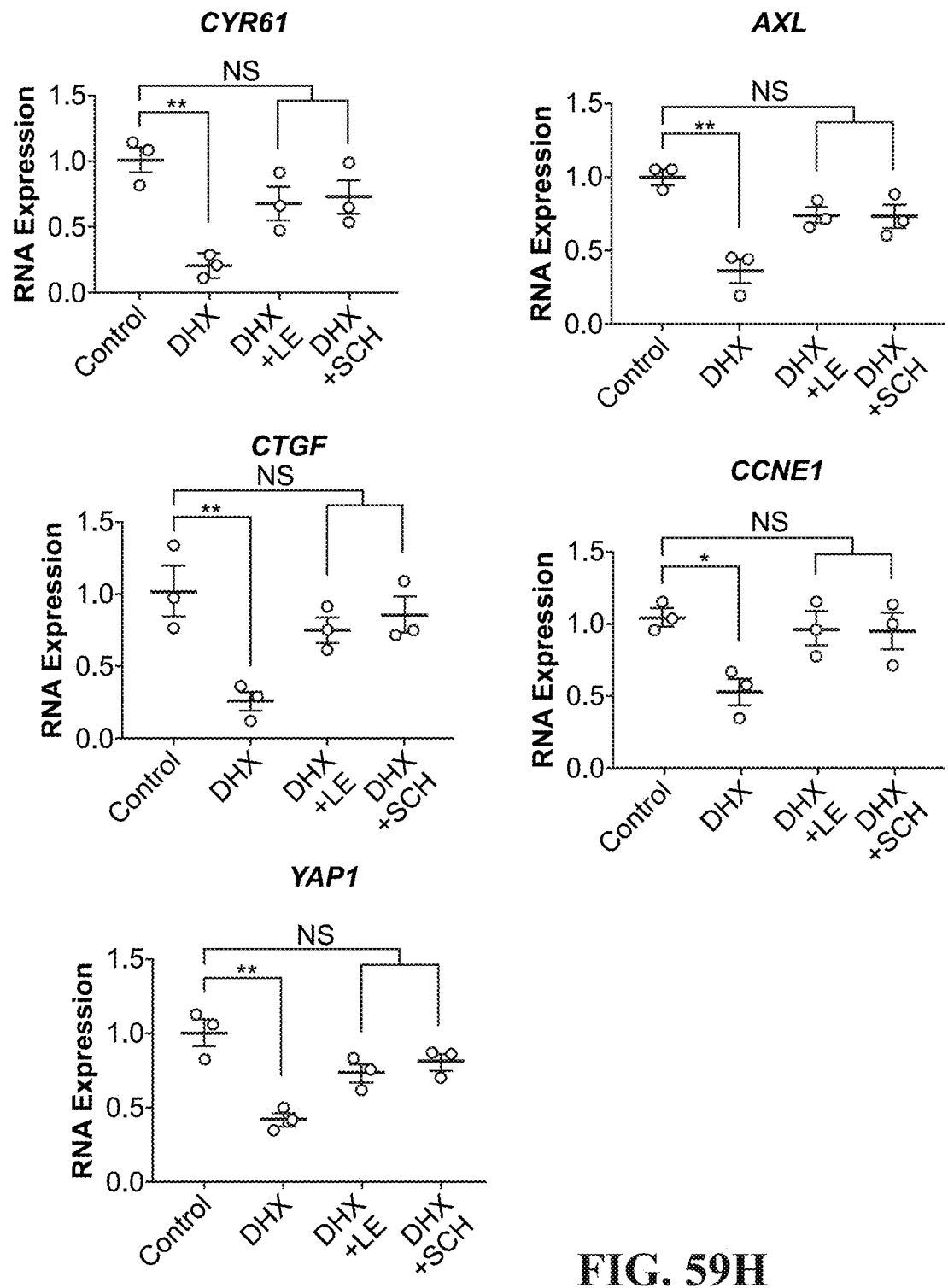
FIG. 59H shows that dopamine receptor D1 antagonists SCH-39166 and LE-300 block DHX's inhibition of YAP/TAZ target genes. N=3, IMR-90 lung fibroblasts.
Figure 60A:
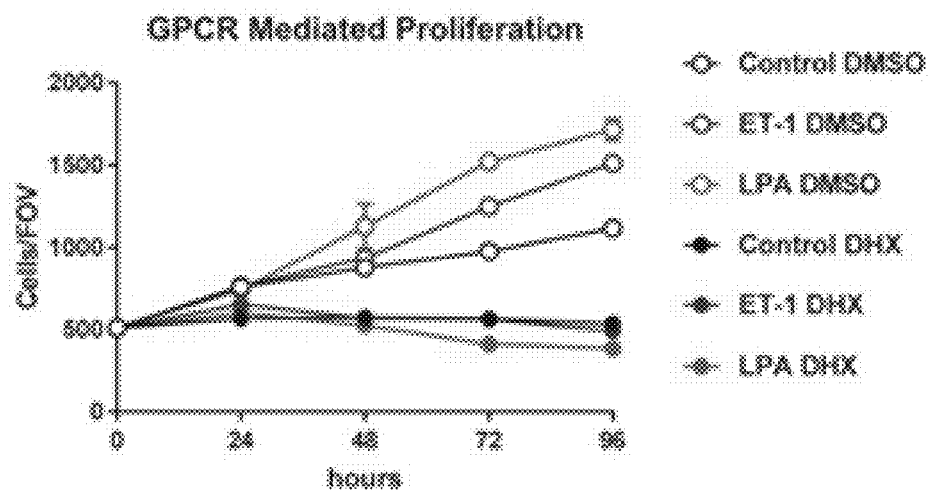
FIG. 60A shows that DHX blocks proliferation and primes lung fibroblasts for apoptosis. Proliferation of lung fibroblasts (IMR-90 cells) measured for 4 days in the presence of GPCR agonists ET-1 (100 nM) and LPA (10 µM)+/−10 µM DHX. Cells were fixed and counted with DAPI at the end of each day. N=3 technical triplicates.
Figure 60B:
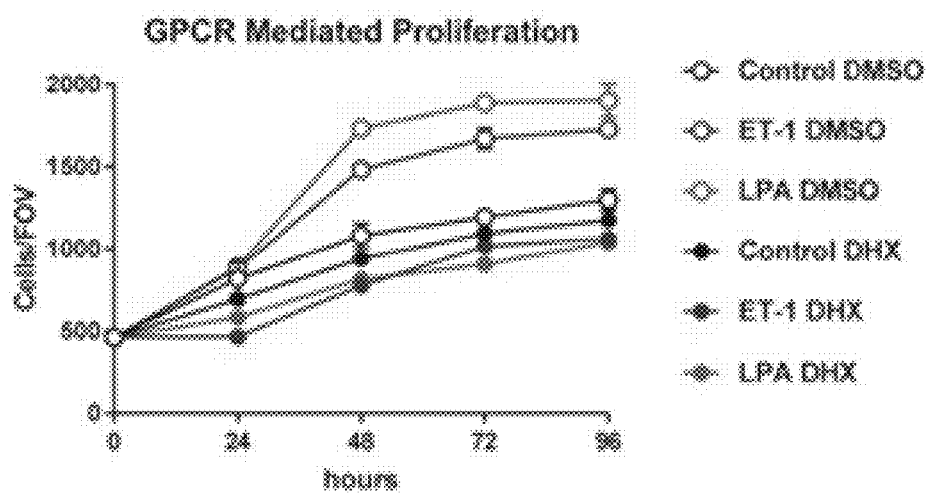
FIG. 60B shows results of an experiment where proliferation of lung fibroblasts (IPF Patient-Derived Lung fibroblasts) measured for 4 days in the presence of GPCR agonists ET-1 (100 nM) and LPA (10 µM)+/−10 µM DHX. Cells were fixed and counted with DAPI at the end of each day. N=3 technical triplicates.
Figure 60C:
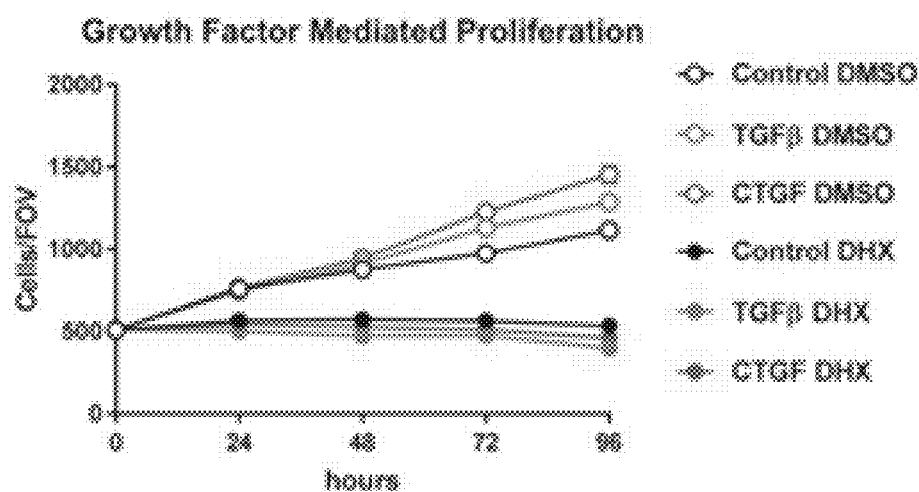
FIG. 60C shows results of an experiment where proliferation of lung fibroblasts (IMR-90 cells) was measured for 4 days in the presence of growth factor TGFβ (2 ng/mL)+/−10 µM DHX. Cells were fixed and counted with DAPI at the end of each day. N=3 technical triplicates.
Figure 60D:
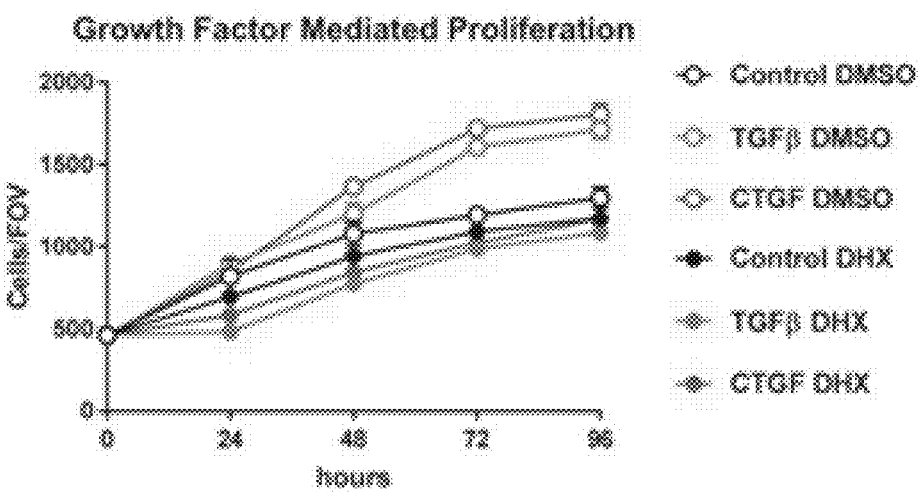
FIG. 60D shows results of an experiment where proliferation of lung fibroblasts (IPF Patient-Derived Lung fibroblasts) measured for 4 days in the presence of growth factor CTGF (100 ng/mL)+/−10 µM DHX. Cells were fixed and counted with DAPI at the end of each day. N=3 technical triplicates.
Figure 60E:
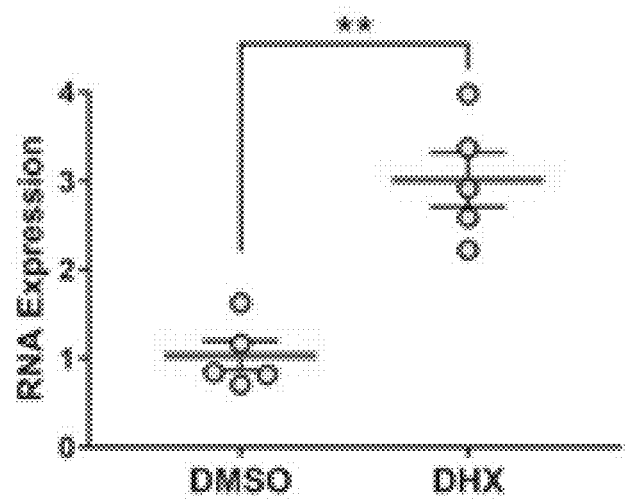
FIG. 60E shows results of an experiment where RNA Expression of pro-apoptotic factor BIM was assessed following 24 treatment with DHX (10 µM). N=4. IMR-90 cells.
Figure 60F:
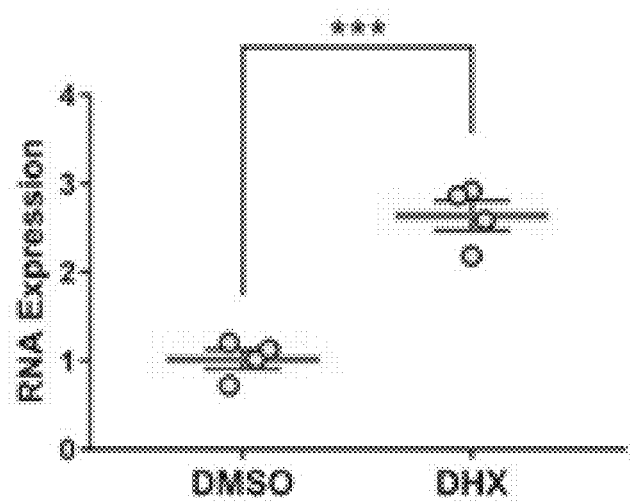
FIG. 60F shows results of an experiment where RNA Expression of pro-apoptotic factor BIM was assessed following 24 treatment with DHX (10 µM). N=4. IPF Patient-Derived Lung fibroblasts.
Figure 60G:
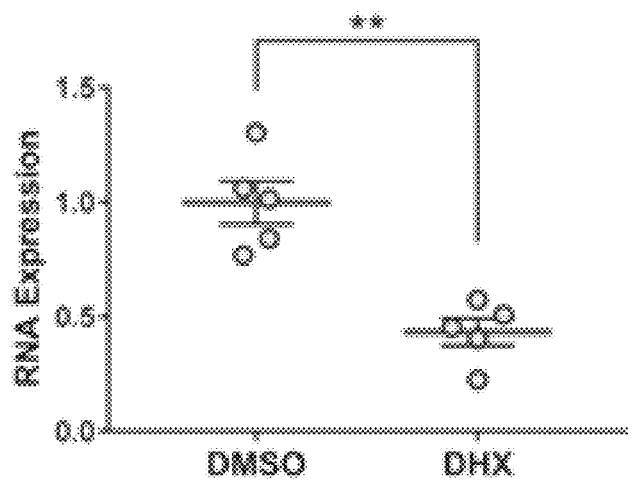
FIG. 60G shows results of an experiment where RNA Expression of anti-apoptotic factor BCL2 was assessed following 24 treatment with DHX (10 µM). N=4. IMR-90 cells.
Figure 60H:
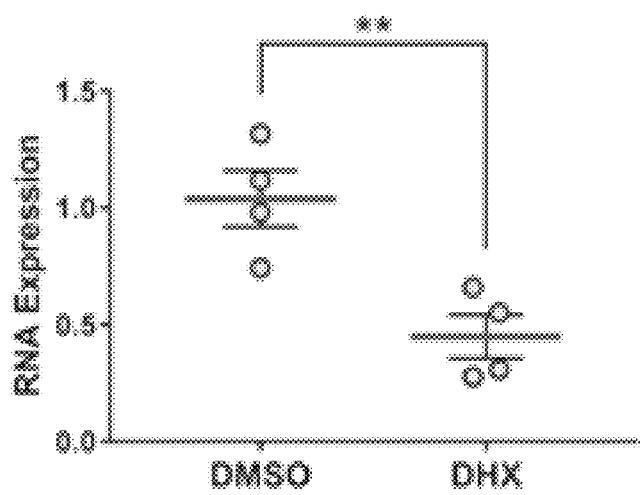
FIG. 60H shows results of an experiment where RNA Expression of anti-apoptotic factor BCL2 was assessed following 24 treatment with DHX (10 µM). N=4. IPF Patient-Derived Lung fibroblasts.

Example 3—Dopamine Receptor Agonist (e.g., DHX) Reduces Fibroblast Activation and Matrix Deposition To test whether DHX-mediated inhibition of YAP/TAZ nuclear localization translates into altered mesenchymal cell activation, we first demonstrated that expression of hallmark profibrotic genes CTGF, COL1A1, ACTA2, and FN1 was reduced in IPF patient-derived lung fibroblasts by DHX treatment, recapitulating effects of YAP/TAZ knockdown (See e.g., Ref. 1-4) (FIG. 11). These effects could be blocked with a DRD1 antagonist (FIG. 11) as well as DRD1-siRNA (FIG. 27-28). Stimulating fibroblasts cultured on stiff tissue culture plastic for 72 hours with TGFβ further enhances their myofibroblastic transition, as detected by αSMA+ stress fibers; treating fibroblasts with DHX from 48-72 hours in the presence of TGFβ reversed this transition (FIG. 12). Similarly, DHX dose-dependently reversed fibroblast-mediated, TGFβ-stimulated accumulation of collagen I and fibronectin (FIG. 13). To validate that this effect is dependent on inhibition of YAP/TAZ, NIH-3T3 cells were employed which stably express a doxycycline-inducible, constitutively active, mutant TAZ (TAZ4SA) (See, e.g., Ref. 2, 36). In these cells, DHX had no effect on profibrotic gene expression or extracellular matrix accumulation (FIG. 29, 30). Finally, traction force microscopy (TFM) demonstrated that DHX significantly and dose-dependently reduced the contractile forces generated by fibroblasts (FIG. 14).

Example 4—Extracellular Matrix Remodeling by Dopamine Receptor Agonist (e.g., DHX)

Figure 15:
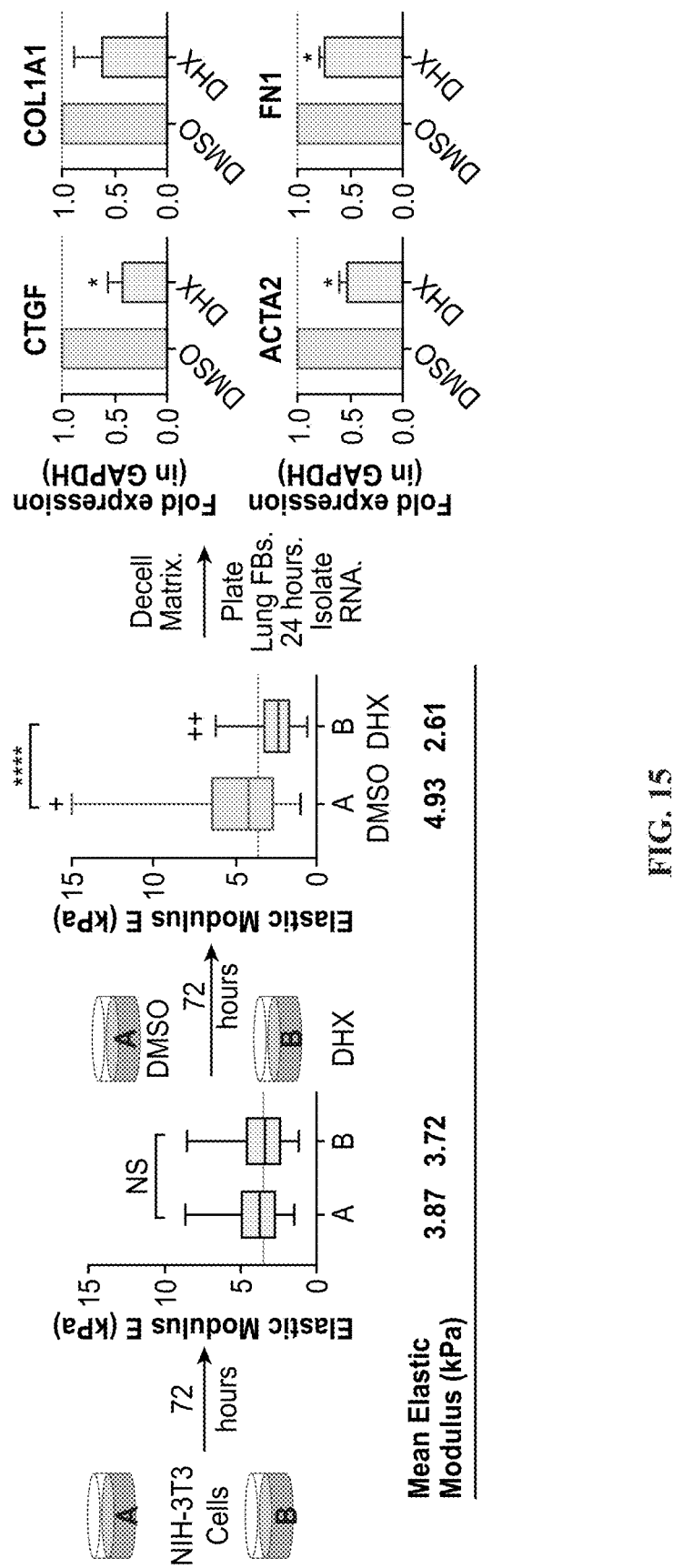
FIG. 15 shows that D1 agonist (e.g., DHX) reverses extracellular matrix stiffening. NIH-3T3 cells plated onto gelatin-coated tissue culture plates stimulated to deposit matrix with 2 ng/mL TGFβ and 20 µM ascorbic acid for 72 hours prior to AFM microindentation analysis to measure stiffness (elastic modulus). The same dishes were then treated +/−10 µM DHX in the same media for another 72 hours and AFM analysis. The matrices were decellularized and passage 3 NHLFs were plated onto the matrices; after 24 hours RNA was collected and expression of profibrotic genes was analyzed. AFM analysis N=2. 75 indentation measurements were made for each plate. The box and whisker plots show min to max, quartile, and mean from one representative experiment (****p<0.0001 vs. 0.1% DMSO vehicle control) (++p<0.01, +p<0.05 vs. the same culture plate after the first 72 hour incubation). Measurement of RNA from cell plated onto decellularized matrices N=3. (*p<0.05 vs. 0.1% DMSO vehicle control).

The results above were consistent with DHX not only attenuating key aspects of fibroblast pro-fibrotic activation, but potentially shifting their phenotype toward one that promotes fibrosis clearance and resolution. To test this concept directly, an in vitro matrix remodeling assay was developed. Fibroblasts (NIH-3T3 cells) were first plated at confluence (A and B in FIG. 15), following an approach developed for studying cell-derived matrices. Cells on both plates were cultured with TGFβ and ascorbic acid to promote matrix synthesis and deposition. After 72 hours the stiffness of the cells and their cell-derived matrix were measured using atomic force microscopy (AFM). To test the ability of DHX to induce cell-mediated matrix remodeling, TGFβ and ascorbic acid were maintained but also DHX was added to B (vehicle control was added to A) for an additional 72 hours before probing the matrix again with AFM. While the cells and matrix in control plate A continued to stiffen over time, DHX treatment effectively reversed this trend and significantly reduced the observed stiffness. To confirm that DHX introduced a matrix remodeling effect, the matrices were decellularized and plated low passage primary human adult lung fibroblasts for 24 hours onto the decellularized matrices, then RNA was isolated to measure changes in profibrotic gene expression. CTGF, COL1A1, ACTA2 and FN1 expression were all decreased in the cells plated onto the matrix which had previously been treated with DHX, identifying a pharmaco-footprint left behind in the extracellular matrix by cellular remodeling.

Figure 16:
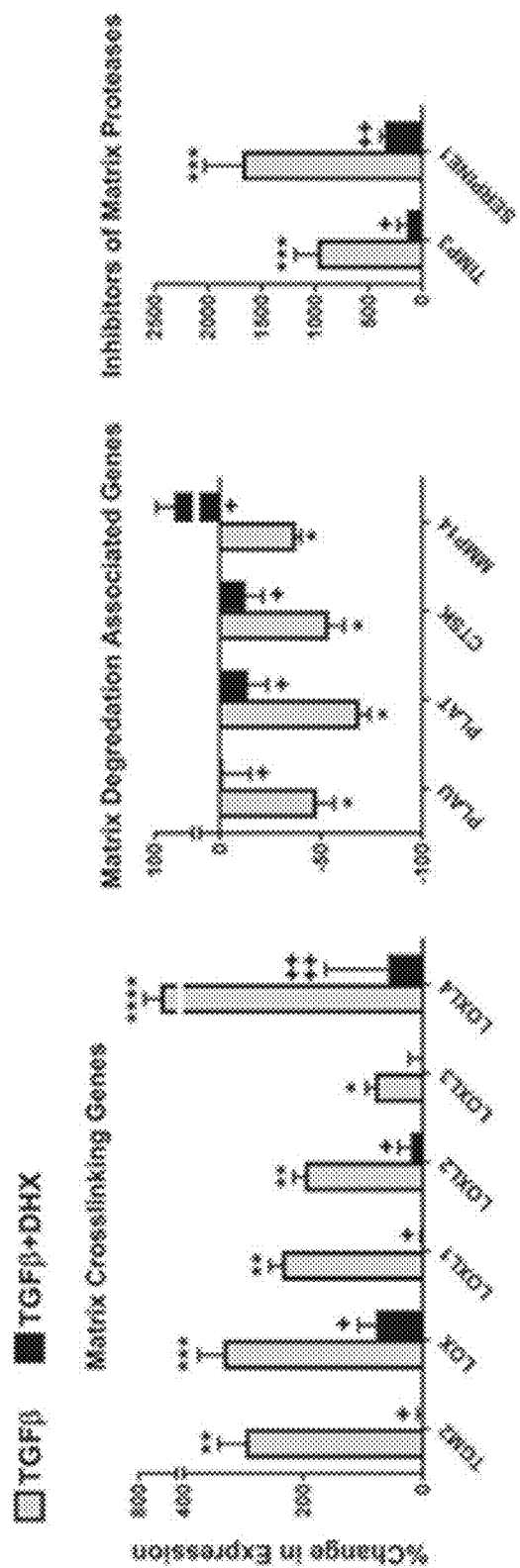
FIG. 16 shows that D1 agonist (e.g., DHX) modulates matrix deposition vs. matrix degradation gene program. IPF patient-derived fibroblasts cultured in media containing 0.1% FBS were stimulated for 24 hours with 2 ng/mL TGFβ and 10 µM DHX prior to RNA isolation. Genes which encode for ECM crosslinking: transglutaminase 2 (TGM2), lysyl oxidase and lysyl oxidase-like enzymes (LOX and LOXL1-4), ECM degradation: uPA (PLAU), tPa (PLAT), cathepsin K (CTSK), and matrix metalloprotease-14 (MMP14) and ECM protease inhibitors: metalloprotease inhibitor 3 (TIMP3), and plasminogen activator inhibitor 1 (SERPINE1) were measured. N=3. (**p<0.0001, *p<0.001, **p<0.01, *p<0.05 vs. 0.1% DMSO vehicle control non-TGFβ treated), (++++p<0.0001, ++p<0.01, +p<0.05 vs. 0.10% DMSO vehicle control TGFβ treated).

Based on these matrix remodeling effects of DHX, it was determined whether efficacy of this pathway extends to inducing matrix degradation/remodeling action in fibroblasts which could reverse the disease rather than simply slow its progression (an important utility of fibroblasts). First, the effect or dopamine receptor agonist (e.g., DHX) was investigated on expression of genes associated with matrix remodeling (FIG. 3f). IPF patient derived fibroblasts treated with TGFβ showed enhanced expression of matrix crosslinking genes and inhibitors of matrix protease enzymes but also showed reduced expression of several genes associated with matrix clearance (FIG. 16). In each case, DHX treatment reversed the effects of TGFβ, reducing expression of crosslinking and protease inhibitors but enhancing expression of matrix degradation associated enzymes. There doesn't appear to be a single driver gene by which DHX effects matrix remodeling, suggesting that the observed effect is a broader fibroblast program shift.

Example 5—Dopamine Receptor Agonist (e.g., DHX) Efficacy In Vivo

Figure 17:
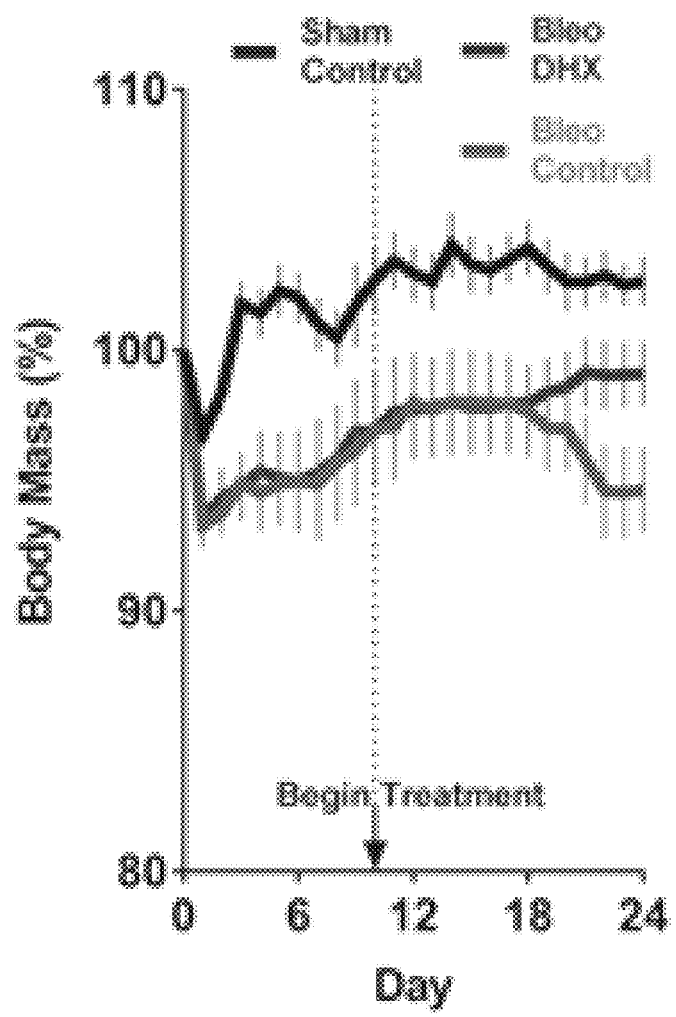
FIG. 17 shows that D1 agonist (e.g., DHX) therapeutically reverses bleomycin-induced pulmonary fibrosis. Weight change as a result of bleomycin induced lung injury and DHX therapeutic benefit. Female mice were intratracheally administered Bleomycin on Day 0; treatment was initiated on Day 10 (5 mg/kg DHX i.n., daily) and continued until day 24.
Figure 18:
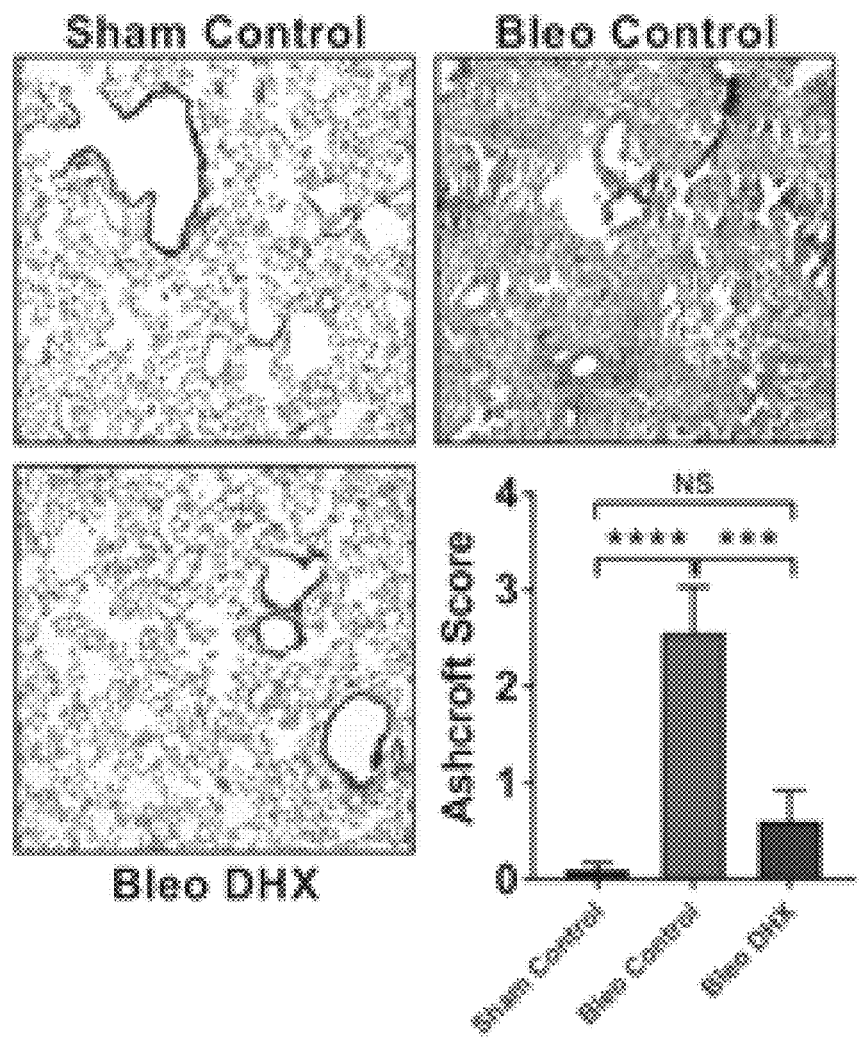
FIG. 18 shows H&E staining to visualize collagen and architectural changes. Paraffin embedded lung sections were stained and analyzed in a blinded fashion by a pulmonary pathologist and scored using the Ashcroft method.
Figure 19:
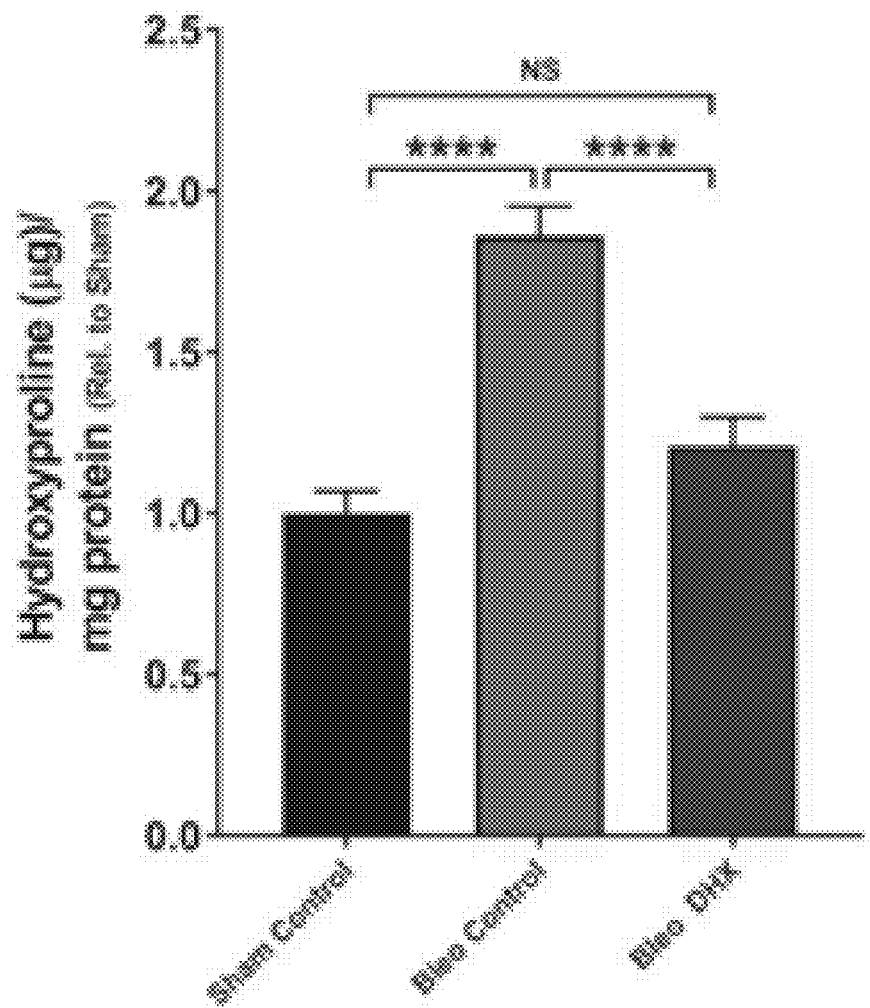
FIG. 19 shows results of hydroxyproline assay to measure collagen deposition in the lungs. Snap frozen lung tissue was biochemically analyzed for collagen abundance using the hydroxyproline assay.
Figure 20:
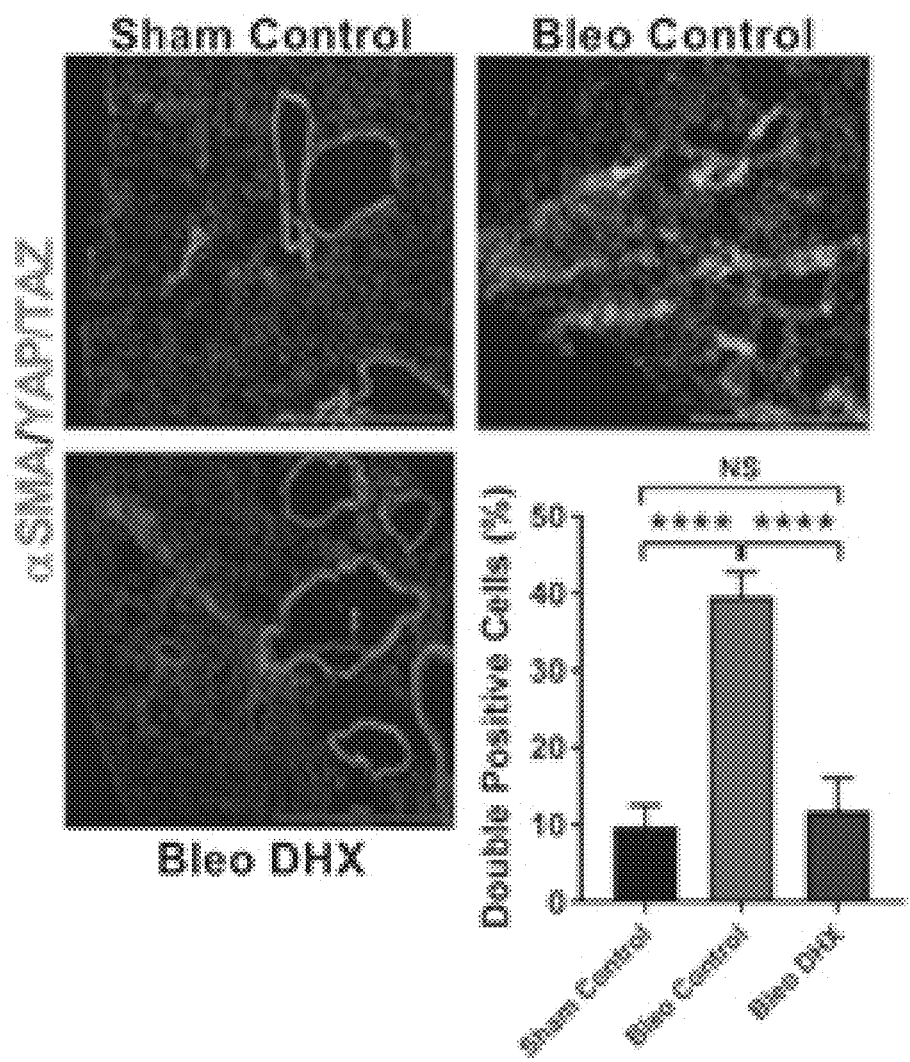
FIG. 20 contains immunofluorescence imaging of lung sections for αSMA and Yap/Taz. Lung sections were stained immune-probed for αSMA and Yap/Taz. Cells which were double positive for both αSMA and Yap/Taz were quantified using automated software.
Figure 21:
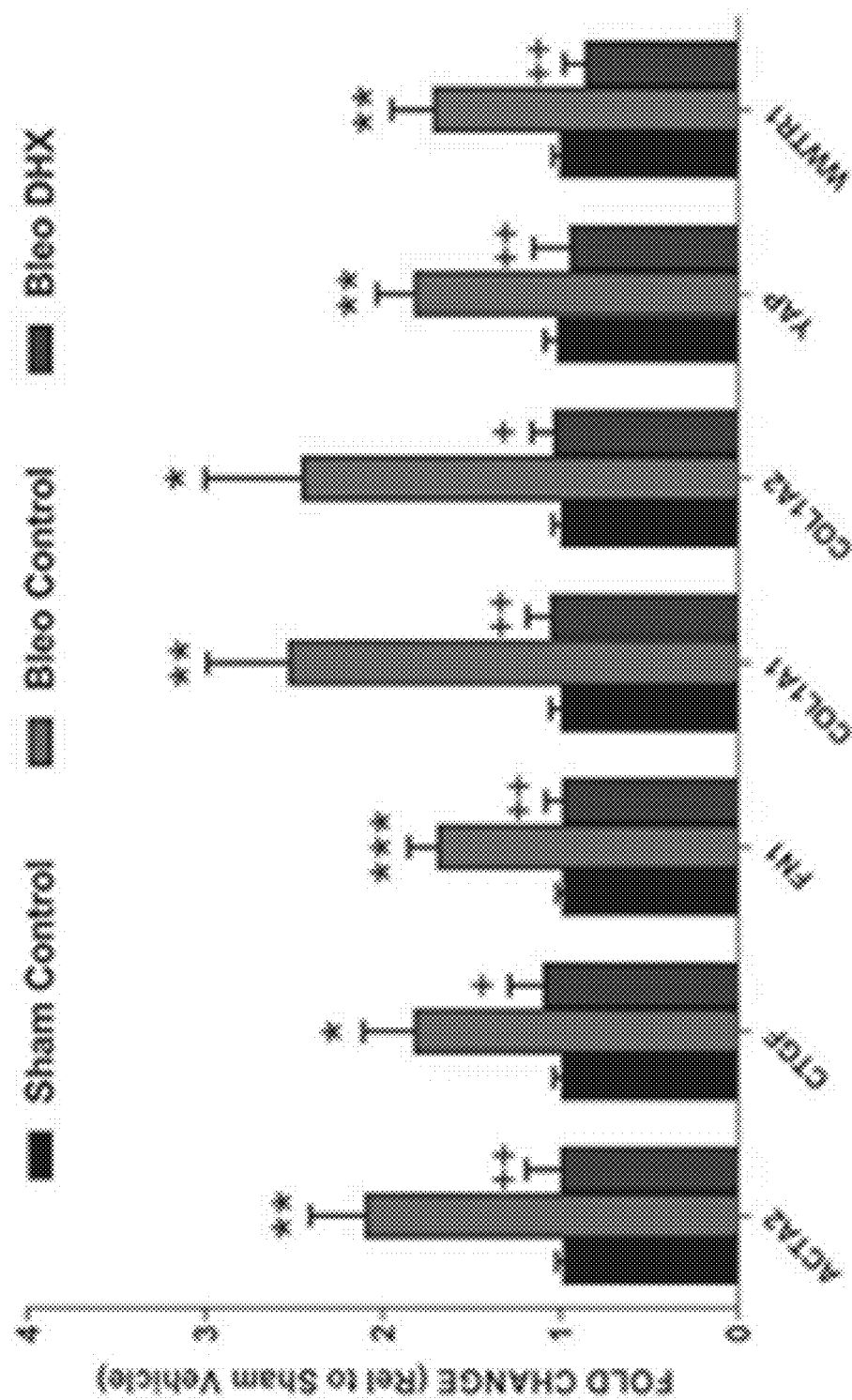
FIG. 21 shows changes in pro-fibrotic gene expression, Yap and Taz (Wwtr1) in whole lung homogenates. Sham Control N=15, Bleo Control N=17, and Bleo DHX N=17. (**p<0.0001, *p<0.001, **p<0.01, *p<0.05 vs. Sham Control) (++p<0.01, +p<0.05 vs. the respective Bleo Control).
Figure 22:
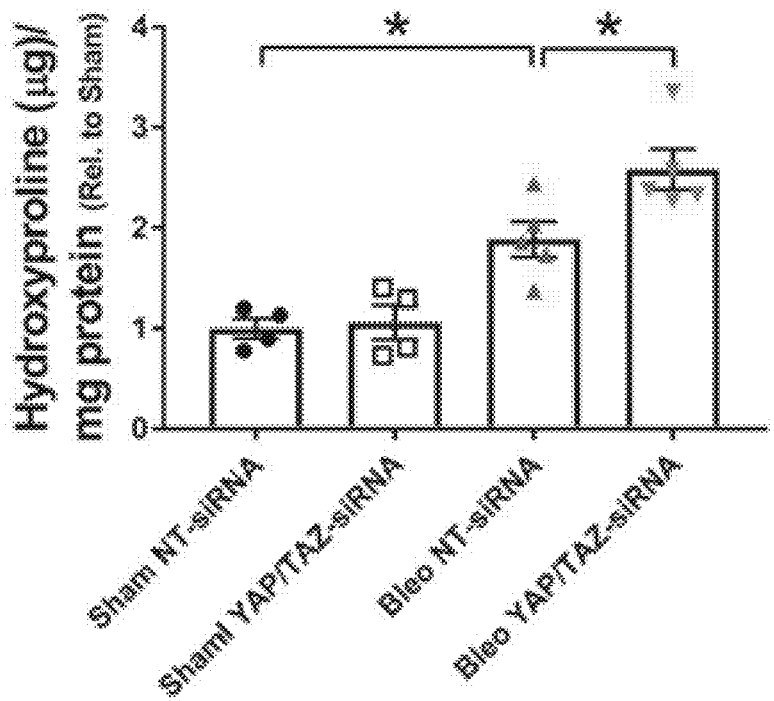
FIG. 22 shows that intratracheally administered YAP/TAZ siRNA worsens bleomycin induced lung injury and fibrosis. Mice were administered bleomycin on Day 0 and then intratracheally administered siRNA for Yap and Taz on Day 14. On Day 21 BAL fluid was collected and lungs were harvested for analysis. Yap/Taz siRNA enhanced collagen deposition. Sham treated mice N=4, Bleo treated mice N=6 (**p<0.0001, *p<0.001, **p<0.01, *p<0.05 vs. Sham NT-siRNA).
Figure 23A:
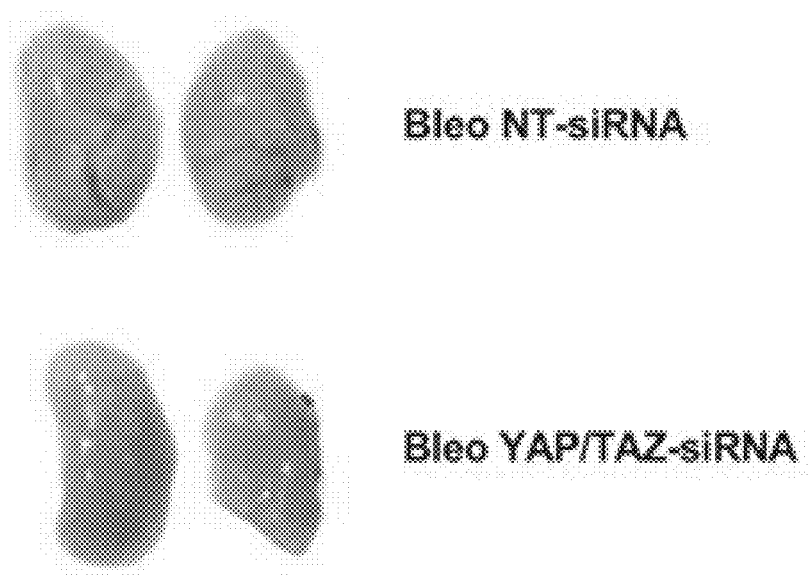
FIG. 23A contains images of lungs treated with bleomycin and YAP/TAZ siRNA.
Figure 23B:
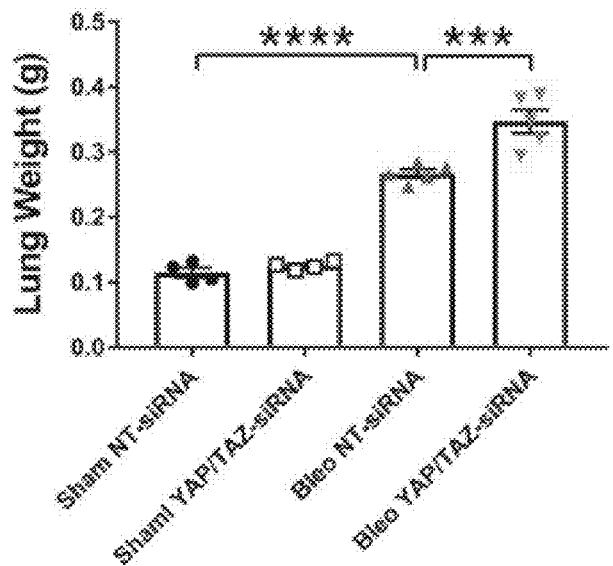
FIG. 23B contains a bar graph showing weight of sham- and bleo-treated lungs.
Figure 23C:
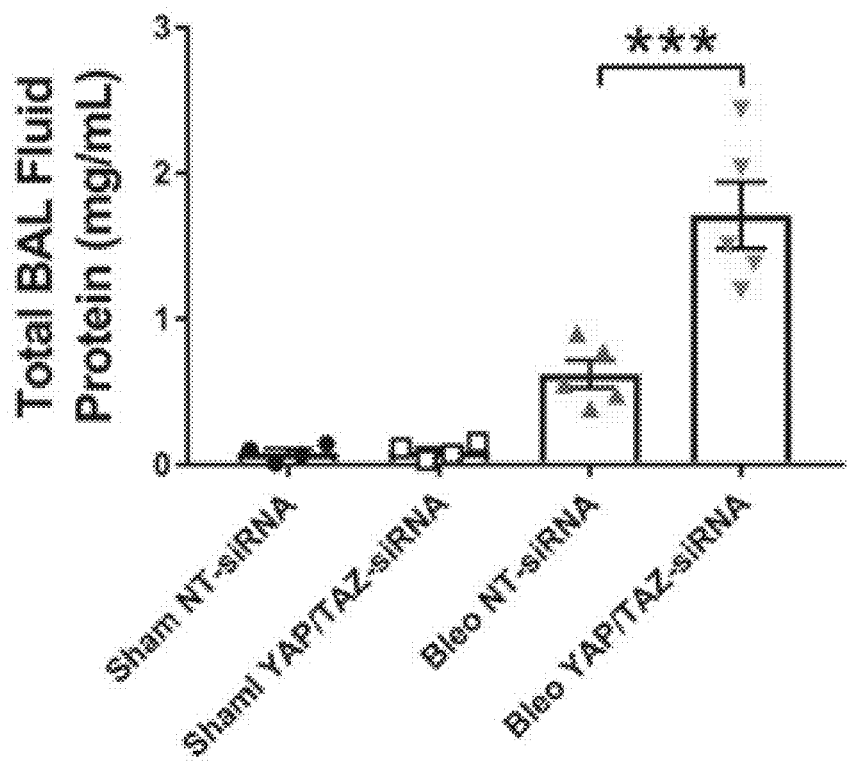
FIG. 23C contains a bar graph showing total BAL fluid protein in sham- and bleo-treated lungs.
Figure 24:
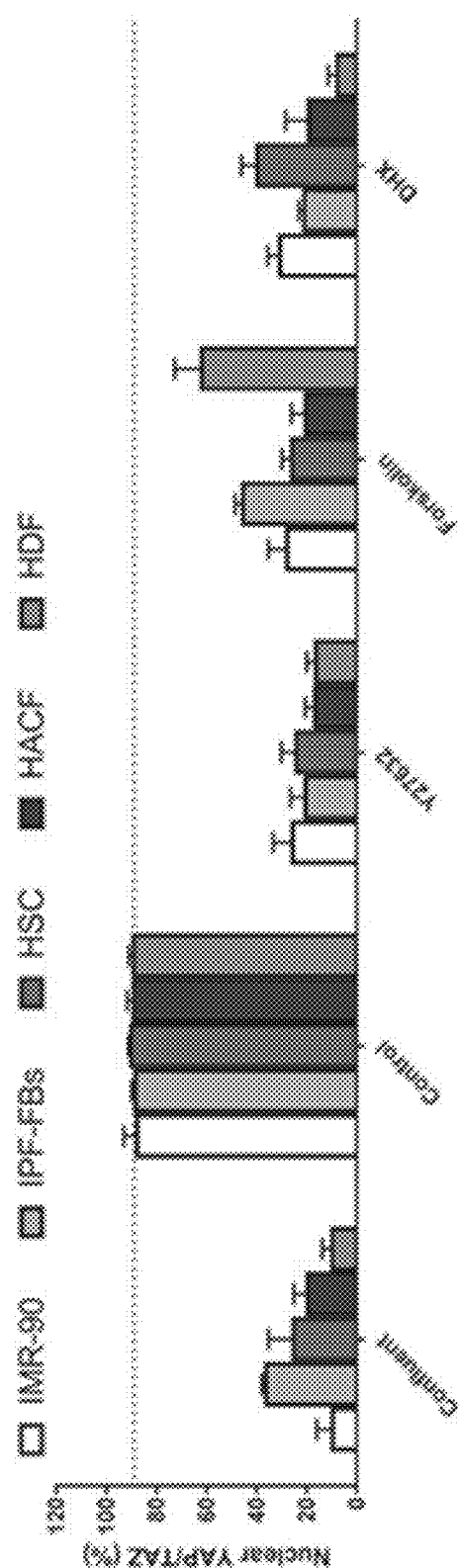
FIG. 24 shows that D1 agonist (e.g., DHX) inhibits YAP/TAZ localization in fibroblasts from multiple tissues. Mesenchymal cells derived from lung (IMR-90 and IPF-FBs) hepatic stellate cells (HSC), human adult cardiac fibroblasts, (HACF) and human dermal fibroblasts (HDF) were plated densely (Confluent) or sparsely (Control and all remaining conditions) onto plastic cell culture plates for 24 hours in media containing 0.10% FBS, treated for 2 hours with Rho kinase inhibitor Y27632, adenylate cyclase activator forskolin and DHX. N=4, Cells that were positive for nuclear YAP/TAZ were quantified by automated image analysis.
Figure 25:
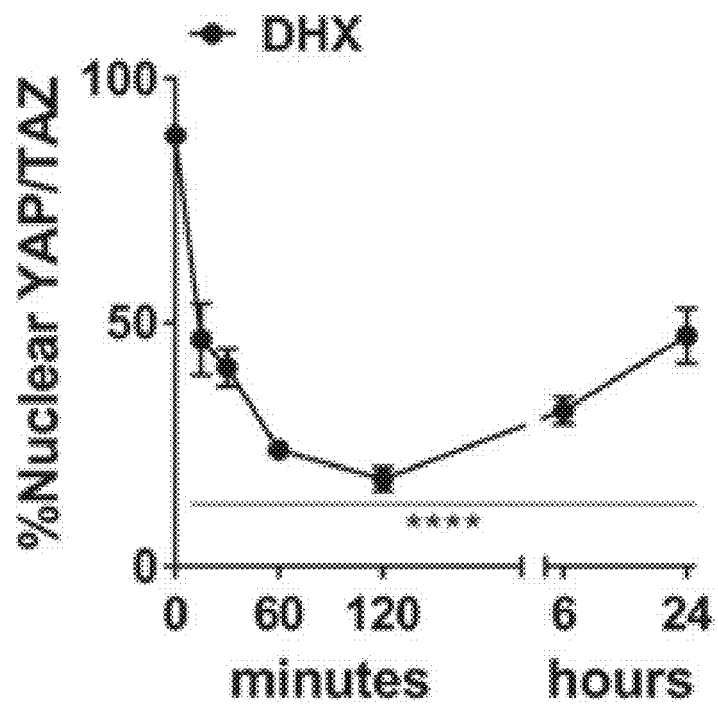
FIG. 25 shows time course for D1 agonist (e.g., DHX) inhibition of YAP/TAZ nuclear localization. IMR-90 cells, N=3 (***$p<0.001$ vs. 0.1% DMSO vehicle control).
Figure 26:
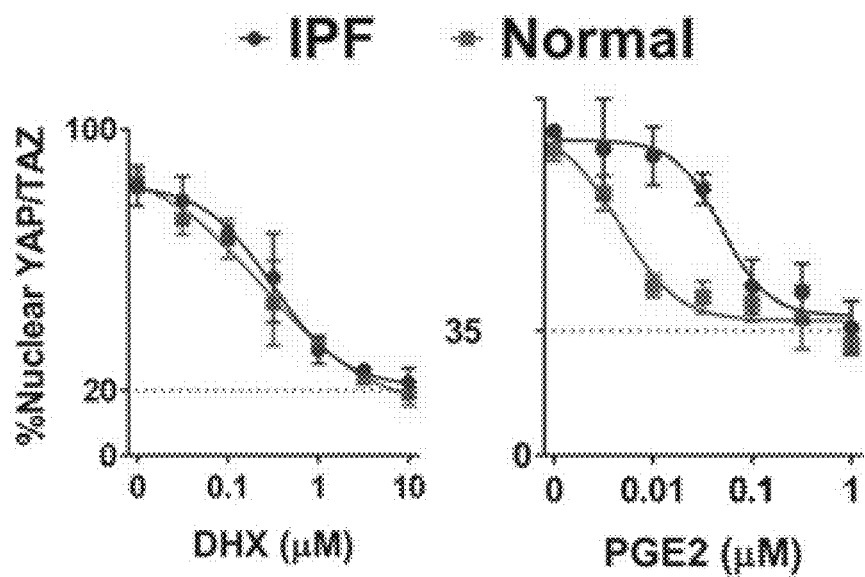
FIG. 26 shows that D1 agonist (e.g., DHX) does not lose potency in IPF derived fibroblasts, unlike PGE2. N=3.

Bleomycin model of pulmonary fibrosis was used to test the efficacy of DHX in vivo in experimental fibrosis. Mice were administered bleomycin intratracheally at Day 0. On Day 10 injury and inflammation typically subside and fibrosis is ongoing. At Day 10 mice were randomized into two groups, one receiving DHX (5 mg/kg once daily i.n.) and the other, vehicle control. The Bleo DHX group lost significantly less weight than the Bleo control group (FIG. 17). At day 24 the mice were sacrificed and compared using histology, hydroxyproline and qPCR. Histologically, the Bleo DHX group was nearly completely protected from lung remodeling compared to the Bleo control group and sham uninjured mice, as assessed by a blinded pathologist (FIG. 18). Total collagen in the lungs of Bleo DHX mice was nearly identical to sham treated mice, and significantly reduced compared to Bleo control mice (FIG. 19). Bleomycin increased staining for YAP and TAZ in the lungs and this was attenuated by DHX treatment (FIG. 20). The Bleo Control group also showed enhanced transcript levels for profibrotic genes Acta2, Ctgf, Fn1, Col1a1, and Col1a2, as well as Yap and Taz themselves, all of which were significantly attenuated in the Bleo DHX group (FIG. 21). To assess whether DHX adversely effects lung remodeling in the absence of fibrosis, we also exposed control mice to DHX following an identical time course and route of exposure. The lungs of Sham DHX mice did not differ from those of control mice using any of these measurements (FIG. 31-34).

Example 6—Effect of Dopamine Receptor Agonist (e.g., DHX) on Hepatic Stellate Cells Based on the efficacy of DHX in attenuating YAP/TAZ nuclear localization across an array of mesenchymal cells, we sought to extend our findings to hepatic stellate cells and liver fibrosis. Preferential expression of DRD1 in hepatic stellate cells (HSCs) compared to hepatocytes (FIG. 35-38) was confirmed, with results similar to those obtained for lung tissue in the previous examples. Ability of DHX to reduce TGFβ-mediated HSC expression of SMA and FN protein was then tested by western blotting, and observed significant reversal of both. Efficacy of DHX in the bile duct ligation model of cholestatic injury and liver fibrosis was then tested. Bile duct ligation was performed at Day 0 and treatment with DHX or vehicle began at Day 7 and continued for 14 days. DHX significantly improved histological fibrosis caused by the BDL and exhibited a trend toward reduced collagen deposition (FIG. 35-38).

Previous work demonstrated that TAZ mediates fibrotic effects in hepatocytes in a model of non-alcoholic steatohepatitis (Ref. 37), that verteporfin (an inhibitor of YAP/TAZ-TEAD interactions) has limited beneficial effects in models of liver fibrosis models (Ref. 19), and that YAP/TAZ are essential in liver regeneration (nonspecific YAP knockdown in liver promotes hepatocyte necrosis (Ref. 38)). The experimental results presented here demonstrate the efficacy of a GPCR-based approach to selective inhibition of YAP/TAZ in experimental liver fibrosis.

Figure 61A:
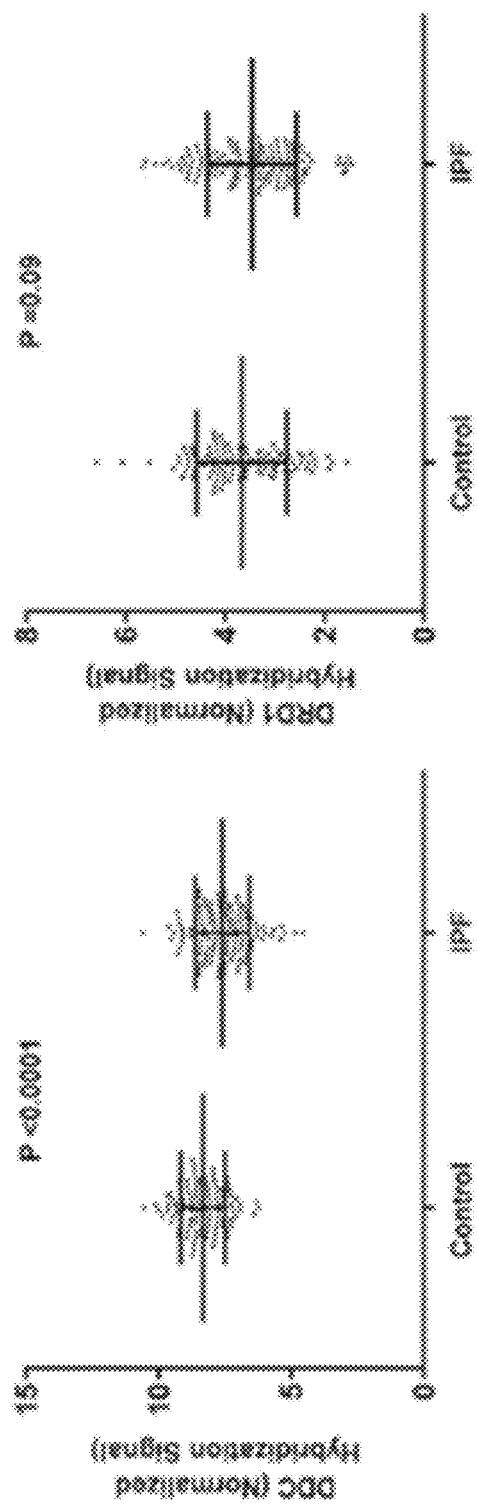
FIG. 61A DOPA decarboxylase is decreased in IPF, and correlates with worsening disease severity Expression levels for DDC and DRD1 were queried from microarray analyses of IPF (n=134) and control (n=108) lungs. Each data point represents expression levels from an individual. Bars indicate mean and standard deviation.
Figure 61B:
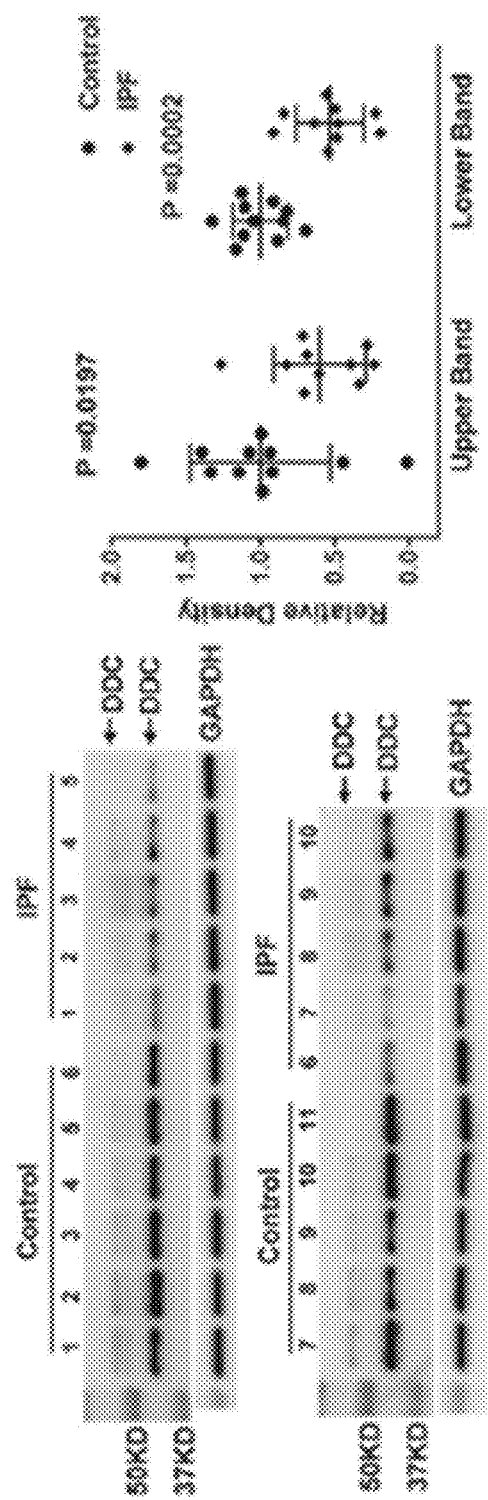
FIG. 61B shows results of an experiment where western blotting was used to detect DDC protein expression in whole lung homogenates from IPF (n=10) and control (n=11) lungs. Bars indicate mean and standard deviation.
Figure 61C:
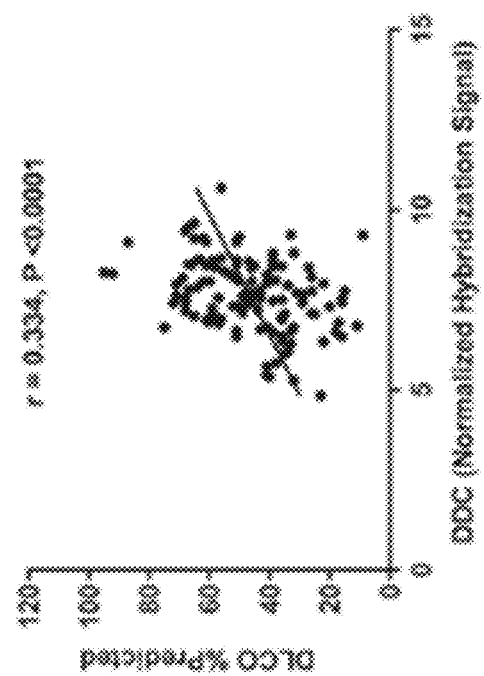
FIG. 61C shows results of an experiment where univariate analysis of the correlation of DDC expression with forced vital capacity (FVC) and diffusing capacity of the lung for carbon monoxide (DLCO) was performed using the Pearson's correlation coefficient (r). Each data point represents expression levels and lung function (expressed a percent predicted based on age, sex and ideal body weight) from an individual. P values are as indicated for each figure panel.
Figure 61C:
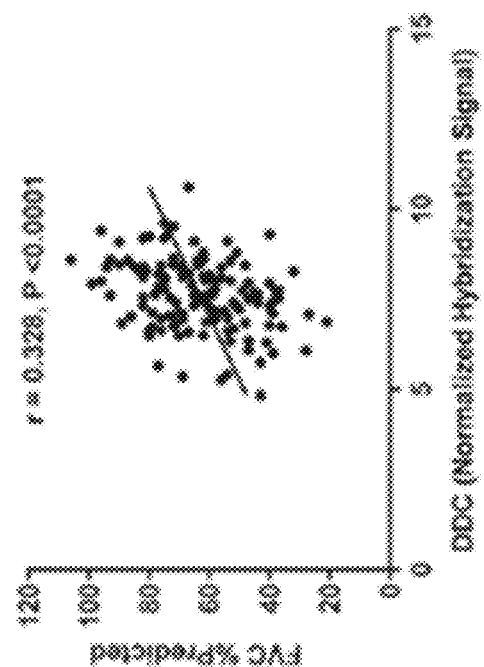
Figure 62A:
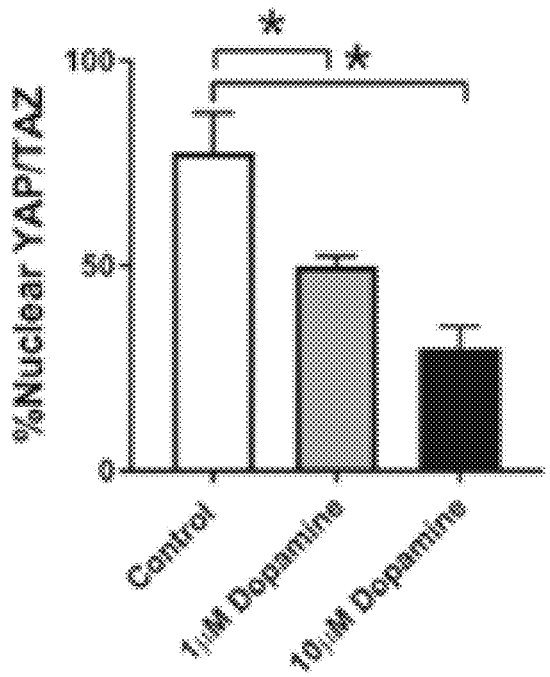
FIG. 62A shows that dopamine promotes anti-fibrotic effects. Dopamine inhibits YAP/TAZ nuclear localization in low density IPF-patient derived fibroblasts plated onto tissue culture plastic. N=2.
Figure 62B:
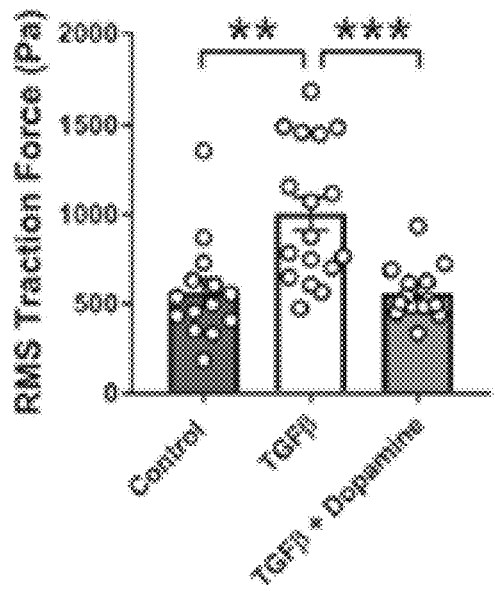
FIG. 62B shows that dopamine attenuates IPF fibroblast contractility measured by traction force microscopy (**$p<0.0001$, *$p<0.001$, **$p<0.01$, *$p<0.05$ vs. the indicated group).
Figure 62C:
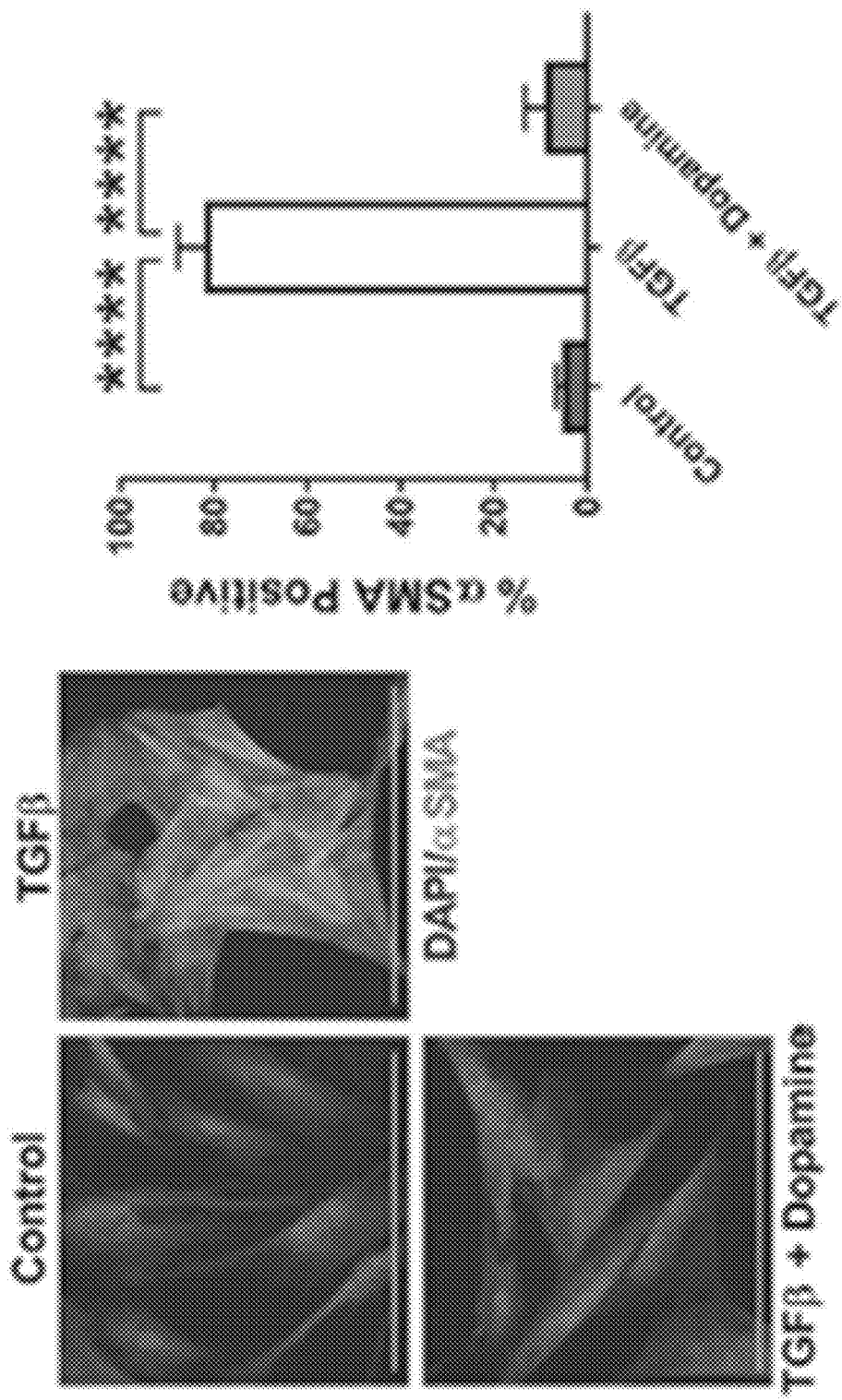
FIG. 62C shows that dopamine reverses αSMA+ stress fiber formation. IPF-patient derived fibroblasts, pre-stimulated with 2 ng/mL TGFβ for 48 hours, then treated with dopamine (1 μM)+2 ng/mL TGFβ for additional 24 hours. N=4. Scale bar represents 500 μm.
Figure 63:
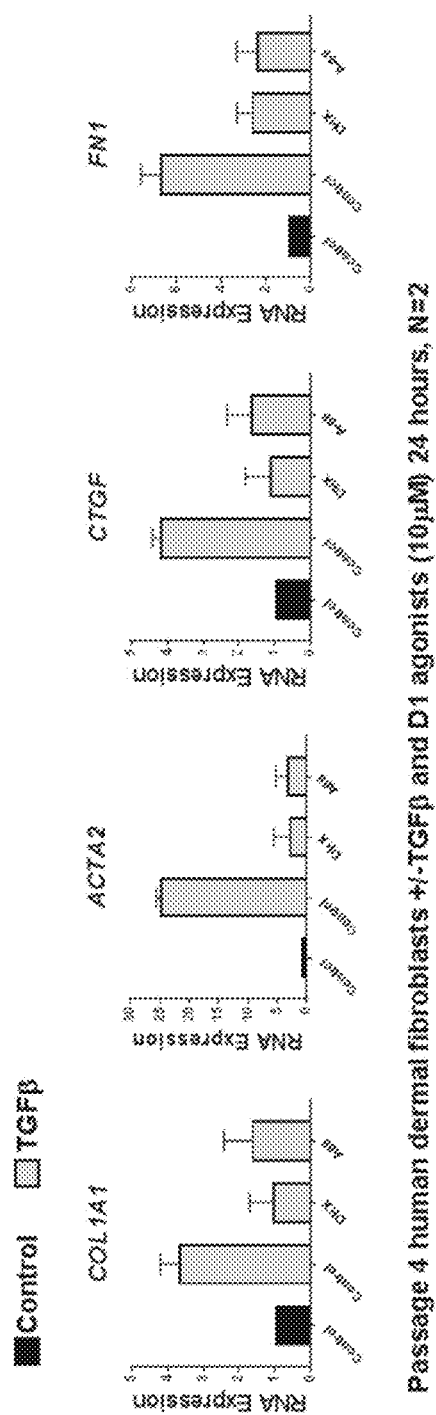
FIG. 63 shows that DRD1 agonism blocks profibrotic gene expression in human dermal fibroblasts. Human dermal fibroblasts treated for 24 hours+/−2 ng/mL TGFβ and D1 agonists: DHX and A68930 prior to RNA isolation. N=2.
Figure 64:
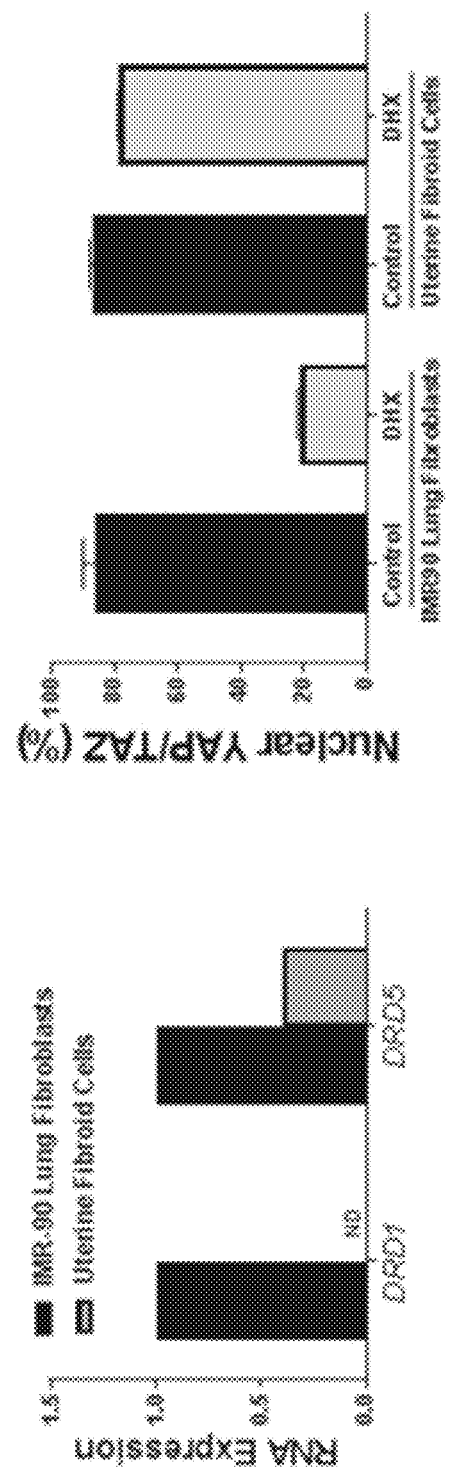
FIG. 64 shows that dihydrexidine (DHX) efficacy depends on expression of D1 like dopamine receptors (DRD1, DRD5). IMR-90 lung fibroblasts express higher levels of DRD1 and DRD5 than mesenchymal cells derived from uterine fibroids which results in marginal inhibition of YAP/TAZ nuclear localization by DHX in these cells. ND refers to the gene not being detected.
Figure 65:
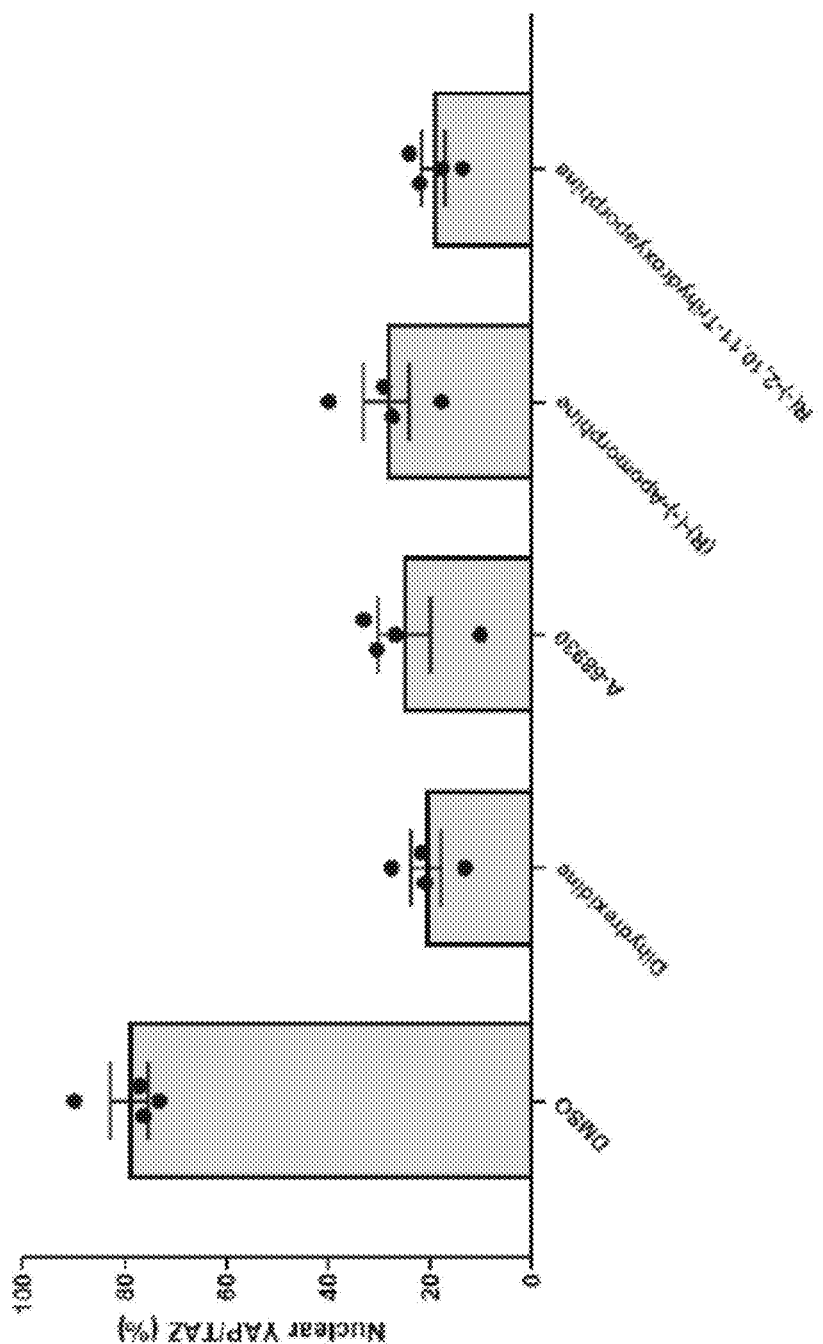
FIG. 65 contains a bar graph showing nuclear YAP/TAZ/DAPI inhibition by D1 agonists dihydrexidine (DHX), A-68930, (R)-(−)-apomorphine, and R(−)-2,10,11-trihydroxyaporphine. (10 μM) N=4 IPF-patient derived lung fibroblasts.
Figure 66:
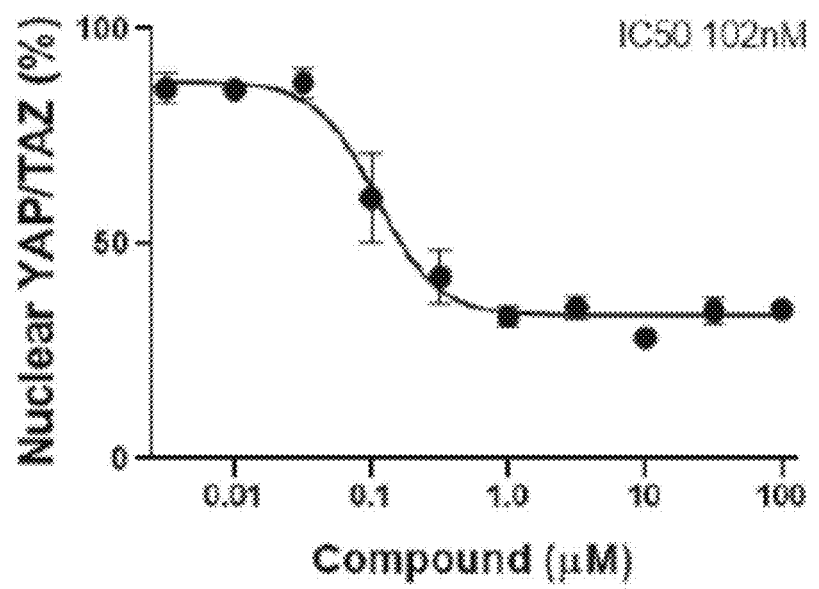
FIG. 66 contains a line plot showing that compound CTC-3 inhibits YAP/TAZ nuclear localization. Adult lung fibroblasts (N=2) sparsely plated into 96-well plates. Treated for 2 hours with compounds prior to fixing and immunostaining for YAP/TAZ. Imaging and quantification of nuclear YAP/TAZ performed through automation using a Cytation 5 ($IC_{50}$ is 102 nM).
Figure 66:
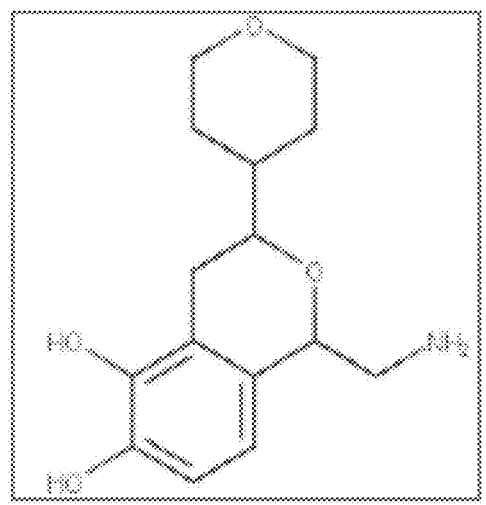
Figure 67:
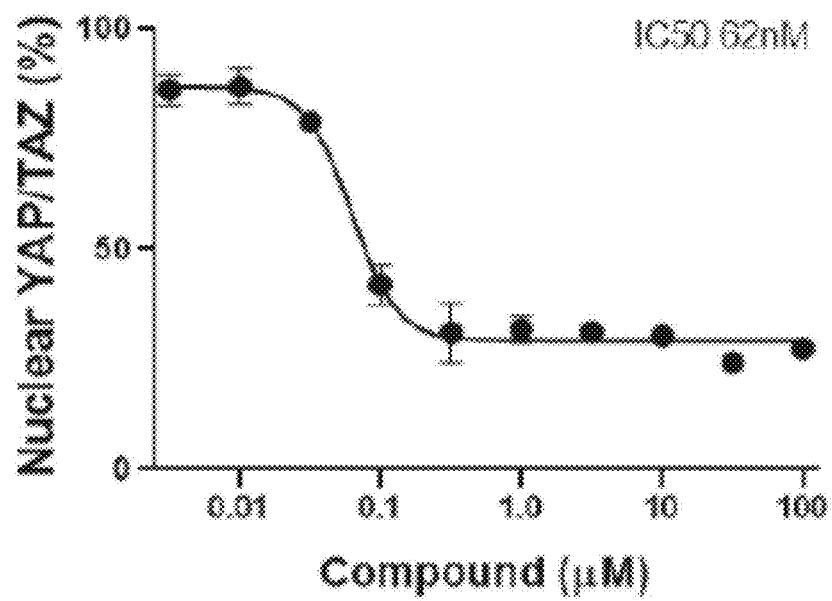
FIG. 67 contains a line plot showing that compound CTC-6 inhibits YAP/TAZ nuclear localization. Adult lung fibroblasts (N=2) sparsely plated into 96-well plates. Treated for 2 hours with compounds prior to fixing and immunostaining for YAP/TAZ. Imaging and quantification of nuclear YAP/TAZ performed through automation using a Cytation 5 ($IC_{50}$ is 62 nM).
Figure 67:
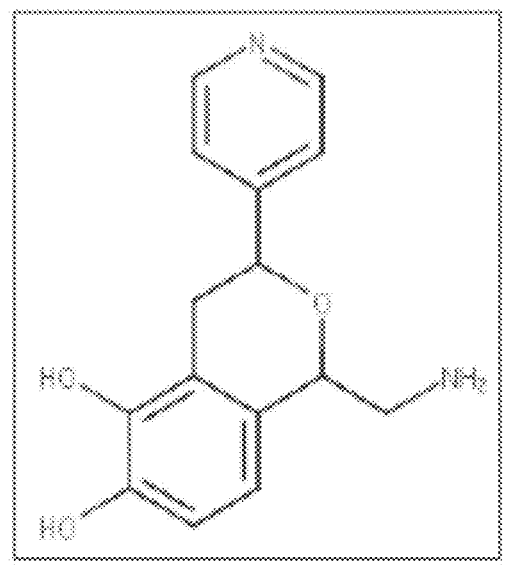
Figure 68:
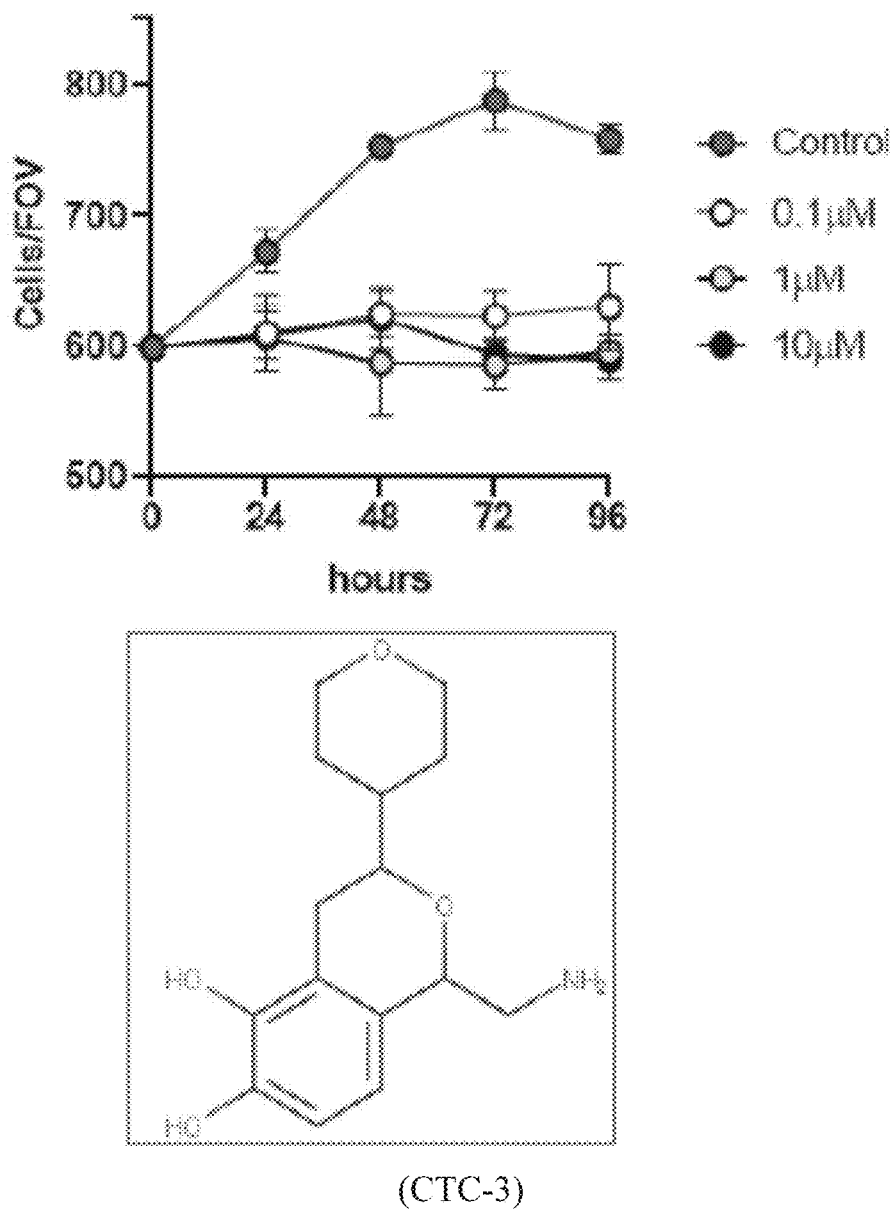
FIG. 68 contains a line plot showing that compound CTC-3 inhibits fibroblast proliferation. Adult lung fibroblasts plated into 96-well plates, stimulated with 2 ng/mL TGFβ and compounds at the indicated concentration. Proliferation determined by fixing and counting DAPI nuclei using a Cytation 5. N=2.
Figure 69:
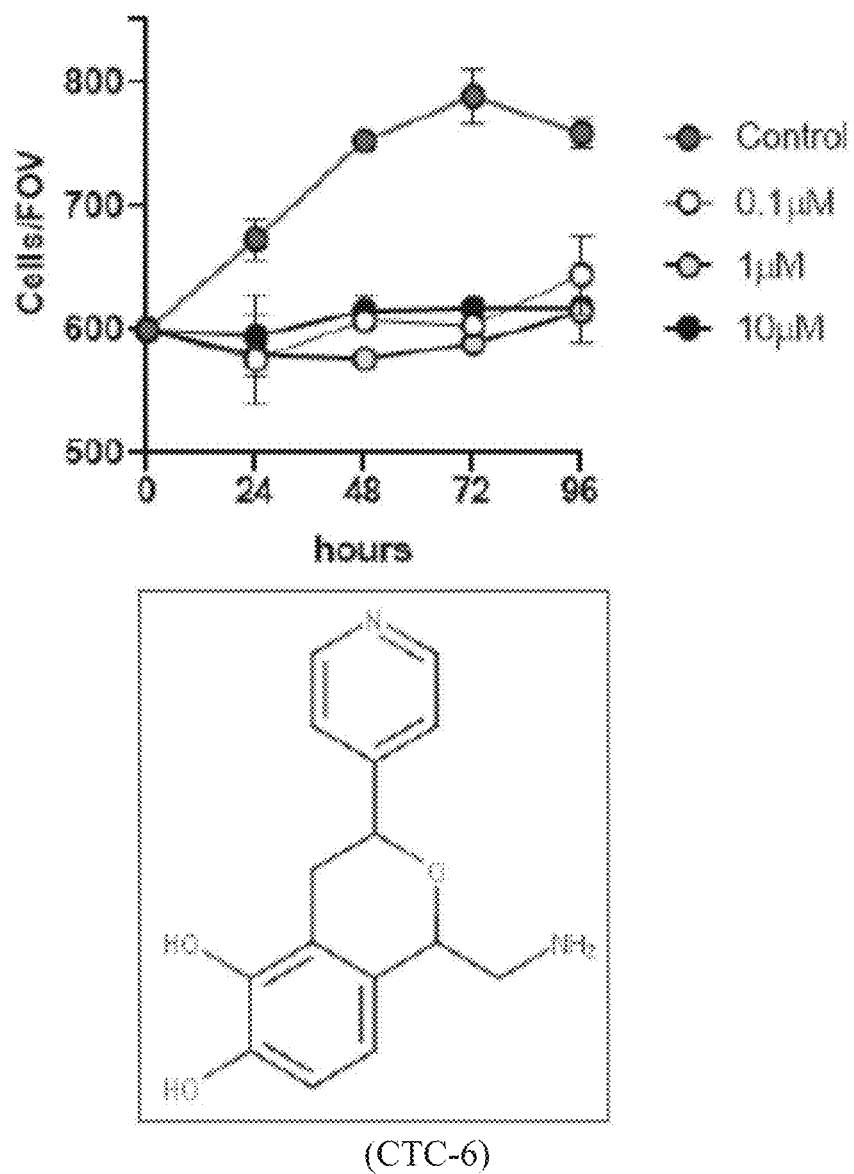
FIG. 69 contains a line plot showing that compound CTC-6 inhibits fibroblast proliferation. Adult lung fibroblasts plated into 96-well plates, stimulated with 2 ng/mL TGFβ and compounds at the indicated concentration. Proliferation determined by fixing and counting DAPI nuclei using a Cytation 5. N=2.
Figure 70:
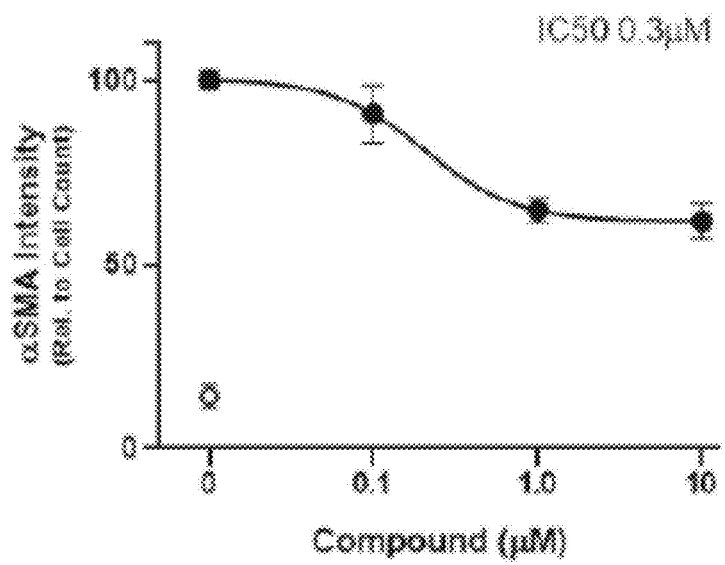
FIG. 70 contains a line plot showing that compound CTC-3 inhibits fibroblast activation. Adult lung fibroblasts plated into 96-well plates, stimulated with 2 ng/mL TGFβ for 96 hours and treated with the indicated concentration of compounds every 48 hours. Imaging and quantification of αSMA intensity performed through automation using a Cytation 5. ($IC_{50}$ is 0.3 μM).
Figure 70:
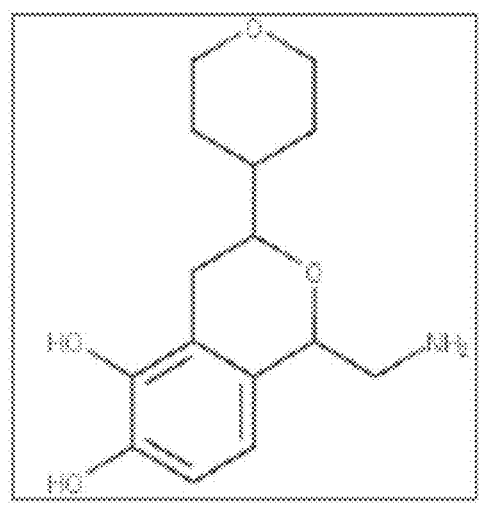
Figure 71:
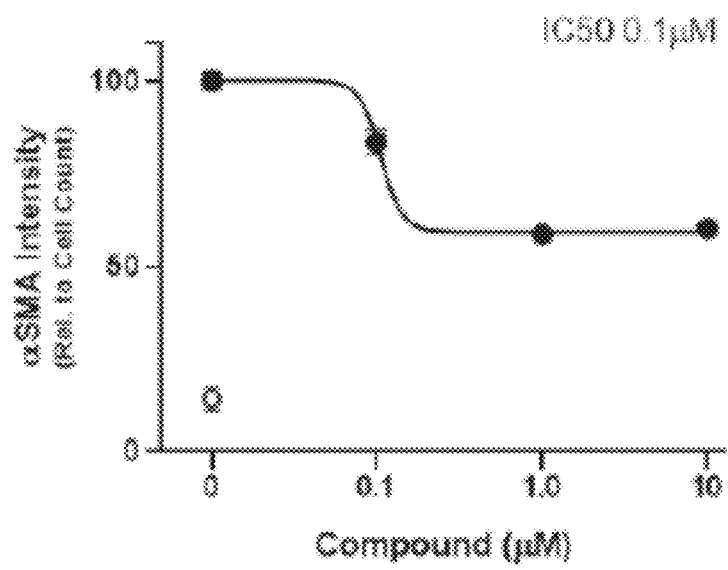
FIG. 71 contains a line plot showing that compound CTC-6 inhibits fibroblast activation. Adult lung fibroblasts plated into 96-well plates, stimulated with 2 ng/mL TGFβ for 96 hours and treated with the indicated concentration of compounds every 48 hours. Imaging and quantification of αSMA intensity performed through automation using a Cytation 5. ($IC_{50}$ is 0.1 μM).
Figure 71:
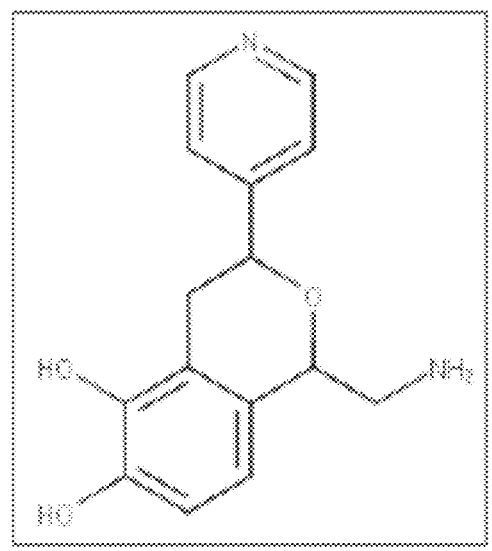
Figure 72:
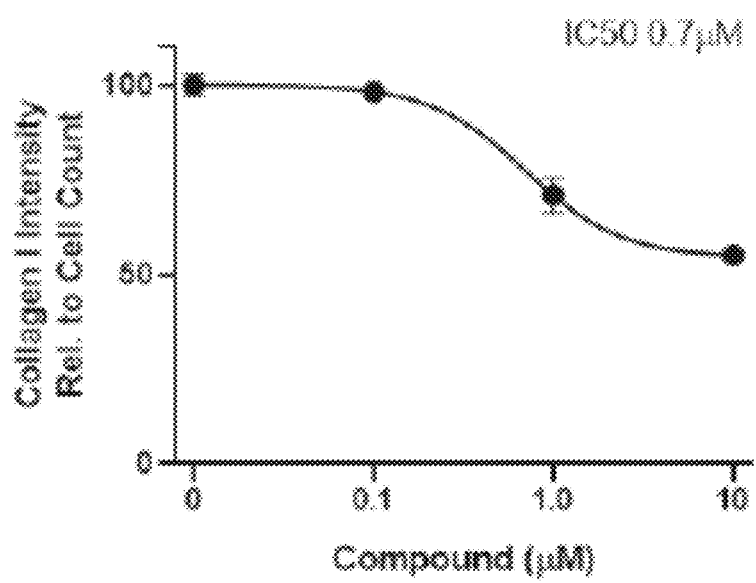
FIG. 72 contains a line plot showing that compound CTC-3 inhibits Collagen I deposition. Adult lung fibroblasts plated into 96-well plates, stimulated with 2 ng/mL TGFβ for 96 hours and treated with the indicated concentration of compounds every 48 hours. Imaging and quantification of Collagen I intensity performed through automation using a LI-COR Odyssey. ($IC_{50}$ is 0.7 μM).
Figure 72:
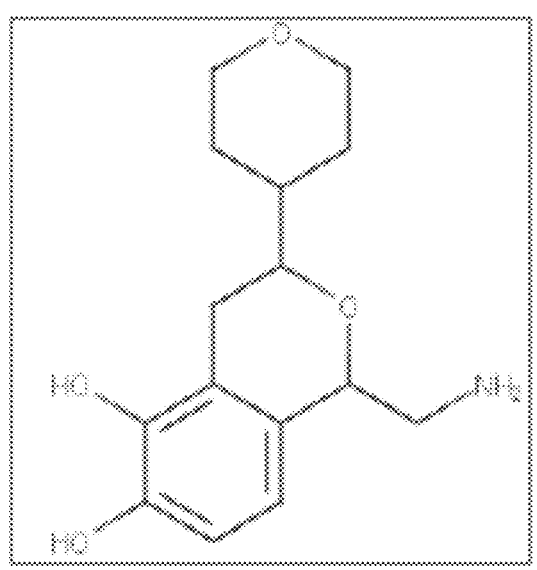
Figure 73:
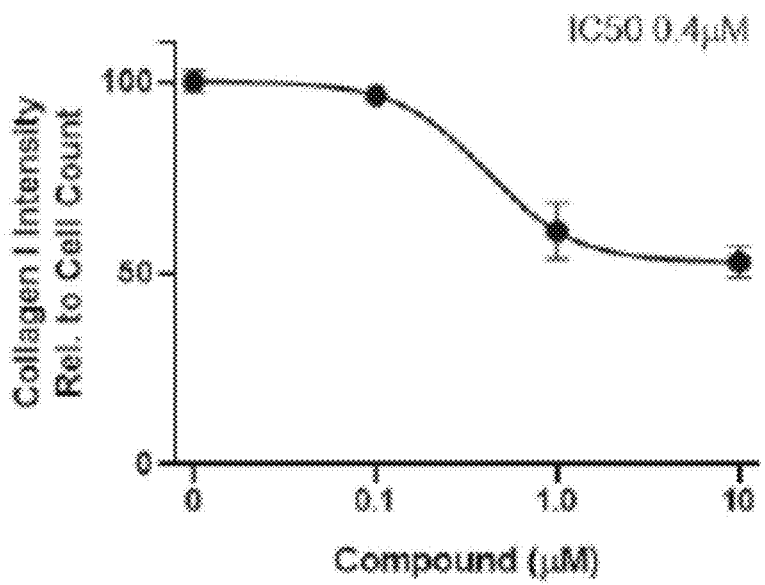
FIG. 73 contains a line plot showing that compound CTC-6 inhibits Collagen I deposition. Adult lung fibroblasts plated into 96-well plates, stimulated with 2 ng/mL TGFβ for 96 hours and treated with the indicated concentration of compounds every 48 hours. Imaging and quantification of Collagen I intensity performed through automation using a LI-COR Odyssey. ($IC_{50}$ is 0.4 μM).
Figure 73:
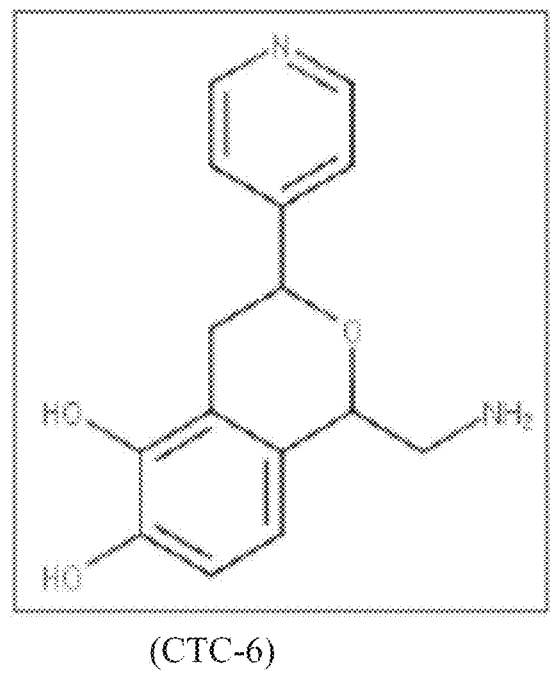
Figure 74:
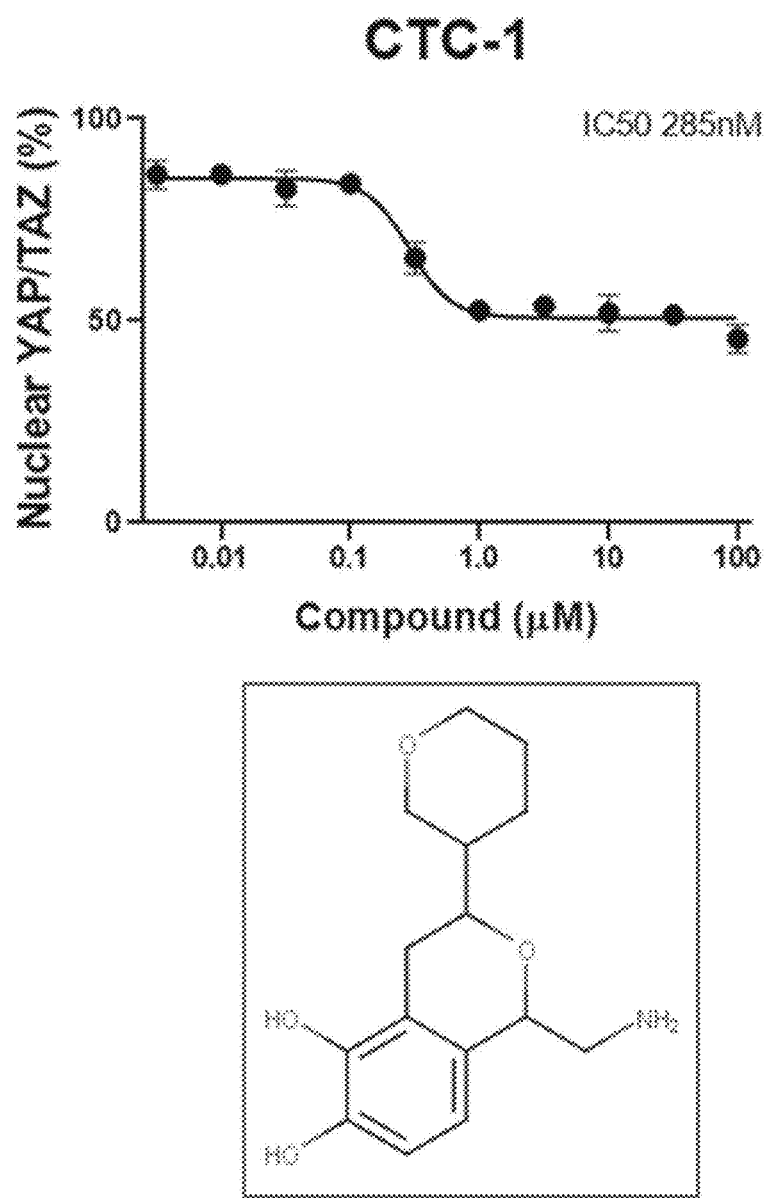
FIG. 74 contains a line plot showing that compound CTC-1 inhibits YAP/TAZ nuclear localization. Adult lung fibroblasts (N=2) sparsely plated into 96-well plates. Treated for 2 hours with compounds prior to fixing and immunostaining for YAP/TAZ. Imaging and quantification of nuclear YAP/TAZ performed through automation using a Cytation 5 ($IC_{50}$ is 285 nM).
Figure 75:
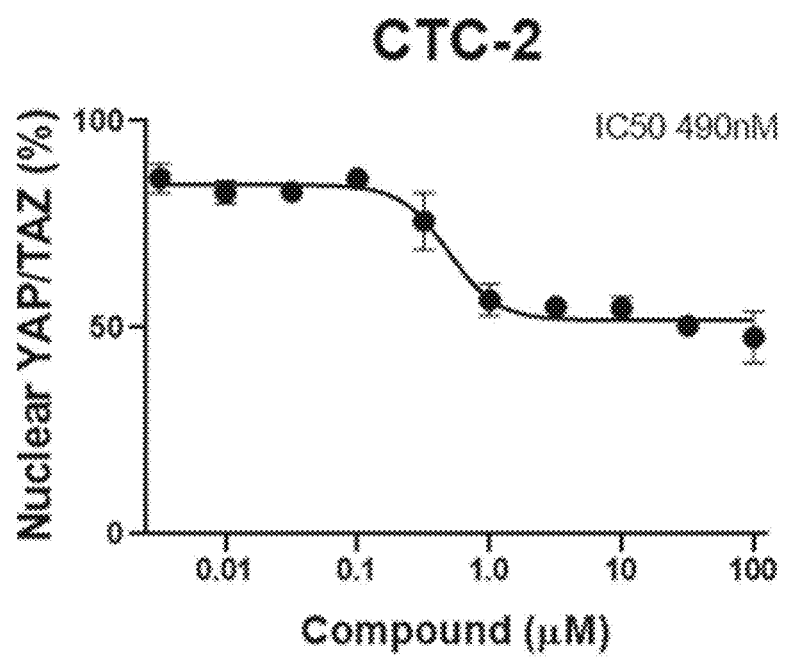
FIG. 75 contains a line plot showing that compound CTC-2 inhibits YAP/TAZ nuclear localization. Adult lung fibroblasts (N=2) sparsely plated into 96-well plates. Treated for 2 hours with compounds prior to fixing and immunostaining for YAP/TAZ. Imaging and quantification of nuclear YAP/TAZ performed through automation using a Cytation 5 ($IC_{50}$ is 490 nM).
Figure 75:
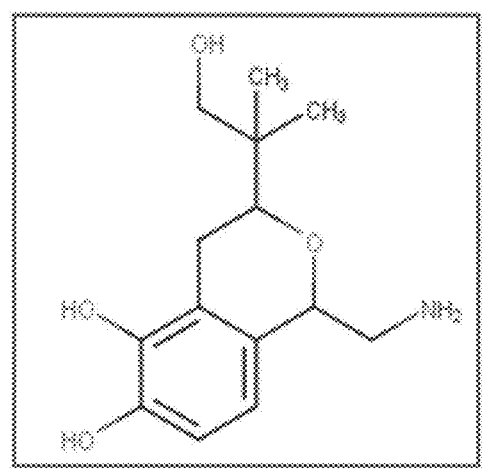
Figure 76:
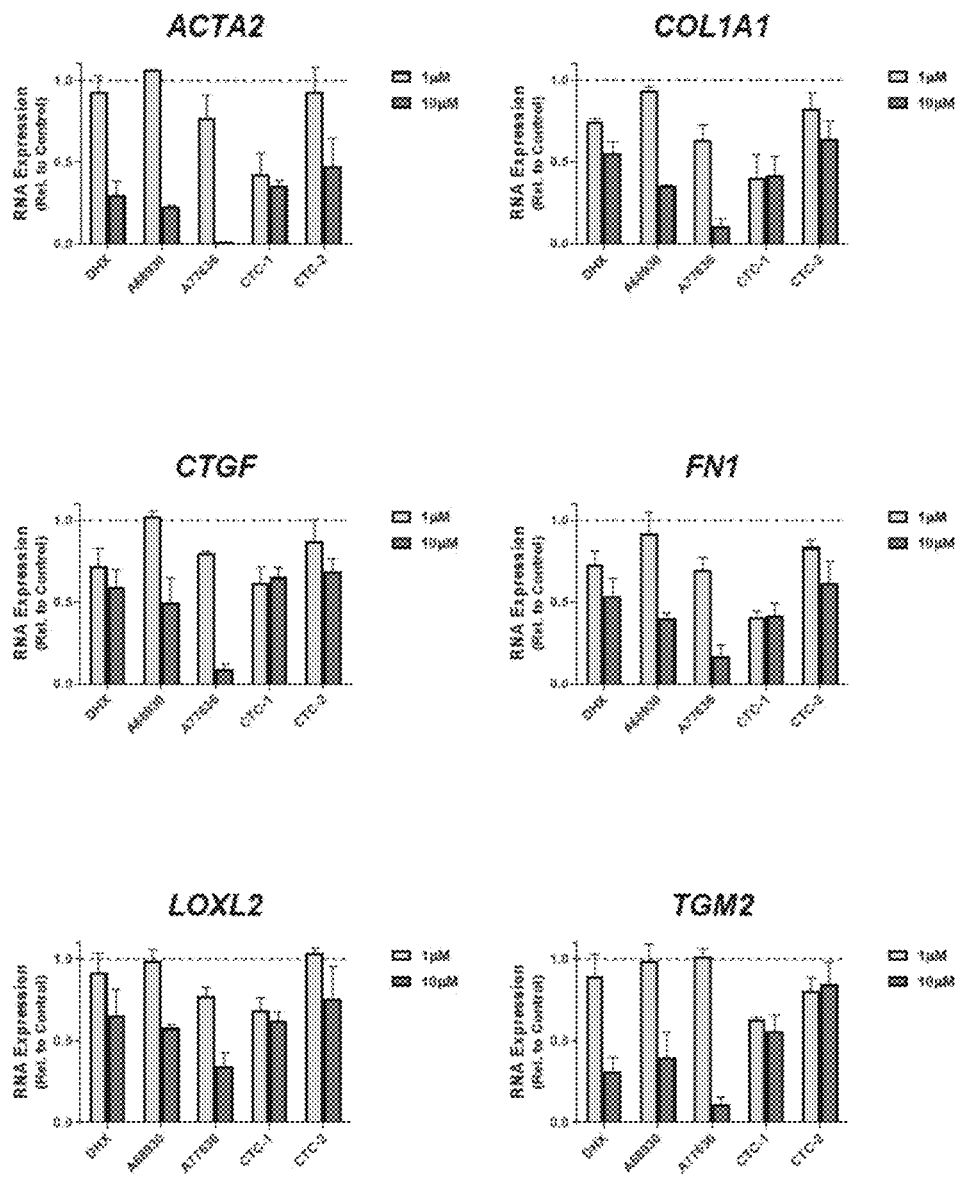
FIG. 76 contains bar graphs showing inhibition of profibrotic gene expression by compounds CTC-1 and CTC-2. IMR-90 lung fibroblasts, treated for 24 hours with the indicated concentration of compound. N=3.
Figure 77A:
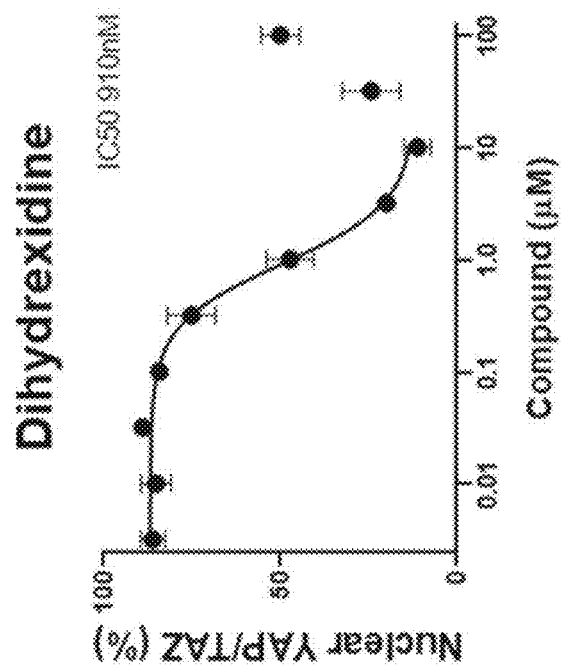
FIG. 77A contains structure and YAP/TAZ inhibition efficacy of dihydrexidine ("DHX"). Human lung fibroblasts were treated for 2 hours with the indicated concentration of dihydrexidine prior to imaging and quantifying YAP/TAZ localization.
Figure 77A:
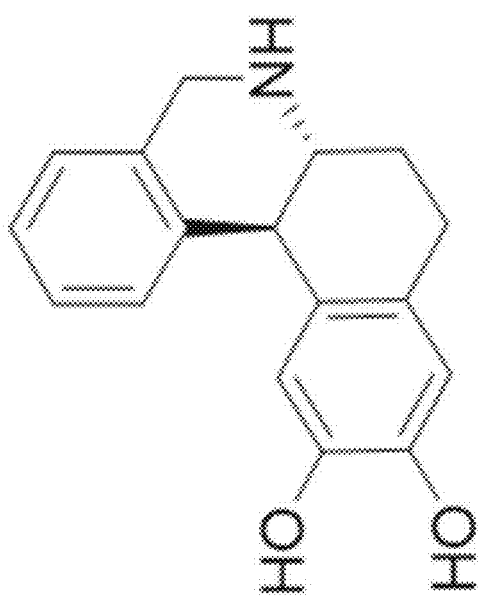
Figure 77B:
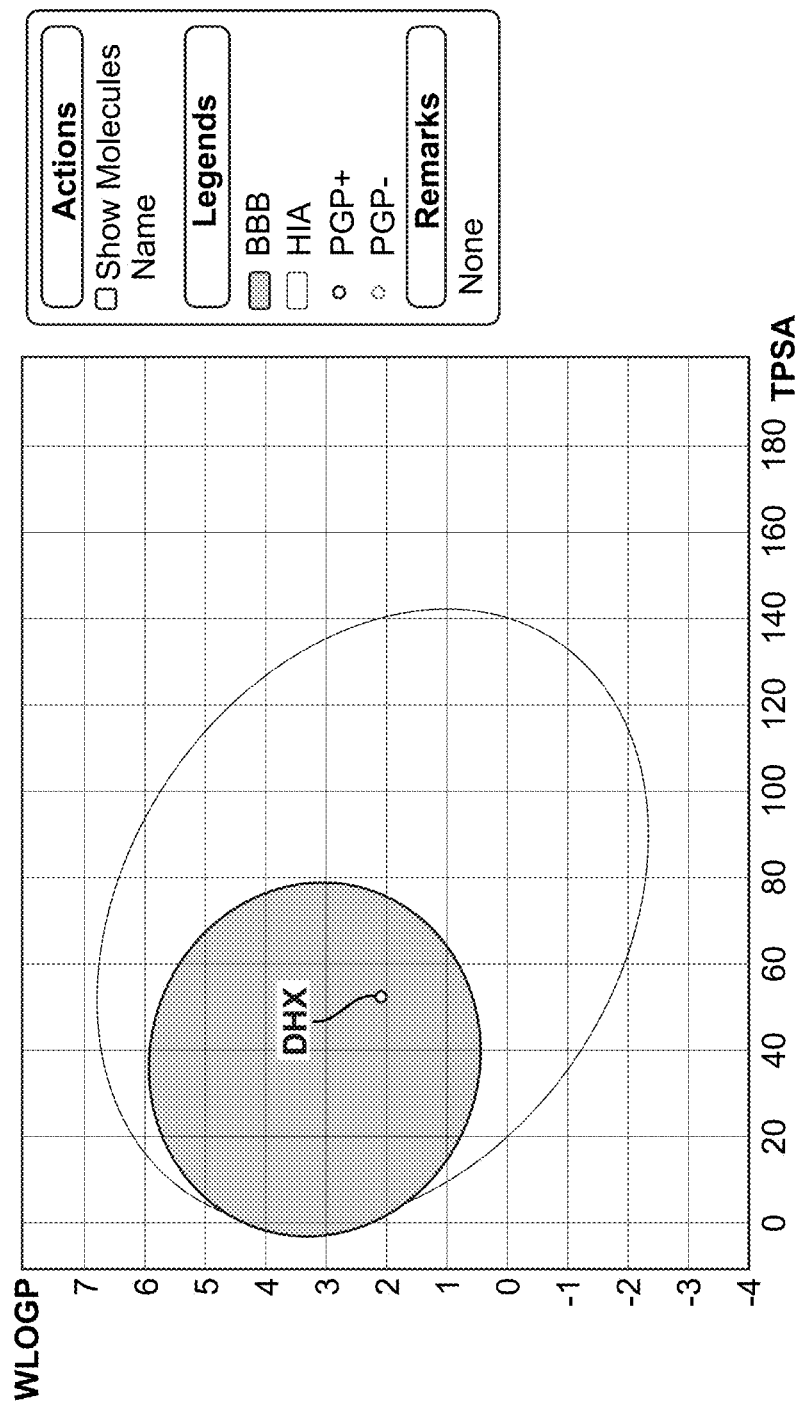
FIG. 77B contains an image of fried eggs model of predicted BBB penetration for DHX using TPSA and WLOGP properties. Compounds which fit into the "yolk" are predicted to enter the CNS. These predictions correlate with in vitro models of BBB penetration.
Figure 78:
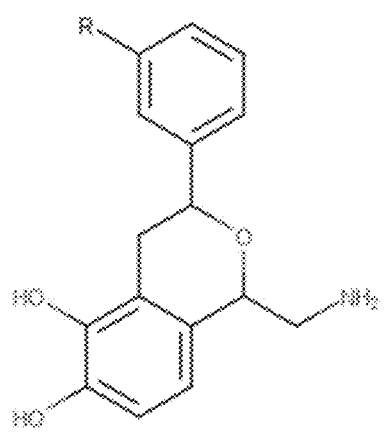
FIG. 78 contains structures and efficacy data for phenyl containing analogs of A-68930. Potency and Efficacy of 3-substituted A-68930 analogs. Measurements were obtained using gold-fish retina or rat striatum, per U.S. Pat. No. 5,621,133.
Figure 79:
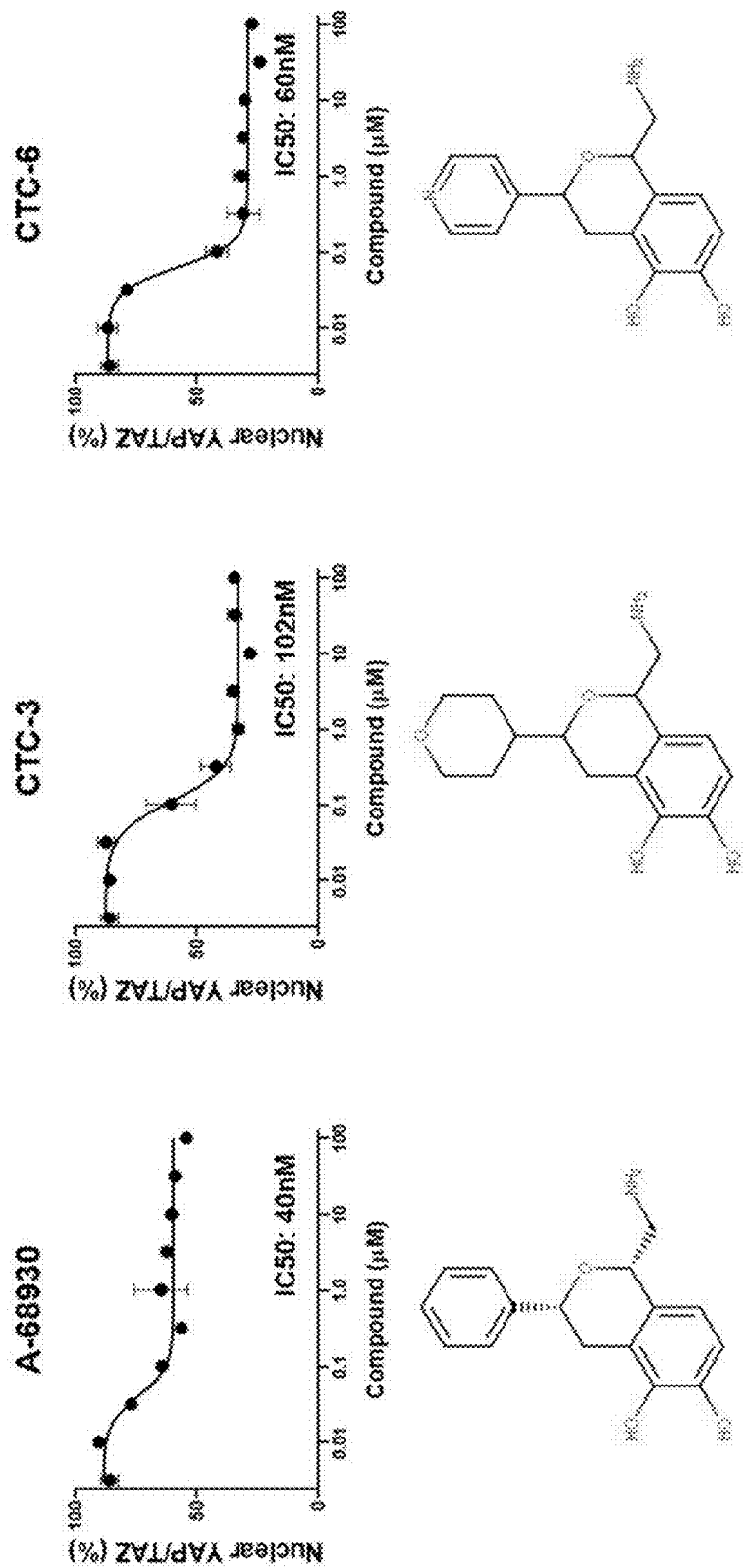
FIG. 79 contains comparative YAP/TAZ nuclear localization inhibition between A-68930 and D1 agonists of the present disclosure. Adult lung fibroblasts (N=2) sparsely plated into 96-well plates. Treated for 2 hours with compounds prior to fixing and immunostaining for YAP/TAZ. Imaging and quantification of nuclear YAP/TAZ performed through automation using a Cytation 5. A-68390 was tested as an optically pure stereoisomer. CTC-3 and CTC-6 are both 1:1 mixtures of active and inactive stereoisomers (the observed potency is 2-fold higher). The major drawback of A-68930 is it lacks full efficacy to elevate cAMP.
Figure 80:
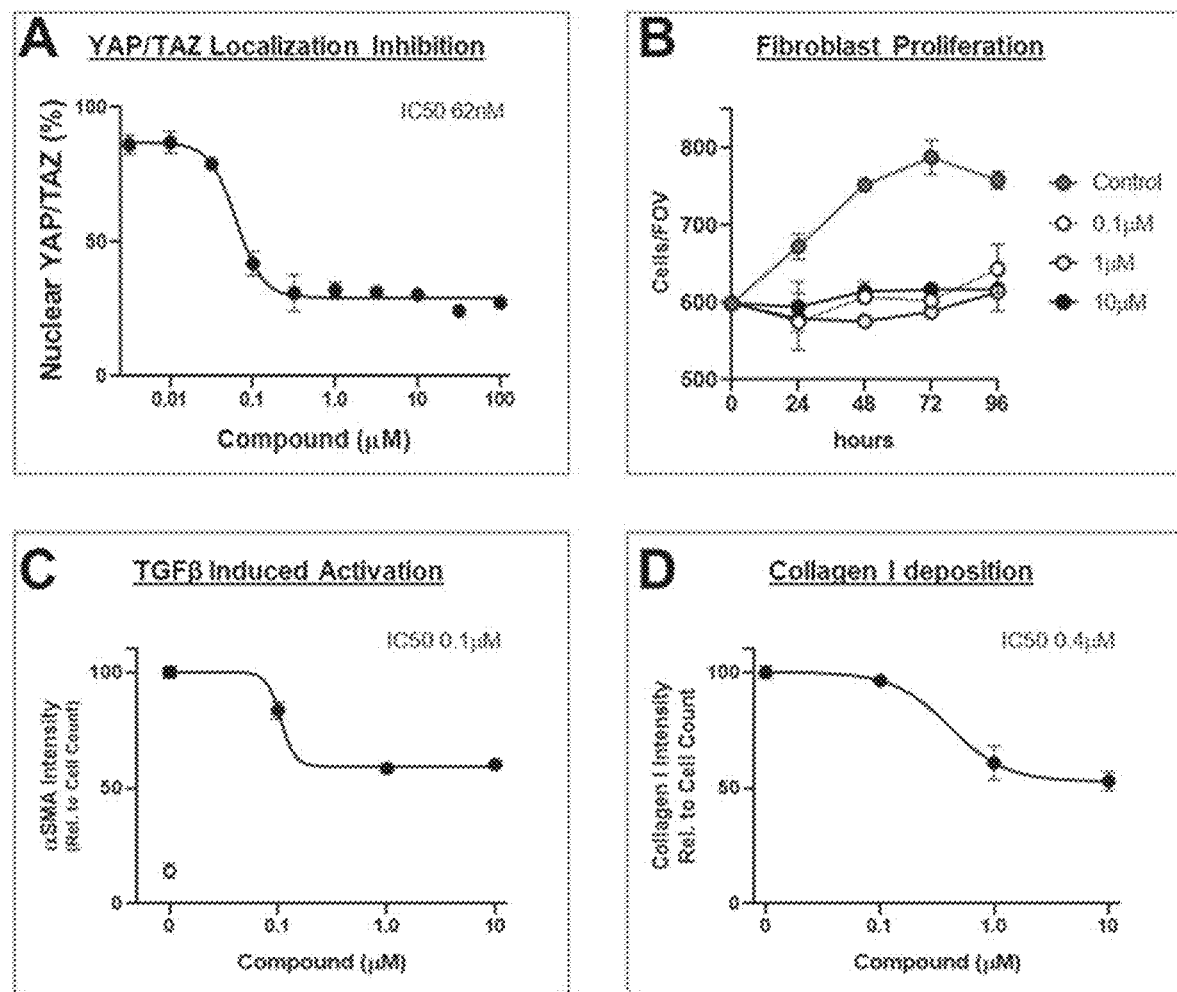
FIG. 80 contains line plots efficacy of CTC-6 in vitro. A. Dose-response curve for CTC-6 inhibiting YAP/TAZ localization in lung fibroblasts. B. Human lung fibroblasts were stimulated for 4 days with 2 ng/mL TGFβ and cell number was measured daily by counting DAPI nuclei from fixed cells treated with the indicated concentration of CTC-6. C. Expression of αSMA intensity measured by immunocytochemistry D. Collagen deposition measured using a "in-cell Western blot" technique developed by our group. Important to note: these data were collected using a racemic mixture of CTC-6. The active stereoisomer is 2-fold more potent that the inactive stereoisomer.
Figure 81A:
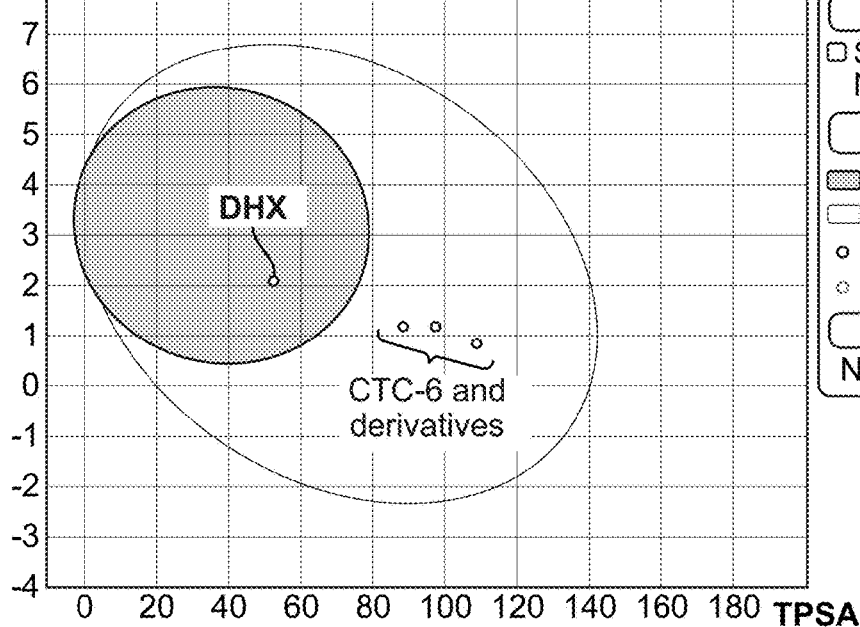
FIG. 81A contains fried eggs model of predicted BBB penetration using TPSA and WLOGP properties. Compounds which fit into the "yolk" are predicted to enter the CNS. DHX and CTC-6 are plotted along with the other compounds of the present disclosure.
Figure 81B:
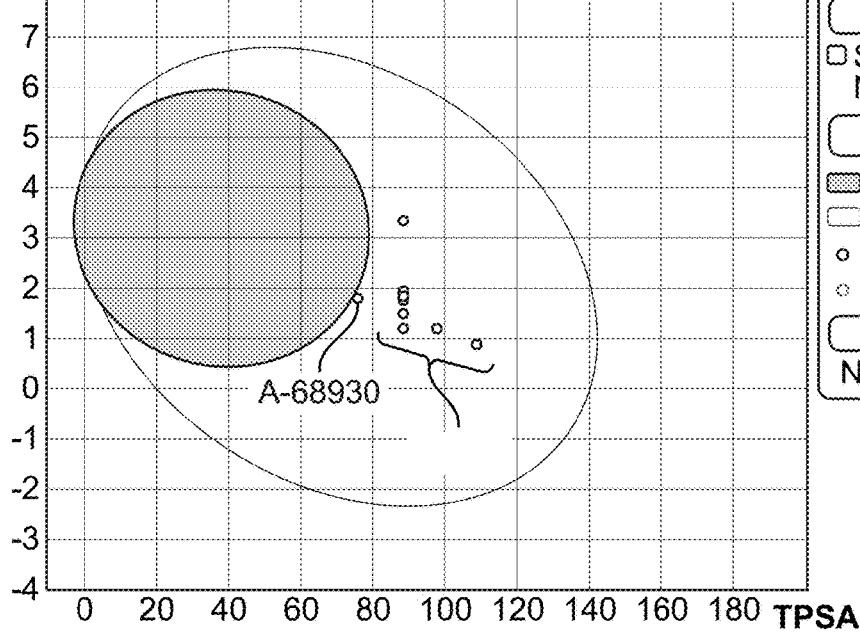
FIG. 81B contains fried eggs model of predicted BBB penetration using TPSA and WLOGP properties. Compounds which fit into the "yolk" are predicted to enter the CNS. A-68930 and CTC-6 are plotted along with the other compounds of the present disclosure.
Figure 82:
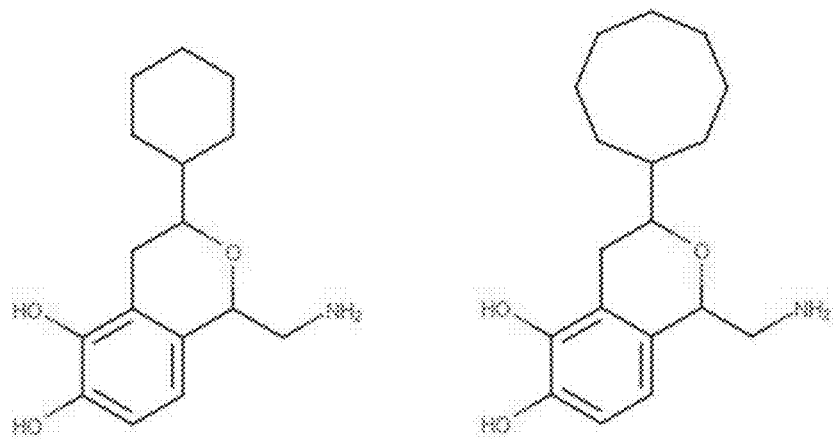
FIG. 82 contains compound structures and data from cyclohexane and cyclooctane derivatives of DHX. Potency appears to be maintained and the efficacy is dramatically increased in the cycloctane. Measurements were obtained using gold-fish retina or rat striatum according to published patent and manuscript.
Figure 83:
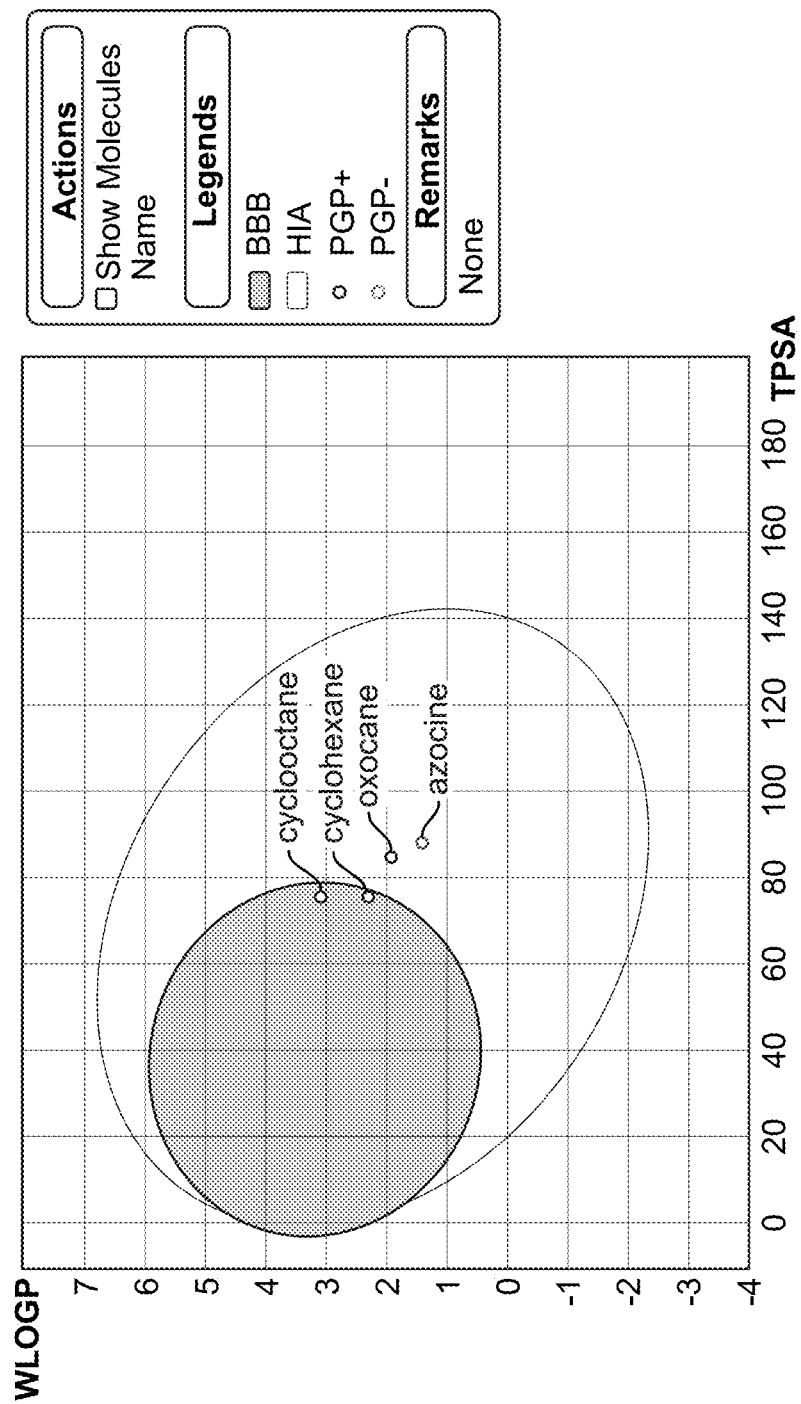
FIG. 83 contains a fried eggs model of predicted BBB penetration using TPSA and WLOGP properties for the compounds of example 9 having various heterocyclis in position $R^1$ of Formula (I).
Figure 84:
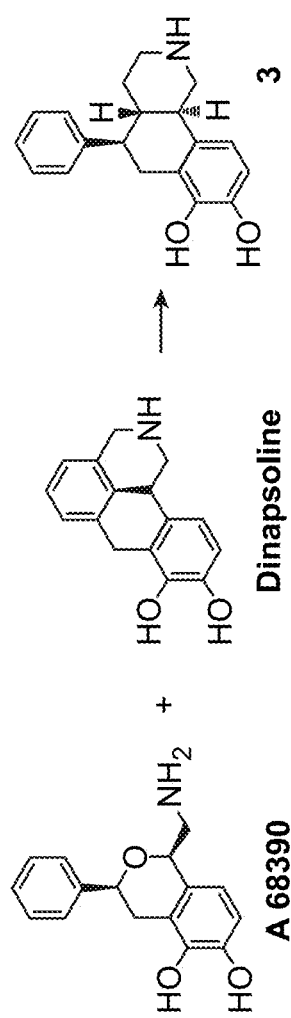
FIG. 84 shows compounds having dinapsoline/A-68930 hybrid scaffold (3), which is more potent than DHX and more efficacious than A-68930. Dinapsoline/A-68930 hybrid scaffolds were previously described by a group at Purdue University in 2010. This hybrid is ~6× more potent than DHX and shows full efficacy at elevating cAMP.
Figure 85:
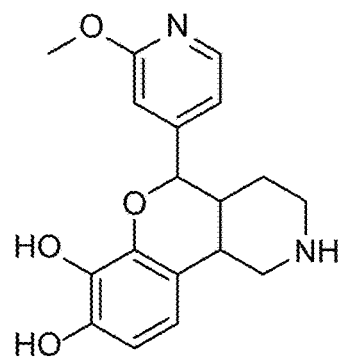
FIG. 85 shows fried eggs model of predicted BBB penetration using TPSA and WLOGP properties of compound of Example 2. Chemical structure of the compound is also shown.
Figure 85:
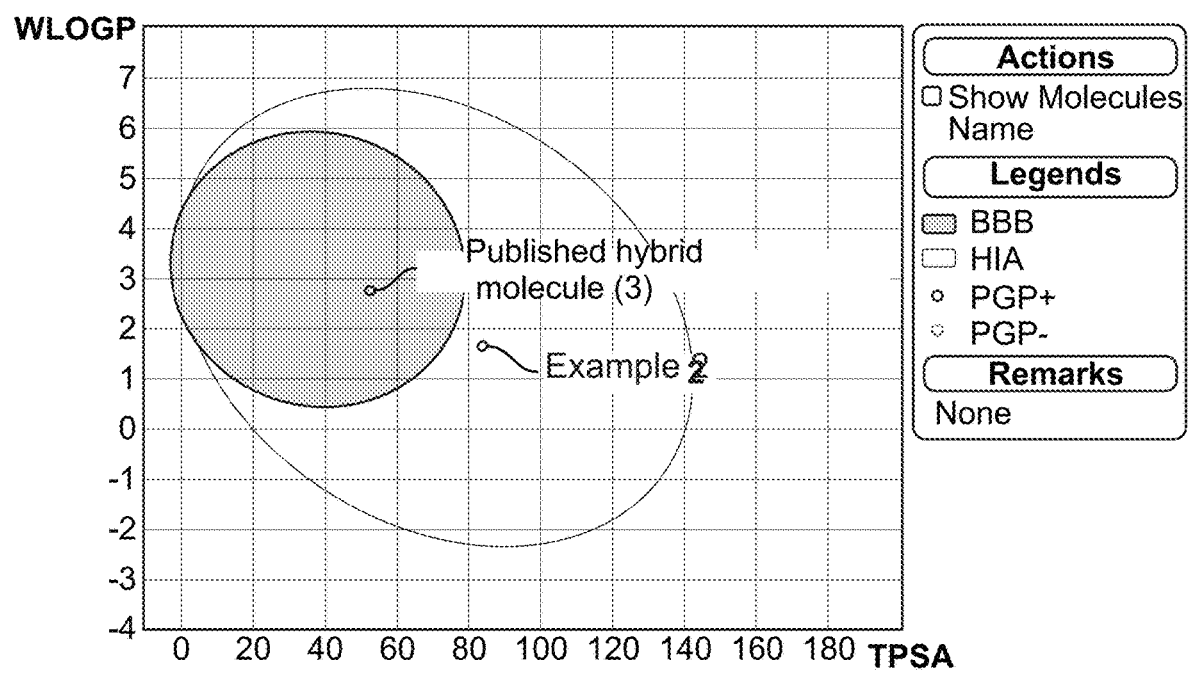
Figure 86:
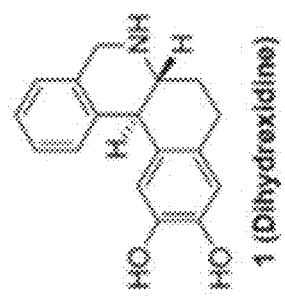
FIG. 86 shows that dinapsoline and dinoxyline display similar D1 binding affinity as dihydrexidine. Not shown in the figure, all three compounds produced full magnitude cAMP response (full efficacy) in published manuscripts. Dinapsoline (DNS) and dinoxyline (DNX) are dihydrexidine (DHX) framework mimics discovered in the late 1990s and early 2000s by the same group from Purdue University.
Figure 86:
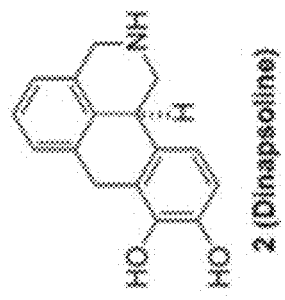
Figure 86:
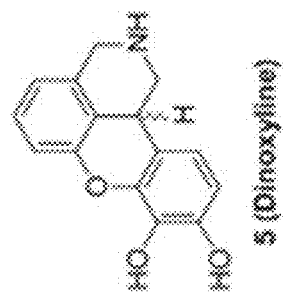
Figure 87:
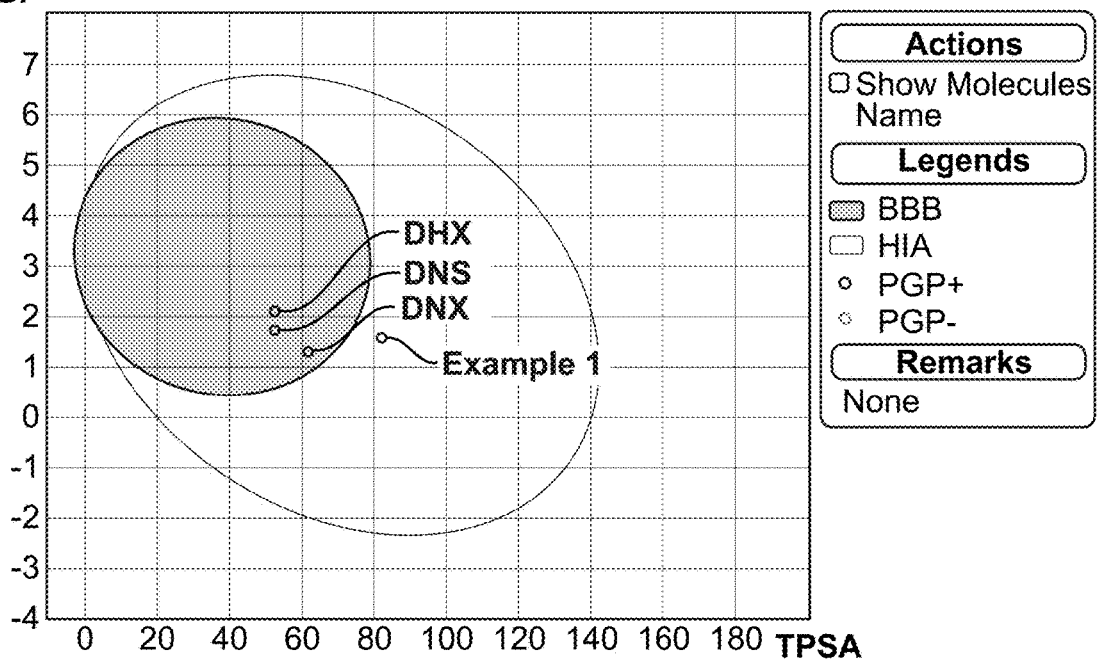
FIG. 87 shows fried eggs model of predicted BBB penetration using TPSA and WLOGP properties of compound of Example 1 and dinapsoline (DNS), dinoxyline (DNX), and dihydrexidine (DHX). Chemical structure of the compound of example 1 is also shown.
Figure 87:
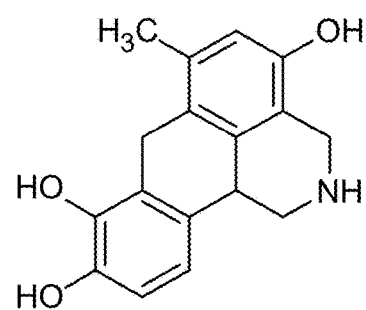
Figure 88:
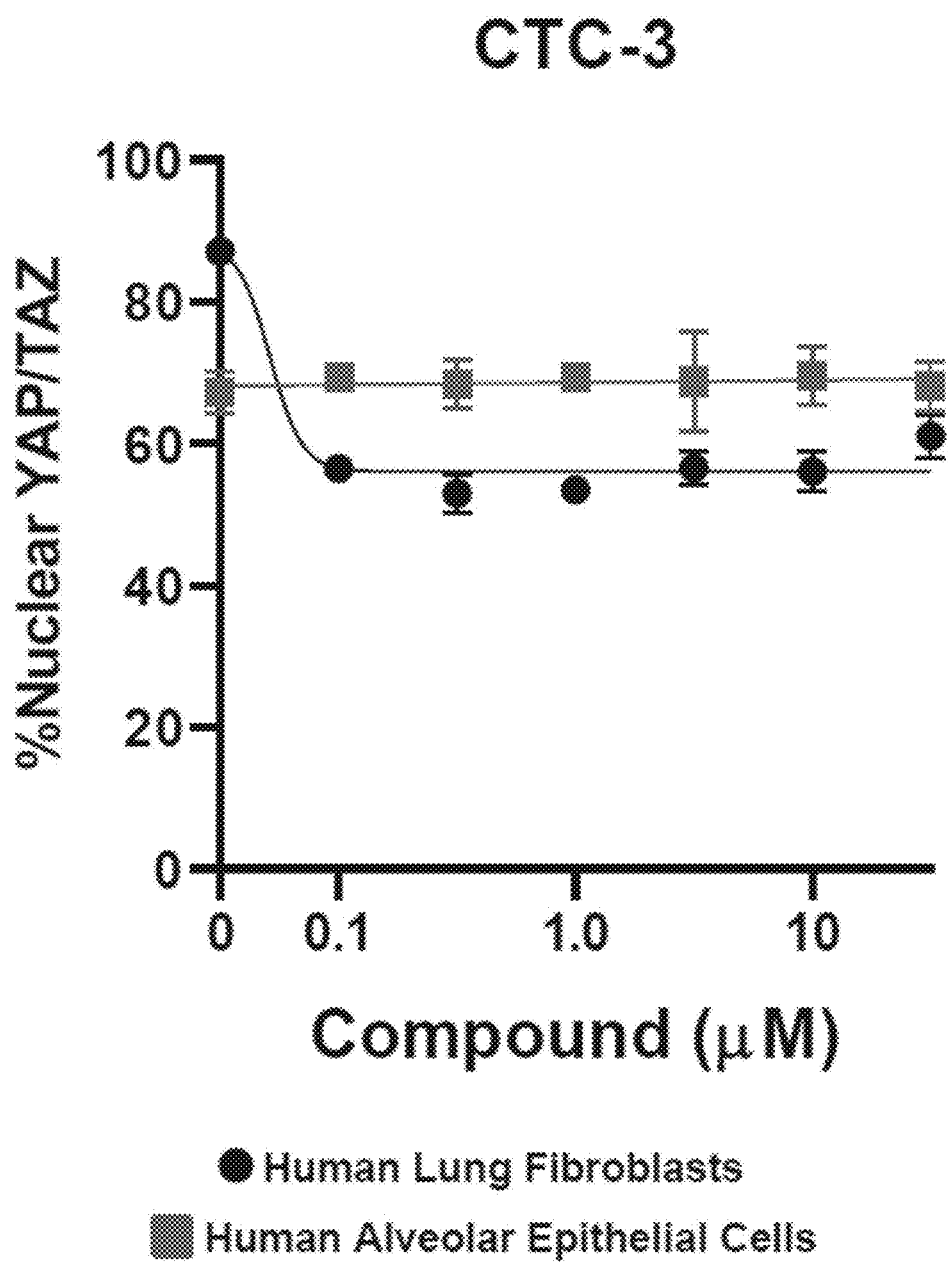
FIG. 88 contains line plots showing % nuclear YAP/TAZ for compound CTC-3 in human lung fibroblasts and human alveolar epithelial cells.
Figure 89:
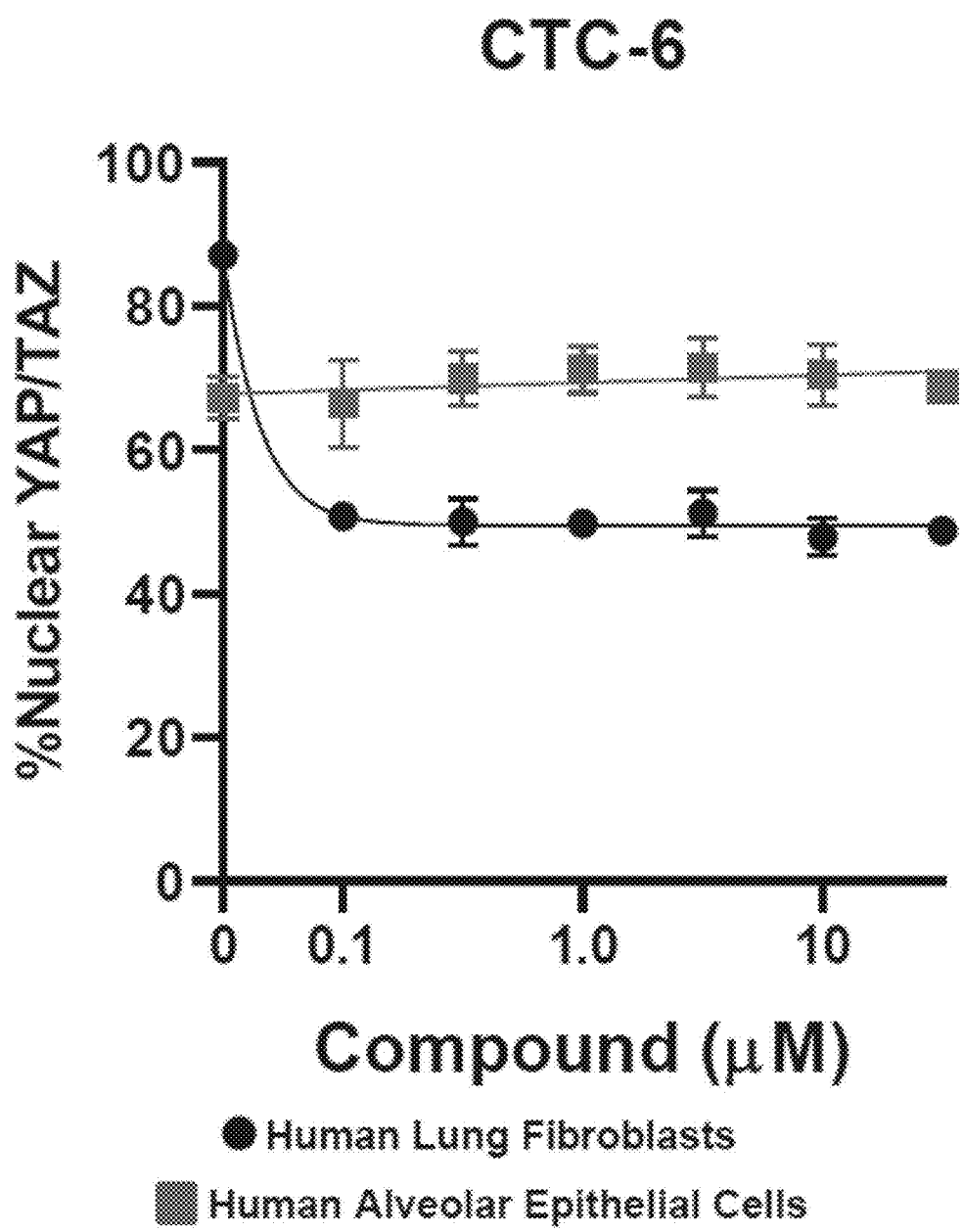
FIG. 89 contains line plots showing % nuclear YAP/TAZ for compound CTC-6 in human lung fibroblasts and human alveolar epithelial cells.

Example 7—DOPA Decarboxylase is Decreased in IPF, and Correlates with Worsening Disease Severity It was discovered that IPF patient lungs express less dopa decarboxylase (DDC) (enzyme that takes part in dopamine synthesis) than non-IPF lungs and the lower level of DDC expression correlates with decreased lung function consistent with an endogenous, protective role for dopamine signaling that is lost in pulmonary fibrosis (FIG. 61A-C). In support of this, it was also shown that dopamine is antifibrotic in in vitro assessments of fibroblast activity (FIG. 62A-C).

Taken together, the experimental results and data presented in Examples 1-7 demonstrate that GPCR agonism (e.g., dopamine receptor agonism) can be used to pharmacologically target YAP and TAZ in selective cell populations to exert beneficial effects on tissue fibrosis. $Ga_s$ agonism (e.g., dopamine receptor agonism) and YAP/TAZ inhibition reverses the matrix deposition and stiffening phenotype of activated fibroblasts toward a matrix remodeling phenotype that promotes fibrosis resolution, showing that $Ga_s$ agonism (e.g., dopamine receptor agonism) and YAP/TAZ inhibition is an valuable approach to treat patients with fibrotic diseases.

Example 8—Compounds CTC-1, CTC-2, CTC-3, CTC-6, and CTC-7 Potently Inhibit Models of Tissue Fibrosis As shown in FIGS. 66-76, compounds CTC-1, CTC-2, CTC-3, and CTC-6 inhibit YAP/TAZ nuclear localization, inhibit fibroblast proliferation, inhibit fibroblast activation, inhibit Collagen I deposition, and inhibition of profibrotic gene expression.

Example 9—Bioactivity of Exemplified Compounds

The compounds described in this disclosure are useful as D1 dopamine receptor agonists for the treatment of idiopathic pulmonary fibrosis. This receptor is preferentially expressed on lung fibroblasts relative to other major resident cell types, providing a mechanism to selectively inhibit the YAP/TAZ transcription program in lung fibroblasts to promote antifibrotic/pro-resolving phenotypes. As shown in the previous example, compounds CTC-3 and CTC-6 potently inhibit the localization of YAP/TAZ in cultured lung fibroblasts ($IC_{50}$ 50-100 nM) and their physical and chemical properties suggest marginal ability to cross the blood-brain-barrier. The compounds of this example maintain or improve the potency of CTC-3/6 while enhancing the intrinsic activity (efficacy) at the D1 receptor.

Most exemplified D1 receptor agonists of the present disclosure contain a catechol moiety. At physiological pH, catechols are sometimes rapidly oxidized into quinones, and for several D1 agonists, a bulk of the drug clearance is a result of this oxidation, not liver metabolism. Fenoldopam is a clinically approved dopamine receptor agonist for the treatment of acute hypertension which contains the chloride substituted catechol ring. The chlorine substitution sometimes has a protecting effect which results in fenoldopam being stable at physiological pH and no reported metabolism through oxidation. Of note, chloride substitution at this site also enhances dopamine receptor potency. In sum, halogen substitutions to the catechol moiety in the exemplified compounds enhances their efficacy and plasma stability, e.g., by preventing oxidation. Chemical structures of exemplified compounds are shown in the tables below.

TABLE 9a

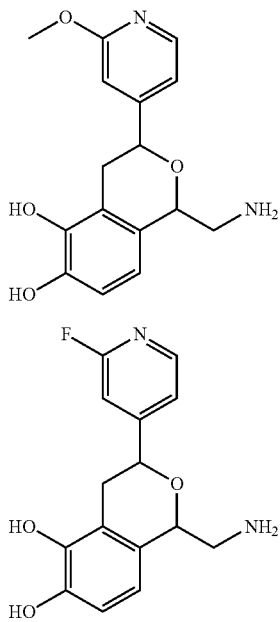

TABLE 9a-continued

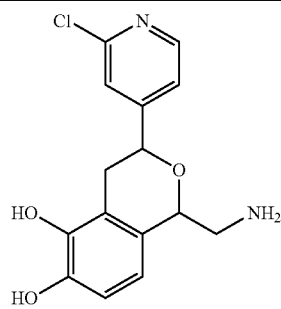

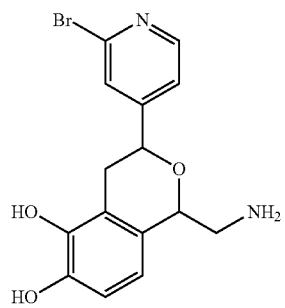 [SMILES: NCC1OC(c2ccnc(Br)c2)Cc2c1ccc(O)c2O]

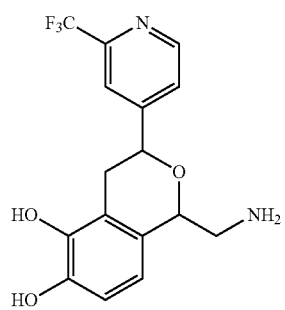 [SMILES: NCC1OC(c2ccnc(C(F)(F)F)c2)Cc2c1ccc(O)c2O]

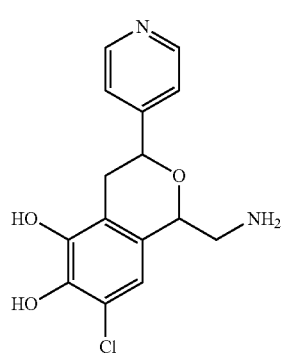 [SMILES: NCC1OC(c2ccncc2)Cc2c1cc(Cl)c(O)c2O]

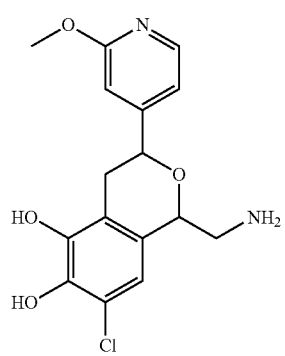 [SMILES: COc1cc(C2Cc3c(cc(Cl)c(O)c3O)C(CN)O2)ccn1]

TABLE 9a-continued
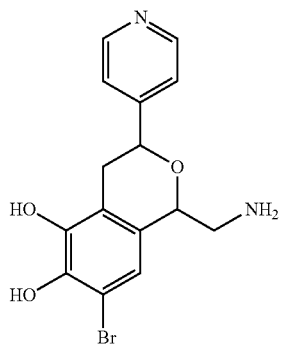
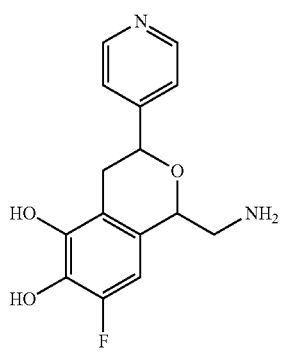
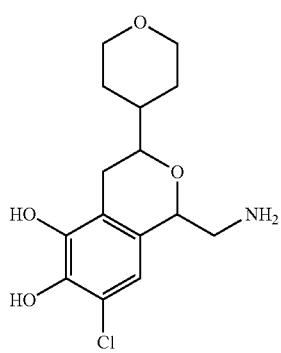 [SMILES: NCC1OC(C2CCOCC2)Cc2c1cc(Cl)c(O)c2O]
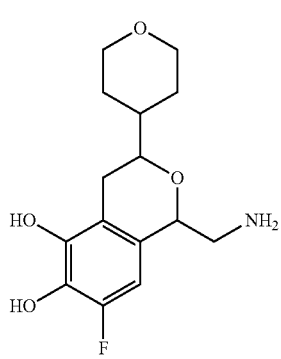 [SMILES: NCC1OC(C2CCOCC2)Cc2c1cc(F)c(O)c2O]
TABLE 9a-continued
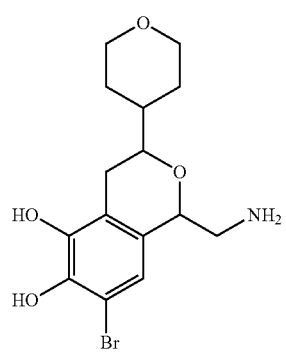
TABLE 9b
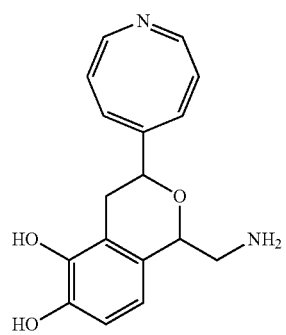 [SMILES: NCC1OC(C2=C/C=C\N=C/C=C\2)Cc2c1ccc(O)c2O]
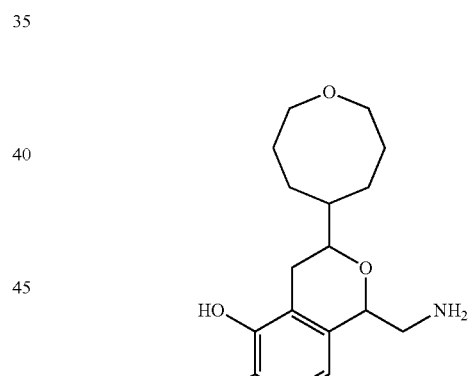
TABLE 9c
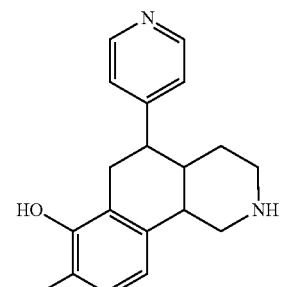

TABLE 9c-continued
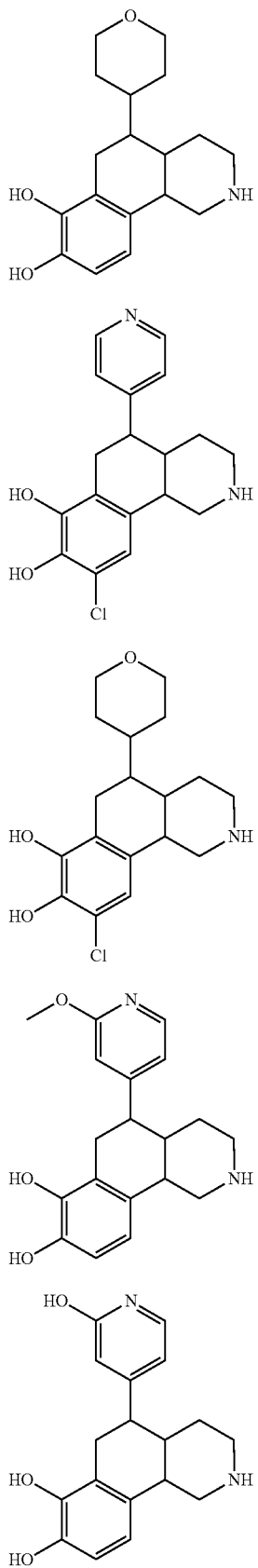
TABLE 9c-continued
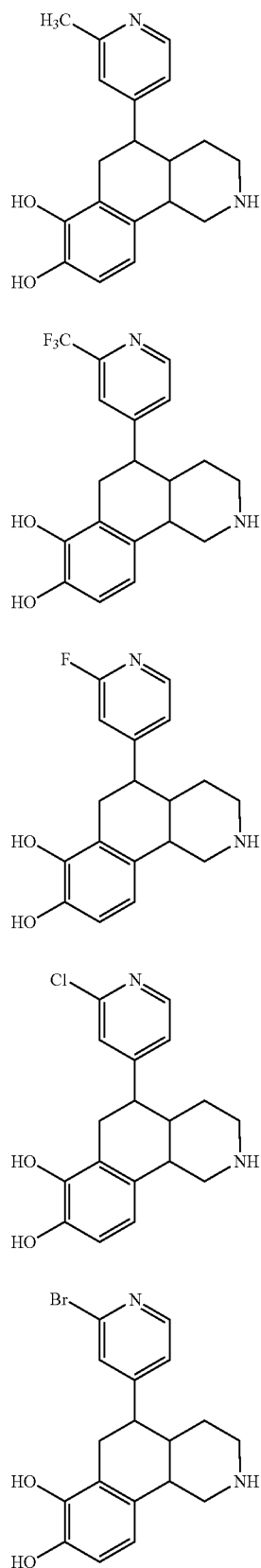

TABLE 9c-continued
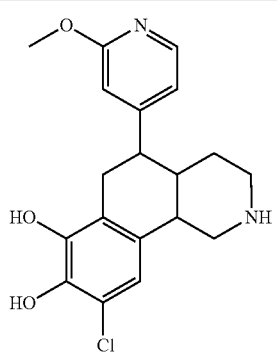 [SMILES: COc1cc(C2Cc3c(cc(Cl)c(O)c3O)C3CNCCC23)ccn1]
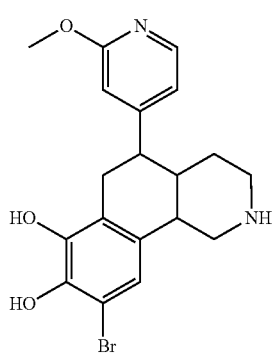 [SMILES: COc1cc(C2Cc3c(cc(Br)c(O)c3O)C3CNCCC23)ccn1]
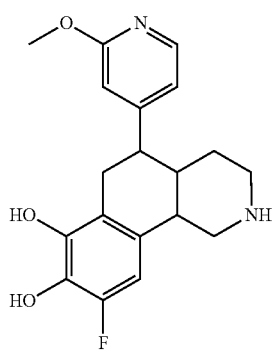 [SMILES: COc1cc(C2Cc3c(cc(F)c(O)c3O)C3CNCCC23)ccn1]
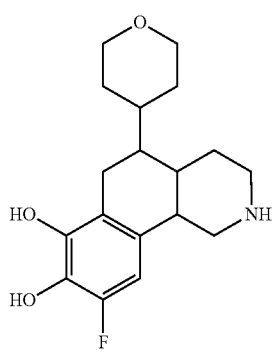 [SMILES: Oc1c(F)cc2c(c1O)CC(C1CCOCC1)C1CCNCC21]
TABLE 9d
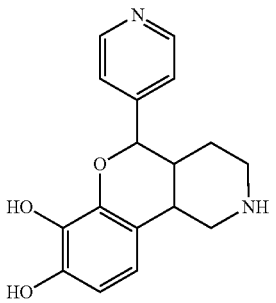 [SMILES: Oc1ccc2c(c1O)OC(c1ccncc1)C1CCNCC21]
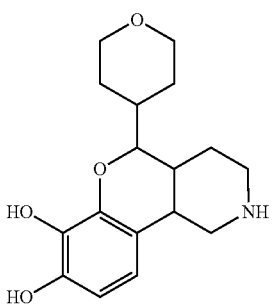 [SMILES: Oc1ccc2c(c1O)OC(C1CCOCC1)C1CCNCC21]
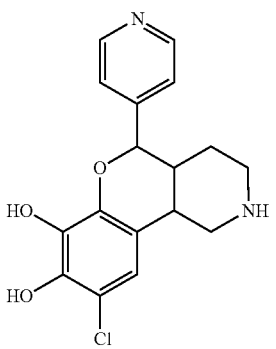 [SMILES: Oc1c(Cl)cc2c(c1O)OC(c1ccncc1)C1CCNCC21]
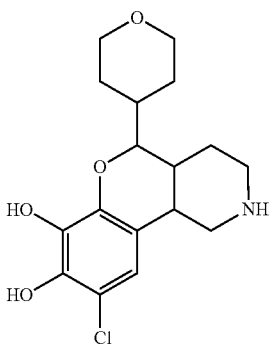 [SMILES: Oc1c(Cl)cc2c(c1O)OC(C1CCOCC1)C1CCNCC21]
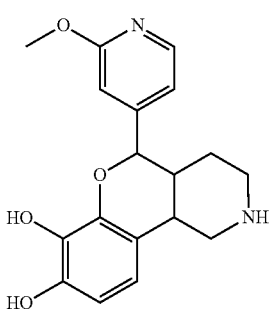 [SMILES: COc1cc(C2Oc3c(ccc(O)c3O)C3CNCCC32)ccn1]

TABLE 9d-continued
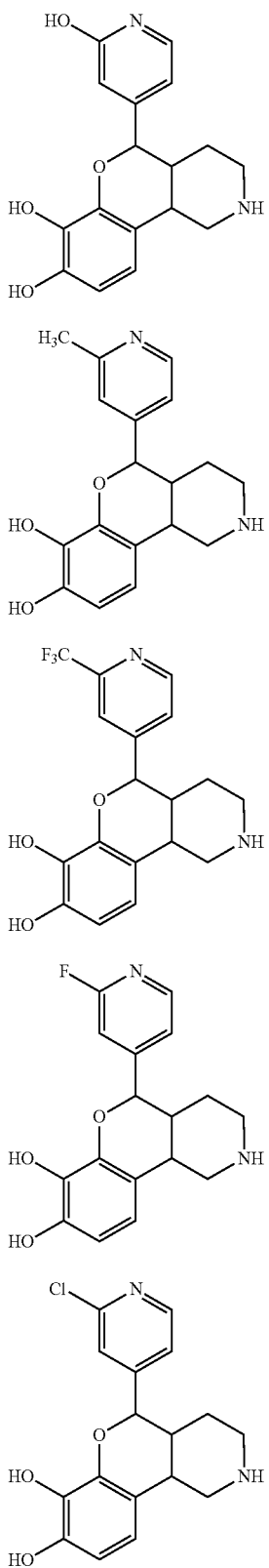
(example 2)
TABLE 9d-continued
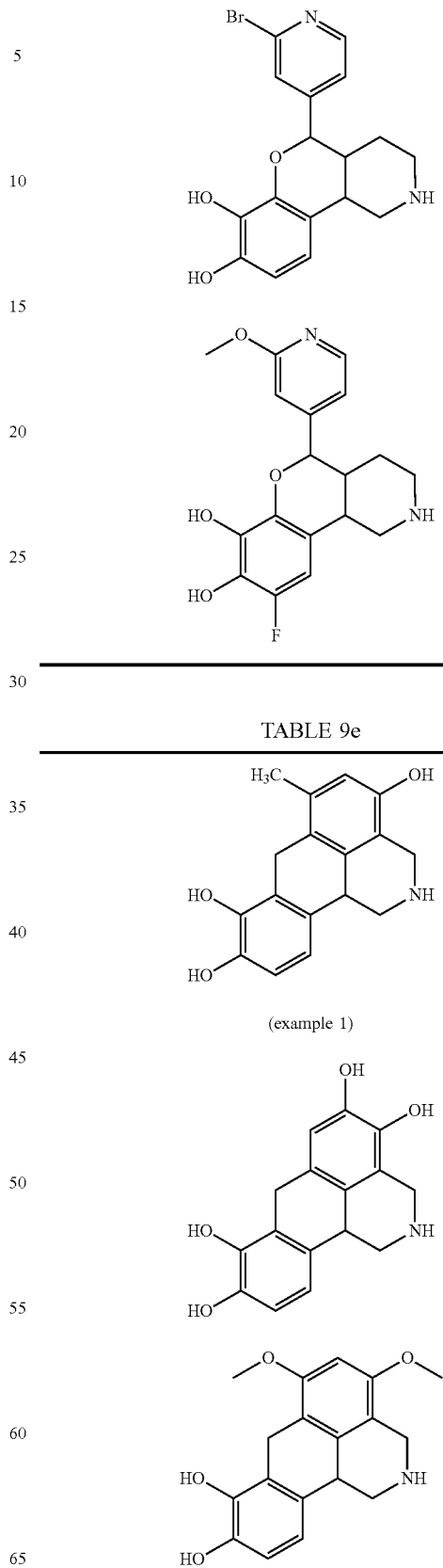
TABLE 9e
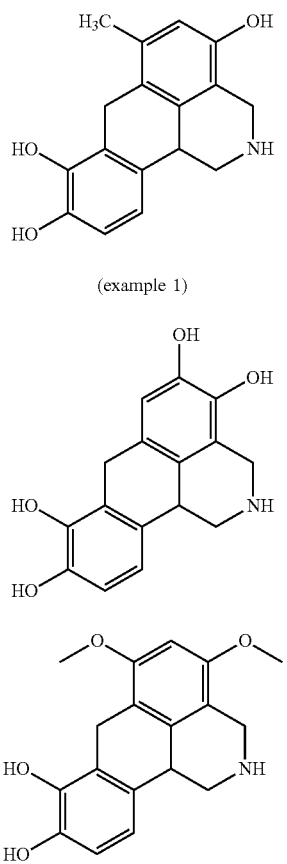
(example 1)

TABLE 9e-continued
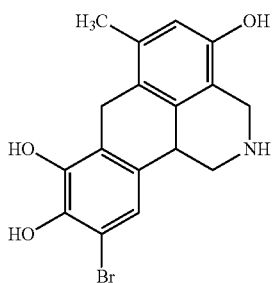 [SMILES: Cc1cc(O)c2c3c1Cc1c(cc(Br)c(O)c1O)C3CNC2]
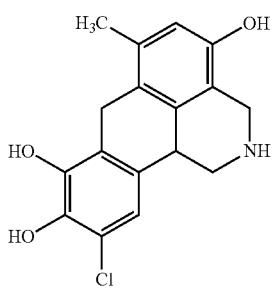 [SMILES: Cc1cc(O)c2c3c1Cc1c(cc(Cl)c(O)c1O)C3CNC2]
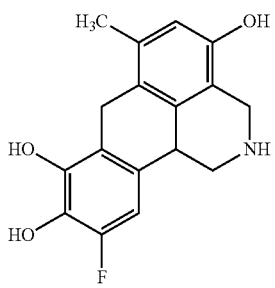 [SMILES: Cc1cc(O)c2c3c1Cc1c(cc(F)c(O)c1O)C3CNC2]
TABLE 9f
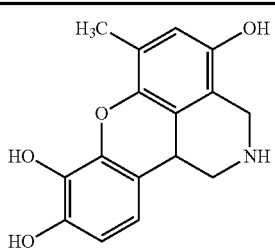
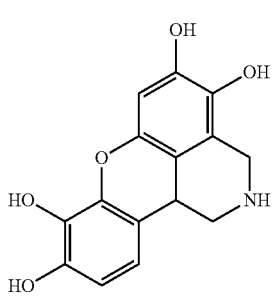 [SMILES: Oc1cc2c3c(c1O)CNCC3c1ccc(O)c(O)c1O2]
TABLE 9f-continued
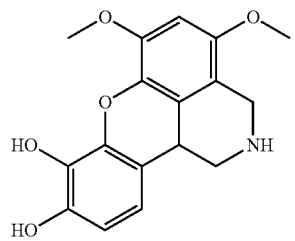 [SMILES: COc1cc(OC)c2c3c1CNCC3c1ccc(O)c(O)c1O2]
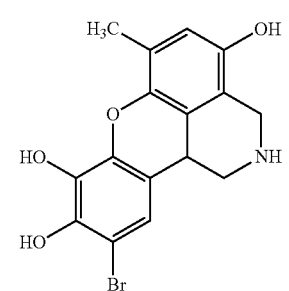 [SMILES: Cc1cc(O)c2c3c1Oc1c(cc(Br)c(O)c1O)C3CNC2]
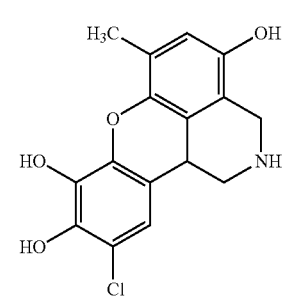 [SMILES: Cc1cc(O)c2c3c1Oc1c(cc(Cl)c(O)c1O)C3CNC2]
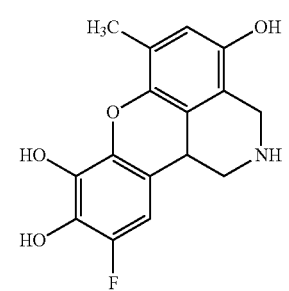 [SMILES: Cc1cc(O)c2c3c1Oc1c(cc(F)c(O)c1O)C3CNC2]
TABLE 9g
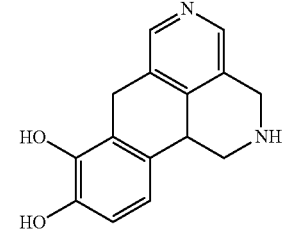

TABLE 9g-continued
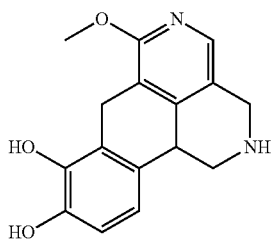 [SMILES: COc1ncc2c3c1Cc1c(ccc(O)c1O)C3CNC2]
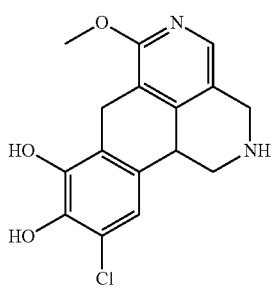 [SMILES: COc1ncc2c3c1Cc1c(cc(Cl)c(O)c1O)C3CNC2]
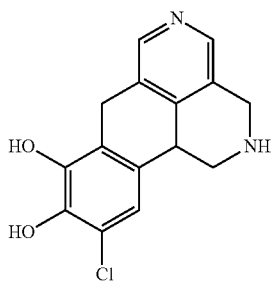
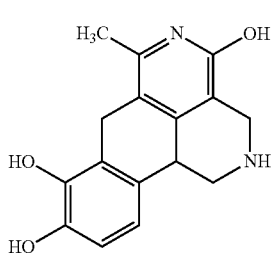 [SMILES: Cc1nc(O)c2c3c1Cc1c(ccc(O)c1O)C3CNC2]
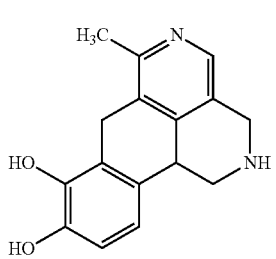 [SMILES: Cc1ncc2c3c1Cc1c(ccc(O)c1O)C3CNC2]
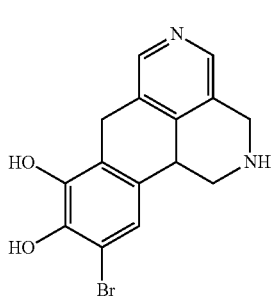 [SMILES: Oc1c(Br)cc2c(c1O)Cc1cncc3c1C2CNC3]
TABLE 9g-continued
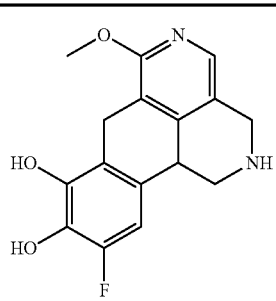
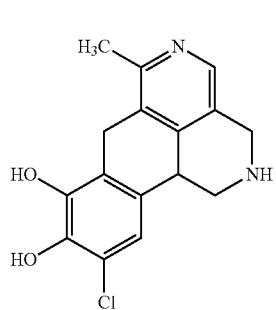
TABLE 9h
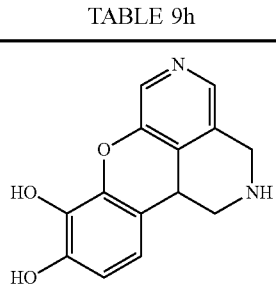
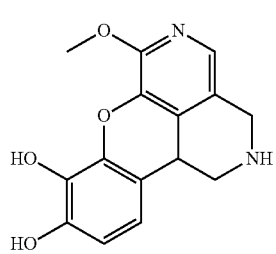 [SMILES: COc1ncc2c3c1Oc1c(ccc(O)c1O)C3CNC2]
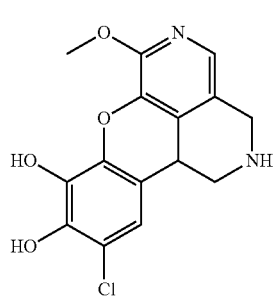 [SMILES: COc1ncc2c3c1Oc1c(cc(Cl)c(O)c1O)C3CNC2]

TABLE 9h-continued

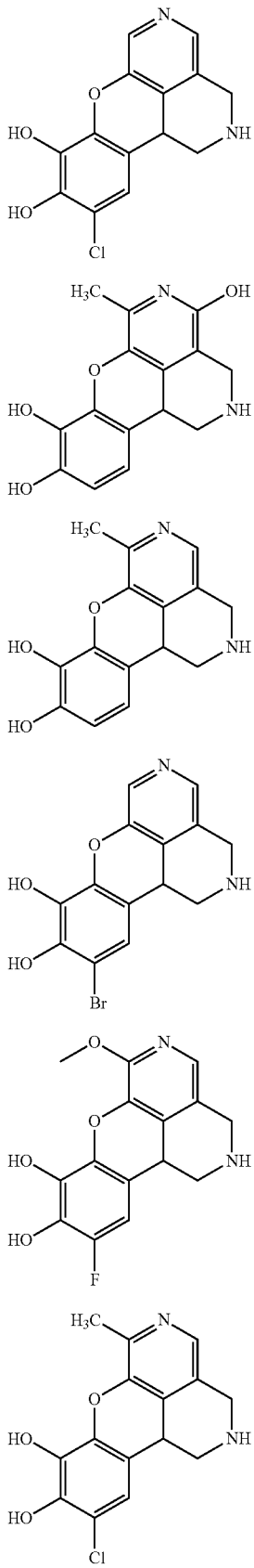

Example 10—Compound 1 (MS-9) Potently Inhibits Models of Tissue Fibrosis

Figure 90:
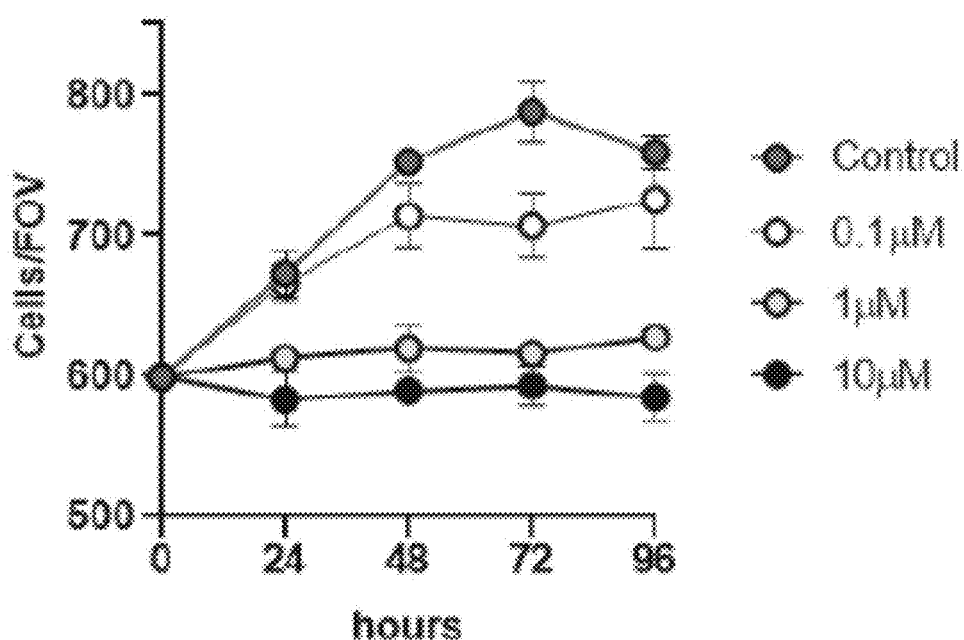
FIG. 90 contains chemical structure of compound 1 and also contains a line plot showing that compound 1 inhibits fibroblast proliferation. Adult lung fibroblasts plated into 96-well plates, stimulated with 2 ng/mL TGFβ and compounds at the indicated concentration. Proliferation determined by fixing and counting DAPI nuclei using a Cytation 5. N=2.
Figure 90:
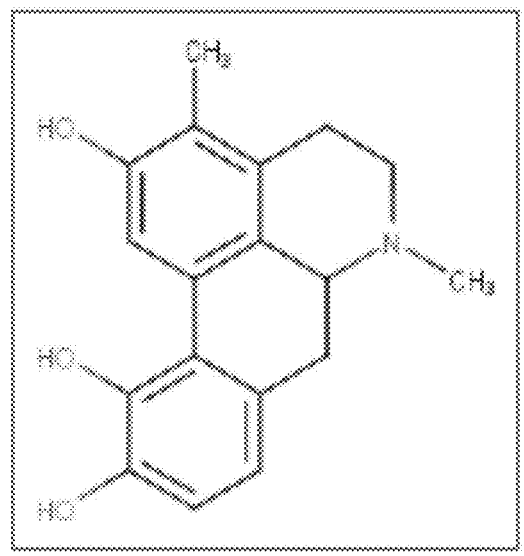

As shown in FIG. 90, compound 1 (MS-9) potently inhibits fibroblast proliferation. Fibroblasts were stimulated with 2 ng/mL TGFβ and treated with compound 1 (MS-9) at the indicated concentration (0.1 μM, 1 μM, and 10 μM). Proliferation determined by fixing and counting DAPI nuclei using a Cytation.

Figure 91A:
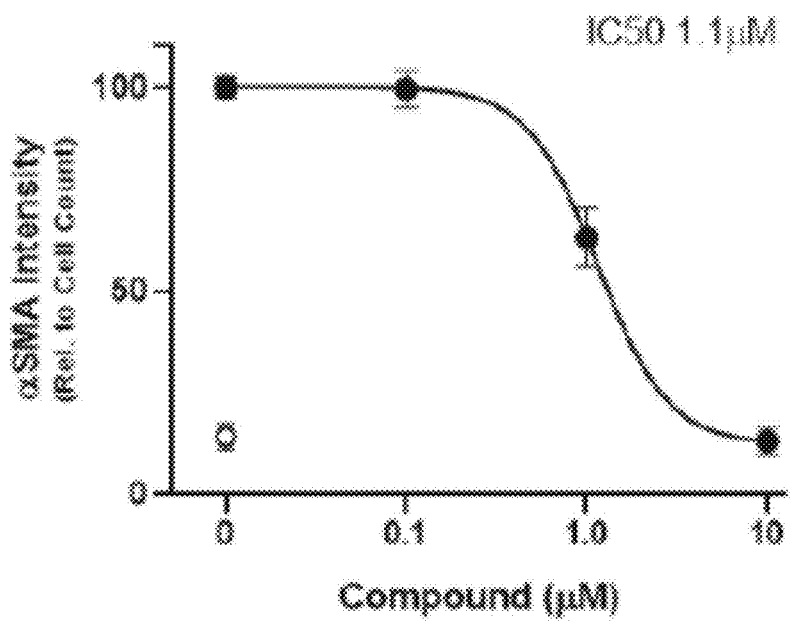
FIG. 91A contains a line plot showing that compound 1 inhibits fibroblast activation. Adult lung fibroblasts plated into 96-well plates, stimulated with 2 ng/mL TGFβ for 96 hours and treated with the indicated concentration of compounds every 48 hours. Imaging and quantification of αSMA intensity performed through automation using a Cytation 5.

Alpha-smooth muscle actin (αSMA) staining is a well-defined marker of fibroblast activation observed in wound healing and tissue fibrosis. As shown in FIG. 91A, compound 1 (MS-9) potently inhibits fibroblast activation. Fibroblasts were stimulated with 2 ng/mL TGFβ and treated with the indicated concentration of compound 1 (MS-9) every 48 hours ($IC_{50}$ is 1.1 μM). Imaging and quantification of αSMA intensity performed through automation using a Cytation 5.

Figure 91B:
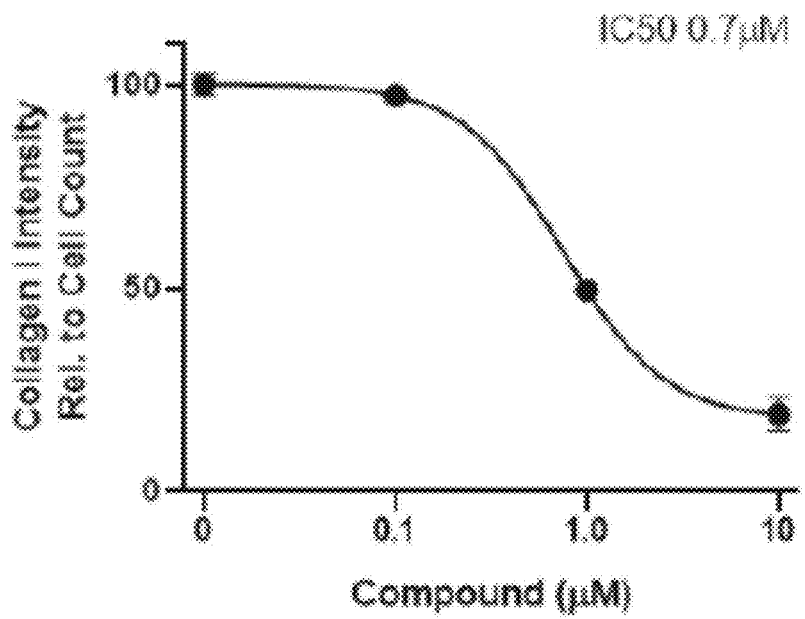
FIG. 91B contains a line plot showing that compound 1 inhibits Collagen I deposition. Adult lung fibroblasts plated into 96-well plates, stimulated with 2 ng/mL TGFβ for 96 hours and treated with the indicated concentration of compounds every 48 hours. Imaging and quantification of Collagen I intensity performed through automation using a LI-COR Odyssey.

As shown in FIG. 91B, compound 1 (MS-9)) potently inhibits collagen 1 deposition. Fibroblasts were stimulated with 2 ng/mL TGFβ and treated with the indicated concentration of compound 1 every 48 hours ($IC_{50}$ is 0.7 μM). Imaging and quantification of collagen I intensity performed through automation using a LI-COR Odyssey.

Figure 92A:
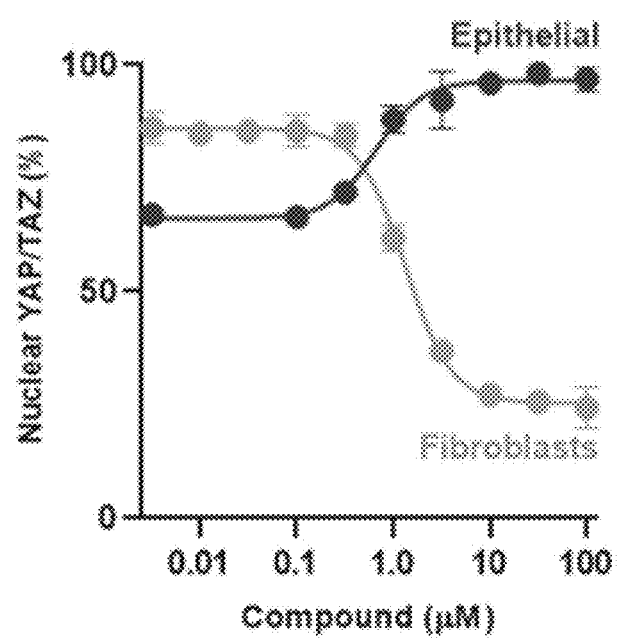
FIG. 92A shows in vitro efficacy of compound 1 (MS-9). Human lung fibroblasts and alveolar epithelial cells are treated with MS-9 and influence on YAP/TAZ localization is determined.
Figure 92B:
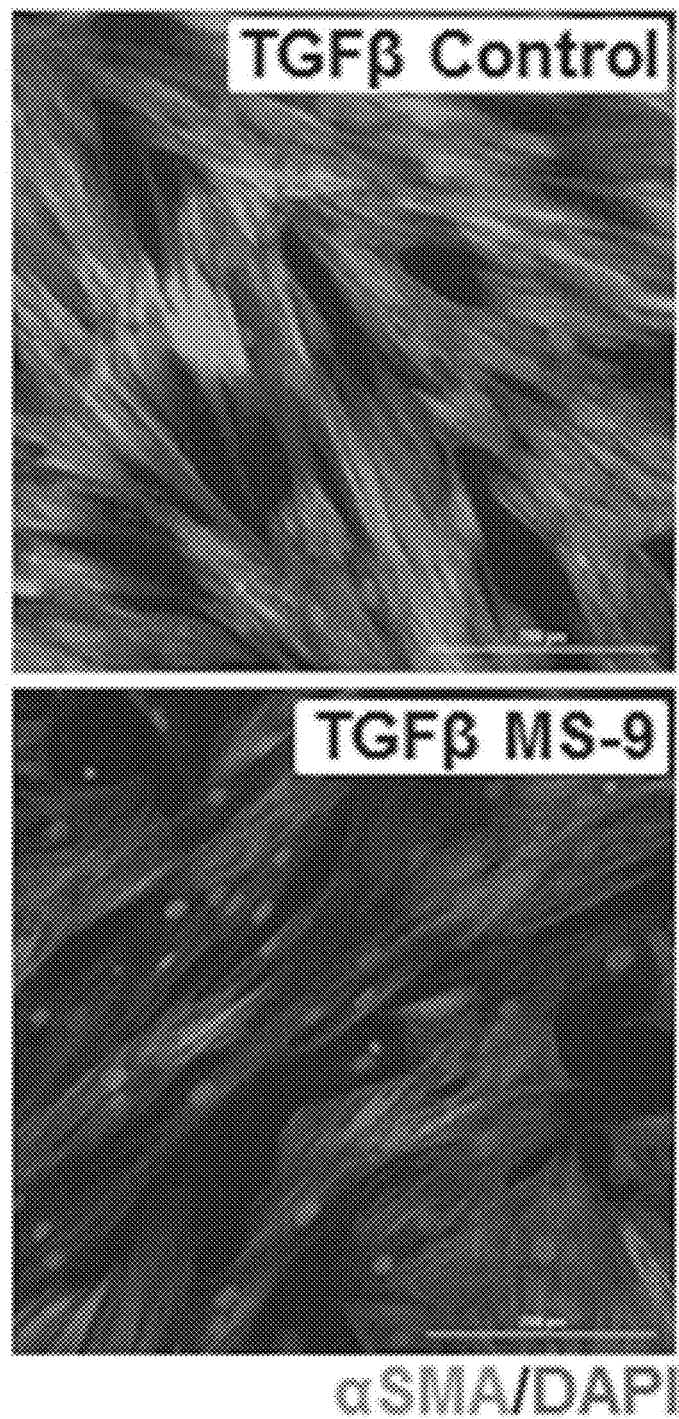
FIG. 92B shows in vitro efficacy of compound 1 (MS-9) blocks expression of TGFβ.
Figure 92C:
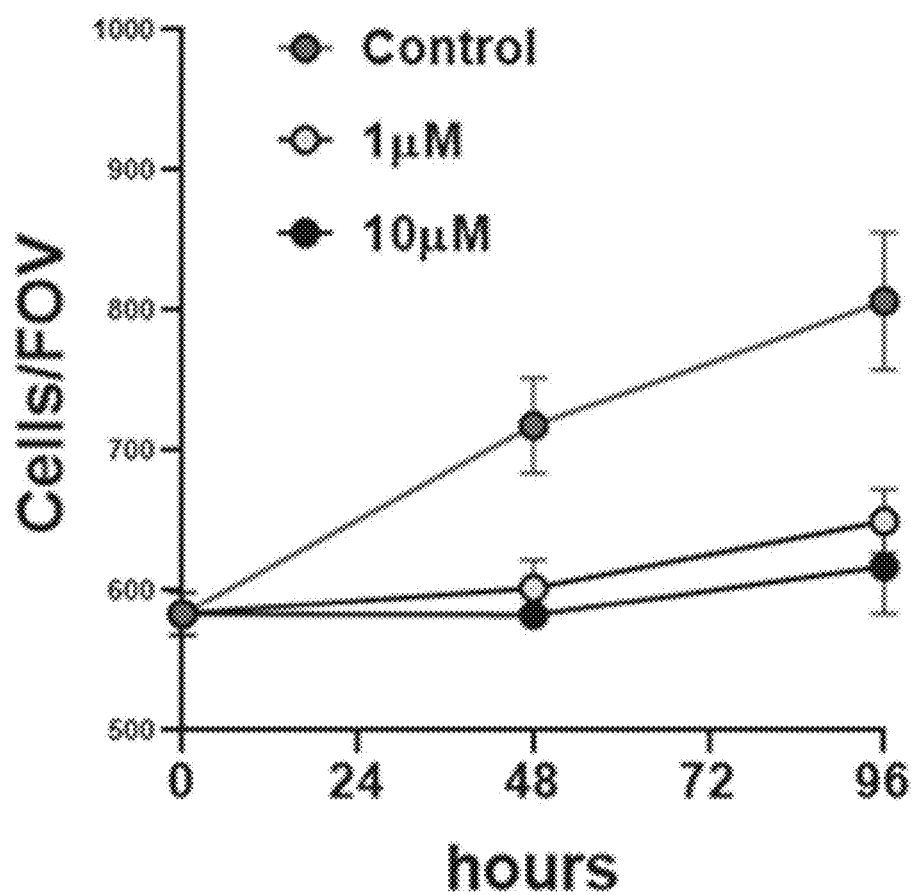
FIG. 92C contains a line plot showing cell count (filed of view) for 1 μM and 10 μM of compound 1 (MS-9).

In cell culture studies, MS-9 potently blocks YAP/TAZ nuclear localization in fibroblasts but promotes YAP/TAZ nuclear localization in epithelial cells and effectively inhibits fibroblast activation in models of lung fibrosis. See FIGS. 92A-92C.

At physiological pH apomorphine is oxidized into the inactive quinone, representing a majority of its metabolism:

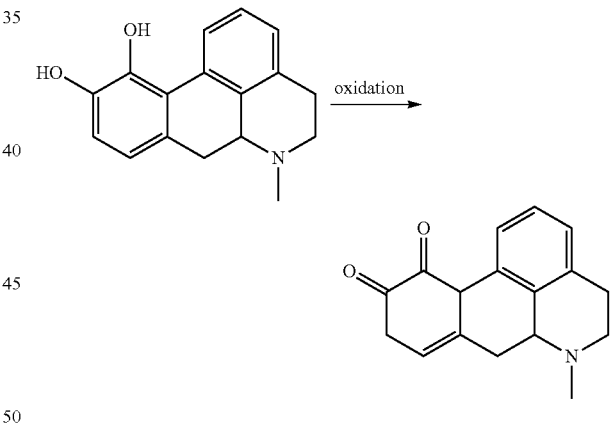

MS-21-9 has a chloride substitution, which stabilizes the catechol while enhancing dopamine receptor potency. As such, MS-21-9 has a longer half-life compared to compounds lacking halogen on the catechol moiety.

Additional exemplified compounds are shown in the table below:

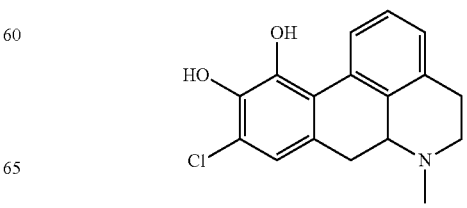

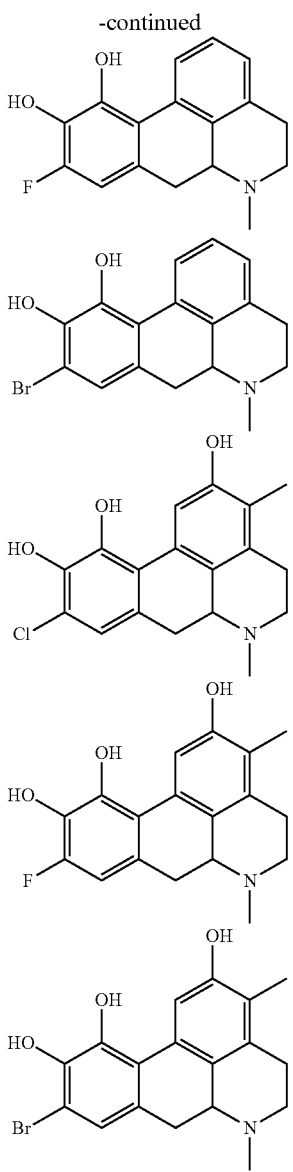

REFERENCES

1 Tschumperlin, D. J., Liu, F. & Tager, A. M. Biomechanical regulation of mesenchymal cell function. *Curr Opin Rheumatol* 25, 92-100, doi:10.1097/BOR.0b013e32835b13cd (2013).
2 Liu, F. et al. Mechanosignaling through YAP and TAZ drives fibroblast activation and fibrosis. *Am J Physiol-Lung C* 308, L344-L357, doi:10.1152/ajplung.00300.2014 (2015).
3 Martin, K. et al. PAK proteins and YAP-1 signalling downstream of integrin beta-1 in myofibroblasts promote liver fibrosis. *Nat Commun* 7, 12502, doi:10.1038/ncomms12502 (2016).
4 Szeto, S. G. et al. YAP/TAZ Are Mechanoregulators of TGF-beta-Smad Signaling and Renal Fibrogenesis. *J Am Soc Nephrol*, doi:10.1681/ASN.2015050499 (2016).
5 Piersma, B., Bank, R. A. & Boersema, M. Signaling in Fibrosis: TGF-beta, WNT, and YAP/TAZ Converge. *Front Med* (Lausanne) 2, 59, doi:10.3389/fmed.2015.00059 (2015).
6 Hansen, C. G., Moroishi, T. & Guan, K. L. YAP and TAZ: a nexus for Hippo signaling and beyond. *Trends Cell Biol* 25, 499-513, doi:10.1016/j.tcb.2015.05.002 (2015).
7 Zanconato, F., Battilana, G., Cordenonsi, M. & Piccolo, S. YAP/TAZ as therapeutic targets in cancer. *Curr Opin Pharmacol* 29, 26-33, doi:10.1016/j.coph.2016.05:002 (2016).
8 Zhao, B., Li, L., Lei, Q. & Guan, K. L. The Hippo-YAP pathway in organ size control and tumorigenesis: an updated version. *Genes Dev* 24, 862-874, doi:24/9/862 [pii] 10.1101/gad.1909210 (2010).
9 Elbediwy, A., Vincent-Mistiaen, Z. I. & Thompson, B. J. YAP and TAZ in epithelial stem cells: A sensor for cell polarity, mechanical forces and tissue damage. *Bioessays* 38, 644-653, doi:10.1002/bies.201600037 (2016).
10 Lin, C. W. et al. YAP is essential for mechanical force production and epithelial cell proliferation during lung branching morphogenesis. *Elife* 6, doi:ARTN e21130 10.7554/eLife.21130 (2017).
11 Imajo, M., Ebisuya, M. & Nishida, E. Dual role of YAP and TAZ in renewal of the intestinal epithelium. *Nature Cell Biology* 17, 7-+, doi:10.1038/ncb3084 (2015).
12 Kim, J. et al. YAP/TAZ regulates sprouting angiogenesis and vascular barrier maturation. *J Clin Invest* 127, 3441-3461, doi:10.1172/JCI93825 (2017).
13 Wang, L. et al. Integrin-YAP/TAZ-JNK cascade mediates atheroprotective effect of unidirectional shear flow. *Nature*, doi:10.1038/nature20602 (2016).
14 Tang, Y. & Weiss, S. J. Snail/Slug-YAP/TAZ complexes cooperatively regulate mesenchymal stem cell function and bone formation. *Cell Cycle* 16, 399-405, doi:10.1080/15384101.2017.1280643 (2017).
15 Levasseur, A., St-Jean, G., Paquet, M., Boerboom, D. & Boyer, A. Targeted disruption of YAP and TAZ impairs the maintenance of the adrenal cortex. *Endocrinology*, doi: 10.1210/en.2017-00098 (2017).
16 Totaro, A. et al. YAP/TAZ link cell mechanics to Notch signalling to control epidermal stem cell fate. *Nat Commun* 8, 15206, doi:10.1038/ncomms15206 (2017).
17 Grove, M. et al. YAP/TAZ initiate and maintain Schwann cell myelination. *Elife* 6, doi:10.7554/eLife.20982 (2017).
18 Elbediwy, A. et al. Integrin signalling regulates YAP and TAZ to control skin homeostasis. *Development* 143, 1674-1687, doi:10.1242/dev.133728 (2016).
19 Martin, K. et al. PAK proteins and YAP-1 signalling downstream of integrin beta-1 in myofibroblasts promote liver fibrosis. *Nat Commun* 7, 12502, doi:10.1038/ncomms12502 (2016).
20 Zhang, K. et al. omega-3 PUFAs ameliorate liver fibrosis and inhibit hepatic stellate cells proliferation and activation by promoting YAP/TAZ degradation. *Sci Rep* 6, 30029, doi:10.1038/srep30029 (2016).
21 Perumal, N., Perumal, M., Halagowder, D. & Sivasithamparam, N. Morin attenuates diethylnitrosamine-induced rat liver fibrosis and hepatic stellate cell activation by co-ordinated regulation of Hippo/Yap and TGF-beta 1/Smad signaling. *Biochimie* 140, 10-19, doi:10.1016/j.biochi.2017.05.017 (2017).
22 Liang, M. et al. Yap/Taz Deletion in Gli+ Cell-Derived Myofibroblasts Attenuates Fibrosis. *J Am Soc Nephrol*, doi:10.1681/ASN.2015121354 (2017).
23 Miranda, M. Z. et al. TGF-beta1 regulates the expression and transcriptional activity of TAZ protein via a Smad3-independent, myocardin-related transcription factor-mediated mechanism. *J Biol Chem* 292, 14902-14920, doi: 10.1074/jbc.M117.780502 (2017).

24 Szeto, S. G. et al. YAP/TAZ Are Mechanoregulators of TGF-beta-Smad Signaling and Renal Fibrogenesis. *J Am Soc Nephrol* 27, 3117-3128, doi:10.1681/ASN.2015050499 (2016).

25 Liang, M. et al. Yap/Taz Deletion in Gli(+) Cell-Derived Myofibroblasts Attenuates Fibrosis. *J Am Soc Nephrol* 28, 3278-3290, doi:10.1681/ASN.2015121354 (2017).

26 Hauser, A. S., Attwood, M. M., Rask-Andersen, M., Schioth, H. B. & Gloriam, D. E. Trends in GPCR drug discovery: new agents, targets and indications. *Nat Rev Drug Discov*, doi: 10.1038/nrd.2017.178 (2017).

27 Zhou, X., Wang, Z., Huang, W. & Lei, Q. Y. G protein-coupled receptors: bridging the gap from the extracellular signals to the Hippo pathway. *Acta Biochim Biophys Sin (Shanghai)* 47, 10-15, doi:10.1093/abbs/gmu108 (2015).

28 Yu, F. X. et al. Regulation of the Hippo-YAP pathway by G-protein-coupled receptor signaling. *Cell* 150, 780-791, doi:10.1016/j.cell.2012.06.037 (2012).

29 Yu, F. X. et al. Protein kinase A activates the Hippo pathway to modulate cell proliferation and differentiation. *Genes Dev* 27, 1223-1232, doi:10.1101/gad.219402.113 (2013).

30 Kim, M. et al. cAMP/PKA signalling reinforces the LATS-YAP pathway to fully suppress YAP in response to actin cytoskeletal changes. *Embo J* 32, 1543-1555, doi: 10.1038/emboj.2013.102 (2013).

31 Insel, P. A. et al. GPCR expression in tissues and cells: Are the optimal receptors being used as drug targets? *Brit J Pharmacol* 165, 1613-1616, doi:10.1111/j.1476-5381.2011.01434.x (2012).

32 Flock, T. et al. Selectivity determinants of GPCR-G-protein binding. *Nature* 545, 317-322, doi:10.1038/nature22070 (2017).

33 Southan, C. et al. The IUPHAR/BPS Guide to PHARMACOLOGY in 2016: towards curated quantitative interactions between 1300 protein targets and 6000 ligands. *Nucleic Acids Res* 44, D1054-D1068, doi:10.1093/nar/gkv1037 (2016).

34 Wilborn, J. et al. Cultured Lung Fibroblasts Isolated from Patients with Idiopathic Pulmonary Fibrosis Have a Diminished Capacity to Synthesize Prostaglandin E(2), and to Express Cyclooxygenase-2. *Journal of Clinical Investigation* 95, 1861-1868, doi:Doi 10.1172/Jci117866 (1995).

35 Snead, A. N., He, S. & Insel, P. A. G protein-coupled receptor (GPCR) regulation of cardiac fibrosis. *Faseb J* 26 (2012).

36 Jorgenson, A. J. et al. TAZ activation drives fibroblast spheroid growth, expression of profibrotic paracrine signals, and context-dependent ECM gene expression. *Am J Physiol Cell Physiol* 312, C277-C285, doi:10.1152/ajpcell.00205.2016 (2017).

37 Wang, X. B. et al. Hepatocyte TAZ/WWTR1 Promotes Inflammation and Fibrosis in Nonalcoholic Steatohepatitis. *Cell Metab* 24, 848-862, doi:10.1016/j.cmet.2016.09.016 (2016).

38 Bai, H. et al. Yes-associated protein regulates the hepatic response after bile duct ligation. *Hepatology* 56, 1097-1107, doi:10.1002/hep.25769 (2012).

39. LeWitt, P. A., Subcutaneously administered apomorphine: pharmacokinetics and metabolism. Neurology, 2004. 62(6 Suppl 4): p. S8-11.

40. Trissel, L. A., Y. Zhang, and M. B. Baker, Stability of fenoldopam mesylate in two infusion solutions. Am J Health Syst Pharm, 2002. 59(9): p. 846-8.

41. Brogden, R. N. and A. Markham, Fenoldopam: a review of its pharmacodynamic and pharmacokinetic properties and intravenous clinical potential in the management of hypertensive urgencies and emergencies. Drugs, 1997. 54(4): p. 634-50.

42. Klecker, R. W. and J. M. Collins, Stereoselective metabolism of fenoldopam and its metabolites in human liver microsomes, cytosol, and slices. J Cardiovasc Pharmacol, 1997. 30(1): p. 69-74.

43. Andersen, P. H. and J. A. Jansen, Dopamine receptor agonists: selectivity and dopamine D1 receptor efficacy. Eur J Pharmacol, 1990. 188(6): p. 335-47.

44. Hahn, R. A., et al., Characterization of the peripheral and central effects of SK&F 82526, a novel dopamine receptor agonist. J Pharmacol Exp Ther, 1982. 223(2): p. 305-13.

Numbered Paragraphs

In some embodiments, the invention of the present disclosure can be described by reference to the following numbered paragraphs:

Paragraph 1. A compound of Formula (I):

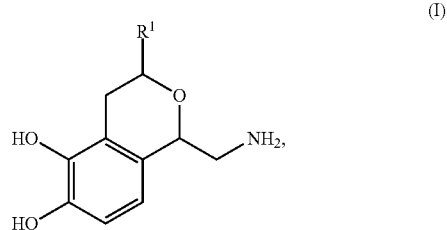

or a pharmaceutically acceptable salt thereof, wherein:

$R^1$ is selected from HO—$C_{1-6}$ alkyl, $NH_2$—$C_{1-6}$ alkyl, 5-6-membered heteroaryl ring comprising 1 or 2 heteroatoms selected from N, O, and S, and 3-7-membered heterocycloalkyl ring comprising 1 or 2 heteroatoms selected from N, O, and S;

wherein said heteroaryl ring and heterocycloalkyl ring are each optionally substituted with 1, 2, or 3 substituents independently selected from $R^2$; and each $R^2$ is independently selected from OH, SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino, and di($C_{1-3}$ alkyl)amino.

Paragraph 2. The compound of paragraph 1, wherein $R^1$ is 5-6-membered heteroaryl ring comprising 1 or 2 heteroatoms selected from N, O, and S, which is optionally substituted with 1, 2, or 3 substituents independently selected from $R^2$.

Paragraph 3. The compound of paragraph 2, wherein $R^1$ is selected from pyridinyl, pyrimidinyl, and pyrazinyl, each of which is optionally substituted with 1, 2, or 3 substituents independently selected from $R^2$.

Paragraph 4. The compound of paragraph 2, wherein $R^1$ is pyridinyl, optionally substituted with 1, 2, or 3 substituents independently selected from $R^2$.

Paragraph 5. The compound of paragraph 4, wherein the compound of Formula (I) is selected from:

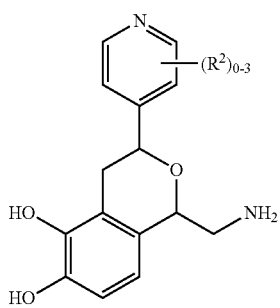

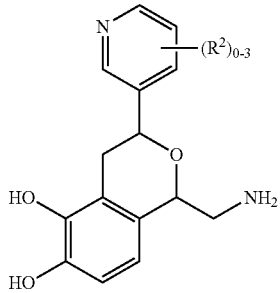

or a pharmaceutically acceptable salt thereof.

Paragraph 6. The compound of paragraph 1, wherein $R^1$ is 3-7-membered heterocycloalkyl ring comprising 1 or 2 heteroatoms selected from N, O, and S, which is optionally substituted with 1, 2, or 3 substituents independently selected from $R^2$.

Paragraph 7. The compound of paragraph 6, wherein $R^1$ is selected from tetrahydropyranyl, piperidinyl, tetrahydrofuranyl, and pyrrolidinyl, each of which is optionally substituted with 1, 2, or 3 substituents independently selected from $R^2$.

Paragraph 8. The compound of paragraph 6, wherein $R^1$ is tetrahydropyranyl, optionally substituted with 1, 2, or 3 substituents independently selected from $R^2$.

Paragraph 9. The compound of paragraph 8, wherein the compound of Formula (I) is selected from:

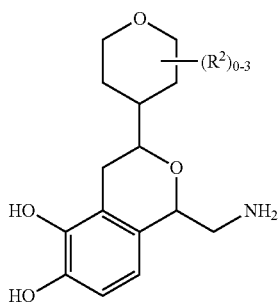

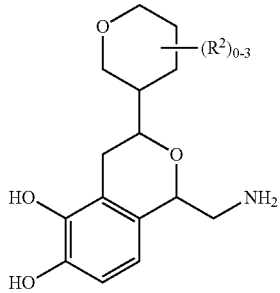

or a pharmaceutically acceptable salt thereof.

Paragraph 10. The compound of paragraph 1, wherein $R^1$ is selected from HO—$C_{1-6}$ alkyl and $NH_2$—$C_{1-6}$ alkyl.

Paragraph 11. The compound of paragraph 1, wherein $R^1$ is HO—$C_{1-6}$ alkyl.

Paragraph 12. The compound of any one of paragraphs 1-9, wherein each $R^2$ is independently selected from OH, $NH_2$, $C_{1-3}$ alkyl, HO—$C_{1-3}$ alkyl, and $NH_2$—$C_{1-3}$ alkyl.

Paragraph 13. The compound of paragraph 1, wherein the compound of Formula (I) is selected from any one of the following compounds:

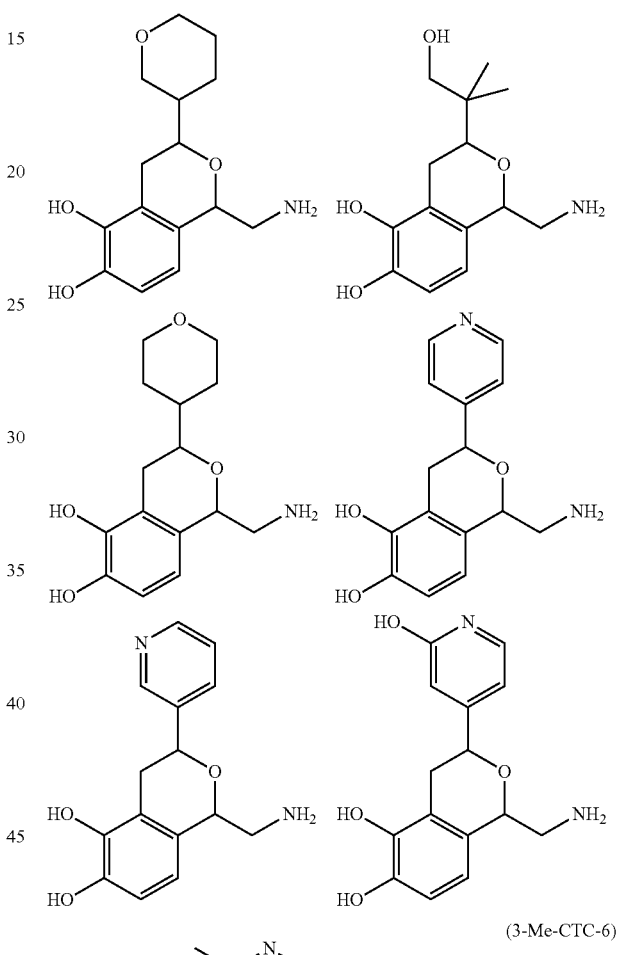

or a pharmaceutically acceptable salt thereof.

Paragraph 14. A pharmaceutical composition comprising a compound of any one of paragraphs 1-13, or a pharmaceutically acceptable salt thereof, and a pharmaceutically acceptable carrier.

Paragraph 15. A method of:
agonizing a Gα_S protein coupled receptor in a cell; and/or
promoting YAP/TAZ phosphorylation in a cell; and/or
inhibiting YAP/TAZ function in a cell; and/or
inhibiting expression of a profibrotic gene in a cell; and/or
reducing nuclear localization of YAP/TAZ in a cell; and/or
inhibiting expressing of α-smooth muscle actin (αSMA) in a cell; and/or
inhibiting extra-cellular matrix production and deposition by a cell; and/or
enhancing extra-cellular matrix degradation by a cell;
the method comprising contacting the cell with an effective amount of a compound of any one of paragraphs 1-13, or a pharmaceutically acceptable salt thereof.

Paragraph 16. The method of paragraph 15, wherein the profibrotic gene is selected from the group consisting of: CTGF, COL1A1, ACTA2, and FN.

Paragraph 17. The method of paragraph 15 or 16, wherein the Gα_S protein coupled receptor is a dopamine receptor.

Paragraph 18. The method of paragraph 17, wherein the dopamine receptor is dopamine receptor D1 (DRD1).

Paragraph 19. The method of paragraph 18, wherein the method comprises selectively agonizing D1 dopamine receptor, as compared to D2, D3, D4, or D5 dopamine receptor, or any combination thereof.

Paragraph 20. The method of any one of paragraphs 15-19, wherein the cell is a mesenchymal cell.

Paragraph 21. The method of paragraph 20, wherein the mesenchymal cell is selected from a fibroblast and a stellate cell.

Paragraph 22. A method of treating or preventing a fibrotic pathology, the method comprising administering to a subject in need thereof a therapeutically effective amount of a compound of any one of paragraphs 1-13, or a pharmaceutically acceptable salt thereof, or a pharmaceutical composition of paragraph 14.

Paragraph 23. The method of paragraph 22, wherein the fibrotic pathology is interstitial lung disease (ILD).

Paragraph 24. The method of paragraph 22, wherein the fibrotic pathology is selected from pulmonary fibrosis (PF) and idiopathic pulmonary fibrosis (IPF).

Paragraph 25. The method of paragraph 22, wherein the fibrotic pathology is selected from liver tissue fibrosis, cardiac fibrosis, kidney fibrosis, and skin tissue fibrosis.

Paragraph 26. The method of any one of paragraphs 22-25, further comprising administering to the subject a therapeutically effective amount of an additional therapeutic agent useful in treating a fibrotic pathology.

Paragraph 27. The method of paragraph 26, wherein the additional therapeutic agent is dopamine, or a pharmaceutically acceptable salt thereof.

Paragraph 28. The method of paragraph 26, wherein the additional therapeutic agent is a dopamine receptor agonist.

Paragraph 29. The method of claim 28, wherein the dopamine receptor agonist is selected from: ABT-413, A-86929, dihydrexidine (DHX), dinapsoline, dinoxyline, doxanthrine, SKF-81297, SKF-82958, SKF-38393, fenoldopam, 6-Br-APB, stepholidine, A-68930, A-77636, CY-208-243, SKF-89145, SKF-89626, 7,8-dihydroxy-5-phenyl-octahydrobenzo[h]isoquinoline, cabergoline, pergolide, R(−)-2,10,11-trihydroxyaporphine, (R)-(−)-apomorphine, R(−)-propylnoraporphine, R(+)-6-bromo-APB, R(−)-2,10,11-trihydroxy-N-propyl-noraporphine, 6,7-ADTN, mesulergine, N-methyldopamine, 4-hydroxyphenethylamine, cabergoline, 3-hydroxyphenethylamine, pramipexole, PD-168077, fenoldopam, (+)-PD 128-907, (+)-2-(N-phenylethyl-N-propyl)amino-5-hydroxytetralin, bromocriptine, ropinirole, LY-163-502, dipropyldopamine, B-HT 920, piribedil, (+)-UH 232, pergolide, (−)-quinpirole, R(−)-2,11-dihydroxy-10-methoxyapomorphine, or a pharmaceutically acceptable salt thereof.

Paragraph 30. A compound of Formula (II):

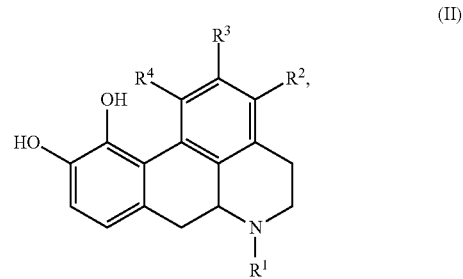

(II)

or a pharmaceutically acceptable salt thereof, wherein:
$R^1$ is selected from H and $C_{1-3}$ alkyl, wherein said $C_{1-3}$ alkyl is optionally substituted with OH, SH, $NH_2$, $C_{1-3}$ alkylamino, or di($C_{1-3}$ alkyl)amino;
$R^2$, $R^3$, and $R^4$ are each independently selected from H, OH, SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino, and di($C_{1-3}$ alkyl)amino;
provided that:
(i) at least one of $R^2$, $R^3$, and $R^4$ is not H;
(ii) if $R^2$ is H and $R^3$ is OH, then $R^4$ is not H or OH; and
(iii) if $R^2$ is OH, then at least one of $R^3$ and $R^4$ is not H.

Paragraph 31. The compound of paragraph 30, wherein $R^1$ is H.

Paragraph 32. The compound of paragraph 30, wherein $R^1$ is $C_{1-3}$ alkyl.

Paragraph 33. The compound of paragraph 30, wherein $R^1$ is selected from HO—$C_{1-3}$ alkyl and $NH_2$—$C_{1-3}$ alkyl.

Paragraph 34. The compound of any one of paragraphs 30-33, wherein at least one of $R^2$, $R^3$, and $R^4$ is selected from SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino and di($C_{1-3}$ alkyl)amino.

Paragraph 35. The compound of any one of paragraphs 30-33, wherein at least one of $R^2$, $R^3$, and $R^4$ is selected from $NH_2$, $C_{1-3}$ alkyl, HO—$C_{1-3}$ alkyl, and $NH_2$—$C_{1-3}$ alkyl.

Paragraph 36. The compound of any one of paragraphs 30-33, wherein at least one of $R^2$, $R^3$, and $R^4$ is $C_{1-3}$ alkyl.

Paragraph 37. The compound of any one of paragraphs 30-33, wherein:
$R^3$ is OH; and
$R^2$ is selected from SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino and di($C_{1-3}$ alkyl)amino.

Paragraph 38. The compound of any one of paragraphs 30-33, wherein:
$R^3$ is OH; and
$R^2$ is selected from OH, $NH_2$, $C_{1-3}$ alkyl, HO—$C_{1-3}$ alkyl, and $NH_2$—$C_{1-3}$ alkyl.

Paragraph 39. The compound of any one of paragraphs 30-33, wherein:

R³ is OH; and
R⁴ is selected from SH, NH₂, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, NH₂, $C_{1-3}$ alkylamino and di($C_{1-3}$ alkyl)amino.

Paragraph 40. The compound of any one of paragraphs 30-33, wherein:
R³ is OH; and
R⁴ is selected from NH₂, $C_{1-3}$ alkyl, HO—$C_{1-3}$ alkyl, and NH₂—$C_{1-3}$ alkyl.

Paragraph 41. The compound of any one of paragraphs 30-33, wherein:
R⁴ is OH; and
R³ is selected from H, SH, NH₂, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, NH₂, $C_{1-3}$ alkylamino and di($C_{1-3}$ alkyl)amino.

Paragraph 42. The compound of any one of paragraphs 30-33, wherein:
R⁴ is OH; and
R³ is selected from H, NH₂, $C_{1-3}$ alkyl, HO—$C_{1-3}$ alkyl, and NH₂—$C_{1-3}$ alkyl.

Paragraph 43. The compound of any one of paragraphs 30-33, wherein:
R² is OH; and
at least one of R³ and R⁴ is selected from OH, SH, NH₂, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, NH₂, $C_{1-3}$ alkylamino and di($C_{1-3}$ alkyl)amino.

Paragraph 44. The compound of any one of paragraphs 30-33, wherein:
R² is OH; and
at least one of R³ and R⁴ is selected from OH, NH₂, $C_{1-3}$ alkyl, HO—$C_{1-3}$ alkyl, and NH₂—$C_{1-3}$ alkyl.

Paragraph 45. The compound of paragraph 30, wherein the compound of Formula (II) is:

(compound 1)

or a pharmaceutically acceptable salt thereof.

Paragraph 46. The compound of paragraph 30, wherein the compound of Formula (II) is:

(compound 2)

or a pharmaceutically acceptable salt thereof.

Paragraph 47. A pharmaceutical composition comprising a compound of any one of paragraphs 30-46, or a pharmaceutically acceptable salt thereof, and a pharmaceutically acceptable carrier.

Paragraph 48. A method of
agonizing a $G\alpha_S$ protein coupled receptor in a cell; and/or
promoting YAP/TAZ phosphorylation in a cell; and/or
inhibiting YAP/TAZ function in a cell; and/or
inhibiting expression of a profibrotic gene in a cell; and/or
reducing nuclear localization of YAP/TAZ in a cell; and/or
inhibiting expressing of α-smooth muscle actin (αSMA) in a cell; and/or
inhibiting extra-cellular matrix production and deposition by a cell; and/or
enhancing extra-cellular matrix degradation by a cell;
the method comprising contacting the cell with an effective amount of a compound of any one of paragraphs 30-46, or a pharmaceutically acceptable salt thereof.

Paragraph 49. The method of paragraph 48, wherein the profibrotic gene is selected from the group consisting of: CTGF, COL1A1, ACTA2, and FN.

Paragraph 50. The method of paragraph 48 or 49, wherein the $G\alpha_S$ protein coupled receptor is a dopamine receptor.

Paragraph 51. The method of paragraph 50, wherein the dopamine receptor is dopamine receptor D1 (DRD1).

Paragraph 52. The method of paragraph 51, wherein the method comprises selectively agonizing D1 dopamine receptor, as compared to D2, D3, D4, or D5 dopamine receptor, or any combination thereof.

Paragraph 53. The method of any one of paragraphs 48-52, wherein the cell is a mesenchymal cell.

Paragraph 54. The method of paragraph 53, wherein the mesenchymal cell is selected from a fibroblast and a stellate cell.

Paragraph 55. A method of treating or preventing a fibrotic pathology, the method comprising administering to a subject in need thereof a therapeutically effective amount of a compound of any one of paragraphs 30-46, or a pharmaceutically acceptable salt thereof, or a pharmaceutical composition of paragraph 47.

Paragraph 56. The method of paragraph 55, wherein the fibrotic pathology is interstitial lung disease (ILD).

Paragraph 57. The method of paragraph 56, wherein the fibrotic pathology is selected from pulmonary fibrosis (PF) and idiopathic pulmonary fibrosis (IPF).

Paragraph 58. The method of paragraph 55, wherein the fibrotic pathology is selected from liver tissue fibrosis, cardiac fibrosis, kidney fibrosis, and skin tissue fibrosis.

Paragraph 59. The method of any one of paragraphs 55-58, further comprising administering to the subject a therapeutically effective amount of an additional therapeutic agent useful in treating a fibrotic pathology.

Paragraph 60. The method of paragraph 59, wherein the additional therapeutic agent is dopamine, or a pharmaceutically acceptable salt thereof.

Paragraph 61. The method of paragraph 59, wherein the additional therapeutic agent is a dopamine receptor agonist.

Paragraph 62. The method of paragraph 61, wherein the dopamine receptor agonist is selected from: ABT-413, A-86929, dihydrexidine (DHX), dinapsoline, dinoxyline, doxanthrine, SKF-81297, SKF-82958, SKF-38393, fenoldopam, 6-Br-APB, stepholidine, A-68930, A-77636, CY-208-243, SKF-89145, SKF-89626, 7,8-dihydroxy-5-phenyl-octahydrobenzo[h]isoquinoline, cabergoline, pergolide, R(−)-2,10,11-trihydroxyaporphine, (R)-(−)-apomorphine, R(−)-propylnorapomorphine, R(+)-6-bromo-APB, R(−)-2,10,11- trihydroxy-N-propyl-noraporphine, 6,7-ADTN, mesulergine, N-methyldopamine, 4-hydroxyphenethylamine, cabergoline, 3-hydroxyphenethylamine, pramipexole, PD-168077, fenoldopam, (±)-PD 128-907, (±)-2-(N-phenylethyl-N-propyl)amino-5-hydroxytetralin, bromocriptine, ropinirole, LY-163-502, dipropyldopamine, B-HT 920, piribedil, (+)-UH 232, pergolide, (−)-quinpirole, R(−)-2,11-dihydroxy-10-methoxyapomorphine, or a pharmaceutically acceptable salt thereof.

Other Embodiments

It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

What is claimed is:

1. A compound of Formula (I):

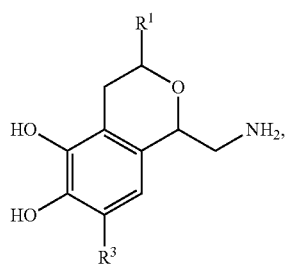

(I)

or a pharmaceutically acceptable salt thereof, wherein:

$R^1$ is selected from 5-6-membered heteroaryl ring comprising 1 to 5 heteroatoms selected from N, O, and S; wherein said heteroaryl ring is optionally substituted with 1, 2, or 3 substituents independently selected from $R^2$;

each $R^2$ is independently selected from halo, OH, $C_{1-3}$ alkoxy, SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, $C_{1-3}$ alkoxy, SH, $NH_2$, $C_{1-3}$ alkylamino, and di($C_{1-3}$ alkyl)amino; and $R^3$ is selected from H and halo.

2. The compound of claim 1, wherein the compound of Formula (I) has formula

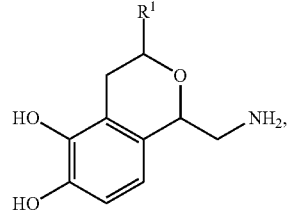

or a pharmaceutically acceptable salt thereof, wherein:

$R^1$ is selected from 5-6-membered heteroaryl ring comprising 1 or 2 heteroatoms selected from N, O, and S; wherein said heteroaryl ring is optionally substituted with 1, 2, or 3 substituents independently selected from $R^2$; and each $R^2$ is independently selected from OH, SH, $NH_2$, $C_{1-3}$ alkylamino, di($C_{1-3}$ alkyl)amino, $C_{1-3}$ alkyl, and $C_{1-3}$ haloalkyl, wherein said $C_{1-3}$ alkyl is optionally substituted with OH, SH, $NH_2$, $C_{1-3}$ alkylamino, and di($C_{1-3}$ alkyl)amino.

3. The compound of claim 1, wherein $R^1$ is 5-6-membered heteroaryl ring comprising 1 or 2 heteroatoms selected from N, O, and S, which is optionally substituted with 1, 2, or 3 substituents independently selected from $R^2$.

4. The compound of claim 1, wherein $R^1$ is selected from pyridinyl, pyrimidinyl, pyrazinyl, diazinyl, triazinyl, tetrazinyl, and pentazinyl, each of which is optionally substituted with 1, 2, or 3 substituents independently selected from $R^2$.

5. The compound of claim 1, wherein $R^1$ is pyridinyl, optionally substituted with 1, 2, or 3 substituents independently selected from $R^2$.

6. The compound of claim 5, wherein the compound of Formula (I) is selected from:

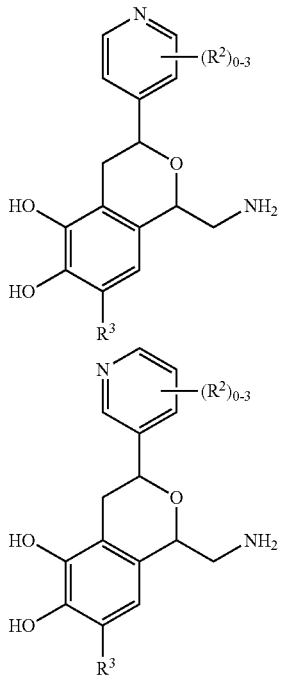

or a pharmaceutically acceptable salt thereof.

7. The compound of claim 5, wherein the compound of Formula (I) is selected from:

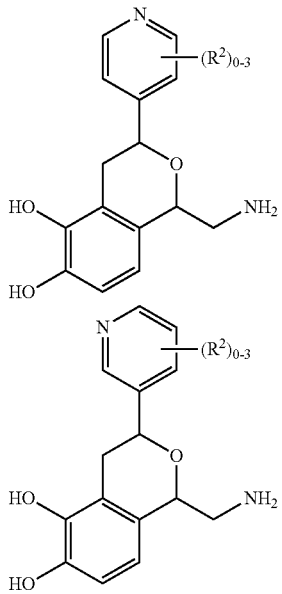

or a pharmaceutically acceptable salt thereof.

8. The compound of claim 1, wherein $R^1$ is selected from HO—$C_{1-6}$ alkyl and $NH_2$-$C_{1-6}$ alkyl.

9. The compound of claim 1, wherein each $R^2$ is independently selected from OH, $NH_2$, $C_{1-3}$ alkyl, HO—$C_{1-3}$ alkyl, and $NH_2$-$C_{1-3}$ alkyl.

10. The compound of claim 1, wherein $R^3$ is selected from Cl, F, and Br.

11. The compound of claim 1, wherein the compound of Formula (I) is selected from any one of the following compounds:

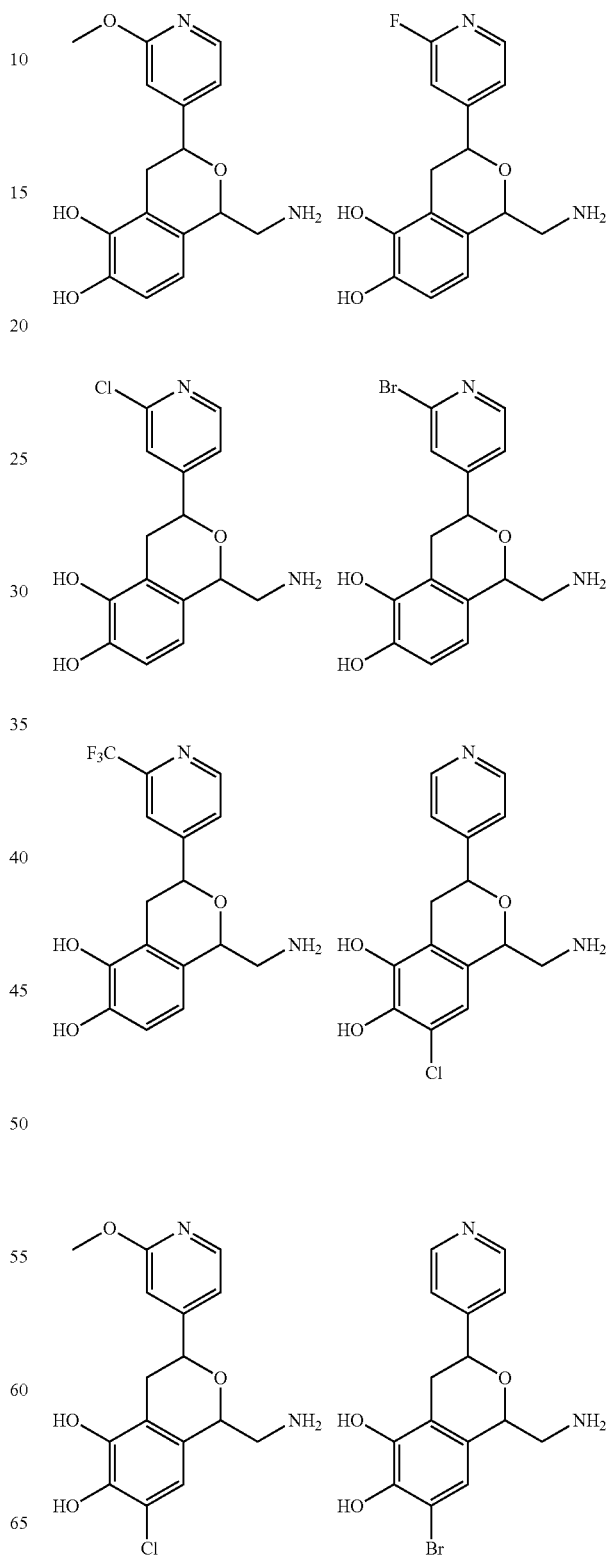

-continued

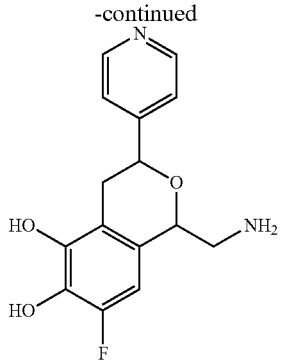

or a pharmaceutically acceptable salt thereof.

12. The compound of claim 1, wherein the compound of Formula (I) is selected from any one of the following compounds:

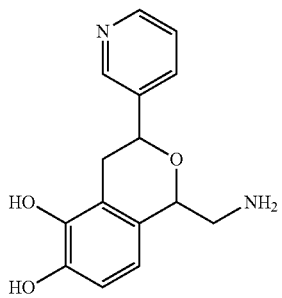

-continued

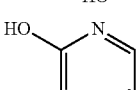

(CTC-6)

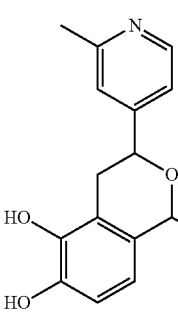

or a pharmaceutically acceptable salt thereof.

13. A pharmaceutical composition comprising a compound of claim 1, or a pharmaceutically acceptable salt thereof, and a pharmaceutically acceptable carrier.

* * * * *

UNITED STATES PATENT AND TRADEMARK OFFICE
CERTIFICATE OF CORRECTION

PATENT NO. : 12,264,163 B2
APPLICATION NO. : 17/625244
DATED : April 1, 2025
INVENTOR(S) : Daniel J. Tschumperlin and Andrew J. Haak Page 1 of 1

It is certified that error appears in the above-identified patent and that said Letters Patent is hereby corrected as shown below:

In the Claims

Column 122, Line 1, In Claim 10, after from insert -- H, --.

Signed and Sealed this
Twenty-seventh Day of May, 2025

Coke Morgan Stewart
*Acting Director of the United States Patent and Trademark Office*

SEQUENCE LISTING

```
<160> NUMBER OF SEQ ID NOS: 54

<210> SEQ ID NO 1
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 1 cccagccta tcagtcatat tg                                              22

<210> SEQ ID NO 2
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 2
aggattcatc tgcgagttca g                                              21

<210> SEQ ID NO 3
<211> LENGTH: 17
<212> TYPE: DNA
<213> ORGANISM: Artificial
<220> FEATURE:
<223> OTHER INFORMATION: synthetic oligonucleotide primer

<400> SEQUENCE: 3
gtccagcacg aggctca                                                   17

<210> SEQ ID NO 4
<211> LENGTH: 17
<212> TYPE: DNA
<213> ORGANISM: Artificial
<220> FEATURE:
<223> OTHER INFORMATION: synthetic oligonucleotide primer

<400> SEQUENCE: 4
tcgccttcgt ggtcctc                                                   17

<210> SEQ ID NO 5
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 5
aagggacaca gaggtttcag tgg                                            23

<210> SEQ ID NO 6
<211> LENGTH: 24
<212> TYPE: DNA
<213> ORGANISM: Artificial
```

```
<220> FEATURE:
<223> OTHER INFORMATION: synthetic oligonucleotide primer

<400> SEQUENCE: 6
cagcaccagt agcaccatca tttc                                          24

<210> SEQ ID NO 7
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 7
gtgaagaaga ggacagcact g                                             21

<210> SEQ ID NO 8
<211> LENGTH: 18
<212> TYPE: DNA
<213> ORGANISM: Artificial
<220> FEATURE:
<223> OTHER INFORMATION: synthetic oligonucleotide primer

<400> SEQUENCE: 8
cccattccca ccatcacc                                                 18

<210> SEQ ID NO 9
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 9
tgtcagtcaa agcaagcccg                                               20

<210> SEQ ID NO 10
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 10
ttaggacgct cataagtgtc accc                                          24

<210> SEQ ID NO 11
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 11
tcagctacaa tgggatcttg g                                             21

<210> SEQ ID NO 12
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 12
tcagctacaa tgggatcttg g                                             21
```

```
<210> SEQ ID NO 13
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 13
acattcgcta cacaggacat c                                              21

<210> SEQ ID NO 14
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 14
ttcccacttc agaacaccag                                                20

<210> SEQ ID NO 15
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 15
tgccagtgga tcgacataac                                                20

<210> SEQ ID NO 16
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 16
gaaacgtagc gacctgtgta g                                              21

<210> SEQ ID NO 17
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 17
gtgcagcgac aaaaggattc                                                20

<210> SEQ ID NO 18
<211> LENGTH: 19
<212> TYPE: DNA
<213> ORGANISM: Artificial
<220> FEATURE:
<223> OTHER INFORMATION: synthetic oligonucleotide primer

<400> SEQUENCE: 18
gcggtaggtt gagaggatg                                                 19

<210> SEQ ID NO 19
<211> LENGTH: 19
<212> TYPE: DNA
<213> ORGANISM: Artificial
<220> FEATURE:
<223> OTHER INFORMATION: synthetic oligonucleotide primer
```

-continued

<400> SEQUENCE: 19
agcgaaaaga gggtcaacg                                                19

<210> SEQ ID NO 20
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 20
tgtcattggc acgatagaac tc                                            22

<210> SEQ ID NO 21
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 21
gtggcagagt cagatttctc c                                             21

<210> SEQ ID NO 22
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 22
ttgttcctga gacgctgttc                                               20

<210> SEQ ID NO 23
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 23
gggagatgaa gtttgaggtg g                                             21

<210> SEQ ID NO 24
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 24
agatggtctg tatagtccgg g                                             21

<210> SEQ ID NO 25
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 25
aaacccagat cgagactcaa ag                                            22

<210> SEQ ID NO 26

```
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 26
acccattccc aaagtagcag                                          20

<210> SEQ ID NO 27
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 27
ctccttccag ttttacagca aag                                      23

<210> SEQ ID NO 28
<211> LENGTH: 19
<212> TYPE: DNA
<213> ORGANISM: Artificial
<220> FEATURE:
<223> OTHER INFORMATION: synthetic oligonucleotide primer

<400> SEQUENCE: 28
tttccccagt tttctcccc                                           19

<210> SEQ ID NO 29
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 29
tgcctaccga caagattgat g                                        21

<210> SEQ ID NO 30
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 30
atcccttccc agactttgat g                                        21

<210> SEQ ID NO 31
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 31
cccgtagcca ttatgatcgt c                                        21

<210> SEQ ID NO 32
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 32
```

-continued agagcattcg acagggtttc 20

<210> SEQ ID NO 33
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 33
tccttctacc acctcagcga g 21

<210> SEQ ID NO 34
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 34
ccggatggtc actctttagg aag 23

<210> SEQ ID NO 35
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 35
ttgctccaaa ctggcgtcta 20

<210> SEQ ID NO 36
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 36
acgtgatctc cgtgtccttg t 21

<210> SEQ ID NO 37
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 37
ctgccagtcc gaaaatggaa c 21

<210> SEQ ID NO 38
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 38
cttcatccac tggggctatc 20

<210> SEQ ID NO 39
<211> LENGTH: 23
<212> TYPE: DNA

```
<213> ORGANISM: Artificial
<220> FEATURE:
<223> OTHER INFORMATION: synthetic oligonucleotide primer

<400> SEQUENCE: 39
gacagagtta gtgaatggag acc                                          23

<210> SEQ ID NO 40
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 40
aaaagttcgg agagtgtagg c                                            21

<210> SEQ ID NO 41
<211> LENGTH: 18
<212> TYPE: DNA
<213> ORGANISM: Artificial
<220> FEATURE:
<223> OTHER INFORMATION: synthetic oligonucleotide primer

<400> SEQUENCE: 41
gagaagccca gccagtcg                                                18

<210> SEQ ID NO 42
<211> LENGTH: 18
<212> TYPE: DNA
<213> ORGANISM: Artificial
<220> FEATURE:
<223> OTHER INFORMATION: synthetic oligonucleotide primer

<400> SEQUENCE: 42
ctcttgctct gggcttca                                                18

<210> SEQ ID NO 43
<211> LENGTH: 17
<212> TYPE: DNA
<213> ORGANISM: Artificial
<220> FEATURE:
<223> OTHER INFORMATION: synthetic oligonucleotide primer

<400> SEQUENCE: 43
cctgcgaccc acacaag                                                 17

<210> SEQ ID NO 44
<211> LENGTH: 18
<212> TYPE: DNA
<213> ORGANISM: Artificial
<220> FEATURE:
<223> OTHER INFORMATION: synthetic oligonucleotide primer

<400> SEQUENCE: 44
gacccaccga agacacag                                                18

<210> SEQ ID NO 45
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 45
ccagcagcat gatcaaaaca c                                            21
```

<210> SEQ ID NO 46
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 46
ggtggctaca tgttagagtg tc                                              22

<210> SEQ ID NO 47
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 47
atcatagcca taggacatct gg                                              22

<210> SEQ ID NO 48
<211> LENGTH: 18
<212> TYPE: DNA
<213> ORGANISM: Artificial
<220> FEATURE:
<223> OTHER INFORMATION: synthetic oligonucleotide primer

<400> SEQUENCE: 48
ctggacagcc tggacttc                                                   18

<210> SEQ ID NO 49
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 49
ctctgagtga tcctctggtt c                                               21

<210> SEQ ID NO 50
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 50
ccataagaac aagaccacat cct                                             23

<210> SEQ ID NO 51
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 51
cttgctggtg ttggtgattc                                                 20

```
<210> SEQ ID NO 52
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 52
atcagcctct gaatcatgtg aa                                              22

<210> SEQ ID NO 53
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 53 tgcttttcc agggtgtgt t                                                 21

<210> SEQ ID NO 54
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 54
ttacttcctg cactaatttg gca                                             23
```